US012668573B2

(12) United States Patent
Zhou et al.

(10) Patent No.: US 12,668,573 B2
(45) Date of Patent: Jun. 30, 2026

(54) LINKER, ANTIBODY-DRUG CONJUGATE INCLUDING SAME AND USE THEREOF

(71) Applicant: Zhejiang Yangshengtang Institute of Natural Medication Co., Ltd., Zhejiang (CN)

(72) Inventors: Xinbo Zhou, Beijing (CN); Yanming Wang, Beijing (CN); Shiyong Fan, Beijing (CN); Song Li, Beijing (CN); Wu Zhong, Beijing (CN); Junhai Xiao, Beijing (CN); Zhibing Zheng, Beijing (CN); Xingzhou Li, Beijing (CN); Dian Xiao, Beijing (CN); Yunde Xie, Beijing (CN); Xiaokui Wang, Beijing (CN); Ruiyuan Cao, Beijing (CN)

(73) Assignee: Zhejiang Yangshengtang Institute of Natural Medication Co., Ltd., Zhejiang (CN)

( * ) Notice: Subject to any disclaimer, the term of this patent is extended or adjusted under 35 U.S.C. 154(b) by 1428 days.

(21) Appl. No.: 17/268,063

(22) PCT Filed: Aug. 15, 2019

(86) PCT No.: PCT/CN2019/100805
§ 371 (c)(1),
(2) Date: Feb. 11, 2021

(87) PCT Pub. No.: WO2020/035027
PCT Pub. Date: Feb. 20, 2020

(65) Prior Publication Data

US 2021/0261505 A1 Aug. 26, 2021

(30) Foreign Application Priority Data

Aug. 17, 2018 (CN) ......................... 201810939770.0

(51) Int. Cl.

| | |
|---|---|
| ***C07D 207/09*** | (2006.01) |
| ***A61K 47/65*** | (2017.01) |
| ***A61K 47/68*** | (2017.01) |
| ***C07D 207/40*** | (2006.01) |
| ***C07D 207/416*** | (2006.01) |
| ***C07K 5/062*** | (2006.01) |
| *A61K 45/06* | (2006.01) |

(52) U.S. Cl.
CPC .......... *C07D 207/416* (2013.01); *A61K 47/65* (2017.08); *A61K 47/6801* (2017.08); *A61K 47/68031* (2023.08); *C07D 207/09* (2013.01); *C07D 207/40* (2013.01); *C07K 5/06052* (2013.01); *A61K 45/06* (2013.01)

(58) Field of Classification Search
None
See application file for complete search history.

(56) References Cited

U.S. PATENT DOCUMENTS

| | | | | |
|---|---|---|---|---|
| 11,643,469 | B2 * | 5/2023 | Lerchen ............. | C07K 16/2866 424/181.1 |
| 2018/0318437 | A1 | 11/2018 | Lerchen et al. | |
| 2018/0318438 | A1 | 11/2018 | Lerchen et al. | |
| 2019/0388555 | A1 | 12/2019 | Shen et al. | |

FOREIGN PATENT DOCUMENTS

| | | | |
|---|---|---|---|
| CN | 108101825 | A | 6/2018 |
| WO | 2017216028 | A1 | 12/2017 |

OTHER PUBLICATIONS

Shastry et al., Rise of Antibody-Drug Conjugates: The Present and Future. Developmental Therapeutics—Molecularly Targeted Agents and Tumor Biology, 2023, 43, p. 1-15.*
Schafer, S., Kolkhof, P. Failure is an option: learning from unsuccessful proof-of-concept trials. Drug Discovery Today. Nov. 2008, 13, 913-916.*
Horig, H., Pullman, W. From bench to clinic and back: Perspective on the 1st IQPC Translational Research conference. Journal of Translational Medicine. Dec. 2004, 2, 44.*
Federal Register (published on 2011, vol. 76, No. 27, p. 7166).*
International Search Report, Application No. PCT/CN2019/100805, mailed Nov. 13, 2019. ISA/China National Intellectual Property Administration.
EP 19849476.7 Extended European Search Report dated May 4, 2022.
Tumey, L. Nathan, et al., Mild Method for Succinimide Hydrolysis on ADCs: Impact on ADC Potency, Stability, Exposure and Efficacy, Bioconjugate Chemistry, vol. 25, No. 10, pp. 1871-1880, American Chemical Society, Oct. 15, 2014.

* cited by examiner

*Primary Examiner* — Po-Chih Chen
(74) *Attorney, Agent, or Firm* — Honigman LLP

(57) ABSTRACT

Provided are a linker represented by Formula I or I', an antibody-drug conjugate containing the same, and use of thereof, a pharmaceutical composition comprising the antibody-drug conjugate, and use of the antibody-drug conjugate for treating and/or preventing a disease.

I

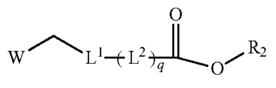

I'

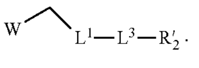

11 Claims, 5 Drawing Sheets stable succinimide ring-opening product

LINKER, ANTIBODY-DRUG CONJUGATE INCLUDING SAME AND USE THEREOF

CROSS-REFERENCE TO RELATED APPLICATIONS

This application is a National Stage Application and claims priority under 35 U.S.C. § 371 to Patent Cooperation Treaty Application No. PCT/CN2019/100805, filed Aug. 15, 2019, which claims the benefit of Chinese Application No. 201810939770.0, filed Aug. 17, 2018. Priority is claimed to both of these applications and the disclosures of these prior applications are considered part of the disclosure of this application and to the extent allowed the entire contents of the aforementioned applications are incorporated herein.

TECHNICAL FIELD

The present application belongs to the field of medicinal chemistry, specifically relates to a linker, a linker-containing antibody-drug conjugate and use of the linker, as well as a pharmaceutical composition comprising the antibody-conjugated drug and use of the antibody-drug conjugate for treating and/or preventing a disease.

BACKGROUND ART

Tumors are still the main cause of human deaths due to diseases. The continuous emergence of new therapies is bringing revolutionary changes to cancer treatment. In recent years, CAR-T cell therapy and PD-1/PD-L1 antibody immunotherapy have made breakthrough progress, however, the indications of CAR-T cell therapy are limited to hematological malignancies, and the objective response rate of PD-1/PD-L1 antibody immunotherapy is only 20% to 30%. For most malignant tumors, the treatment methods are still limited and it is still necessary to expand existing therapies and create synergy by continuous innovation.

In recent years, the strategy for malignant tumor treatment is gradually shifting from traditional chemotherapies to antibody-based targeted therapies. However, in general, traditional treatment methods are still the first choice in clinical practice and chemotherapeutic drugs still occupy the largest share of the cancer treatment market in terms of product numbers. Due to their poor targeting and biodistribution, small-molecule chemotherapeutic drugs are prone to generate serious toxic and side effects, resulting in poor patient compliance and difficulty in obtaining satisfactory clinical benefits. Compared with chemotherapeutic drugs, monoclonal antibody drugs have better targeting and pharmacokinetic properties and have played an increasingly important role in the treatment of malignant tumors, however, they also have deficiencies such as poor tissue penetration, weak biological activity and easiness to produce resistance.

In the context of a serious lack of overall high-quality targets for new drug development, the emergence of antibody-drug conjugates (ADCs) has achieved a strong combination of advantages of small molecule chemotherapeutic drug and antibody and it has become one of the most promising directions besides tumor immunotherapy. The structure of antibody-drug conjugate comprises three parts: an antibody, a small molecule cytotoxin and a linker that realizes the organic combination of the former two parts. By means of the targeting property of antibody, cytotoxin of ADC is accumulated on a tumor target site to achieve the effects of increased efficacy and reduced toxicity and the released cytotoxin can further kill surrounding tumor cells through the bystander effect. The $IC_{50}$ of cytotoxin is usually $10^{-10}$ to $10^{-12}$ mol/L and the common cytotoxins are tubulin inhibitors MMAE and DM1. Compared with conventional chemotherapeutic drug, ADC shows a significantly improved therapeutic index.

In addition to the targeted drug delivery based on antibody, another major advantage of ADC is that the secondary drug resistance caused by monoclonal antibody may be overcome to a certain extent, because the efficacy of ADC mainly depends on cytotoxin rather than antibody, and its targeted binding would not be affected by a certain degree of tumor mutation. For example, ADC drug Kadcyla, which is composed of monoclonal antibody Herceptin and cytotoxin DM1, can still effectively treat $HER2^+$ breast cancer after Herceptin resistance and can substantially prolong the overall survival (OS) by nearly 6 months in comparison with the standard therapy of capecitabine/lapatinib. In addition, the clinical phase III evidence-based medicine studies with code names of MARIANNE, KAMILLA, etc. have confirmed that Kadcyla single drug showed an efficacy not inferior to that of the standard therapies and had better safety. This drug has now been included in the breast cancer guidelines as a first-line alternative anti-HER2 regimen. ADCs are characterized by high activity, low toxic and side effects and long duration of action, and the emergence of such drugs provides a new strategy for the "precision treatment" of tumors.

In biological macromolecules such as antibodies, heavy and light chains are often linked by disulfide bonds at defined positions. The free sulfhydryl groups generated by selective reduction of disulfide bonds between light and heavy chains of antibody molecules have been widely used as antibody modification sites to obtain ADC drugs in which antibody cysteine residues are used as coupling sites, the first successful marketed ADC drug Brentuximab Vedotin (Adcetris®) adopts this coupling method. In addition, the emerging sulfhydryl site-directed mutagenesis engineered antibody (THIOMAB) has an improved uniformity of ADC drug to a certain extent and the coupling site of this type of antibody is also sulfhydryl coupling site. In the preparation process of the above-mentioned various types of ADC, thiosuccinimide may be generated by Michael addition reaction between a free sulfhydryl group in the antibody structure and a maleimide group to realize the small molecule drug modification process of antibody (FIG. 1) and this addition reaction has now become an indispensable tool in the preparation process of ADCs currently on the market and in clinical research.

The structure of thiosuccinimide is widely used in ADC linkers. At present, the two mainstream ADC drugs Adcetris® and Kadcyla® and a large number of clinically researched ADCs all contain thiosuccinimide structural fragments. The wide application of thiosuccinimide structure in biological coupling is mainly based on two points: (1) the structure can be directly obtained through the Michael addition reaction between maleimide structure and sulfhydryl group under mild biological conditions; (2) the addition reaction has high selectivity and good reaction kinetic properties and the coupling process can be quantitatively completed in a very short time without a large excess of substrate.

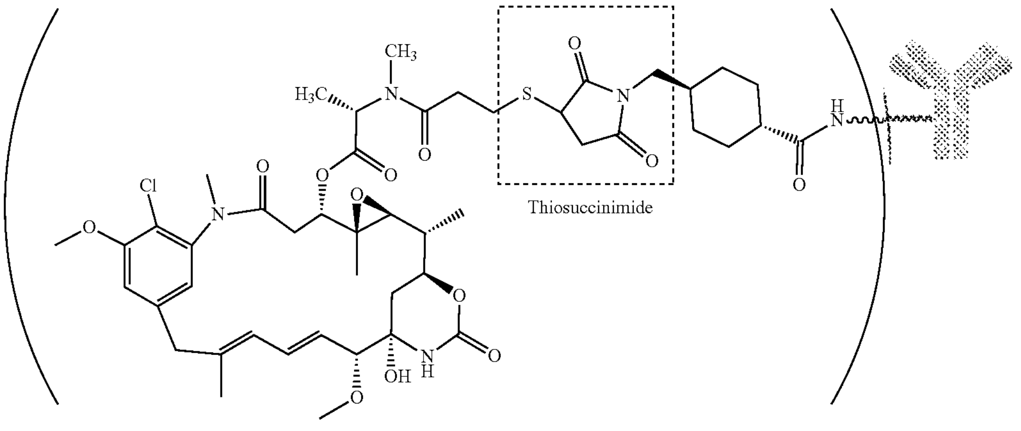

Kadcyla

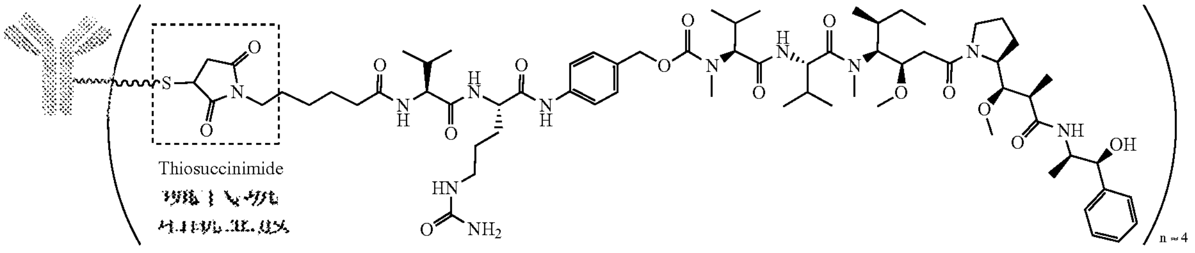

Adcetris

Although thiosuccinimide has obvious advantages and wide applicability, researchers in many biological coupling fields have realized that the spontaneous reverse Michael addition reaction of thiosuccinimide will cause slow decomposition of nearly half of conjugate (FIG. 2), thereby causing the toxin to miss its target. The off-target toxins caused by the above-mentioned instability characteristics will undoubtedly lead to the reduction of ADC efficacy and the increase of toxic and side effects (Nature Biotech., 2014, 32(10): 1059-1062.; *Nature Biotech.,* 2012, 30(2): 184-189.; *Bioconjugate Chem.,* 2008, 19(3): 759-765.; *Bioconjug Chem.,* 2016, 27(7): 1588-1598.; *J Med Chem.,* 2014, 57(19): 7890-7899.).

The process of purifying and preparing various ADCs containing thiosuccinimide is also accompanied by the above reverse Michael addition reaction at all times. Since the addition reaction between the maleimide produced by the reverse Michael addition reaction and the thiol will occur rapidly again, the process is generally undetectable. However, when other thiols are present, the off-target maleimide is transferred from the ADC antibody to any other available thiol. It has been confirmed that this process occurs in plasma, where the maleimide of ADC is transferred to the $34^{th}$ cysteine of serum albumin (*Bioconjugate Chem.,* 2008, 19(3): 759-765.). When substances containing sulfhydryl such as cysteine or glutathione are present, the ADC will also undergo the above-mentioned toxin off-target process (*Nature Biotech.,* 2012, 30(2): 184-189.).

Researchers have long been aware of the off-target problem of toxins in ADC caused by thiosuccinimide and many pharmaceutical companies around the world are also committed to finding solutions to solve the above problem. The research results of Junutula JR, a researcher of ADC pharmaceutical company Genentech, show that when the structure of thiosuccinimide undergoes a reverse Michael addition reaction, a competitive hydrolysis ring-opening reaction occurs at the same time, the structure of the product obtained by the hydrolysis ring-opening reaction is stable, toxins linked to which will not be off-target for a long time (Nature Biotech., 2012, 30(2): 184-189., FIG. 3). Further studies have found that the ring-opening structure is extremely stable and its degradation half-life can be as long as 2 years (*Bioconjug Chem.,* 2015, 26(1): 145-152.). However, the above work of Genentech only involves research and analysis at in vivo pharmacokinetic level and the stable ADC product has not been obtained. The conclusions of literature research and our further experiments confirm that the structure-stable linker ring-opening coupling product cannot be directly prepared by coupling reaction (*Biochem J,* 1979, 179(1): 191-197.).

The problem of ADC instability caused by the succinimide structure has not yet been effectively solved and the preparation of stable ADCs with ring-opening linkers still faces huge challenges. L. Nathan Tumey at Pfizer tried to perform the ring-opening process of the succinimide in the ADC structure by heating under alkaline conditions, so as to obtain the ring-opening product to overcome the off-targeting of toxin caused by the instability of succinimide (FIG. 4). However, heating (at 45° C.) for a long time (48 h) in an alkaline condition (pH=9.2) close to the isoelectric point of antibody caused the destruction of structure and properties of the antibody and about 70% of the antibody had deamidization mutation of asparagine (*Bioconjug Chem.,* 2014, 25(10): 1871-1880.). This method still has significant deficiencies and limitations when used in ADC development.

Lyon RP, a researcher of Seattle Genetics, introduced intramolecular amino groups near the succinimide group to induce and accelerate the ring-opening process of succinimide (*Nature Biotech.,* 2014, 32(10): 1059-1062., FIG. 5).

However, this strategy brought a variety of uncontrollable factors to the preparation process, the changes of structure can bring about various effects on the distribution, metabolism, pharmacokinetics and efficacy of the final product; and the preparation process to induce ring-opening structure was complicated, so that the druggability and drug safety of the resultant new chemical entities need be further confirmed.

In the current research, there is still no ideal choice that can better replace the thiosuccinimide linker structure. How to solve the problem of off-targeting of toxin caused by the thiosuccinimide structure, which is common in mainstream ADCs, still faces huge challenges.

Contents of the Application

The first aspect of the present application relates to a compound represented by Formula I or Formula I', a salt or a solvate thereof,

I

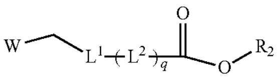

I'

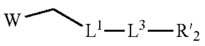

wherein:

W is

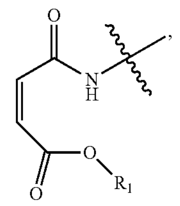

wherein the two carbonyl groups are located on the same side of the C═C double bond, which is a cis structure;

$R_1$ is a $C_{1-6}$ linear or branched alkyl and $R_1$ is optionally mono- or multi-substituted by one or more substituents selected from the group consisting of halogen, $C_{1-4}$ alkoxy;

$L^1$ is selected from the group consisting of $-(CH_2)_m-$, $-(CH_2)_tO-$, $-(CH_2CH_2O)_r-$, $-O-$, $-NH-$, $-S-$, $-S(O)-$, $-S(O)_2-$, $-NCH_3-$, $-NH(CH_2)_2NH-$, $-C(O)-$, $-(CH_2)_e-C(O)NH-(CH_2CH_2O)_f(CH_2)_g-$, $-(CH_2)_h-C(O)NH-CH[(CH_2)_i-NHC(O)-(CH_2CH_2O)_j-(CH_2)_k-CH_3]-$,

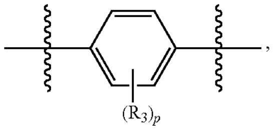,
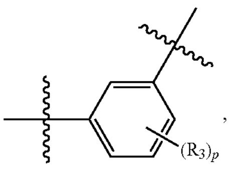,

-continued

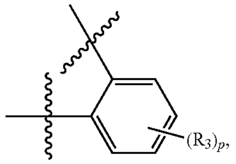
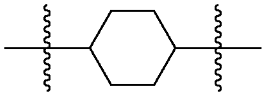,
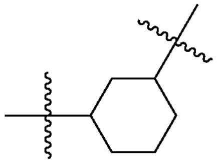,
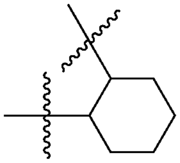 and
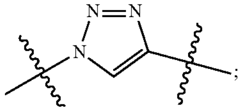;

$L^2$ is

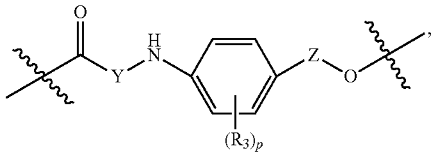, or
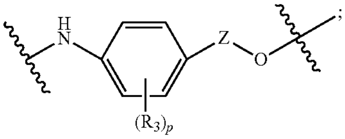;

$L^3$ is

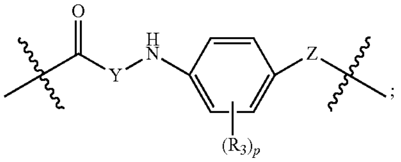;

$R_2$ is selected from the group consisting of

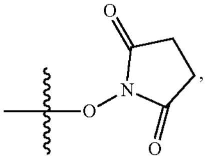,
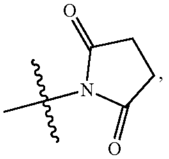,
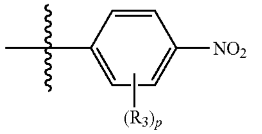 and
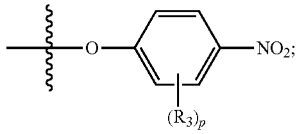;

$R'_2$ is halogen;

$R_3$ is selected from the group consisting of hydrogen, halogen, methyl, ethyl, nitro, methoxy and ethoxy;

q is 0 or 1;

m, r, t, e, f, g, h, i, j and k are each independently selected from the group consisting of 0, 1, 2, 3, 4, 5, 6, 7, 8, 9, 10 and 11;

each p is independently 0, 1, 2, 3 or 4;

Y is an amino acid residue formed by a dipeptide selected from the group consisting of: Val-Cit, Val-Ala, Val-Lys, Val-Gly, Val-Thr, Val-Val, Val-Leu, Val-Ile, Val-Asn and Phe-Lys, wherein the N-terminus is connected to the carbonyl and the C-terminus is connected to the N atom;

Z is $-CH_2-$, $-CH(CH_3)-$ or $-C(CH_3)_2-$.

The second aspect of the present application relates to a compound represented by Formula II or Formula II', a salts or a solvate thereof, wherein:

II

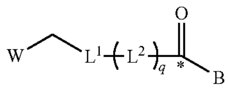

II'

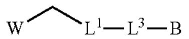

W is

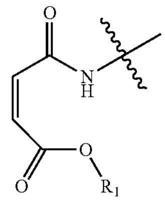, wherein the two carbonyl groups are located on the same side of the C═C double bond, which is a cis structure;

B is an active compound selected from the group consisting of drug, cytotoxin, detection reagent, diagnostic reagent and targeting carrier; preferably, B is a cytotoxin, an anti-tumor drug, an antiviral drug or an anti-infective drug; further preferably, B is a cytotoxin, such as a tubulin inhibitor, a DNA alkylating agent, a DNA intercalator, an enzyme inhibitor, an antimetabolite, a peptide or a nucleotide;

B is coupled to the site * through a N atom or O atom in the active compound molecule; or B is coupled to $L^3$ through a N atom or O atom in the active compound molecule;

$R_1$ is a $C_{1-6}$ linear or branched alkyl and $R_1$ is optionally mono- or multi-substituted by one or more substituents selected from the group consisting of halogen and $C_{1-4}$ alkoxy;

$L^1$ is selected from the group consisting of: $-(CH_2)_m-$, $-(CH_2)_tO-$, $-(CH_2CH_2O)_r-$, $-O-$, $-NH-$, $-S-$, $-S(O)-$, $-S(O)_2-$, $-NCH_3-$, $-NH(CH_2)_2NH-$, $-C(O)-$, $-(CH_2)_e-C(O)NH-(CH_2CH_2O)_f(CH_2)_g-$, $-(CH_2)_h-C(O)NH-CH[(CH_2)_i-NHC(O)-(CH_2CH_2O)_j-(CH_2)_k-CH_3]-$,

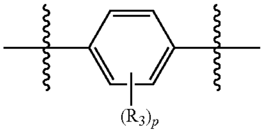, 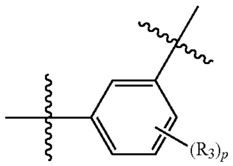,

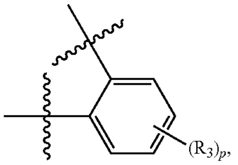 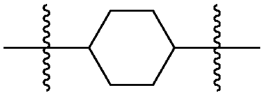,

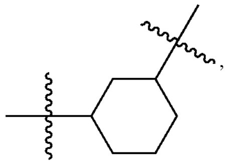, 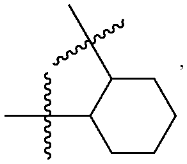, and

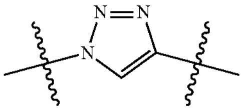;

$L^2$ is

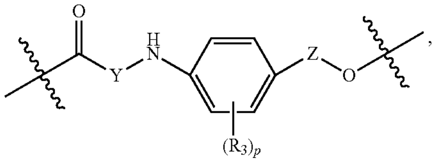, or

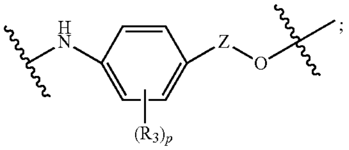;

$L^3$ is

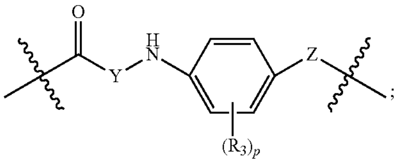;

$R_3$ is selected from the group consisting of: hydrogen, halogen, methyl, ethyl, nitro, methoxy, and ethoxy;

q is 0 or 1;

m, r, t, e, f, g, h, i, j and k are each independently selected from the group consisting of 0, 1, 2, 3, 4, 5, 6, 7, 8, 9, 10 and 11;

each p is independently 0, 1, 2, 3 or 4;

Y is an amino acid residue formed by a dipeptide selected from the group consisting of: Val-Cit, Val-Ala, Val-Lys, Val-Gly, Val-Thr, Val-Val, Val-Leu, Val-Ile, Val-Asn and Phe-Lys, wherein the N-terminus is connected to the carbonyl and the C-terminus is connected to the N atom;

Z is $-CH_2-$, $-CH(CH_3)-$ or $-C(CH_3)_2-$.

The third aspect of the present application relates to a compound represented by Formula III or Formula III', a salt or a solvate thereof,

III

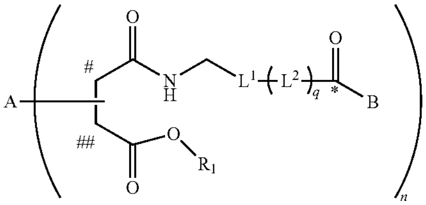

III'

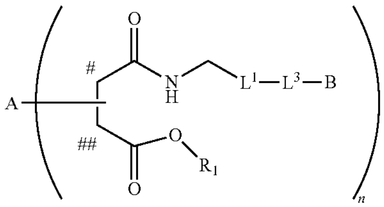

wherein:

A is a targeting compound selected from the group consisting of protein, antibody, polypeptide, enzyme and small molecule; A is coupled to the site # or ## through a S atom in the targeting compound molecule;

B is an active compound selected from the group consisting of drug, cytotoxin, detection reagent, diagnostic reagent and targeting carrier; preferably, B is a cytotoxin, an antitumor drug, an antiviral drug or an anti-infective drug; further preferably, B is a cytotoxin, such as a tubulin inhibitor, a DNA alkylating agent, a DNA intercalator, an enzyme inhibitor, an antimetabolite, a peptide or a nucleotide;

B is coupled to the site * through a N atom or O atom in the active compound molecule; or B is coupled to $L^3$ through a N atom or O atom in the active compound molecule;

n is a number between 0.5 and 8.5, such as a number between 0.8 and 5, a number between 1 and 4, a number between 2 and 6, a number between 3 and 7, a number between 4 and 8, a number between 3.5 and 8.5, a number between 3.5 and 4.5, or a number between 6.5 and 8.5, preferably n is about 4, 5, 6, 7 or 8;

$R_1$ is a $C_{1-6}$ linear or branched alkyl, and $R_1$ is optionally mono- or multi-substituted by one or more substituents selected from the group consisting of halogen and $C_{1-4}$ alkoxy;

$L^1$ is selected from the group consisting of: $-(CH_2)_m-$, $-(CH_2)_tO-$, $-(CH_2CH_2O)_r-$, $-O-$, $-NH-$, $-S-$, $-S(O)-$, $-S(O)_2-$, $-NCH_3-$, $-NH(CH_2)_2NH-$, $-C(O)-$, $-(CH_2)_e-C(O)NH-(CH_2CH_2O)_f(CH_2)_g-$, $-(CH_2)_h-C(O)NH-CH[(CH_2)_i-NHC(O)-(CH_2CH_2O)_j-(CH_2)_k-CH_3]-$,

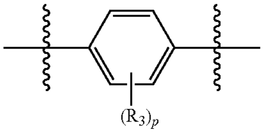,

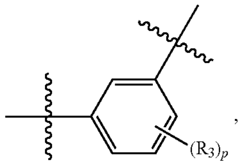,

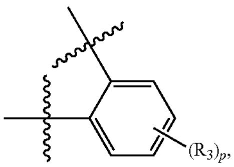,

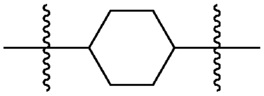,

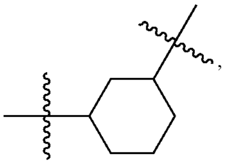,

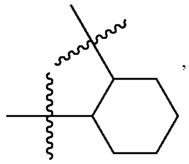, and

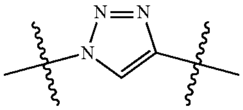;

$L^2$ is

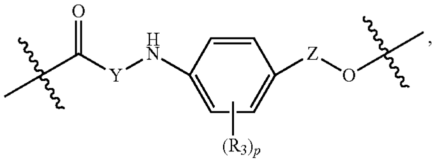, or

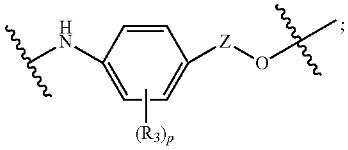;

$L^3$ is

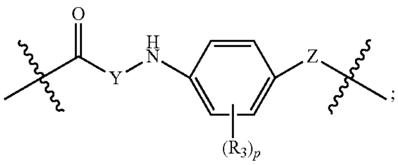;

$R_3$ is selected from the group consisting of: hydrogen, halogen, methyl, ethyl, nitro, methoxy, ethoxy;

q is 0 or 1;

m, r, t, e, f, g, h, i, j and k are each independently selected from the group consisting of 0, 1, 2, 3, 4, 5, 6, 7, 8, 9, 10 and 11;

each p is independently 0, 1, 2, 3 or 4;

Y is an amino acid residue formed by a dipeptide selected from the group consisting of: Val-Cit, Val-Ala, Val-Lys, Val-Gly, Val-Thr, Val-Val, Val-Leu, Val-Ile, Val-Asn and Phe-Lys, wherein the N-terminus is connected to the carbonyl and the C-terminus is connected to the N atom;

Z is $-CH_2-$, $-CH(CH_3)-$ or $-C(CH_3)_2-$.

According to some embodiments of the present application, the present application relates to the compound represented by Formula I, Formula I', Formula II, Formula II', Formula III, Formula III', a salt or a solvate thereof, wherein:

W is

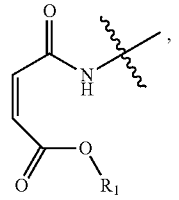

wherein the two carbonyl groups are located on the same side of the C═C double bond, which is a cis structure;

$R_1$ is a $C_{1-6}$ linear or branched alkyl and $R_1$ is optionally mono- or multi-substituted by one or more substituents selected from the group consisting of: halogen and $C_{1-4}$ alkoxy;

$L^1$ is selected from the group consisting of: $-(CH)_m-$, $-(CH_2)_tO-$, $-(CH_2CH_2O)_r-$, $-O-$, $-NH-$, $-S-$, $-S(O)-$, $-S(O)_2-$, $-NCH_3-$, $-NH(CH_2)_2NH-$, $-C(O)-$,

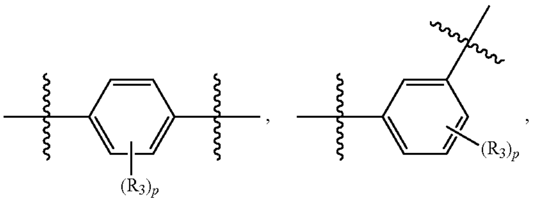

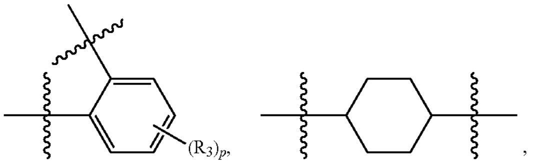

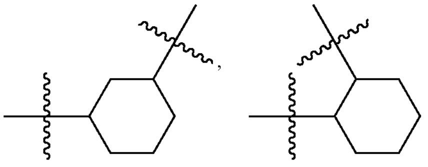

and

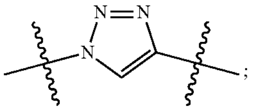

$L^2$ is

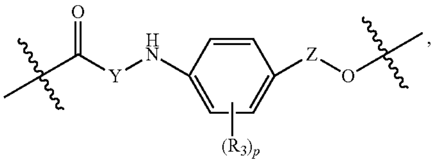

or

-continued

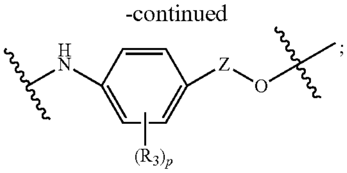

$L^3$ is

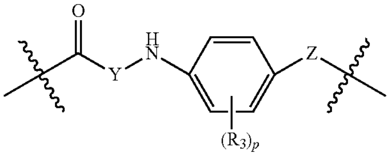

$R_3$ is selected from the group consisting of: hydrogen, halogen, methyl, ethyl, nitro, methoxy, and ethoxy;

q is 0 or 1;

m, t, r are each independently selected from the group consisting of 0, 1, 2, 3, 4, 5, 6, 7, 8, 9, 10 and 11;

each p is independently 0, 1, 2, 3 or 4;

Y is an amino acid residue formed by a dipeptide selected from the group consisting of: Val-Cit, Val-Ala, Val-Lys, Val-Gly, Val-Thr, Val-Val, Val-Leu, Val-Ile, Val-Asn and Phe-Lys, wherein the N-terminus is connected to the carbonyl and the C-terminus is connected to the N atom;

Z is $-CH_2-$, $-CH(CH_3)-$ or $-C(CH_3)_2-$.

According to some embodiments of the present application, the present application relates to the compound represented by Formula I, Formula I', Formula II, Formula II', Formula III, Formula III', a salt or a solvate thereof, wherein:

W is

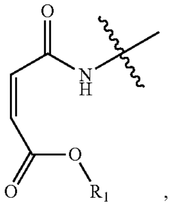

wherein the two carbonyl groups are located on the same side of the C═C double bond, which is a cis structure;

$R_1$ is a $C_{1-6}$ linear or branched alkyl and $R_1$ is optionally mono- or multi-substituted by one or more substituents selected from the group consisting of: halogen and $C_{1-4}$ alkoxy;

$L^1$ is selected from the group consisting of: $-(CH_2)_e-C(O)NH-(CH_2CH_2O)_r(CH_2)_g-$ and $-(CH_2)_h-C(O)NH-CH[(CH_2)_i-NHC(O)-(CH_2CH_2O)_j-(CH_2)_k-CH_3]-$;

$L^2$ is

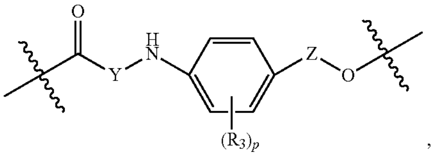

, or

-continued

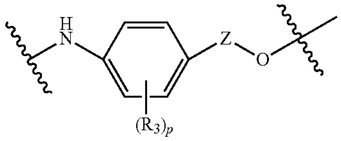

;

$L^3$ is

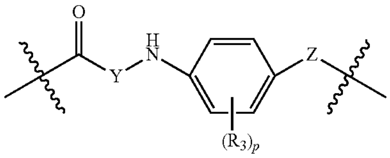

;

$R_3$ is selected from the group consisting of: hydrogen, halogen, methyl, ethyl, nitro, methoxy, and ethoxy;

q is 0 or 1;

e, f, g, h, i, j and k are each independently selected from the group consisting of 0, 1, 2, 3, 4, 5, 6, 7, 8, 9, 10 and 11;

each p is independently 0, 1, 2, 3 or 4;

Y is an amino acid residue formed by a dipeptide selected from the group consisting of: Val-Cit, Val-Ala, Val-Lys, Val-Gly, Val-Thr, Val-Val, Val-Leu, Val-Ile, Val-Asn and Phe-Lys, wherein the N-terminus is connected to the carbonyl and the C-terminus is connected to the N atom;

Z is $-CH_2-$, $-CH(CH_3)-$ or $-C(CH_3)_2-$.

In some embodiments, the present application relates to the compound represented by Formula III or Formula III', a salt or a solvate thereof, wherein: A is coupled to the site # through a S atom in the targeting compound molecule, as shown in Formula III-1 or Formula III'-1:

III-1

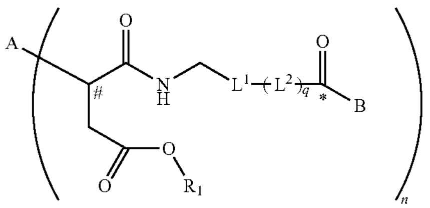

III'-1

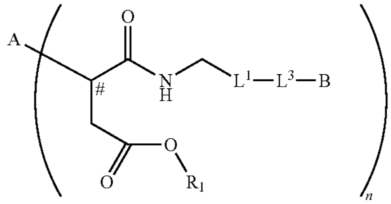

wherein the definitions of substituents are as described in the present application.

In some embodiments, in the compound represented by Formula I, Formula I', Formula II, Formula II', Formula III, Formula III', Formula III-1 or Formula III'-1, a salt or a solvate thereof as described in the present application, $L^1$ is selected from the group consisting of: $-(CH_2)_m-$,

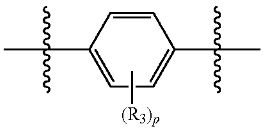

,

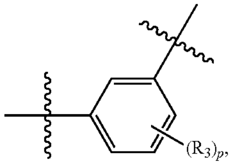

,

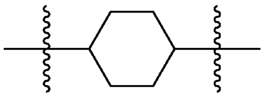

and

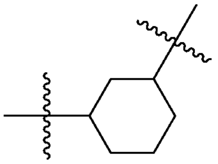

;

$R_3$ is selected from the group consisting of: hydrogen, halogen, methyl, ethyl, nitro, methoxy, and ethoxy; preferably, $R_3$ is selected from the group consisting of: hydrogen, halogen, methyl, and ethyl;

m is selected from the group consisting of 0, 1, 2, 3, 4 and 5; preferably, m is selected from the group consisting of 0, 1, 2, 3, 4;

each p is independently 0, 1, 2, 3 or 4; preferably, each p is independently 0, 1, 2 or 3; more preferably, each p is independently 0, 1 or 2; more preferably, each p is independently 0.

In some embodiments, in the compound represented by Formula I, Formula I', Formula II, Formula II', Formula III, Formula III', Formula III-1 or Formula III'-1, a salt or a solvate thereof as described in the present application.

$L^1$ is selected from the group consisting of: $-(CH_2)_m-$,

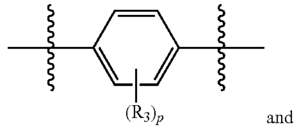

and

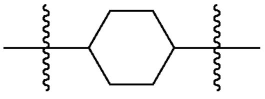

;

$R_3$ is selected from the group consisting of: hydrogen, halogen, methyl, ethyl, nitro, methoxy, and ethoxy; preferably, $R_3$ is selected from the group consisting of: hydrogen, halogen, methyl, and ethyl;

m is selected from the group consisting of 0, 1, 2, 3, 4;

each p is independently 0, 1, 2, 3 or 4; preferably, each p is independently 0, 1, 2 or 3; more preferably, each p is independently 0, 1 or 2; more preferably, each p is independently 0.

In some embodiments, in the compound represented by Formula I, Formula II, Formula III, Formula III-1, a salt or a solvate thereof as described in the present application $L^2$ is

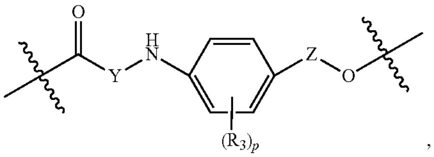

, wherein:

Y is an amino acid residue formed by Val-Cit or Val-Ala, wherein the N-terminus is connected to the carbonyl and the C-terminus is connected to the N atom;

Z is —$CH_2$—;

the definitions of $R_3$ and p are as described in the present application.

In some embodiments, in the compound represented by Formula I, Formula II, Formula III or Formula III-1 as described in the present application, $L^2$ is

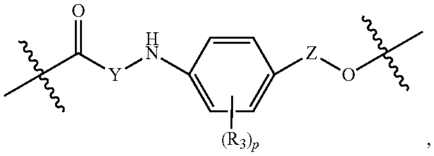

, wherein:

Y is an amino acid residue formed by Val-Cit, wherein the N-terminus is connected to the carbonyl and the C-terminus is connected to the N atom;

the definitions of Z, $R_3$ and p are as described in the present application.

In some embodiments, in the compound represented by Formula I, Formula II, Formula III or Formula III-1 as described in the present application, $L^2$ is

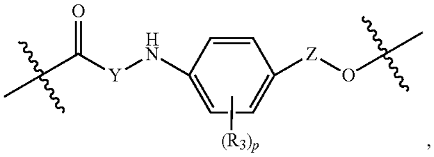

, wherein:

Y is an amino acid residue formed by Val-Ala, wherein the N-terminus is connected to the carbonyl and the C-terminus is connected to the N atom;

the definitions of Z, $R_3$ and p are as described in the present application.

In some embodiments, in the compound represented by Formula I, a salt or a solvate thereof as described in the present application, $R_2$ is selected from the group consisting of:

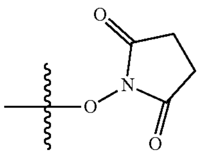

and

-continued

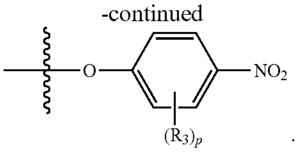

.

In some embodiments, in the compound represented by Formula I, a salt or a solvate thereof as described in the present application, $R_2$ is

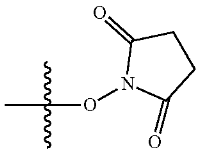

;

q is 0; or $R_2$ is

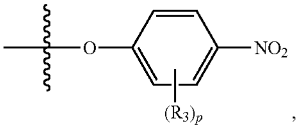

, wherein $R_3$ and p are as described in the present application;

q is 1.

In some embodiments, in the compound represented by Formula I, a salt or a solvate thereof as described in the present application, $R_2$ is

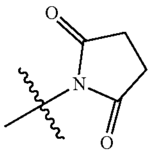

;

q is 0; or $R_2$ is

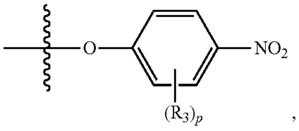

, wherein $R_3$ and p are as described in the present application;

q is 1.

In some embodiments, the present application relates to the compound of Formula I, a salt or a solvate thereof, wherein $R_2$ is

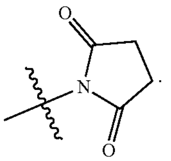 [SMILES: *N1C(=O)CCC1=O]

In some embodiments, the present application relates to the compound of Formula I, a salt or a solvate thereof, wherein $R_2$ is

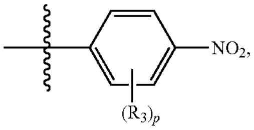

wherein $R_3$ and p are as described in the present application.

In some embodiments, the present application relates to the compound represented by Formula I, a salt or a solvate thereof, wherein the compound is a compound represented by Formula IV, wherein,

IV

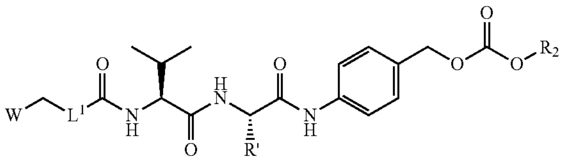

W is

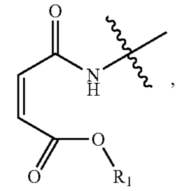

wherein the two carbonyl groups are located on the same side of the C═C double bond, which is cis structure;

$R_1$ is a $C_{1-6}$ linear or branched alkyl and $R_1$ is optionally mono- or poly-substituted by one or more substituents selected from the group consisting of: halogen and $C_{1-4}$ alkoxy;

$L^1$ is selected from the group consisting of: $—(CH_2)_m—$, $—(CH_2)_tO—$, $—(CH_2CH_2O)_r—$, —O—, —NH—, —S—, —S(O)—, $—S(O)_2—$, $—NCH_3—$, $—NH(CH_2)_2NH—$, —C(O)—, $—(CH_2)_e—C(O)NH—(CH_2CH_2O)_f(CH_2)_g—$, $—(CH_2)_h—C(O)NH—CH[(CH_2)_i—NHC(O)—(CH_2CH_2O)_j—(CH_2)_k—CH_3]—$,

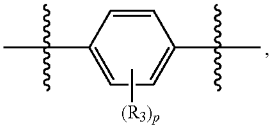

,

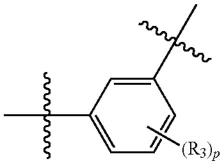

,

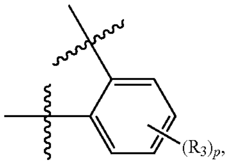

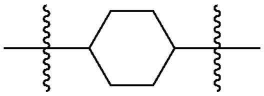

,

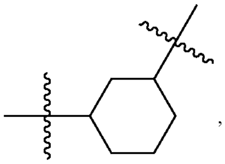

,

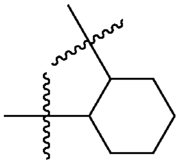

, and

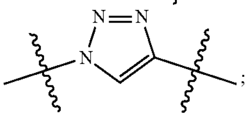

;

preferably, $L^1$ is selected from the group consisting of: $—(CH_2)_m—$,

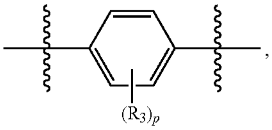

,

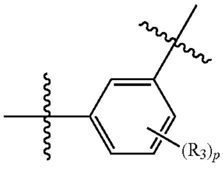

,

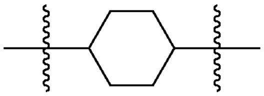

and

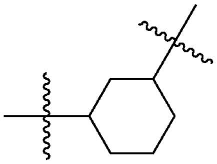

;

R' is a substituent side chain in the variable group (R) of the amino acid residue; R' is $—CH_3$, $—(CH_2)_3NHCONH_2$, $—(CH_2)_4—NH_2$, —H, $—CH(CH_3)—OH$, $—CH—(CH_3)_2$, $—CH_2—CH(CH_3)_2$, $—CH(CH_3)—CH_2—CH_3$, or $—CH_2—CONH_2$, R' preferably is $—CH_3$, or $—(CH_2)_3NHCONH_2$;

$R_2$ is selected from the group consisting of:

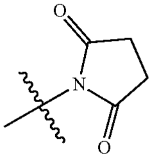

and

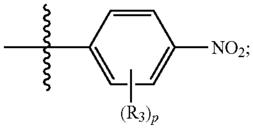

$R_3$ is selected from the group consisting of: hydrogen, halogen, methyl, ethyl, nitro, methoxy, and ethoxy; preferably, $R_3$ is selected from the group consisting of: hydrogen, halogen, methyl, and ethyl;

m, r, t are each independently selected from the group consisting of 0, 1, 2, 3, and 4;

e, f, g, h, i, j and k are each independently selected from the group consisting of 0, 1, 2, 3, 4, 5, 6, 7, 8, 9, and 10;

each p is independently 0, 1, 2, 3 or 4; preferably, each p is independently 0, 1, 2 or 3; more preferably, each p is independently 0, 1 or 2; more preferably, each p is independently 0.

In some embodiments, in the compound represented by Formula IV described in the present application, $L^1$ is selected from the group consisting of:

$-(CH_2)_e-C(O)NH-(CH_2CH_2O)_f-(CH_2)_g-$, and $-(CH_2)_h-C(O)NH-CH[(CH_2)_i-NHC(O)-(CH_2CH_2O)_j-(CH_2)_k-CH_3]-$, wherein e, f, g, h, i, j, k are defined as described in the present application.

In some embodiments, in the compound represented by Formula IV described in the present application, $L^1$ is selected from the group consisting of:

$-(CH_2)_m-$, $-(CH_2)_tO-$, $-(CH_2CH_2O)_r-$, $-O-$, $-NH-$, $-S-$, $-S(O)-$, $-S(O)_2-$, $-NCH_3-$, $-NH(CH_2)_2NH-$, $-C(O)-$,

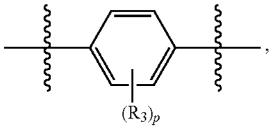,
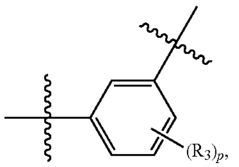,
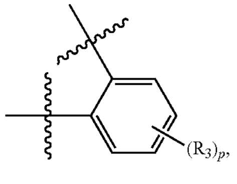,
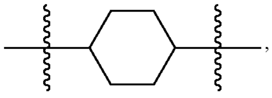,
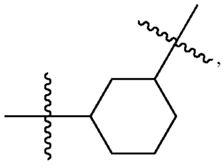,
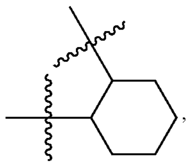, and
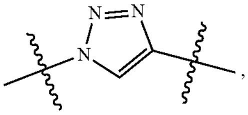, wherein $R_3$ and p are defined as described in the present application.

In some embodiments, the application relates to the compound represented by Formula I', a salt or a solvate thereof, wherein the compound is a compound represented by Formula IV', wherein,

IV'

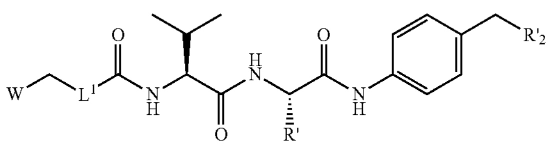

W is

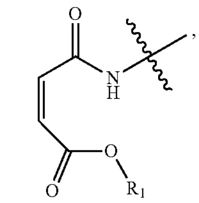, wherein the two carbonyl groups are located on the same side of the C═C double bond, which is cis structure;

$R_1$ is a $C_{1-6}$ linear or branched alkyl and $R_1$ is optionally mono- or poly-substituted by one or more substituents selected from the group consisting of: halogen and $C_{1-4}$ alkoxy;

$L^1$ is selected from the group consisting of: $-(CH_2)_m-$, $-(CH_2)_tO-$, $-(CH_2CH_2O)_r-$, $-O-$, $-NH-$, $-S-$, $-S(O)-$, $-S(O)_2-$, $-NCH_3-$, $-NH(CH_2)_2NH-$, $-C(O)-$, $-(CH_2)_e-C(O)NH-(CH_2CH_2O)_f-(CH_2)_g-$, $-(CH_2)_h-C(O)NH-CH[(CH_2)_i-NHC(O)-(CH_2CH_2O)_j-(CH_2)_k-CH_3]-$,

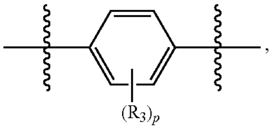,
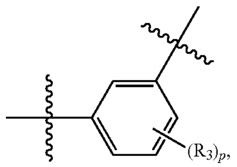,
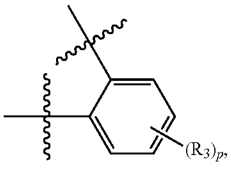,
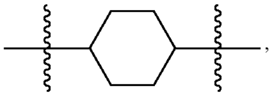,
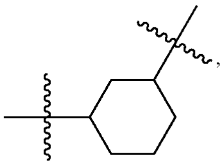,
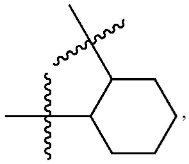, and
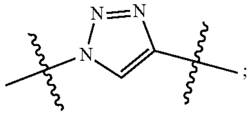;

preferably, $L^1$ is selected from the group consisting of:

$-(CH_2)_m-$,

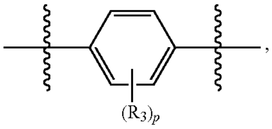

,

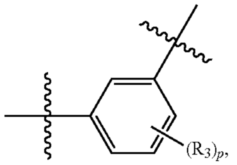

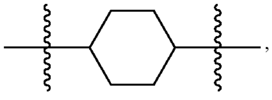

, and

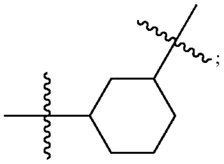

;

R' is a substituent side chain in the variable group (R) of the amino acid residue; R' is $-CH_3$, $-(CH_2)_3NHCONH_2$, $-(CH_2)_4-NH_2$, $-H$, $-CH(CH_3)-OH$, $-CH-(CH_3)_2$, $-CH_2-CH(CH_3)_2$, $-CH(CH_3)-CH_2-CH_3$, or $-CH_2-CONH_2$, R' preferably is $-CH_3$ or $-(CH_2)_3NHCONH_2$;

$R'_2$ is halogen;

$R_3$ is selected from the group consisting of: hydrogen, halogen, methyl, ethyl, nitro, methoxy, and ethoxy; preferably, $R_3$ is selected from the group consisting of: hydrogen, halogen, methyl, and ethyl;

m, r, t are each independently selected from the group consisting of 0, 1, 2, 3, and 4;

e, f, g, h, i, j and k are each independently selected from the group consisting of 0, 1, 2, 3, 4, 5, 6, 7, 8, 9, and 10;

each p is independently 0, 1, 2, 3 or 4; preferably, each p is independently 0, 1, 2 or 3; more preferably, each p is independently 0, 1 or 2; more preferably, each p is independently 0.

In some embodiments, in the compound represented by Formula IV' described in the present application, $L^1$ is selected from the group consisting of:

$-(CH_2)_e-C(O)NH-(CH_2CH_2O)_f(CH_2)_g-$, and $-(CH_2)_h-C(O)NH-CH[(CH_2)_i-NHC(O)-(CH_2CH_2O)_j-(CH_2)_k-CH_3]-$, wherein e, f, g, h, i, j and k are defined as described in the present application.

In some embodiments, in the compound represented by Formula IV' described in the present application, $L^1$ is selected from the group consisting of:

$-(CH_2)_m-$, $-(CH_2)_tO-$, $-(CH_2CH_2O)_r-$, $-O-$, $-NH-$, $-S-$, $-S(O)-$, $-S(O)_2-$, $-NCH_3-$, $-NH(CH_2)_2NH-$, $-C(O)-$,

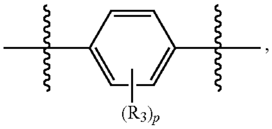

,

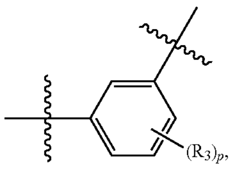

-continued

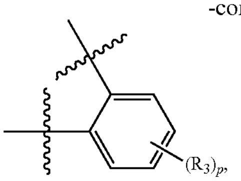

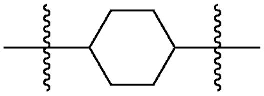

,

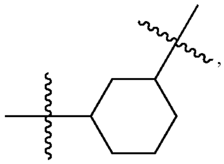

,

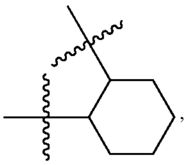

, and

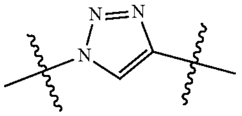

, wherein $R_3$ and p are defined as described in the present application.

In some embodiments, the present application relates to the compound represented by Formula II, a salt or a solvate thereof, wherein the compound is a compound represented by Formula V,

V

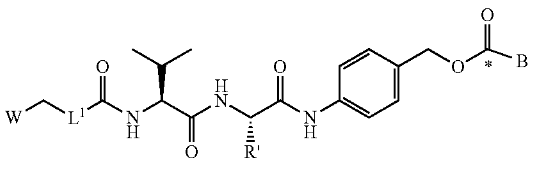

wherein,

W is

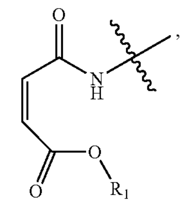

, wherein the two carbonyl groups are located on the same side of the C═C double bond, which is cis structure;

B is an active compound selected from the group consisting of drug, cytotoxin, detection reagent, diagnostic reagent and targeting carrier; preferably, B is a cytotoxin, an anti-tumor drug, an antiviral drug or an anti-infective drug; further preferably, B is a cytotoxin, such as a tubulin inhibitor, a DNA alkylating agent, a DNA intercalator, an enzyme inhibitor, an antimetabolite, a peptide or a nucleotide;

B is coupled to the site * through a N atom or O atom in the active compound molecule;

$R_1$ is a $C_{1-6}$ linear or branched alkyl and $R_1$ is optionally mono- or poly-substituted by one or more substituents selected from the group consisting of: halogen and $C_{1-4}$ alkoxy;

$L^1$ is selected from the group consisting of: $—(CH_2)_m—$, $—(CH_2)_tO—$, $—(CH_2CH_2O)_r—$, $—O—$, $—NH—$, $—S—$, $—S(O)—$, $—S(O)_2—$, $—NCH_3—$, $—NH(CH_2)_2NH—$, $—C(O)—$, $—(CH_2)_e—C(O)NH—(CH_2CH_2O)_r(CH_2)_g—$, $—(CH_2)_h—C(O)NH—CH[(CH_2)_i—NHC(O)—(CH_2CH_2O)_j—(CH_2)_k—CH_3]—$,

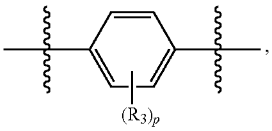,
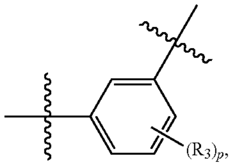
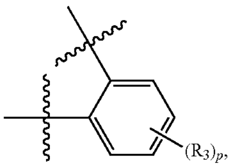
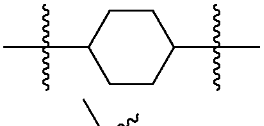,
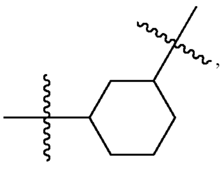,
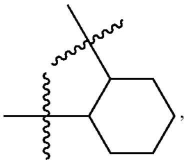, and
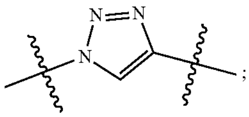;

preferably, $L^1$ is selected from the group consisting of: $—(CH_2)_m—$,

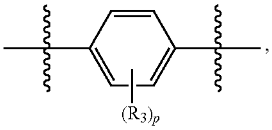,
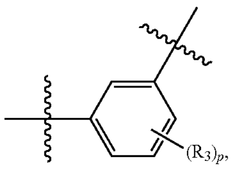
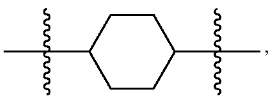, and
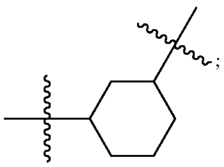;

R' is a substituent side chain in the variable group (R) of the amino acid residue; R' is $—CH_3$, $—(CH_2)_3NHCONH_2$, $—(CH_2)_4—NH_2$, $—H$, $—CH(CH_3)—OH$, $—CH—(CH_3)_2$, $—CH_2—CH(CH_3)_2$, $—CH(CH_3)—CH_2—CH_3$, or $—CH_2—CONH_2$, R' preferably is $—CH_3$, or $—(CH_2)_3NHCONH_2$;

$R_3$ is selected from the group consisting of: hydrogen, halogen, methyl, ethyl, nitro, methoxy, and ethoxy; preferably, $R_3$ is selected from the group consisting of: hydrogen, halogen, methyl, and ethyl;

m, r and t are each independently selected from the group consisting of 0, 1, 2, 3, and 4;

e, f, g, h, i, j and k are each independently selected from the group consisting of 0, 1, 2, 3, 4, 5, 6, 7, 8, 9, and 10;

each p is independently 0, 1, 2, 3 or 4; preferably, each p is independently 0, 1, 2 or 3; more preferably, each p is independently 0, 1 or 2; more preferably, each p is independently 0.

In some embodiments, in the compound represented by Formula V described in the present application, $L^1$ is selected from the group consisting of:

$—(CH_2)_e—C(O)NH—(CH_2CH_2O)_r(CH_2)_g—$, and $—(CH_2)_h—C(O)NH—CH[(CH_2)_i—NHC(O)—(CH_2CH_2O)_j—(CH_2)_k—CH_3]—$, wherein e, f, g, h, i, j and k are defined as described in the present application.

In some embodiments, in the compound represented by formula V described in the present application, $L^1$ is selected from the group consisting of:

$—(CH_2)_m—$, $—(CH_2)_tO—$, $—(CH_2CH_2O)_r—$, $—O—$, $—NH—$, $—S—$, $—S(O)—$, $—S(O)_2—$, $—NCH_3—$, $—NH(CH_2)_2NH—$, $—C(O)—$,

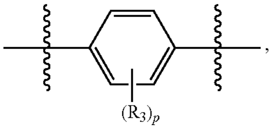,
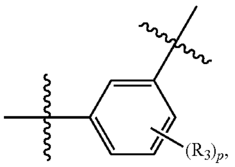
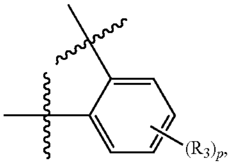
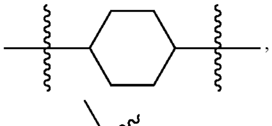,
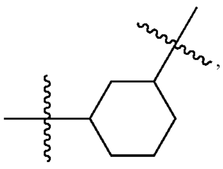,
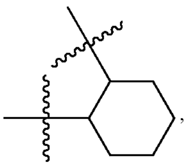, and
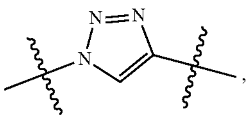, wherein $R_3$ and p are defined as described in the present application.

In some embodiments, the present application relates to the compound of Formula II', a salt or a solvate thereof, wherein the compound is a compound represented by Formula V,

V'

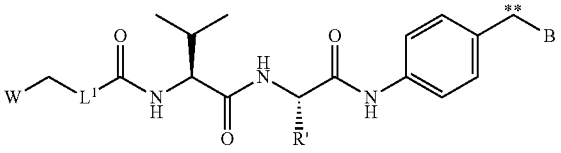

wherein,

W is

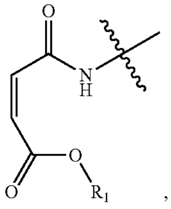
, wherein the two carbonyl groups are located on the same side of the C═C double bond, which is cis structure;

B is an active compound selected from the group consisting of drug, cytotoxin, detection reagent, diagnostic reagent and targeting carrier; preferably, B is a cytotoxin, an antitumor drug, an antiviral drug or an anti-infective drug; further preferably, B is a cytotoxin, such as a tubulin inhibitor, a DNA alkylating agent, a DNA intercalator, an enzyme inhibitor, an antimetabolite, a peptide or a nucleotide;

B is coupled to the site ** through a N atom or O atom in the active compound molecule;

$R_1$ is a $C_{1-6}$ linear or branched alkyl group and $R_1$ is optionally mono- or multi-substituted by one or more substituents selected from the group consisting of: halogen and $C_{1-4}$ alkoxy;

$L^1$ is selected from the group consisting of: $—(CH_2)_m—$, $—(CH_2)_tO—$, $—(CH_2CH_2O)_r—$, —O—, —NH—, —S—, —S(O)—, $—S(O)_2—$, $—NCH_3—$, $—NH(CH_2)_2NH—$, —C(O)—, $—(CH_2)_e—C(O)NH—(CH_2CH_2O)_r(CH_2)_g—$, $—(CH_2)_h—C(O)NH—CH[(CH_2)_i—NHC(O)—(CH_2CH_2O)_j—(CH_2)_k—CH_3]—$,

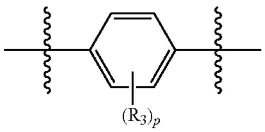
,

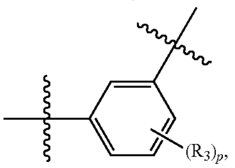

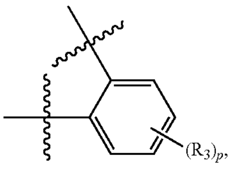

-continued

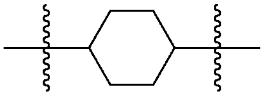
,

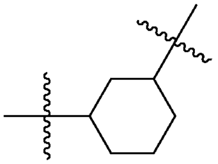
,

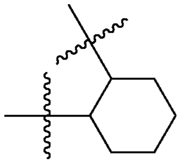
, and

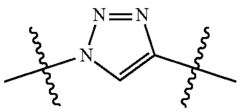
;

preferably, $L^1$ is selected from the group consisting of: $—(CH_2)_m—$,

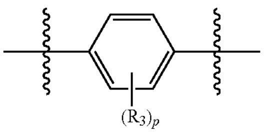
,

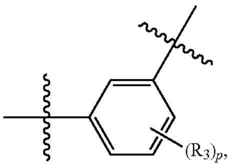

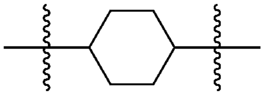
and

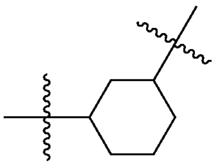
;

R' is a substituent side chain in the variable group (R) of the amino acid residue; R' is $—CH_3$, $—(CH_2)_3NHCONH_2$, $—(CH_2)_4—NH_2$, —H, $—CH(CH_3)—OH$, $—CH—(CH_3)_2$, $—CH_2—CH(CH_3)_2$, $—CH(CH_3)—CH_2—CH_3$, or $—CH_2—CONH_2$, R' preferably is $—CH_3$, or $—(CH_2)_3NHCONH_2$;

$R_3$ is selected from the group consisting of: hydrogen, halogen, methyl, ethyl, nitro, methoxy, and ethoxy; preferably, $R_3$ is selected from the group consisting of: hydrogen, halogen, methyl, and ethyl;

m, r and t are each independently selected from the group consisting of 0, 1, 2, 3, and 4;

e, f, g, h, i, j and k are each independently selected from the group consisting of 0, 1, 2, 3, 4, 5, 6, 7, 8, 9, and 10;

each p is independently 0, 1, 2, 3 or 4; preferably, each p is independently 0, 1, 2 or 3; more preferably, each p is independently 0, 1 or 2; more preferably, each p is independently 0.

In some embodiments, in the compound represented by Formula V' described in the present application, $L^1$ is selected from the group consisting of:

$-(CH_2)_e-C(O)NH-(CH_2CH_2O)_r(CH_2)_g-$, and $-(CH_2)_h-C(O)NH-CH[(CH_2)_i-NHC(O)-(CH_2CH_2O)_j-(CH_2)_k-CH_3]-$, wherein e, f, g, h, i, j and k are defined as described in the present application.

In some embodiments, in the compound represented by Formula V' described in the present application, $L^1$ is selected from:

-continued

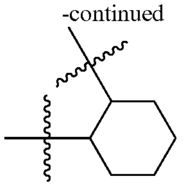

, and

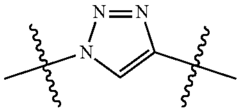

, wherein $R_3$ and p are defined as described in the present application.

In some embodiments, the present application relates to the compound represented by Formula III, a salt or a solvate thereof, wherein the compound is a compound represented by Formula VI,

VI

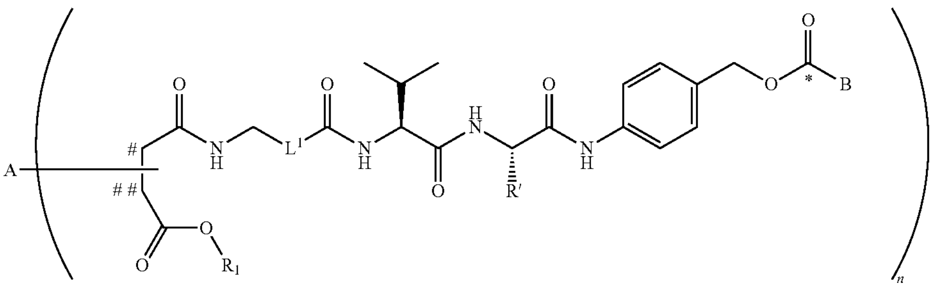

$-(CH_2)_m-$, $-(CH_2)_tO-$, $-(CH_2CH_2O)_r-$, $-O-$, $-NH-$, $-S-$, $-S(O)-$, $-S(O)_2-$, $-NCH_3-$, $-NH(CH_2)_2NH-$, $-C(O)-$,

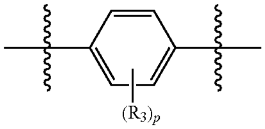

,

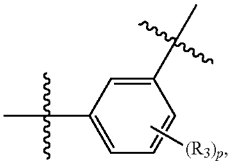

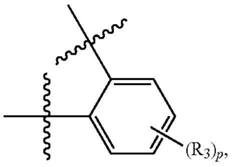

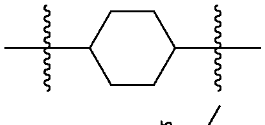

,

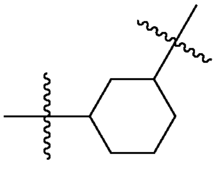

, wherein,

A is a targeting compound selected from the group consisting of protein, antibody, polypeptide, enzyme and small molecule; A is coupled to the site # or ## through a S atom in the targeting compound molecule;

B is an active compound selected from the group consisting of drug, cytotoxin, detection reagent, diagnostic reagent and targeting carrier; preferably, B is a cytotoxin, an antitumor drug, an antiviral drug or an anti-infective drug; further preferably, B is a cytotoxin, such as a tubulin inhibitor, a DNA alkylating agent, a DNA intercalator, an enzyme inhibitor, an antimetabolite, a peptide or a nucleotide; B is coupled to the site * through a N atom or O atom in the active compound molecule;

n is a number between 0.5 and 8.5, such as a number between 0.8 and 5, a number between 1 and 4, a number between 2 and 6, a number between 3 and 7, a number between 4 and 8, a number between 3.5 and 8.5, a number between 3.5 and 4.5, or a number between 6.5 and 8.5, preferably n is about 4, 5, 6, 7 or 8;

$R_1$ is a $C_{1-6}$ linear or branched alkyl group, and $R_1$ is optionally mono- or multi-substituted by one or more substituents selected from the group consisting of: halogen and $C_{1-4}$ alkoxy;

$L^1$ is selected from: $-(CH_2)_m-$, $-(CH_2)_tO-$, $-(CH_2CH_2O)_r-$, $-O-$, $-NH-$, $-S-$, $-S(O)-$, $-S(O)_2-$, $-NCH_3-$, $-NH(CH_2)_2NH-$, $-C(O)-$, $-(CH_2)_e-C(O)NH-(CH_2CH_2O)_r(CH_2)_g-$, $-(CH_2)_h-C(O)NH-CH[(CH_2)_i-NHC(O)-(CH_2CH_2O)_j-(CH_2)_k-CH_3]-$,

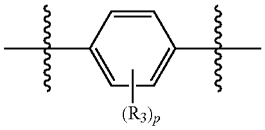
,

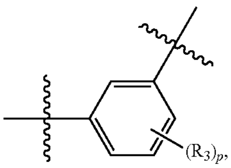

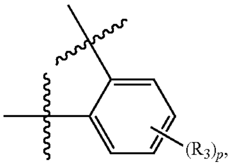

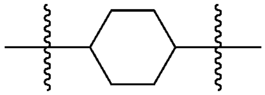
,

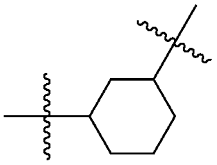
,

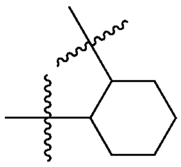
, and

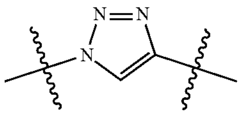
;

preferably, $L^1$ is selected from the group consisting of: $-(CH_2)_m-$,

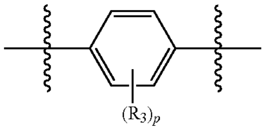
,

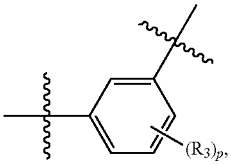

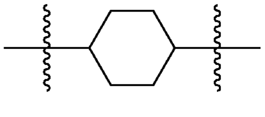
and

-continued

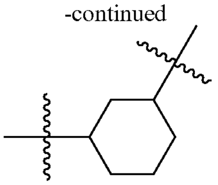
;

R' is a substituent side chain in the variable group (R) of the amino acid residue; preferably, R' is $-CH_3$, $-(CH_2)_3NHCONH_2$, $-(CH_2)_4-NH_2$, —H, $-CH(CH_3)-OH$, $-CH-(CH_3)_2$, $-CH_2-CH(CH_3)_2$, $-CH(CH_3)-CH_2-CH_3$ or $-CH_2-CONH_2$, R' preferably is $-CH_3$ or $-(CH_2)_3NHCONH_2$;

each $R_3$ is independently selected from the group consisting of: hydrogen, halogen, methyl, ethyl, nitro, methoxy, and ethoxy; preferably, each $R_3$ is independently selected from the group consisting of: hydrogen, halogen, methyl, and ethyl;

m, r and t are each independently selected from the group consisting of 0, 1, 2, 3, and 4;

e, f, g, h, i, j and k are each independently selected from the group consisting of 0, 1, 2, 3, 4, 5, 6, 7, 8, 9, and 10;

each p is independently 0, 1, 2, 3 or 4; preferably, each p is independently 0, 1, 2 or 3; more preferably, each p is independently 0, 1 or 2; more preferably, each p is independently 0.

In some embodiments, in the compound represented by Formula VI described in the present application, $L^1$ is selected from the group consisting of:

$-(CH_2)_e-C(O)NH-(CH_2CH_2O)_f(CH_2)_g-$, and $-(CH_2)_h-C(O)NH-CH[(CH_2)_i-NHC(O)-(CH_2CH_2O)_j-(CH_2)_k-CH_3]-$, wherein e, f, g, h, i, j and k are defined as described in the present application.

In some embodiments, in the compound represented by Formula VI described in the present application, $L^1$ is selected from the group consisting of: $-(CH_2)_m-$, $-(CH_2)_tO-$, $-(CH_2CH_2O)_r-$, —O—, —NH—, —S—, —S(O)—, $-S(O)_2-$, $-NCH_3-$, $-NH(CH_2)_2NH-$, —C(O)—,

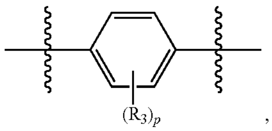
,

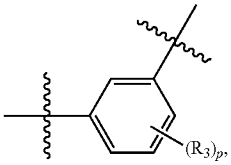

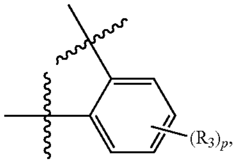

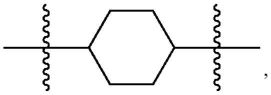
,

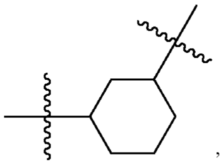
,

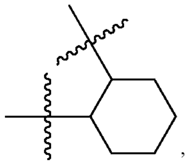
, and

-continued

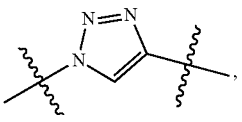

wherein $R_3$ and p are defined as described in the present application.

In some embodiments, the present application relates to the compound represented by Formula III', a salt or a solvate thereof, wherein the compound is a compound of Formula VI',

VI'

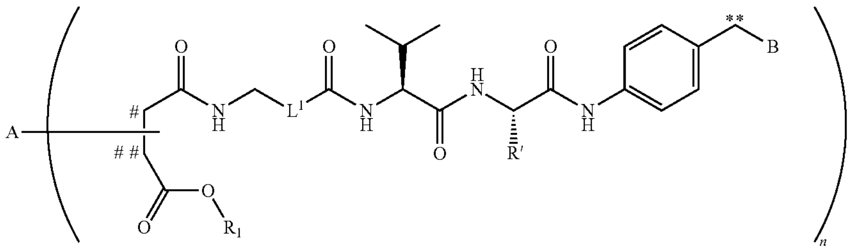

wherein,

A is a targeting compound selected from the group consisting of protein, antibody, polypeptide, enzyme and small molecule; A is coupled to the site # or ## through a S atom in the targeting compound molecule;

B is an active compound selected from the group consisting of drug, cytotoxin, detection reagent, diagnostic reagent and targeting carrier; preferably, B is a cytotoxin, an antitumor drug, an antiviral drug or an anti-infective drug; further preferably, B is a cytotoxin, such as a tubulin inhibitor, a DNA alkylating agent, a DNA intercalator, an enzyme inhibitor, an antimetabolite, a peptide or a nucleotide; B is coupled to the site ** through a N atom or O atom in the active compound molecule;

n is a number between 0.5 and 8.5, such as a number between 0.8 and 5, a number between 1 and 4, a number between 2 and 6, a number between 3 and 7, a number between 4 and 8, a number between 3.5 and 8.5, a number between 3.5 and 4.5, or a number between 6.5 and 8.5, preferably n is about 4, 5, 6, 7 or 8;

$R_1$ is a $C_{1-6}$ linear or branched alkyl group and $R_1$ is optionally mono- or multi-substituted by one or more substituents selected from the group consisting of: halogen and $C_{1-4}$ alkoxy;

$L^1$ is selected from the group consisting of: $—(CH_2)_m—$, $—(CH_2)_tO—$, $—(CH_2CH_2O)_r—$, $—O—$, $—NH—$, $—S—$, $—S(O)—$, $—S(O)_2—$, $—NCH_3—$, $—NH(CH_2)_2NH—$, $—C(O)—$, $—(CH_2)_e—C(O)NH—(CH_2CH_2O)_f(CH_2)_g—$, $—(CH_2)_h—C(O)NH—CH[(CH_2)_i—NHC(O)—(CH_2CH_2O)_j—(CH_2)_k—CH_3]—$,

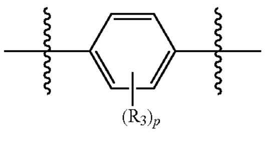

,

-continued

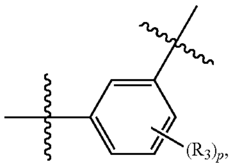

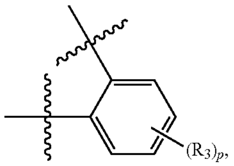

-continued

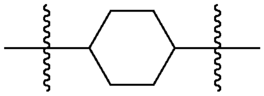

,

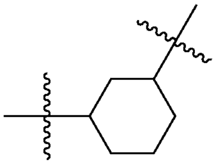

,

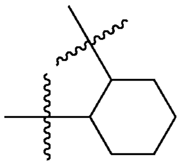

, and

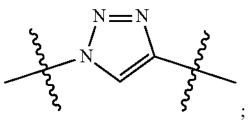

;

preferably, $L^1$ is selected from the group consisting of: $—(CH_2)_m—$,

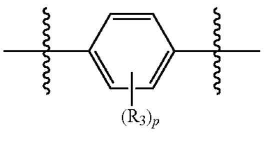

,

-continued

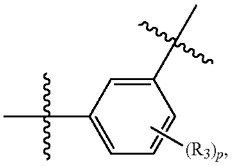

,

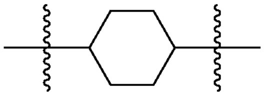

and

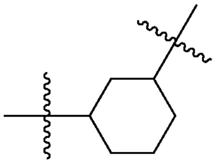

;

R' is a substituent side chain in the amino acid residue; preferably, R' is —$CH_3$, —$(CH_2)_3NHCONH_2$, —$(CH_2)_4$—$NH_2$, —H, —$CH(CH_3)$—OH, —CH—$(CH_3)_2$, —$CH_2$—$CH(CH_3)_2$, —$CH(CH_3)$—$CH_2$—$CH_3$ or —$CH_2$—$CONH_2$, R' preferably is —$CH_3$ or —$(CH_2)_3NHCONH_2$;

each $R_3$ is independently selected from the group consisting of: hydrogen, halogen, methyl, ethyl, nitro, methoxy, and ethoxy; preferably, each $R_3$ is independently selected from the group consisting of: hydrogen, halogen, methyl, and ethyl;

m, r and t are each independently selected from the group consisting of 0, 1, 2, 3, and 4;

e, f, g, h, i, j and k are each independently selected from the group consisting of 0, 1, 2, 3, 4, 5, 6, 7, 8, 9, and 10;

p is 0, 1, 2, 3 or 4; preferably, p is 0, 1, 2 or 3; more preferably, p is 0, 1 or 2; more preferably, p is 0.

In some embodiments, in the compound represented by Formula VI' described in the present application, $L^1$ is selected from the group consisting of:

—$(CH_2)_e$—C(O)NH—$(CH_2CH_2O)_f(CH_2)_g$—, and —$(CH_2)_h$—C(O)NH—$CH[(CH_2)_i$—NHC(O)—$(CH_2CH_2O)_j$—$(CH_2)_k$—$CH_3]$—, wherein, e, f, g, h, i, j and k are defined as described in the present application.

In some embodiments, in the compound represented by Formula VI' described in the present application, $L^1$ is selected from the group consisting of:

—$(CH_2)_m$—, —$(CH_2)_t$O—, —$(CH_2CH_2O)_r$—, —O—, —NH—, —S—, —S(O)—, —$S(O)_2$—, —$NCH_3$—, —$NH(CH_2)_2NH$—, —C(O)—,

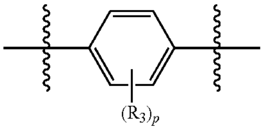

,

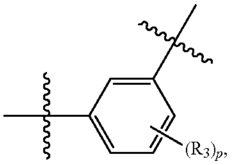

,

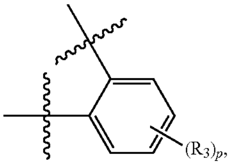

,

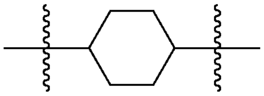

,

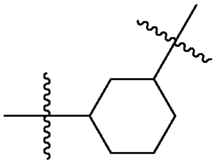

,

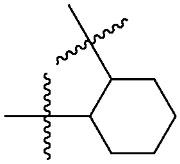

, and

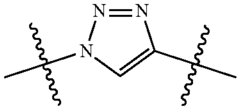

, wherein $R_3$ and p are defined as described in the present application.

In some embodiments, the present application relates to the compound represented by Formula VI or Formula VI', a salt or a solvate thereof, wherein A is coupled to the site # through a S atom in the targeting compound molecule, and the compound is as shown in Formula VI-1 or Formula VI'-1:

VI-1

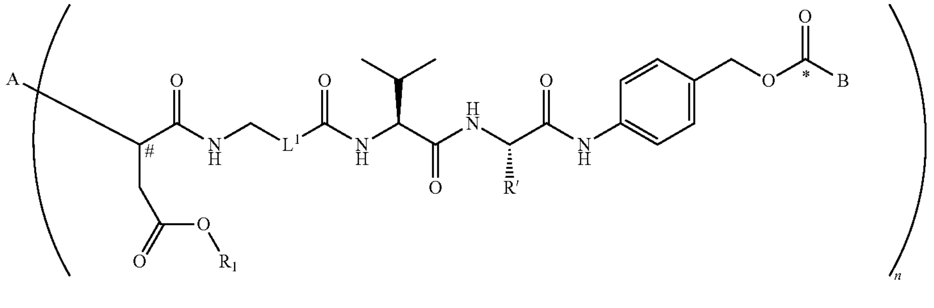

-continued

VI'-1

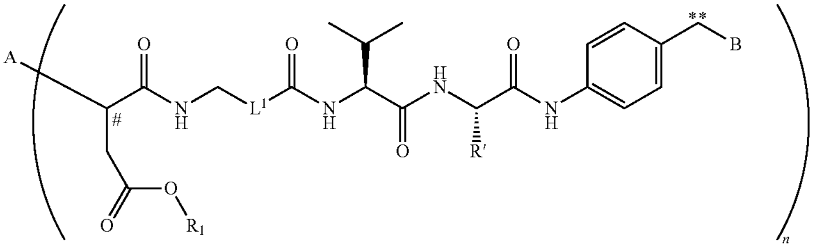

wherein,

A is a targeting compound selected from the group consisting of protein, antibody, polypeptide, enzyme and small molecule; A is coupled to the site # through a S atom in the targeting compound molecule;

B is an active compound selected from the group consisting of drug, cytotoxin, detection reagent, diagnostic reagent and targeting carrier; preferably, B is a cytotoxin, an antitumor drug, an antiviral drug or an anti-infective drug; further preferably, B is a cytotoxin, such as a tubulin inhibitor, a DNA alkylating agent, a DNA intercalator, an enzyme inhibitor, an antimetabolite, a peptide or a nucleotide; B is coupled to the site * or ** through a N atom or O atom in the active compound molecule;

n is a number between 0.5 and 8.5, such as a number between 0.8 and 5, a number between 1 and 4, a number between 2 and 6, a number between 3 and 7, a number between 4 and 8, a number between 3.5 and 8.5, a number between 3.5 and 4.5, or a number between 6.5 and 8.5, preferably n is about 4, 5, 6, 7 or 8;

$R_1$ is a $C_{1-6}$ linear or branched alkyl group and $R_1$ is optionally mono- or multi-substituted by one or more substituents selected from the group consisting of: halogen and $C_{1-4}$ alkoxy;

$L^1$ is selected from the group consisting of: $-(CH_2)_m-$, $-(CH_2)_tO-$, $-(CH_2CH_2O)_r-$, $-O-$, $-NH-$, $-S-$, $-S(O)-$, $-S(O)_2-$, $-NCH_3-$, $-NH(CH_2)_2NH-$, $-C(O)-$, $-(CH_2)_e-C(O)NH-(CH_2CH_2O)_r(CH_2)_g-$, $-(CH_2)_h-C(O)NH-CH[(CH_2)_i-NHC(O)-(CH_2CH_2O)_j-(CH_2)_k-CH_3]-$,

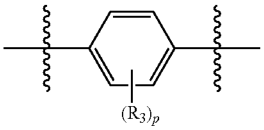

,

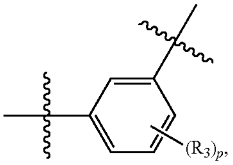

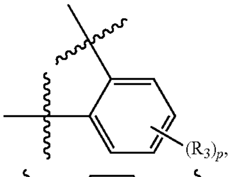

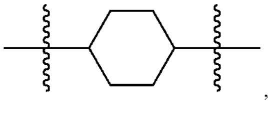

,

-continued

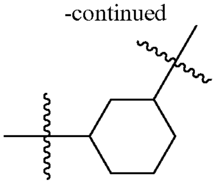

,

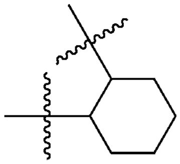

, and

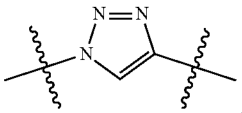

;

preferably, $L^1$ is selected from the group consisting of: $-(CH_2)_m-$,

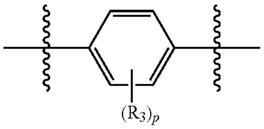

,

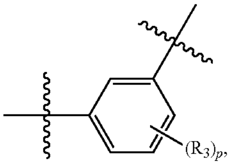

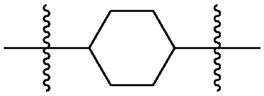

and

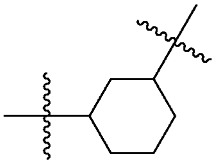

;

R' is a substituent side chain in the variable group (R) in the amino acid residue; R' is $-CH_3$, $-(CH_2)_3NHCONH_2$, $-(CH_2)_4-NH_2$, $-H$, $-CH(CH_3)-OH$, $-CH-(CH_3)_2$, $-CH_2-CH(CH_3)_2$, $-CH(CH_3)-CH_2-CH_3$, or $-CH_2-CONH_2$, R' preferably is $-CH_3$, or $-(CH_2)_3NHCONH_2$;

$R_3$ is selected from the group consisting of: hydrogen, halogen, methyl, ethyl, nitro, methoxy, and ethoxy; preferably, $R_3$ is selected from the group consisting of: hydrogen, halogen, methyl, and ethyl;

m, r and t are each independently selected from the group consisting of 0, 1, 2, 3, and 4;

e, f, g, h, i, j and k are each independently selected from the group consisting of 0, 1, 2, 3, 4, 5, 6, 7, 8, 9, and 10;

each p is independently 0, 1, 2, 3 or 4; preferably, each p is independently 0, 1, 2 or 3; more preferably, each p is independently 0, 1 or 2; more preferably, each p is independently 0.

In some embodiments, in the compound represented by Formula VI'-1 described in the present application, $L^1$ is selected from the group consisting of:

$—(CH_2)_e—C(O)NH—(CH_2CH_2O)_r(CH_2)_g—$, and $—(CH_2)_h—C(O)NH—CH[(CH_2)_i—NHC(O)—(CH_2CH_2O)_j—(CH_2)_k—CH_3]—$, wherein, e, f, g, h, i, j and k are defined as described in the present application.

In some embodiments, in the compound represented by Formula VI'-1 described in the present application, $L^1$ is selected from the group consisting of: $—(CH_2)_m—$, $—(CH_2)_tO—$, $—(CH_2CH_2O)_r—$, —O—, —NH—, —S—, —S(O)—, $—S(O)_2—$, $—NCH_3—$, $—NH(CH_2)_2NH—$, —C(O)—,

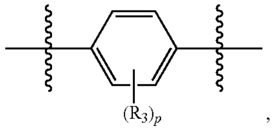
,
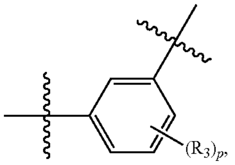
,
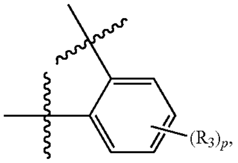
,
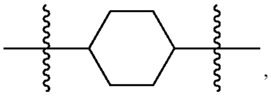
,
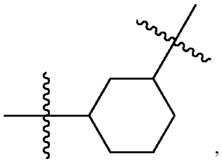
,
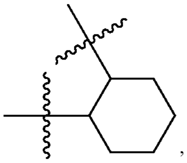
, and
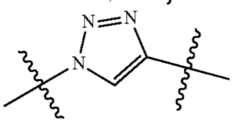
, wherein $R_3$ and p are defined as described in the present application.

In some embodiments, in Formulas I to VI, Formulas I' to VI', Formula III-1, Formula III'-1, Formula VI-1, or Formula VI'-1 described in the present application, $L^1$ is $—(CH_2)_e—C(O)NH—(CH_2CH_2O)_r—(CH_2)_g—$ wherein e, f and g are defined as described in the present application.

In some embodiments, in Formulas I to VI, Formulas I' to VI', Formula III-1, Formula III'-1, Formula VI-1, or Formula VI'-1 described in the present application, $L^1$ is $—(CH_2)_h—C(O)NH—CH[(CH_2)_i—NHC(O)—(CH_2CH_2O)_j—(CH_2)_k—CH_3]—$, wherein h, i, j and k are defined as described in the present application.

In some embodiments, in Formulas I to VI, Formulas I' to VI', Formula III-1, Formula III'-1, Formula VI-1, or Formula VI'-1 described in the present application, e, f and g are each independently selected from the group consisting of 1, 2, 3, 4, 5, 6, 7, 8, 9, and 10.

In some embodiments, in Formulas I to VI, Formulas I' to VI', Formula III-1, Formula III'-1, Formula VI-1, or Formula VI'-1 described in the present application, h, i, j and k are each independently selected from the group consisting of 0, 1, 2, 3, 4, 5, 6, 7, 8, 9, and 10.

In some embodiments, in Formulas I to VI, Formulas I' to VI', Formula III-1, Formula III'-1, Formula VI-1, or Formula VI'-1 described in the present application, e is 1, 2, 3, 4, 5, 6, 7 or 8.

In some embodiments, in Formulas I to VI, Formulas I' to VI', Formula III-1, Formula III'-1, Formula VI-1, or Formula VI'-1 described in the present application, e is 1 or 2.

In some embodiments, in Formulas I to VI, Formulas I' to VI', Formula III-1, Formula III'-1, Formula VI-1, or Formula VI'-1 described in the present application, e is 3 or 4.

In some embodiments, in Formulas I to VI, Formulas I' to VI', Formula III-1, Formula III'-1, Formula VI-1, or Formula VI'-1 described in the present application, e is 5 or 6.

In some embodiments, in Formulas I to VI, Formulas I' to VI', Formula III-1, Formula III'-1, Formula VI-1, or Formula VI'-1 described in the present application, e is 7 or 8.

In some embodiments, in Formulas I to VI, Formulas I' to VI', Formula III-1, Formula III'-1, Formula VI-1, or Formula VI'-1 described in the present application, f is 1, 2, 3, 4, 5, 6, 7, 8, 9, 10 or 11.

In some embodiments, in Formulas I to VI, Formulas I' to VI', Formula III-1, Formula III'-1, Formula VI-1, or Formula VI'-1 described in the present application, f is 1 or 2.

In some embodiments, in Formulas I to VI, Formulas I' to VI', Formula III-1, Formula III'-1, Formula VI-1, or Formula VI'-1 described in the present application, f is 3 or 4.

In some embodiments, in Formulas I to VI, Formulas I' to VI', Formula III-1, Formula III'-1, Formula VI-1, or Formula VI'-1 described in the present application, f is 5 or 6.

In some embodiments, in Formulas I to VI, Formulas I' to VI', Formula III-1, Formula III'-1, Formula VI-1, or Formula VI'-1 described in the present application, f is 7 or 8.

In some embodiments, in Formulas I to VI, Formulas I' to VI', Formula III-1, Formula III'-1, Formula VI-1, or Formula VI'-1 described in the present application, f is 9, 10 or 11.

In some embodiments, in Formulas I to VI, Formulas I' to VI', Formula III-1, Formula III'-1, Formula VI-1, or Formula VI'-1 described in the present application, g is 1, 2, 3, 4, 5 or 6.

In some embodiments, in Formulas I to VI, Formulas I' to VI', Formula III-1, Formula III'-1, Formula VI-1, or Formula VI'-1 described in the present application, g is 1 or 2.

In some embodiments, in Formulas I to VI, Formulas I' to VI', Formula III-1, Formula III'-1, Formula VI-1, or Formula VI'-1 described in the present application, g is 3 or 4.

In some embodiments, in Formulas I to VI, Formulas I' to VI', Formula III-1, Formula III'-1, Formula VI-1, or Formula VI'-1 described in the present application, g is 5 or 6.

In some embodiments, in Formulas I to VI, Formulas I' to VI', Formula III-1, Formula III'-1, Formula VI-1, or Formula VI'-1 described in the present application, h is 1, 2, 3, 4, 5, 6, 7 or 8.

In some embodiments, in Formulas I to VI, Formulas I' to VI', Formula III-1, Formula III'-1, Formula VI-1, or Formula VI'-1 described in the present application, h is 1 or 2.

In some embodiments, in Formulas I to VI, Formulas I' to VI', Formula III-1, Formula III'-1, Formula VI-1, or Formula VI'-1 of the present application, h is 3 or 4.

In some embodiments, in Formulas I to VI, Formulas I' to VI', Formula III-1, Formula III'-1, Formula VI-1 or Formula VI'-1 of the present application, h is 5 or 6.

In some embodiments, in Formulas I to VI, Formulas I' to VI', Formula III-1, Formula III'-1, Formula VI-1 or Formula VI'-1 described in the present application, h is 7 or 8.

In some embodiments, in Formulas I to VI, Formulas I' to VI', Formula III-1, Formula III'-1, Formula VI-1 or Formula VI'-1 described in the present application, i is 1, 2, 3, 4, 5, 6, 7 or 8.

In some embodiments, in Formulas I to VI, Formulas I' to VI', Formula III-1, Formula III'-1, Formula VI-1 or Formula VI'-1 described in the present application, i is 1 or 2.

In some embodiments, in Formulas I to VI, Formulas I' to VI', Formula III-1, Formula III'-1, Formula VI-1 or Formula VI'-1 described in the present application, i is 3 or 4.

In some embodiments, in Formulas I to VI, Formulas I' to VI', Formula III-1, Formula III'-1, Formula VI-1 or Formula VI'-1 described in the present application, i is 5 or 6.

In some embodiments, in Formulas I to VI, Formulas I' to VI', Formula III-1, Formula III'-1, Formula VI-1 or Formula VI'-1 described in the present application, i is 7 or 8.

In some embodiments, in Formulas I to VI, Formulas I' to VI', Formula III-1, Formula III'-1, Formula VI-1 or Formula VI'-1 described in the present application, j is 1, 2, 3, 4, 5, 6, 7, 8, 9, 10 or 11.

In some embodiments, in Formulas I to VI, Formulas I' to VI', Formula III-1, Formula III'-1, Formula VI-1 or Formula VI'-1 described in the present application, j is 1 or 2.

In some embodiments, in Formulas I to VI, Formulas I' to VI', Formula III-1, Formula III'-1, Formula VI-1 or Formula VI'-1 described in the present application, j is 3, 4 or 5.

In some embodiments, in Formulas I to VI, Formulas I' to VI', Formula III-1, Formula III'-1, Formula VI-1 or Formula VI'-1 described in the present application, j is 6 or 7.

In some embodiments, in Formulas I to VI, Formulas I' to VI', Formula III-1, Formula III'-1, Formula VI-1 or Formula VI'-1 described in the present application, j is 8 or 9.

In some embodiments, in Formulas I to VI, Formulas I' to VI', Formula III-1, Formula III'-1, Formula VI-1 or Formula VI'-1 described in the present application, j is 10 or 11.

In some embodiments, in Formulas I to VI, Formulas I' to VI', Formula III-1, Formula III'-1, Formula VI-1 or Formula VI'-1 described in the present application, k is 0, 1, 2, 3, 4 or 5.

In some embodiments, in Formulas I to VI, Formulas I' to VI', Formula III-1, Formula III'-1, Formula VI-1 or Formula VI'-1 described in the present application, k is 0.

In some embodiments, in Formulas I to VI, Formulas I' to VI', Formula III-1, Formula III'-1, Formula VI-1 or Formula VI'-1 described in the present application, k is 1 or 2.

In some embodiments, in Formulas I to VI, Formulas I' to VI', Formula III-1, Formula III'-1, Formula VI-1 or Formula VI'-1 described in the present application, k is 3, 4 or 5.

In some embodiments, in Formulas I to VI, Formulas I' to VI', Formula III-1, Formula III'-1, Formula VI-1 or Formula VI'-1 described in the present application, q is 0.

In some embodiments, in Formulas I to VI, Formulas I' to VI', Formula III-1, Formula III'-1, Formula VI-1 or Formula VI'-1 described in the present application, q is 1.

In some embodiments, in Formulas I to VI, Formulas I' to VI', Formula III-1, Formula III'-1, Formula VI-1 or Formula VI'-1 described in the present application, $R_3$ is hydrogen.

In some embodiments, in Formulas I to VI, Formulas I' to VI', Formula II-1, Formula III'-1, Formula VI-1 or Formula VI'-1 described in the present application, $R_3$ is halogen.

In some embodiments, in Formulas I to VI, Formulas I' to VI', Formula III-1, Formula III'-1, Formula VI-1 or Formula VI'-1 described in the present application, $R_3$ is methyl.

In some embodiments, in Formulas I to VI, Formulas I' to VI', Formula III-1, Formula III'-1, Formula VI-1 or Formula VI'-1 described in the present application, $R_3$ is ethyl.

In some embodiments, in Formulas I to VI, Formulas I' to VI', Formula III-1, Formula III'-1, Formula VI-1 or Formula VI'-1 described in the present application, $R_3$ is nitro.

In some embodiments, in Formulas I to VI, Formulas I' to VI', Formula III-1, Formula III'-1, Formula VI-1 or Formula VI'-1 described in the present application, $R_3$ is methoxy.

In some embodiments, in Formulas I to VI, Formulas I' to VI', Formula III-1, Formula III'-1, Formula VI-1 or Formula VI'-1 described in the present application, $R_3$ is ethoxy.

In some embodiments, in Formulas I to VI, Formulas I' to VI', Formula III-1, Formula III'-1, Formula VI-1 or Formula VI'-1 described in the present application, $L^1$ is $—(CH_2)_m—$, m is 1 or 2.

In some embodiments, in Formulas I to VI, Formulas I' to VI', Formula III-1, Formula III'-1, Formula VI-1 or Formula VI'-1 described in the present application, $L^1$ is $—(CH_2)_m—$, m is 3 or 4.

In some embodiments, in Formulas I to VI, Formulas I' to VI', Formula III-1, Formula III'-1, Formula VI-1 or Formula VI'-1 described in the present application, $L^1$ is $—(CH_2)_m—$, m is 5 or 6.

In some embodiments, in Formulas I to VI, Formulas I' to VI', Formula III-1, Formula III'-1, Formula VI-1 or Formula VI'-1 described in the present application, $L^1$ is $—(CH_2)_m—$, m is 7 or 8.

In some embodiments, in Formulas I to VI, Formulas I' to VI', Formula III-1, Formula III'-1, Formula VI-1 or Formula VI'-1 described in the present application, $L^1$ is

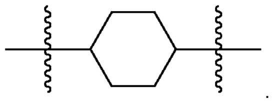 [SMILES: *C1CCC(*)CC1 ; "."]

In some embodiments, in the compound represented by Formula I, Formula II, Formula III, Formula I', Formula II', Formula III', Formula III-1 or Formula III'-1, a salt or a solvate thereof described in the present application, $R_1$ is a Cia alkyl group, such as methyl, ethyl, n-propyl, isopropyl, n-butyl, isobutyl, sec-butyl, tert-butyl, preferably methyl.

In some embodiments, in the compound represented by Formula II, Formula III, Formula II' or Formula III', a salt or a solvate thereof described in the present application, B is selected from the group consisting of: auristatin, methyl-auristatin E (MMAE), maytansine or derivatives thereof (such as maytansinoids, DM1, DM3, DM4), paclitaxel, calicheamicin, duocarmycin, doxorubicin, camptothecin, PBD (pyrrolobenzodiazepines) cytotoxin and derivatives thereof.

In some embodiments, in the compound represented by Formula II, Formula III, Formula II', Formula III', Formula III-1 or Formula III'-1, a salt or a solvate thereof described in the present application, B is monomethyl-auristatin E (MMAE).

In some embodiments, in the compound represented by Formula III, Formula III', Formula III-1 or Formula III'-1, a salt or a solvate thereof, A is a monoclonal antibody (MAB), or A comprises an antibody fragment or an alternative or variant thereof, a protein ligand or a protein scaffold;

preferably, A is coupled to the site # through a S atom in A, preferably, A is coupled to the site # through a S atom of a cysteine residue in A.

In some embodiments, in the compound represented by Formula III, Formula III', Formula III-1 or Formula III'-1, a salt or a solvate thereof, A is a monoclonal antibody with a sulfhydryl as the coupling site, or a monoclonal antibody with site-directed mutation or modification and with sulfhydryl as the coupling site.

In some embodiments, in the compound represented by Formula III, Formula III', Formula III-1 or Formula III'-1, a salt or a solvate thereof, A is selected from the group consisting of anti-HER2 humanized monoclonal antibody mil40, anti-HER2 monoclonal antibodies trastuzumab (HERCEPTIN) and pertuzumab (PERJETA), anti-EGFR monoclonal antibodies cetuximab (ERBITUX) and panitumumab (VECTIBIX), anti-CD20 monoclonal antibody rituximab (RITUXAN), anti-CD52 monoclonal antibody alemtuzumab (CAMPATH), anti-CD20 monoclonal antibody ibritumomab (ZEVALIN), anti-CD20 monoclonal antibody tositumomab (BEXXAR), anti-CD20 monoclonal antibody ofatumumab (ARZERRA), anti-VEGF monoclonal antibody bevacizumab (AVASTIN), anti-CTLA-4 monoclonal antibody ipilimumab (YERVOY), anti-RANKL monoclonal antibody denosumab (XGEVA), anti-PD-1 monoclonal antibodies pembrolizumab (KEYTRUDA), nivolumab (Opdivo) and Avelumab (Bavencio), anti-PD-L1 monoclonal antibodies Atezolizumab (Tecentriq) and durvalumab (Imfinzi), anti-TROP-2 monoclonal antibody sacituzumab, anti-DLL-3 monoclonal antibody rovalpituzumab, and biological analogues thereof.

In some embodiments, in the compound represented by Formula III, Formula III', Formula III-1 or Formula III'-1, a salt or a solvate thereof, A is an anti-HER2 humanized monoclonal antibody mil40.

In some embodiments, the application relates to the compound represented by Formula III, Formula III', Formula III-1, Formula III'-1 or the compound represented by Formula VI, Formula VI', Formula VI-1 or Formula VI'-1, a salt or a solvate thereof, wherein A is monoclonal antibody (MAB), n is DAR (drug/antibody molar ratio).

In some embodiments, the application relates to the compound represented by Formula I, a salt or a solvate thereof, wherein the compound is selected from the group consisting of:

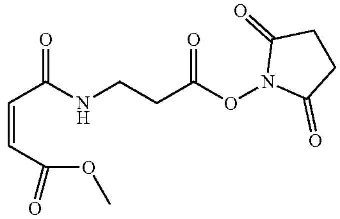
,
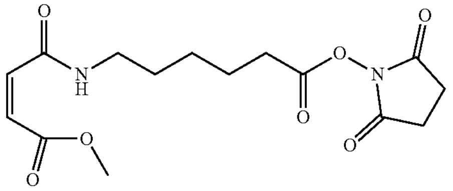
,

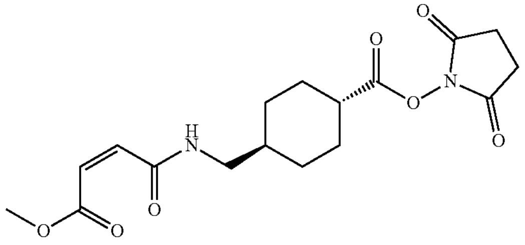
,

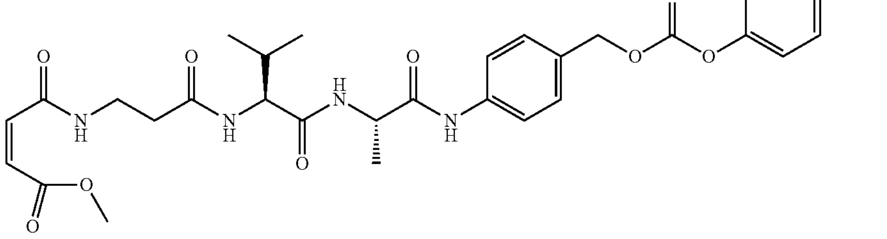
,

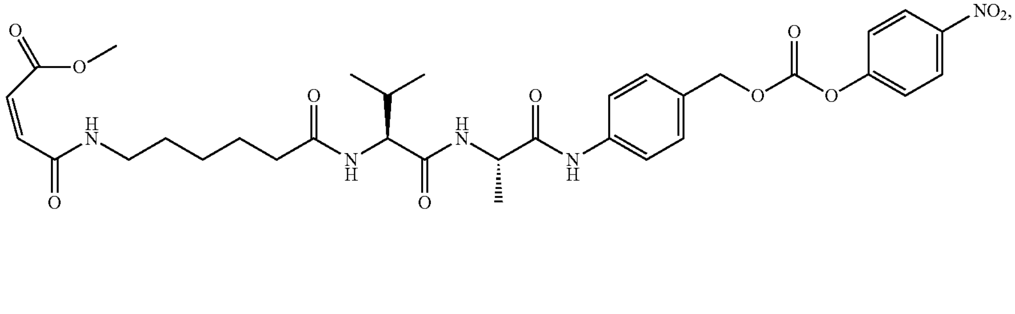
,

-continued
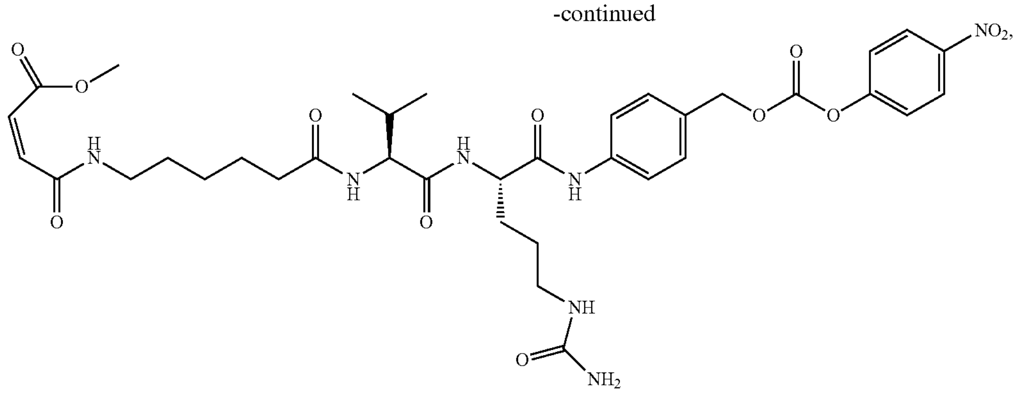
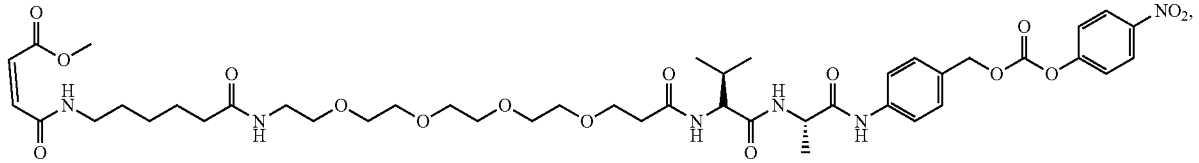
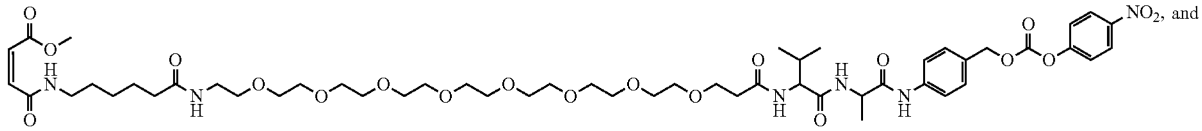
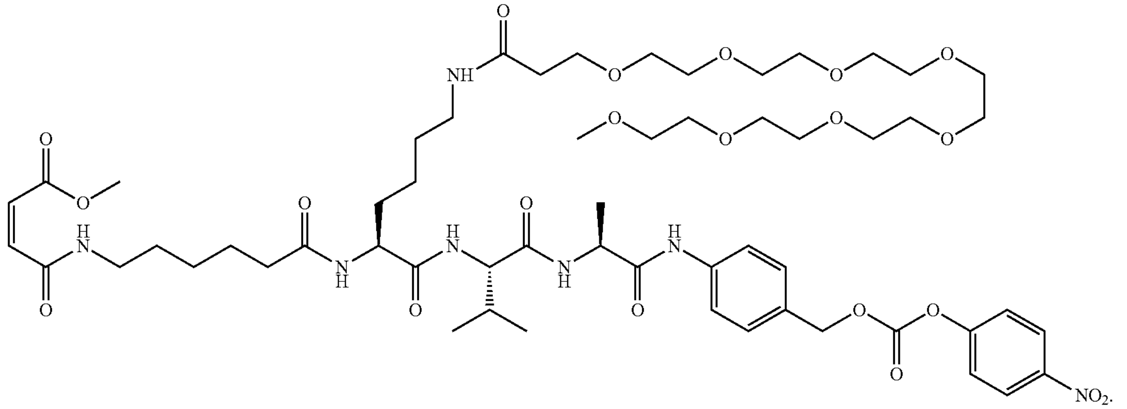 [SMILES: COCCOCCOCCOCCOCCOCCOCCOCCC(=O)NCCCC[C@H](NC(=O)CCCCCNC(=O)/C=C\C(=O)OC)C(=O)N[C@H](C(=O)N[C@@H](C)C(=O)Nc1ccc(COC(=O)Oc2ccc([N+](=O)[O-])cc2)cc1)C(C)C]
In some embodiments, the application relates to the compound represented by Formula II, a salt or a solvate thereof, wherein the compound is selected from the group consisting of:
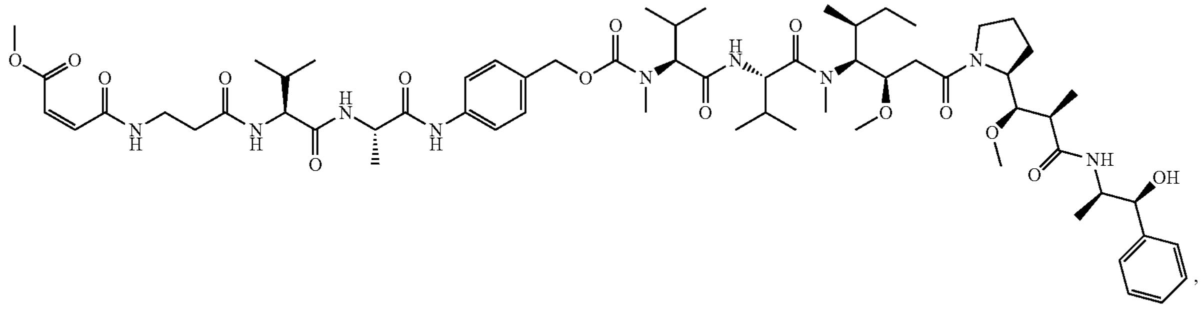

-continued
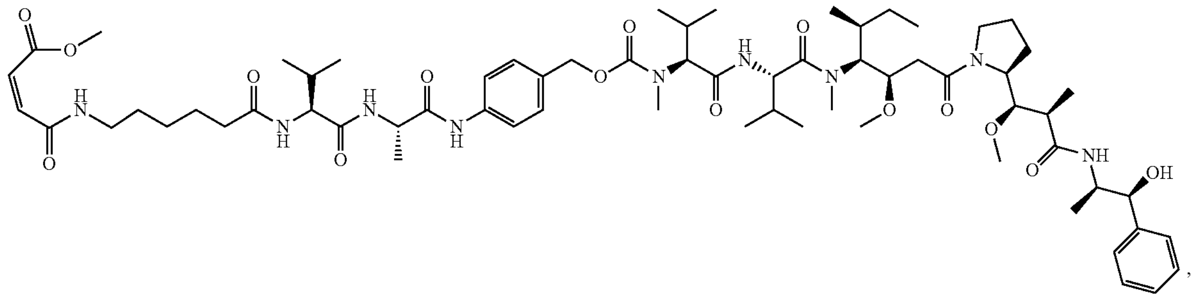
,
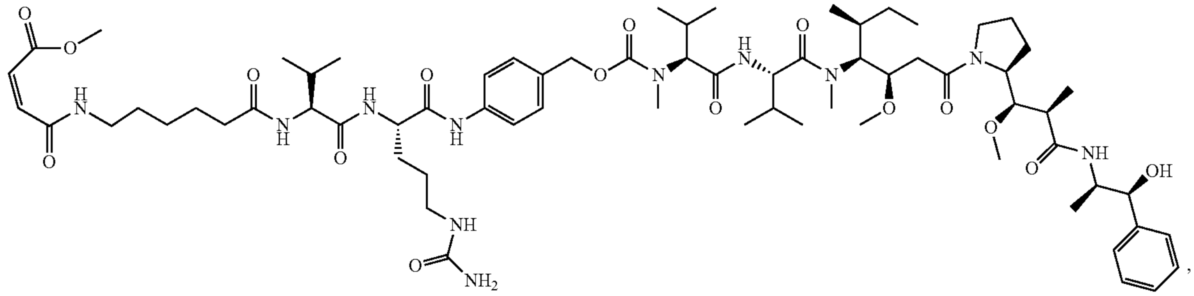
,
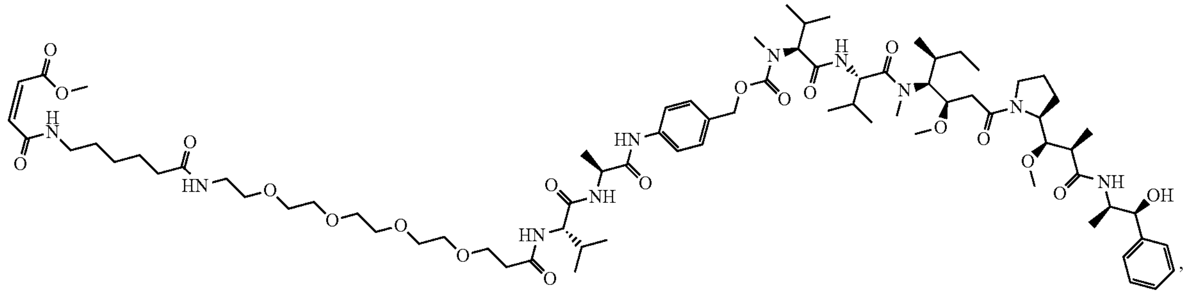
,
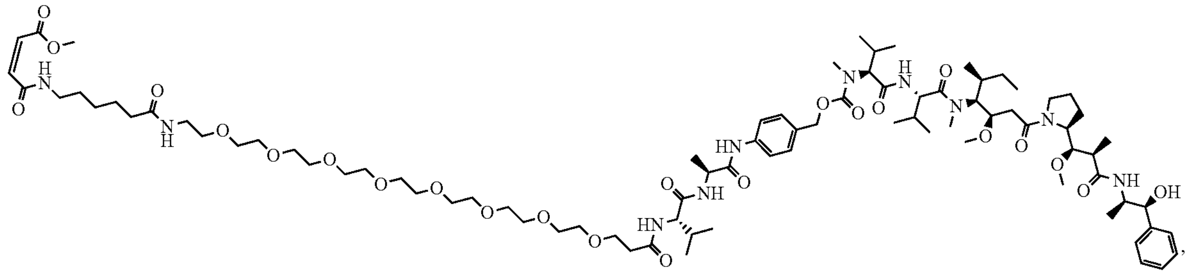
,
and
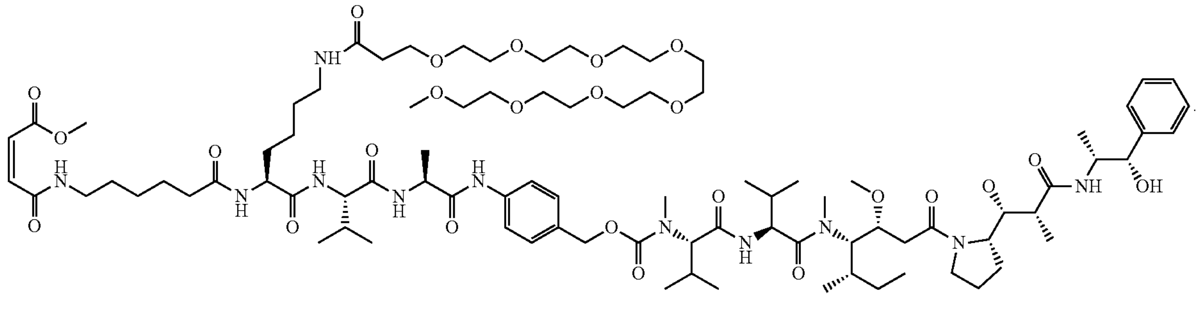
.

In some embodiments, the application relates to the compound represented by Formula III, a salt or a solvate thereof, wherein the compound is selected from the group consisting of:
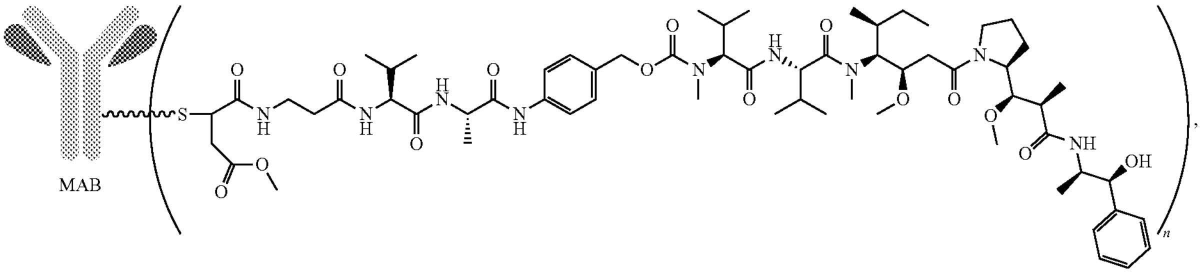
,
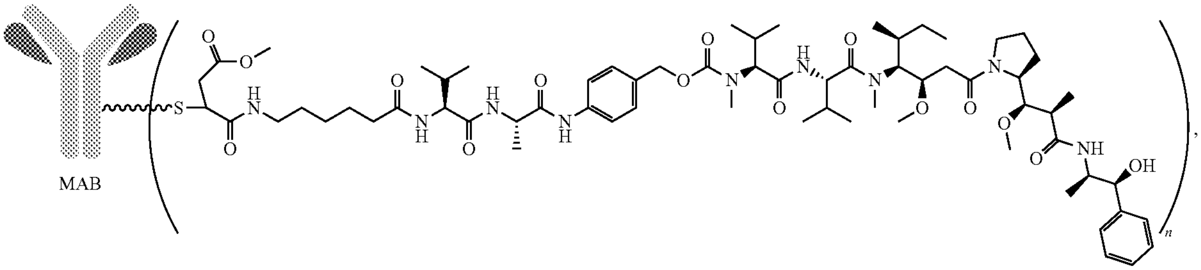
,
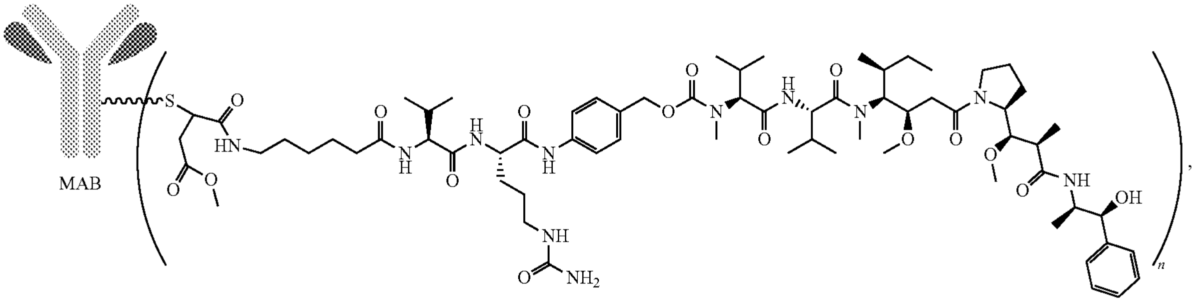
,
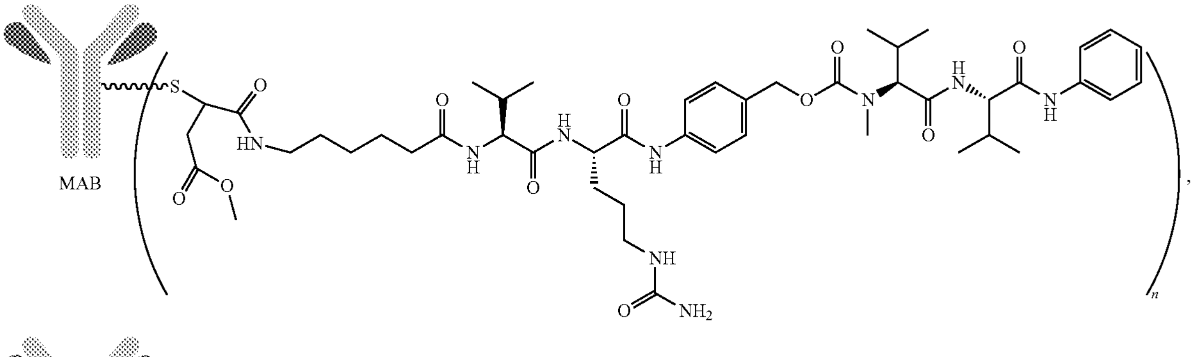
,
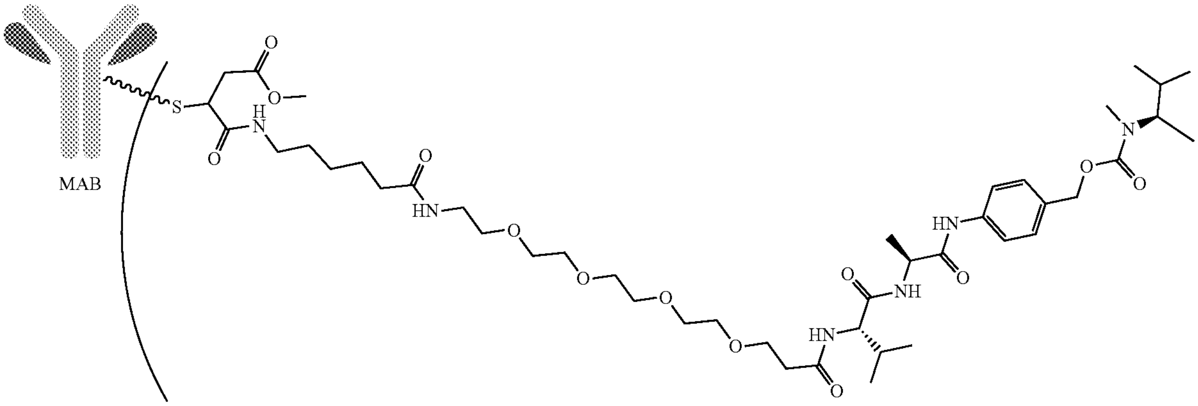

-continued

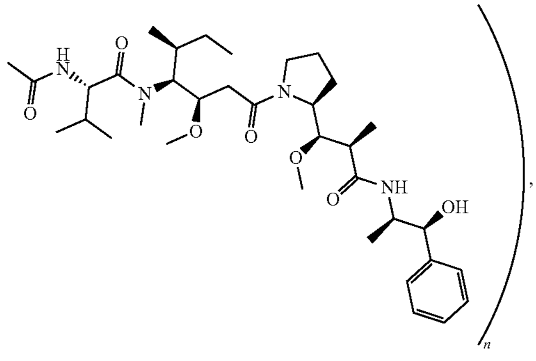

,

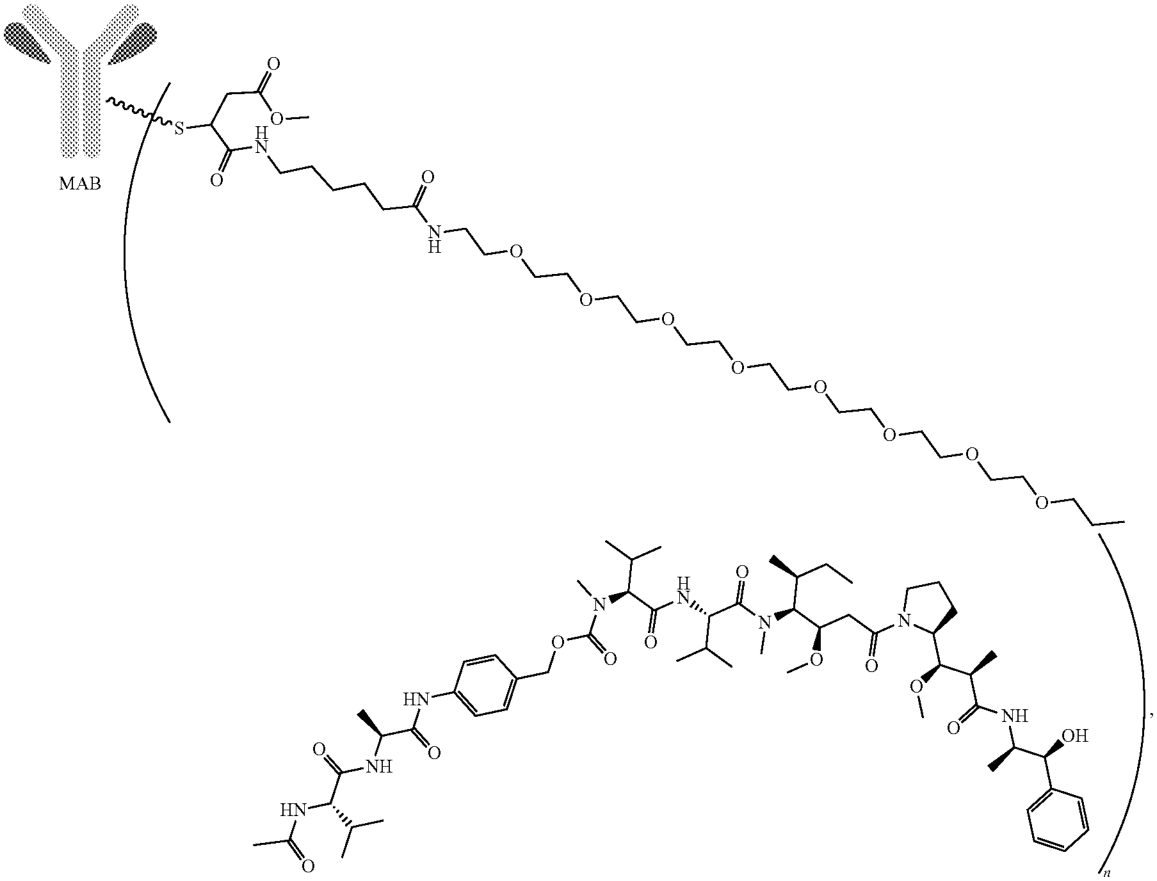

, and

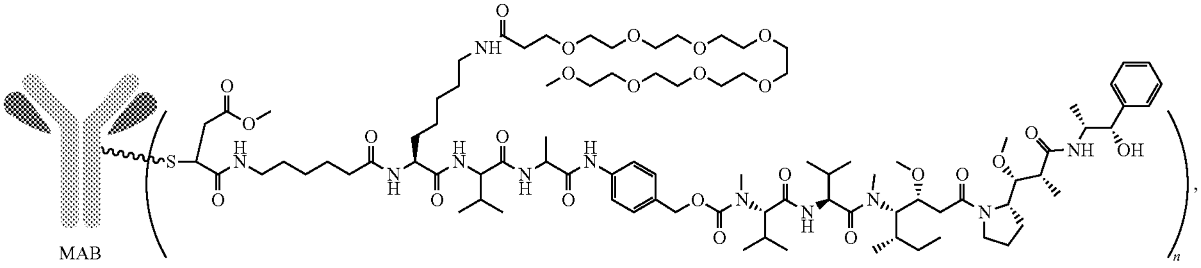

, wherein MAB is an antibody, n is defined as described in the present application, preferably n is about 4 or 8, preferably, MAB is selected from the group consisting of: anti-HER2 humanized monoclonal antibody mil40, trastuzumab (HERCEPTIN), pertuzumab (PERJETA), cetuximab (ERBITUX), panitumumab (VECTIBIX), rituximab (RITUXAN), alemtuzumab (CAMPATH), ibritumomab (ZEVALIN), tositumomab (BEXXAR), ofatumumab (ARZERRA), bevacizumab (AVASTIN), ipilimumab (YERVOY), denosumab (XGEVA), pembrolizumab (KEYTRUDA), nivolumab (Opdivo), Avelumab (Bavencio), Atezolizumab (Tecentriq), durvalumab (Imfinzi), sacituzumab, rovalpituzumab, and biological analogues thereof, more preferably, MAB is an anti-HER2 humanized monoclonal antibody mil40.

The fourth aspect of the present application relates to use of the compound represented by Formula I or Formula I' described in the first aspect of the present application or the compound represented by Formula II or Formula II' described in the second aspect of the present application, or a salt or a solvate thereof in manufacture of an antibody-drug conjugate, preferably, the antibody-drug conjugate is the compound represented by Formula III or Formula III' described in the third aspect of the present application.

The present application also relates to use of the compound represented by Formula I' or the compound represented by Formula II', or a salt or a solvate thereof in manufacture of an antibody-drug conjugate; preferably, the antibody-drug conjugate is the compound represented by Formula III-1 or Formula III'-1 described in the present application.

The fifth aspect of the present application relates to a method for preparing the compound represented by Formula I, or a salt or a solvate thereof described in the first aspect of the present application, 1) if q is 0, and $R_2$ is

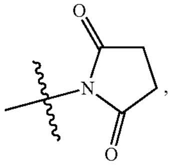 [SMILES: *N1C(=O)CCC1=O]

the preparation method comprises the following steps:

a) reacting maleic anhydride with a compound represented by Formula i to produce a compound represented by Formula ii;

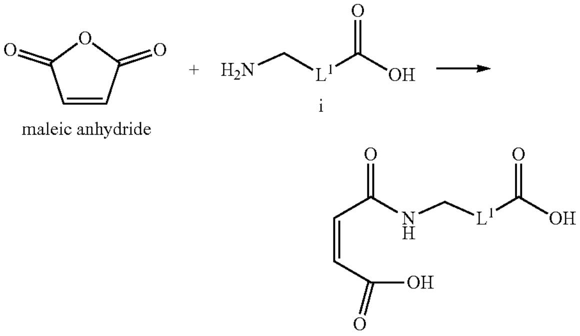

maleic anhydride i ii b) reacting the compound represented by Formula ii with N-hydroxysuccinimide (SuOH) to produce a compound represented by Formula iii;

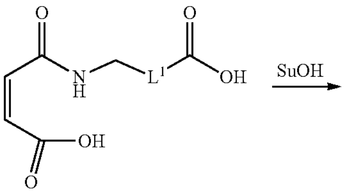

ii

-continued

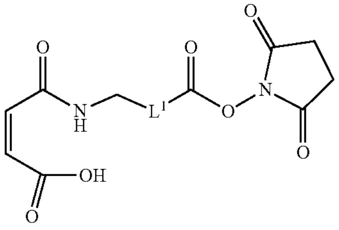

iii c) reacting the compound represented by Formula iii with an iodoalkyl $R_1$—I to produce a target compound I-1;

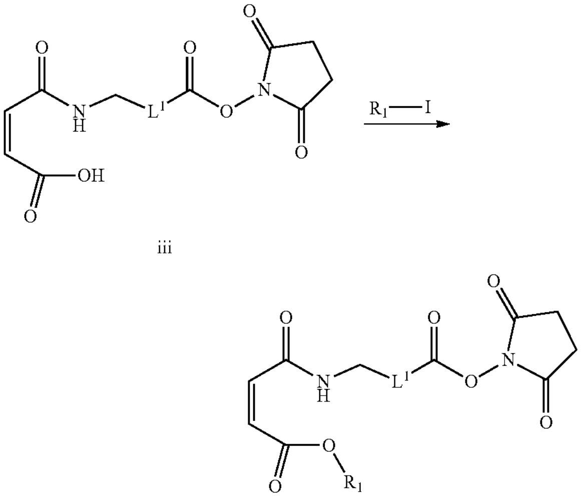

iii

I-1

2) if q is 1, and $R_2$ is

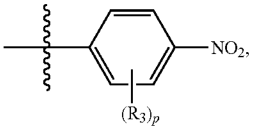

the preparation method comprises the following steps:

a) reacting Fmoc-Y—OH with a compound represented by Formula iv to produce a compound represented by Formula v;

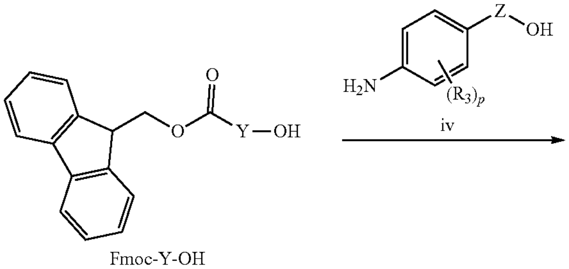

iv

Fmoc-Y-OH

-continued

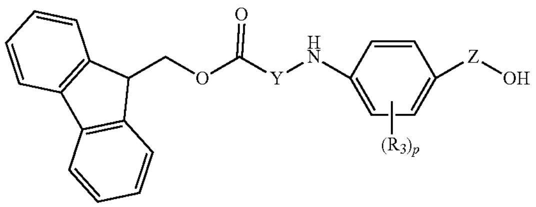

v b) removing Fmoc protecting group from the compound represented by Formula v to obtain a compound represented by Formula vi;

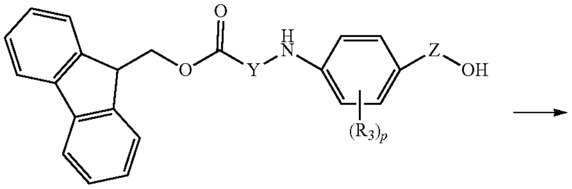

v

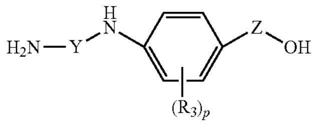

vi c) reacting Compound I-1 with the compound represented by Formula vi to produce a compound represented by Formula vii;

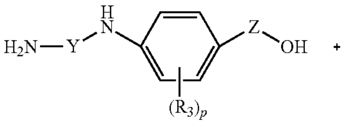

vi

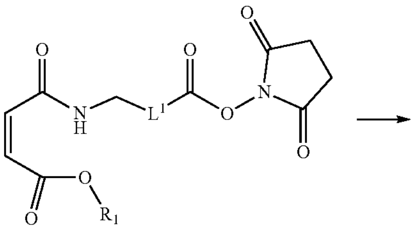

I-1

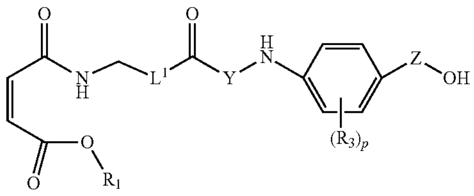

vii d) reacting the compound represented by Formula vii with a compound represented by Formula viii to produce a target Compound I-2;

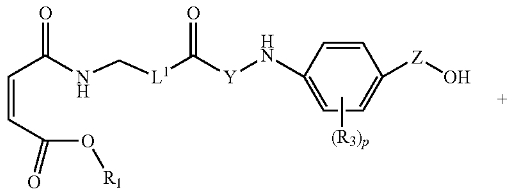

vii

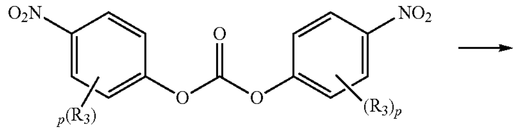

viii

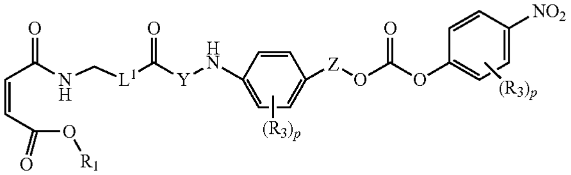

I-2 wherein, $L^1$, Y, Z, $R_1$, $R_3$ and p are defined as described in the present application.

The sixth aspect of the present application relates to a method for preparing the compound represented by Formula II or Formula II', a salt or a solvate thereof as described in the second aspect of the present application, which comprises the following steps:

reacting the compound represented by Formula I or Formula I' or a salt or a solvate thereof described in the first aspect of the present application with a drug, cytotoxin, detection reagent, diagnostic reagent or targeting carrier represented by B to obtain the compound represented by Formula II or Formula II',

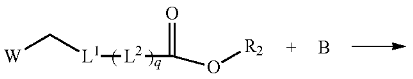

I

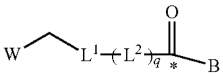

II

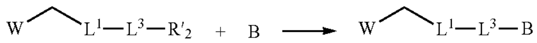

I' II' wherein the substituents are each defined as described in the present application.

The seventh aspect of the present application relates to a method for preparing the compound represented by Formula III or Formula III' or a salt or a solvate thereof described in the third aspect of the present application, which comprises the following steps:

reacting the compound represented by Formula II or Formula II' or a salt or a solvate thereof described in the second aspect of the present application with A, wherein A is coupled to the site # or ## through a S atom in the targeting compound molecule to obtain the compound represented by Formula III or Formula III',

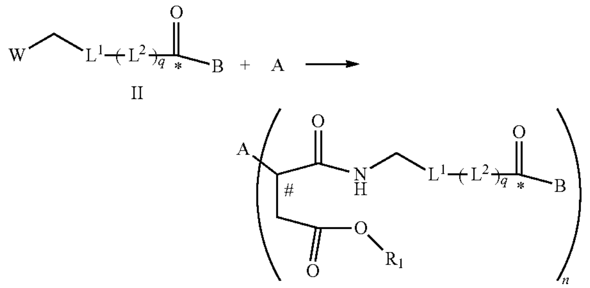

III

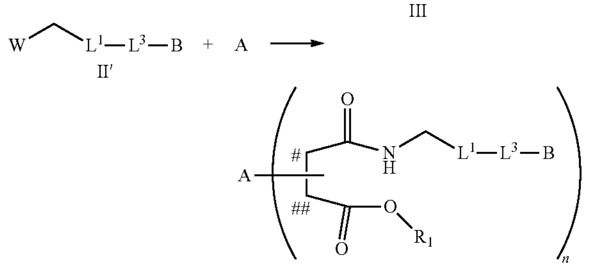

III' preferably, the reaction is carried out under conditions of pH=5 to 10 and temperature of 0° C. to 40° C.;

wherein the substituents are each defined as described in the present application.

The eighth aspect of the present application relates to a pharmaceutical composition, which comprises at least one compound represented by Formula III or Formula III' or a salt or a solvate thereof described in the third aspect of the present application, and one or more pharmaceutical carriers or excipients.

The ninth aspect of the present application relates to use of the compound represented by Formula III or Formula III' or a salt or a solvate thereof described in the third aspect of the present application in manufacture of a medicament for the diagnosis, prevention or treatment of a disease or condition or reduction of severity of the disease or condition.

The tenth aspect of the present application relates to a method for diagnosis, prevention or treatment of a disease or condition or reduction of severity of the disease or condition, the method comprising administering to a patient in need of such treatment a therapeutically effective amount of the compound represented by Formula III or Formula III' or a salt or a solvate thereof.

The eleventh aspect of the present application relates to the compound represented by Formula III or Formula III' or a salt or a solvate thereof, for use in the diagnosis, prevention or treatment of a disease or condition or reduction of severity of the disease or condition.

The present application also relates to a method for diagnosis, prevention or treatment of a disease or condition, comprising administering to a patient in need of such treatment a therapeutically effective amount of the compound represented by Formula III or Formula III' or a salt or a solvate thereof.

In some embodiments, the disease or condition described in the present application is selected from the group consisting of tumor, infectious disease, hematological disease, metabolic disease, inflammation, preferably, the tumor is selected from cancer, lymphoma, lymphoid tumor, blastoma, sarcoma and leukemia, preferably, the cancer is selected from the group consisting of: breast cancer (for example, HER2-positive breast cancer); squamous cell carcinoma (for example, epithelial squamous cell carcinoma); lung cancer, including small cell lung cancer, non-small cell lung cancer, adenocarcinoma of lung and squamous cell carcinoma of lung; peritoneal cancer; liver cancer; gastric cancer; gastrointestinal cancer; pancreatic cancer; glioblastoma; cervical cancer; ovarian cancer; liver cancer; bladder cancer; urethral cancer; hepatocellular tumor; breast cancer; intestinal cancer; colon cancer; rectal cancer; colorectal cancer; endometrial cancer; uterine cancer; salivary gland cancer; renal or kidney cancer; prostate cancer; vulvar cancer; thyroid cancer; liver cancer; anal cancer; penile cancer; melanoma; multiple myeloma and B-cell lymphoma; brain cancer; gallbladder cancer; esophageal cancer; cholangiocarcinoma; head and neck cancer and related metastatic tumor.

DEFINITIONS

As used herein, the term "antibody" is a common immunoglobulin, and a Y-shaped protein used by the immune system to recognize and neutralize foreign objects (e.g., bacteria and viruses). Antibody can specifically recognize the unique part of foreign target (called antigen), because each tip of the Y-shaped protein antibody contains a site that can specifically recognize the antigen. After the antibody binds to the specific antigen, it can mediate multiple related biological effects. Antibody is composed of two identical heavy chains and two identical light chains, and the chains are connected by disulfide bonds formed by sulfhydryl groups in cysteine residues. "Monoclonal antibody" is a single specific antibody in which all antibody molecules are composed of the same immune cells that are clones of the only parent cell, so all antibody molecules are the same.

As used herein, the term "cytotoxin" refers to a molecule that can be toxic to a cancer cell after being released in the cell. The toxins of particular concern in the present application include methyl-auristatin E (MMAE), auristatin, maytansinoids or their derivatives (e.g., maytansinoids, DM1, DM3, DM4), calicheamicin, duocarmycin, doxorubicin, camptothecin or PBD type cytotoxins.

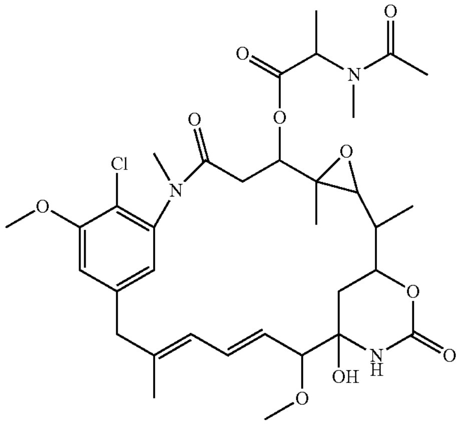

Maytansine

-continued

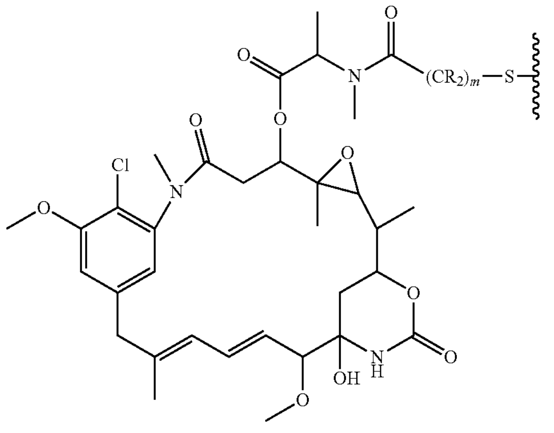

Maytansinoids

DM1

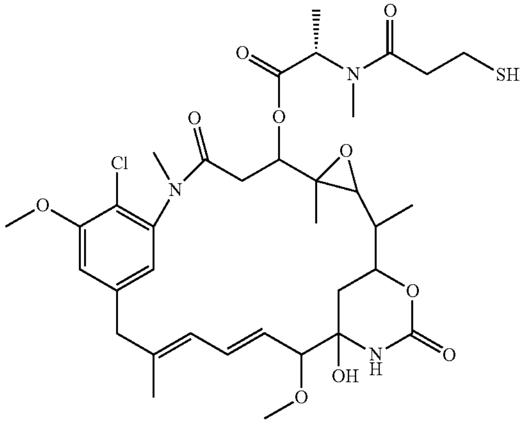

DM3

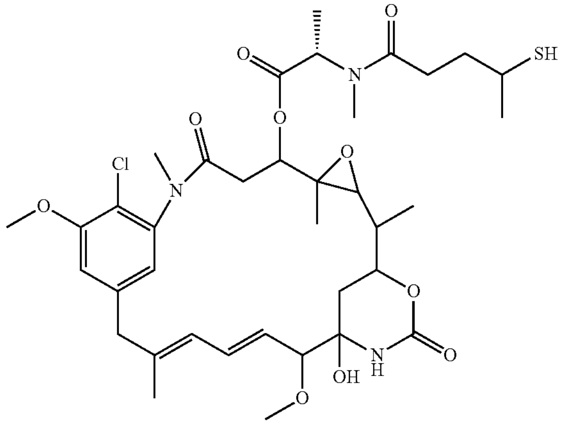

-continued

DM4

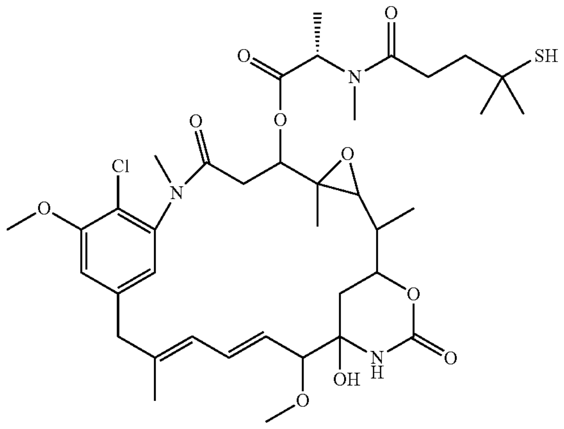

As used herein, the term "linker" is a molecule with two reactive ends, one end of which can be coupled to an antibody and the other end is used to couple to an active compound, such as a cytotoxin. The antibody coupling end of the linker is usually a site that can be coupled through a sulfhydryl of cysteine or an amino of lysine in the antibody, and the toxin coupling end of the linker is usually a site that can be coupled through an active site such as sulfhydryl, amino, carboxyl or hydroxyl in the toxin molecule. When the term "linker" is used to describe a linker in the coupling form, since the linker has reacted with one or two of the antibody and cytotoxin to form covalent bond, it can no longer comprise one or two reactive sites at reactive ends (e.g., a leaving group for sulfhydryl reactive group, a leaving group for amino reactive group).

As used herein, the term "antibody-drug conjugate" or "ADC" is a product formed by an antibody molecule on which multiple molecules (usually 1 to 8) of cytotoxin are each coupled via linker, i.e., an antibody conjugated to one or more cytotoxins. The antibody is usually a monoclonal antibody showing a selectivity to a cancer-specific antigen.

As used herein, the term "about" can be understood as a value which is within +/−20%, +/−18%, +/−15%, +/−12%, +/−10%, +/−9%, +/−8%, +/−7%, +/−6%, +/−5%, +/−4%, +/−3%, +/−2%, +/−1%, +/−0.5%, +/−0.4%, +/−0.3%, +/−0.2%, +/−0.1% of the mentioned value. Unless obvious from the context, all numerical values provided herein are modified by the term "about."

The definitions of abbreviations used in herein are as follows:

ADC: antibody-drug conjugate;
Ala: Alanine;
Boc: tert-Butyloxy carbonyl;
Cit: Citrulline;
DAR (Drug-antibody ratio): drug/antibody molar ratio;
DCC: Dicyclohexylcarbodiimide;
DCM: Dichloromethane;
DIPEA: N,N-Diisopropylethylamine;
DMAC: N,N-Dimethylacetamide;
DMF: N,N-Dimethylformamide;
DMSO: Dimethyl sulfoxide;
EEDQ: N-Ethoxycarbonyl-2-ethoxy-1,2-dihydroquinoline;
Fmoc: Fluorenylmethyloxycarbonyl;
HER2: Human epidermal growth factor receptor 2;
HIC: Hydrophobic interaction chromatography;
His: Histidine;

mM: Millimoles;
Ma: Maleimide;
Maa: Maleic acid amide;
Mm: Methyl maleate;
Mf: Methyl fumarate;
MAB: Monoclonal antibody
MMAE: Monomethyl-auristatin E;
NHS/SuOH: N-Hydroxysuccinimide;
NMM: N-Methylmorpholine;
NAC (N-Acetyl-L-cysteine): N-Acetylcysteine;
PAB: p-Aminobenzyl alcohol;
Su: Succinimide;
TCEP: Tris(2-carboxyethyl)phosphine;
TFA: trifluoroacetic acid;
THE: Hetrahydrofuran;
Tris: Tris(hydroxymethyl)aminomethane;
VA (Valine-Alanine, Val-Ala): valine-alanine dipeptide;
Val: valine;
VC (Valine-Citrulline, Val-Cit): valine-citrulline dipeptide;
DCU: dicyclohexylurea;
HOBT: 1-hydroxybenzotriazole;
EDCI: 1-(3-dimethylaminopropyl)-3-ethylcarbodiimide hydrochloride;
TEA: triethylamine;
Lys: lysine;
Gly: glycine;
Thr: threonine;
Leu: leucine;
Ile: isoleucine;
Asn: asparagine;
Phe: phenylalanine.

As used herein, the term "salt" refers to a salt that retains the biological effectiveness and properties of a compound from which the salt is derived. In many cases, the compound disclosed herein is capable of forming an acid and/or base salt through the presence of amino and/or carboxyl or a similar group. Acid addition salt can be formed with an inorganic acid or organic acid. The inorganic acid that can be derivatized to form the salt includes, for example, hydrochloric acid, hydrobromic acid, sulfuric acid, nitric acid, phosphoric acid, etc. The organic acid that can be derivatized to form the salt includes, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, etc. Base addition salt can be formed with an inorganic base or organic base. The inorganic base that can be derivatized to form the salt includes, for example, sodium, potassium, lithium, ammonium, calcium, magnesium, iron, zinc, copper, manganese, aluminum, etc.; particularly preferred are salts of ammonium, potassium, sodium, calcium and magnesium. The organic base that can be derivatized to form the salt includes, for example, primary, secondary and tertiary amines, substituted amines, including naturally-occurring substituted amines, cyclic amines, basic ion exchange resins, etc., specifically including, for example, isopropylamine, trimethylamine, diethylamine, triethylamine, tripropylamine and ethanolamine.

As used herein, in the term "$C_{1-6}$ linear or branched alkyl", "1" and "6" refer to the number of carbon atoms in the group. That is, the "$C_{1-6}$ linear or branched alkyl" can contain carbon atoms in number of from "1" to "6". Therefore, for example, "$C_{1-4}$ alkyl" refers to all alkyl groups that have 1 to 4 carbon atoms, i.e., $CH_3$—, $CH_3CH_2$—, $CH_3CH_2CH_2$—, $(CH_3)_2CH$—, $CH_3CH_2CH_2CH_2$—, $CH_3CH_2$ $CH(CH_3)$— and $(CH_3)_3C$—.

As used herein, the term "$C_{1-6}$ alkoxy" refers to a group having a structure of "$C_{1-6}$ alkyl-O—", wherein $C_{1-6}$ alkyl has the same meaning as the aforementioned "$C_{1-6}$ linear or branched alkyl". For example, $C_{1-4}$ alkoxy, $C_{1-2}$ alkoxy, $C_1$ alkoxy, $C_2$ alkoxy, $C_3$ alkoxy, $C_4$ alkoxy, $C_5$ alkoxy or $C_6$ alkoxy, preferably $C_{1-4}$ alkoxy. Specific examples include, but are not limited to, methoxy, ethoxy, propoxy, n-butoxy, 2-butoxy, isopropoxy, sec-butoxy, tert-butoxy, n-pentoxy, n-hexyloxy, etc.

As used herein, the term "halogen" or "halo" refers to any one of the radioactively stable atoms in Column 7 of the periodic table, for example, fluorine, chlorine, bromine, iodine, etc.

The pharmaceutical composition as described herein comprises the compound represented by Formula III or Formula III' or a salt or a solvate thereof described in the present application, and a conventional pharmaceutical carrier or excipient. The pharmaceutical composition can be administered by, for example, oral or parenteral administration.

As used herein, the term "effective amount" refers to an amount sufficient to achieve a desired therapeutic effect, for example, an amount that achieves alleviation of a symptom associated with a disease to be treated.

In addition, it should be pointed out that the dosage and usage of the compound of the present application depend on many factors, including age, weight, gender, natural health status and nutritional status of patient, active strength of compound, time of administration, metabolic rate, severity of disease, and subjective judgment of physician in diagnosis and treatment. The preferred dosage is between 0.01 to 100 mg/kg body weight/day.

In some embodiments, the typical synthetic route of the Val-Cit dipeptide-containing ring-opening ADC involved in the present application is as follows:

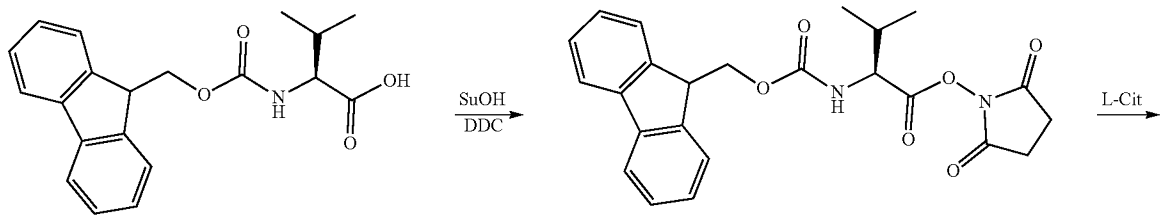

N-F-moc-L-Val
Fmoc-Val-OSu

-continued
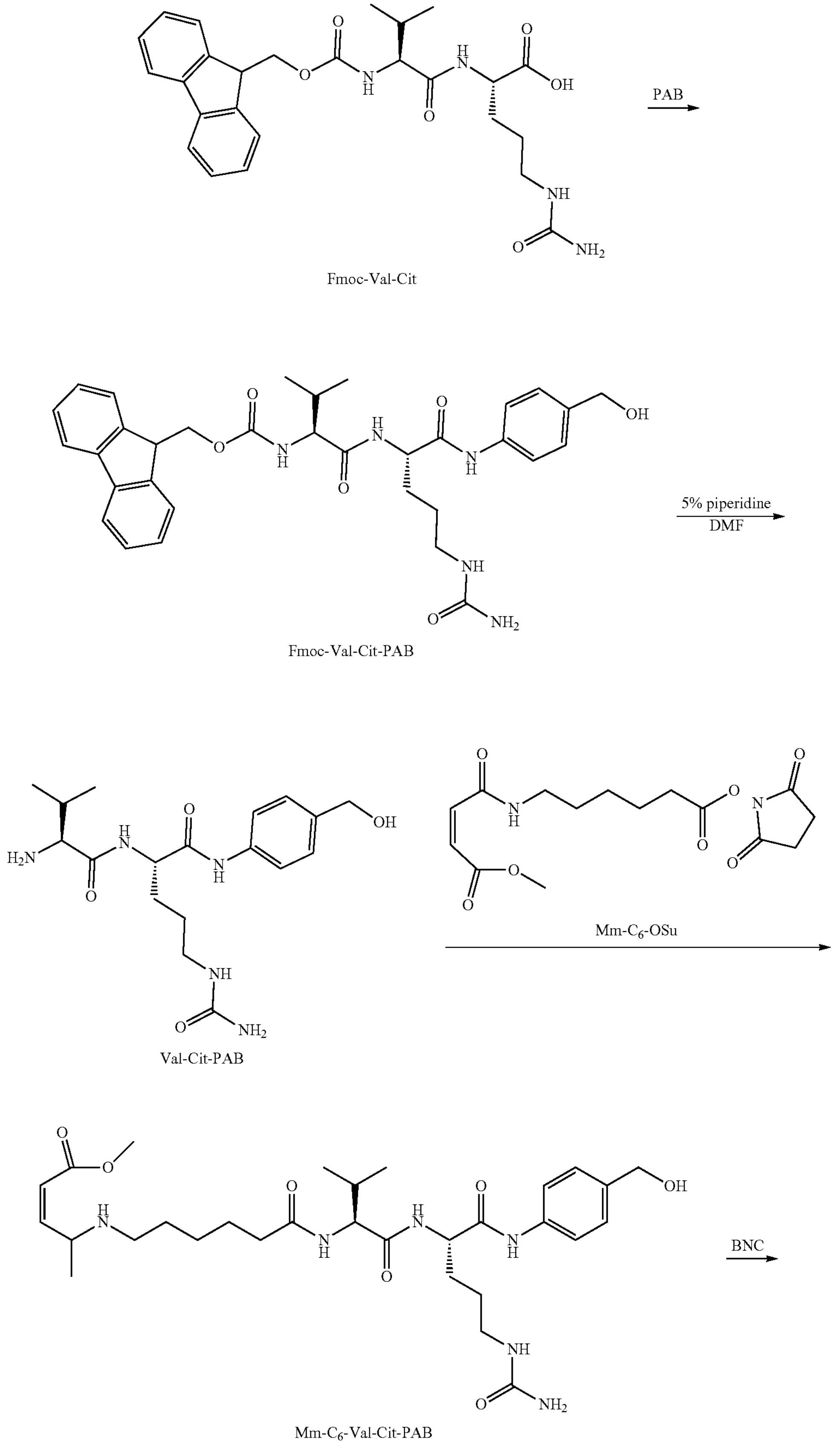
Fmoc-Val-Cit
Fmoc-Val-Cit-PAB
Val-Cit-PAB
Mm-$C_6$-OSu
Mm-$C_6$-Val-Cit-PAB -continued

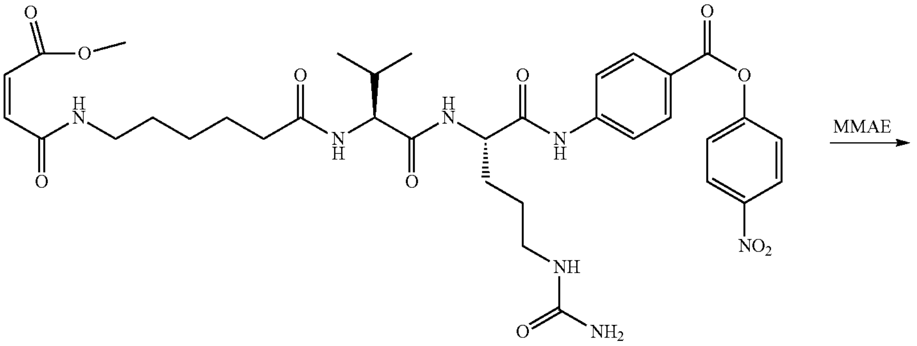

Mm-$C_6$-Val-Cit-PAB-PNP

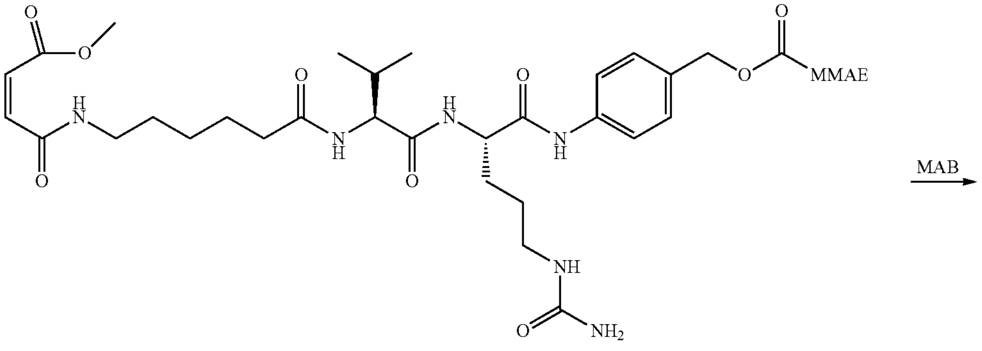

Mm-$C_6$-Val-Cit-PAB-MMAE

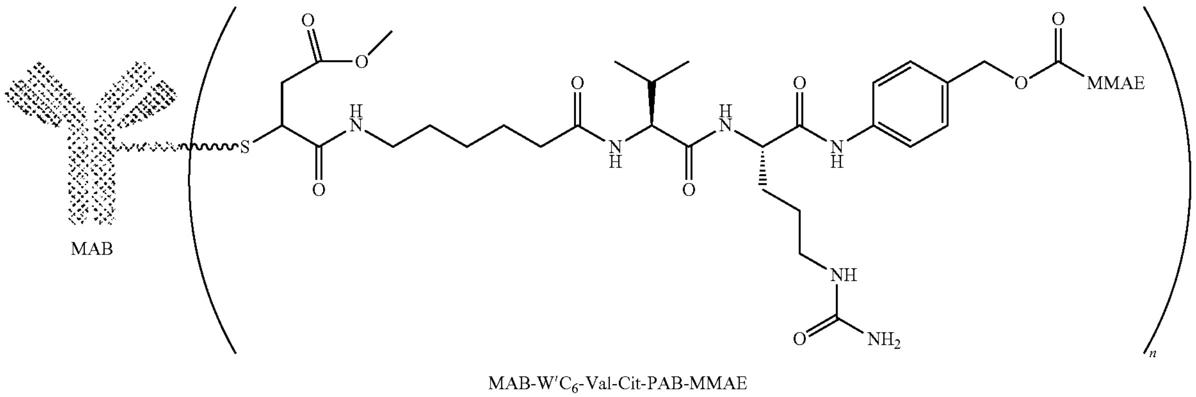

MAB-W'$C_6$-Val-Cit-PAB-MMAE

N-Fmoc-L-Val is condensed with SuOH (NHS) under the action of a DCC condensing agent to form active ester Fmoc-Val-OSu, the active ester Foc-Val-OSu and L-Cit undergo acylation reaction to obtain Fmoc-Val-Cit, the Fmoc-Val-Cit is condensed with p-aminobenzyl alcohol (PAB) under the action of EEDQ to form Fmoc-Val-Cit-PAB, the Fmoc-Val-Cit-PAB undergoes the removal of protective group under alkaline condition to obtain Val-Cit-PAB, the Val-Cit-PAB reacts with active ester linker Mm-$C_6$-OSu containing methyl maleate structure to obtain Mm-$C_6$-Val-Cit-PAB, the Mm-$C_6$-Val-Cit-PAB further reacts with bis(p-nitrophenyl) carbonate to obtain linker Mm-$C_6$-Val-Cit-PAB-PNP, the linker reacts with cytotoxin MMAE to obtain a small molecule load Mm-$C_6$-Val-Cit-PAB-MMAE of ADC, and finally the Mm-$C_6$-Val-Cit-PAB-MMAE is coupled with an antibody to obtain ADC MAB-W'—$C_6$-Val-Cit-PAB-MMAE with a stable linker W'.

In some embodiments, the general synthetic route of the Val-Cit dipeptide-containing ring-closing ADC control substance involved in the present application is as follows:

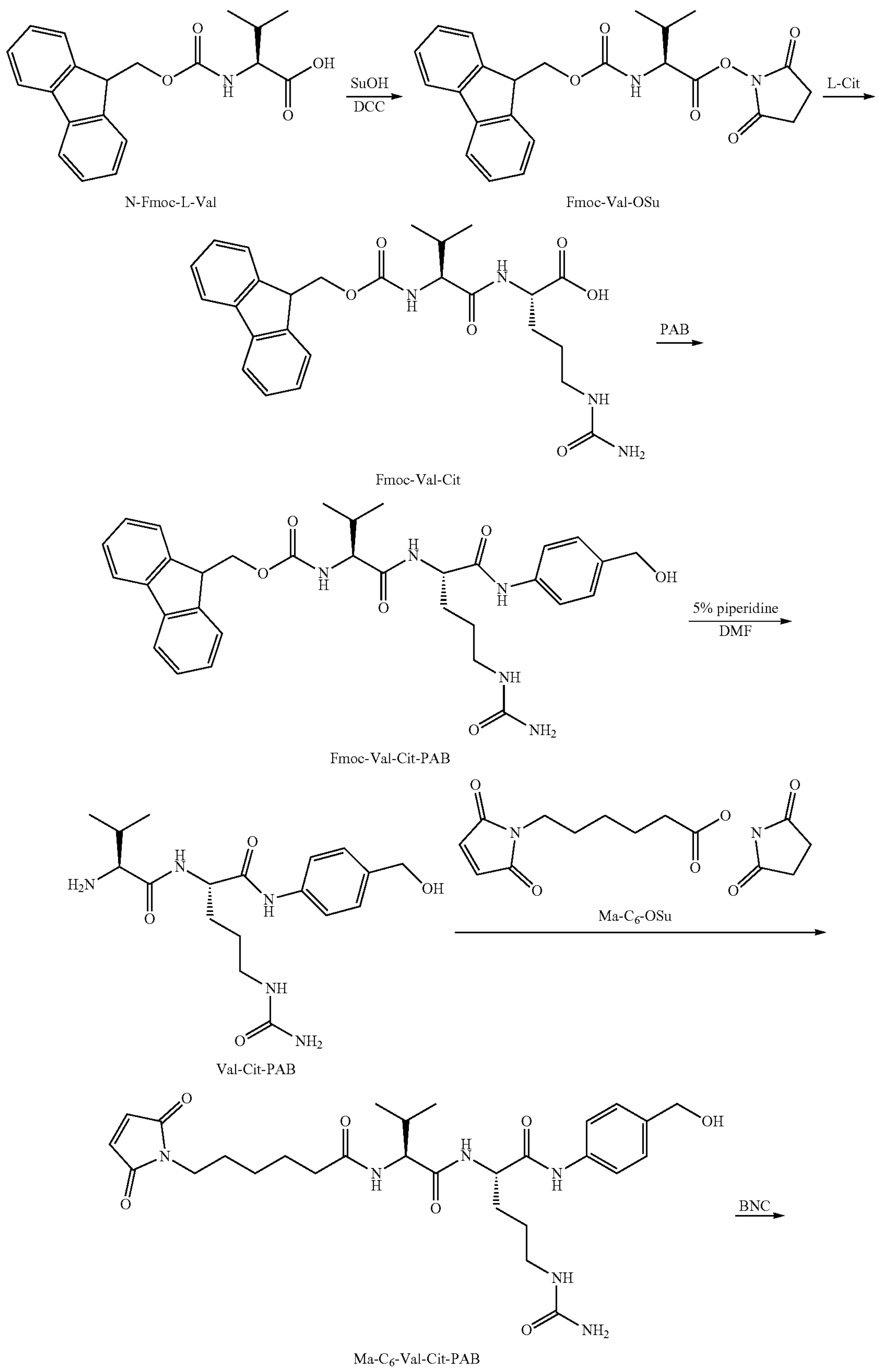
SuOH
DCC
L-Cit
N-Fmoc-L-Val
Fmoc-Val-OSu
PAB
Fmoc-Val-Cit
5% piperidine
DMF
Fmoc-Val-Cit-PAB
Ma-$C_6$-OSu
Val-Cit-PAB
BNC
Ma-$C_6$-Val-Cit-PAB -continued

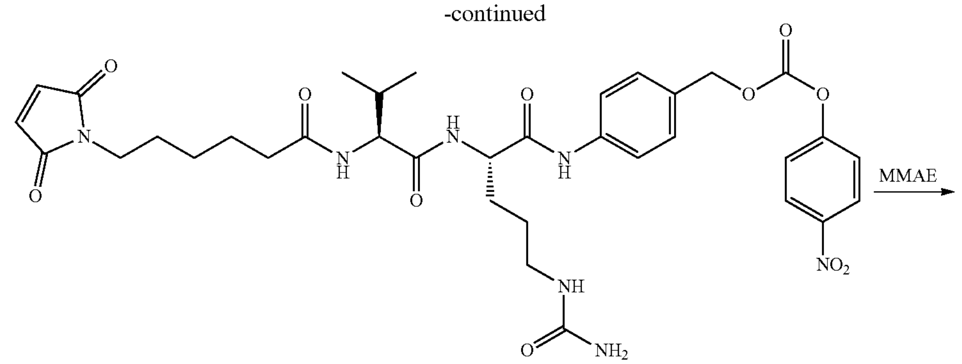

Ma-$C_6$-Cal-Cit-PAB-PNP

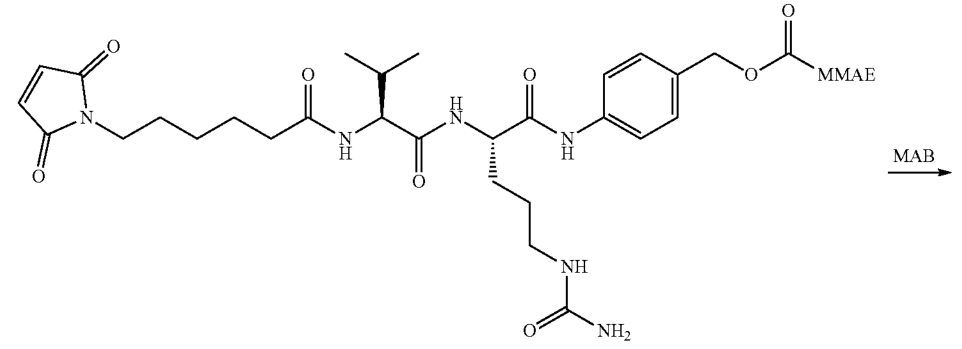

Ma-$C_6$-Val-Cit-PAB-MMAE

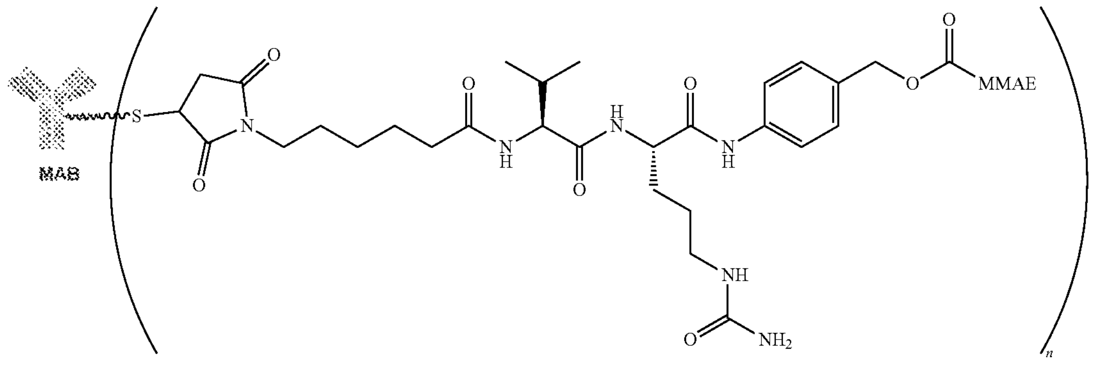

MAB-Su-$C_6$-Val-Cit-PAB-MMAE

N-Fmoc-L-Val is condensed with SuOH (NHS) under the action of a DCC condensing agent to form active ester Fmoc-Val-OSu, the active ester Fmoc-Val-OSu and L-Cit undergo acylation reaction to obtain Fmoc-Val-Cit, the Fmoc-Val-Cit is condensed with p-aminobenzyl alcohol (PAB) under the action of EEDQ to form Fmoc-Val-Cit-PAB, the Fmoc-Val-Cit-PAB undergoes the removal of protective group under alkaline conditions to obtain Val-Cit-PAB, the Val-Cit-PAB reacts with active ester linker Ma-$C_6$-OSu containing maleimide structure to obtain Ma-$C_6$-Val-Cit-PAB, the Ma-$C_6$-Val-Cit-PAB further reacts with bis(p-nitrophenyl) carbonate to obtain linker Ma-$C_6$-Val-Cit-PAB-PNP, the linker reacts with cytotoxin MMAE to obtain a small molecule load Ma-$C_6$-Val-Cit-PAB-MMAE of ADC, and finally the Ma-$C_6$-Val-Cit-PAB-MMAE is coupled with an antibody to obtain ADC MAB-Su-$C_6$-Val-Cit-PAB-MMAE with a stable linker structure.

In some embodiments, the preparation route of the Val-Ala dipeptide-containing stable ring-opening ADC involved in the present application can also be:

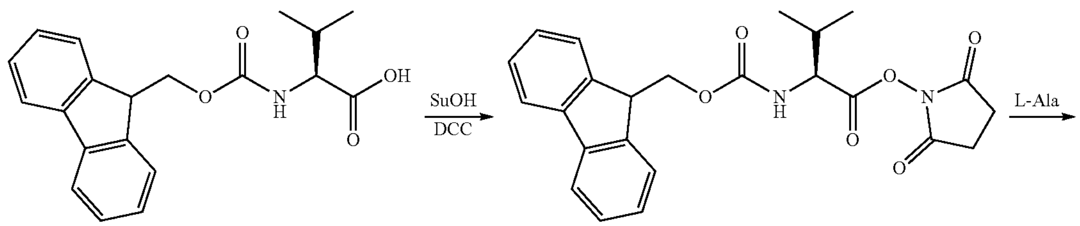
N-Fmoc-L-Val
Fmoc-Val-OSu
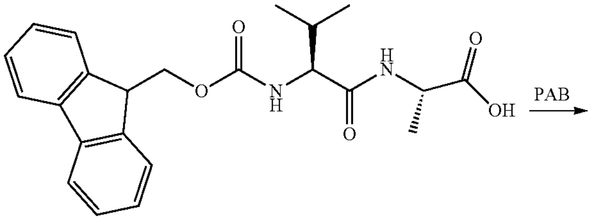
Fmoc-Val-Ala
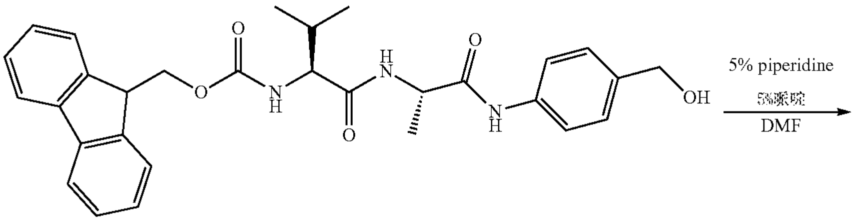
Fmoc-Val-Cit-PAB
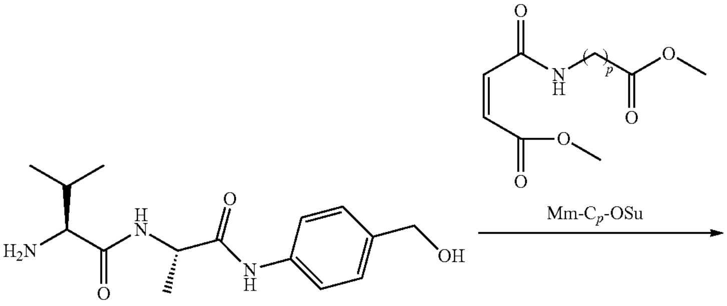
Val-Cit-PAB
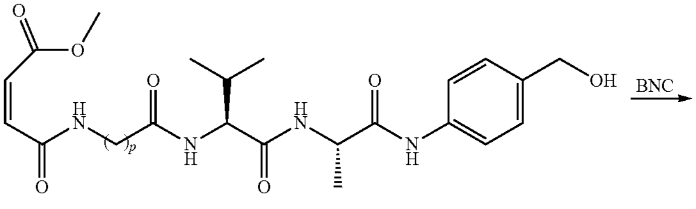
Mm-$C_p$-Val-Ala-PAB
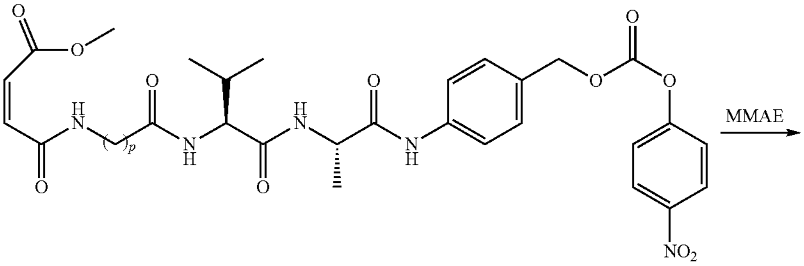
Mm-$C_p$-Val-Ala-PAB-PNP -continued

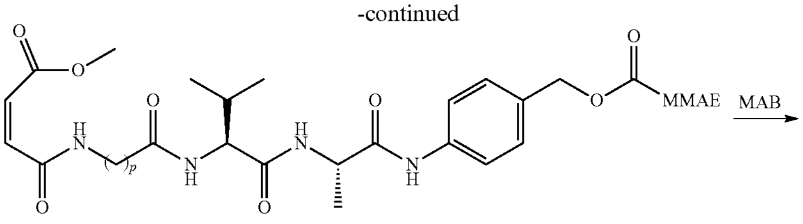

Mm-$C_p$-Val-Ala-PAB-MMAE

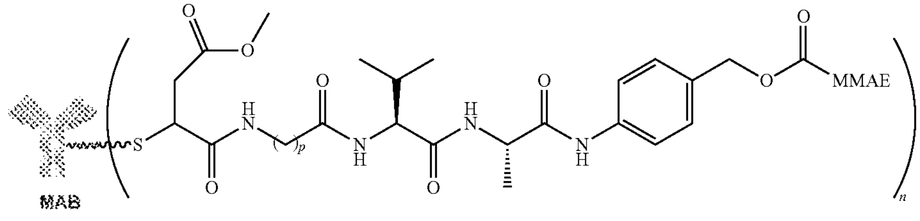

MAB-W′-$C_p$-Val-Ala-PAB-MMAE

N-Fmoc-L-Val is condensed with SuOH (NHS) under the action of a DCC condensing agent to form active ester Fmoc-Val-OSu, the active ester Fmoc-Val-OSu and L-Ala undergo acylation reaction to obtain Fmoc-Val-Ala, the Fmoc-Val-Ala is condensed with p-aminobenzyl alcohol (PAB) under the action of EEDQ to form Fmoc-Val-Ala-PAB, the Fmoc-Val-Ala-PAB undergoes the removal of protecting group under alkaline condition to obtain Val-Ala-PAB, the Val-Ala-PAB reacts with active ester linker Mm-$C_6$-OSu or Mm-$C_3$-OSu containing methyl maleate structure to obtain Mm-$C_6$-Val-Ala-PAB or Mm-$C_3$-Val-Ala-PAB, the Mm-$C_6$-Val-Ala-PAB or Mm-$C_3$-Val-Ala-PAB further reacts with bis(p-nitrophenyl) carbonate to obtain linker Mm-$C_6$-Val-Ala-PAB-PNP or Mm-$C_3$-Val-Ala-PAB-PNP, the above-mentioned linker reacts with cytotoxin MMAE to obtain a small molecule load Mm-$C_6$-Val-Ala-PAB-MMAE or Mm-$C_3$-Val-Ala-PAB-MMAE of ADC, and finally the Mm-$C_6$-Val-Ala-PAB-MMAE or Mm-$C_3$-Val-Ala-PAB-MMAE is coupled with an antibody to obtain ADC MAB-Mm-$C_6$-Val-Ala-PAB-MMAE or MAB-Mm-$C_3$-Val-Ala-PAB-MMAE with a stable linker structure.

In some embodiments, the preparation route of the Val-Ala dipeptide-containing ring-closing ADC control substance involved in the present application is as follows:

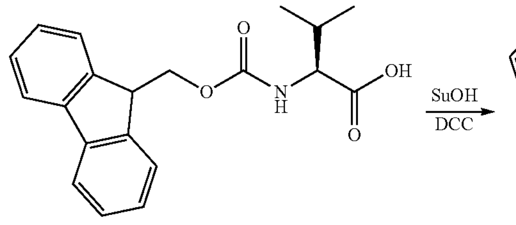

N-Fmoc-L-Val

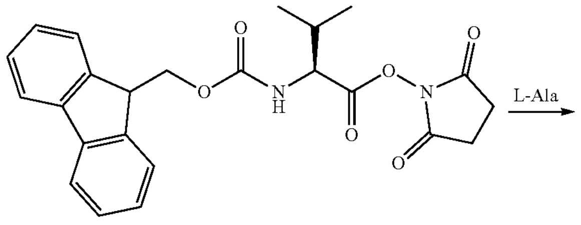

Fmoc-Val-OSu

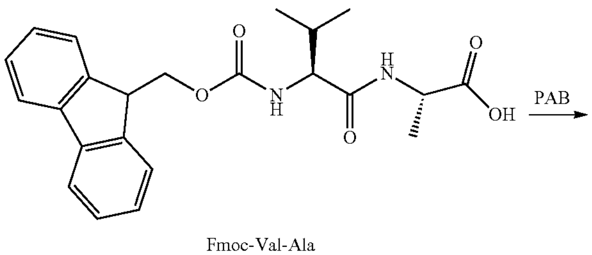

Fmoc-Val-Ala

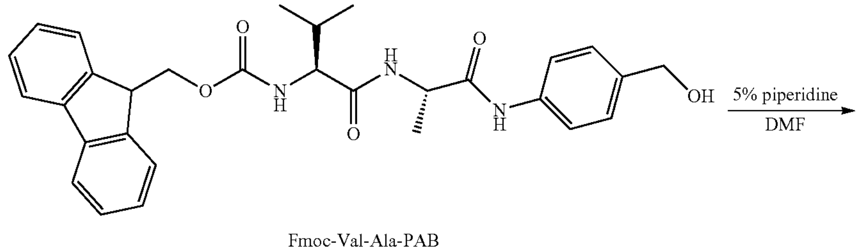

Fmoc-Val-Ala-PAB

-continued

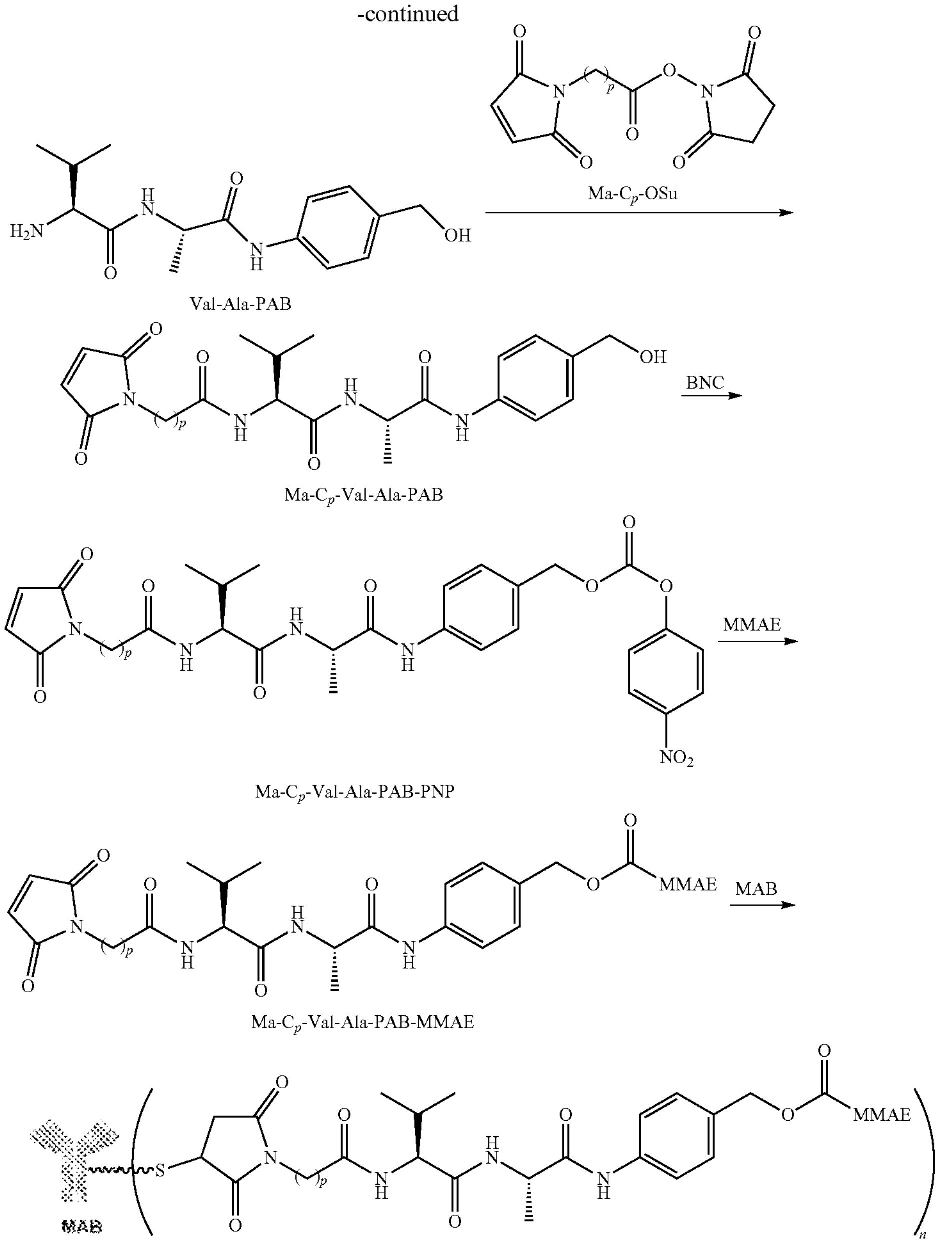

Val-Ala-PAB

Ma-$C_p$-Val-Ala-PAB

Ma-$C_p$-Val-Ala-PAB-PNP

Ma-$C_p$-Val-Ala-PAB-MMAE

MAB-Su-$C_p$-Val-Ala-PAB-MMAE

N-Fmoc-L-Val is condensed with SuOH (NHS) under the action of a DCC condensing agent to form active ester Fmoc-Val-OSu, the active ester Fmoc-Val-OSu and L-Ala undergo acylation reaction to obtain Fmoc-Val-Ala, the Fmoc-Val-Ala is condensed with p-aminobenzyl alcohol (PAB) under the action of EEDQ to form Fmoc-Val-Ala-PAB, the Fmoc-Val-Ala-PAB undergoes the removal of protecting group under alkaline condition to obtain Val-Ala-PAB, the Val-Ala-PAB reacts with reactive ester linker Ma-$C_6$-OSu or Ma-$C_3$-OSu containing methyl maleate structure to obtain Ma-$C_6$-Val-Ala-PAB or Ma-$C_3$-Val-Ala-PAB, the Ma-$C_6$-Val-Ala-PAB or Ma-$C_3$-Val-Ala-PAB further reacts with bis(p-nitrophenyl) carbonate to obtain linker Ma-$C_6$-Val-Ala-PAB-PNP or Ma-$C_3$-Val-Ala-PAB-PNP, the above-mentioned linker reacts with cytotoxin MMAE to obtain small molecule load Ma-$C_6$-Val-Ala-PAB-MMAE or Ma-$C_3$-Val-Ala-PAB-MMAE of ADC, and finally the Ma-$C_6$-Val-Ala-PAB-MMAE or Ma-$C_3$-Val-Ala-PAB-MMAE is coupled with an antibody to obtain ADC MAB-Su-$C_6$-Val-Ala-PAB-MMAE or MAB-Su-$C_3$-Val-Ala-PAB-MMAE with a stable linker structure.

Beneficial Technical Effects

The present application provides a class of compounds represented by Formula III or Formula III' with an ring-opening linker, and the compounds can be quickly prepared under mild conditions similar to biological characteristics. The compounds have high stability and can effectively overcome the toxin off-targeting problem caused by the instability of thiosuccinimide, which is common in ADCs at the present stage.

SPECIFIC MODELS FOR CARRYING OUT THE APPLICATION

Figure 1:
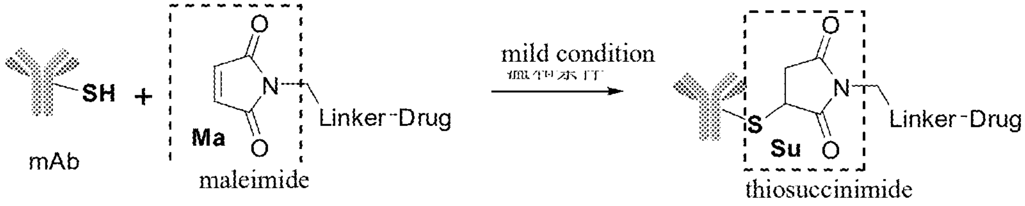
FIG. 1 shows a schematic diagram of the process of generating thiosuccinimide during antibody coupling.
Figure 2:
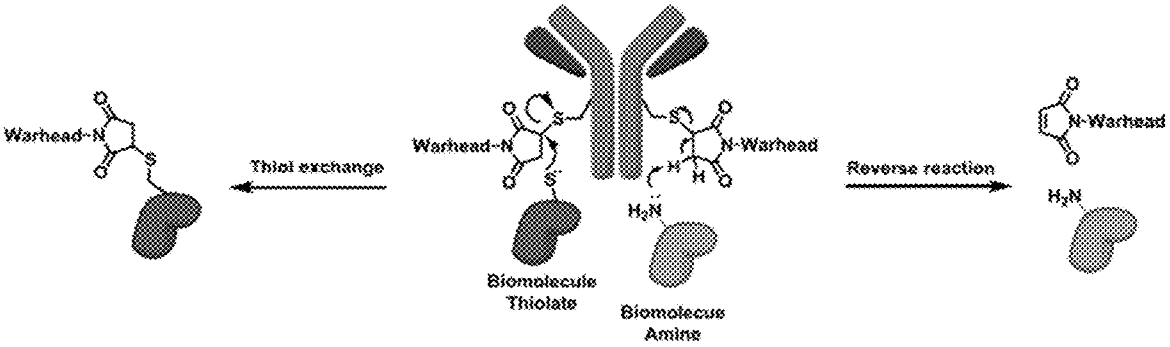
FIG. 2 shows a schematic diagram of the toxin off-targeting caused by instability of thiosuccinimide structure.
Figure 3:
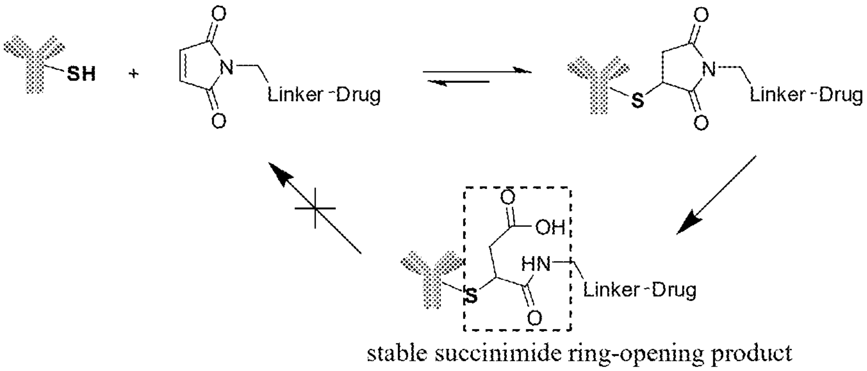
FIG. 3 shows a schematic diagram of two degradation modes of thiosuccinimide structure.
Figure 4:
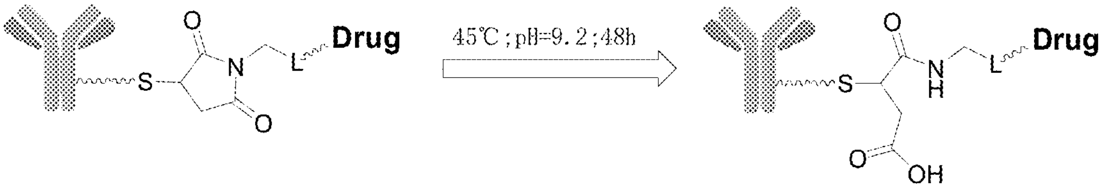
FIG. 4 shows a schematic diagram of the hydrolysis of succinimide under non-mild conditions.
Figure 5:
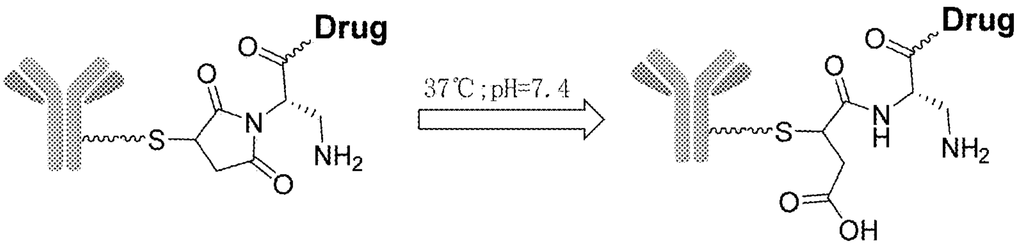
FIG. 5 shows a schematic diagram of introducing an amino group near succinimide group to induce and accelerate the ring-opening process of succinimide.

The embodiments of the present application will be described in detail below in combination with examples, but those skilled in the art will understand that the following examples are only used to illustrate the present application and should not be regarded as limiting the scope of the present application. If specific conditions are not indicated in the examples, they shall be carried out in accordance with conventional conditions or conditions recommended by the manufacturers. The reagents or instruments used without giving manufacturers are all conventional products that were commercially available.

Example 1: Synthesis of Linker Mm-$C_3$-OSu

1) Preparation of Maa-$C_3$—OH:

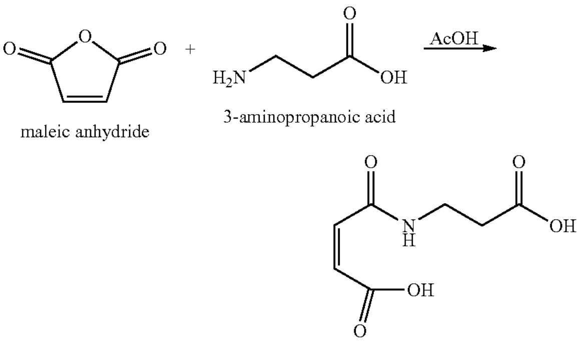

maleic anhydride 3-aminopropanoic acid

Maa-$C_3$—OH

3-Aminopropionic acid (4.13 g, 46.35 mM) was dissolved in acetic acid (200 mL), stirred to dissolve, maleic anhydride (5.0 g, 51 mM) was added, and stirred at room temperature, the resulting reaction solution was clear and transparent, and reacted under stirring for 1 hour, then white insoluble substance was precipitated out, the reaction was continued for 10 hours, and then filtration was carried out, the filter cake was washed with acetonitrile to obtain a white powdery solid, the white powdery solid was weighed as 7.72 g, and the yield was 89%. $^1$H-NMR (400M, DMSO-d6): δ 14.28 (br, 1H), 12.72 (br, 1H), 9.09 (s, 1H), 6.40 (d, J=12.6 Hz, 1H), 6.24 (d, J=12.6, 1H), 3.37 (t, 2H), 2.47 (t, 2H). MS m/z 186.04 ([M−H]$^-$).

2) Preparation of Maa-$C_3$-OSu:

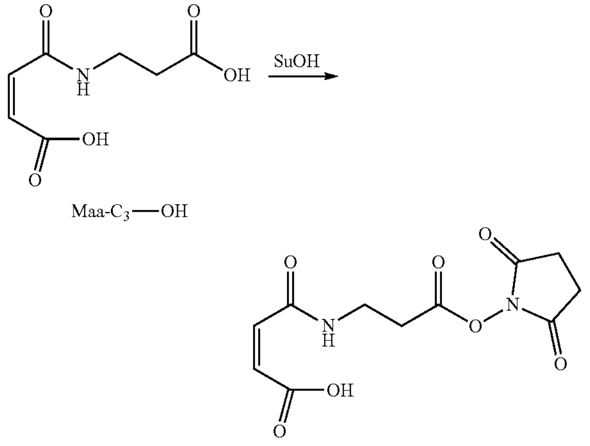

Maa-$C_3$—OH

Maa-$C_3$—OSu

Maa-$C_3$—OH (2.0 g, 10.68 mM, 1 eq) was dissolved in N,N-dimethylformamide (DMF, 45 mL), stirred to dissolve, N-hydroxysuccinimide (SuOH, 2.46 g, 21.37 mM, 2 eq) was added, stirred at room temperature, placed in a −5° C. cold trap to cool for 20 minutes, then 2,4,6-trimethylpyridine (4.21 mL, 32.04 mM, 3 eq) was added and stirred continuously for 20 minutes at −5° C. Trifluoroacetic anhydride (4.50 mL, 3 eq) was slowly added dropwise within half an hour. After the addition was completed, the reaction solution was dropped into 1 mol/L hydrochloric acid solution (HCl) and then extracted with chloroform for 3 to 4 times. The organic phases were combined, washed 3 times with water, washed 2 times with 1 mol/L HCl, washed 3 times with saturated brine, dried with anhydrous magnesium sulfate, and the organic phase was concentrated to obtain the target product as a colorless oil, which became a white solid when placed at low temperature, after being dried, the white solid was weighed as 2.5 g, and the yield was 81%. $^1$H-NMR (400M, DMSO-d6): δ 8.22 (t, 1H), 6.39 (d, J=12.6 Hz, 1H), 6.33 (d, J=12.6 Hz, 1H), 2.95 (q, 2H), 2.89 (s, 4H). MS m/z 283.2 ([M−H]$^-$); 285.2 ([M+H]$^+$).

Preparation of Mm-$C_3$-OSu:

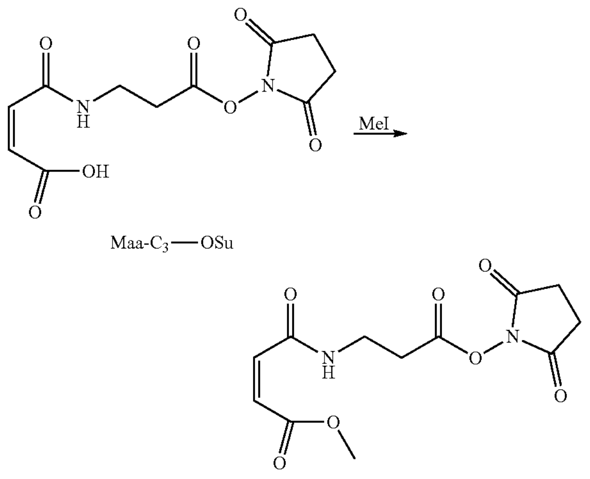

Maa-$C_3$—OSu

Mm-$C_3$—OSu

Maa-$C_3$-OSu (2.4 g, 9.27 mM, 1 eq) was dissolved in DMF (30 mL), stirred to dissolve, anhydrous potassium carbonate (2.56 g, 18.53 mM, 2 eq) was added, and then iodomethane (2.63 g, 18.53 mM, 2 eq) was added dropwise, and reacted at room temperature for 2 hours. After the reaction was completed, the insoluble substance was removed by filtration. The solvent was removed by concentration under reduced pressure, ethyl acetate was added to dissolve the residue, and then filtered, the filtrate was washed with saturated brine for 3 times, dried over anhydrous magnesium sulfate, and concentrated to obtain a white semi-solid substance, which was crude product of Mm-$C_3$-OSu.

Example 2: Synthesis of Linker Mm-$C_6$-OSu

1) Preparation of Maa-$C_6$—OH:

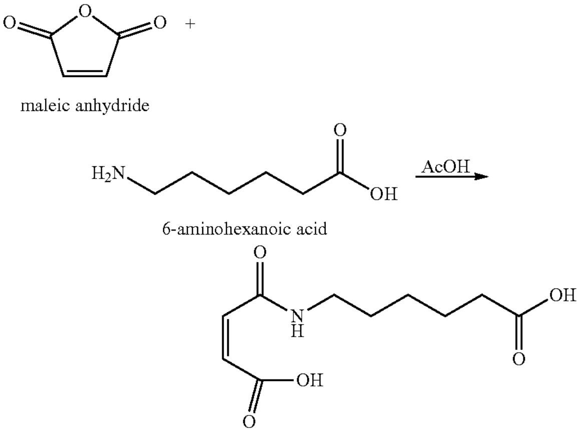

maleic anhydride 6-aminohexanoic acid

Maa-$C_6$—OH

6-Aminohexanoic acid (3.94 g, 30 mM) was dissolved in acetic acid (100 mL), stirred to dissolve, maleic anhydride (2.94 g, 30 mM) was added, stirred at room temperature, the resulting reaction solution was clear and transparent, and stirred continuously to react at room temperature for 1 hour, a white insoluble substance was precipitated out. The reaction was continued for 10 hours, filtration was carried out, and the filter cake was washed with acetonitrile to obtain a white powdery solid, the white powdery solid was weighed as 5.7 g, and the yield was 82%. $^1$H-NMR (400M, DMSO-d6): δ 15.08 (br, 1H), 11.92 (br, 1H), 9.12 (t, 1H), 6.40 (d, J=12.6 Hz, 1H), 6.25 (d, J=12.6 Hz, 1H), 3.16 (t, 2H), 2.20 (t, 2H), 1.54-1.43 (m, 4H), 1.29 (m, 2H). MS m/z 228 ([M−H]$^-$).

2) Preparation of Maa-$C_6$-OSu:

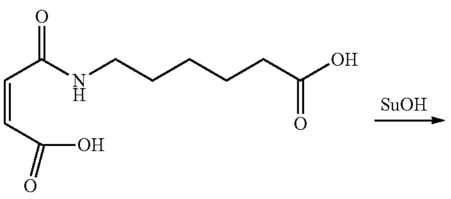

Maa-$C_6$—OH

-continued

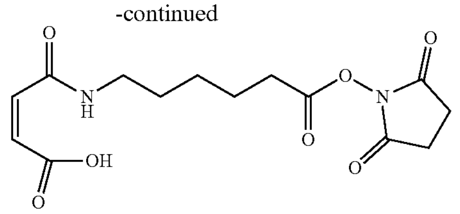

Maa-$C_6$—OSu

Maa-$C_6$—OH (4.00 g, 17.45 mM, 1 eq) was dissolved in DMF (70 mL), stirred to dissolve, N-hydroxysuccinimide (8.03 g, 69.80 mM, 4 eq) was added, stirred at room temperature, placed in a −5° C. cold trap to cool for 20 minutes, then 2,4,6-trimethylpyridine (9.31 mL, 69.80 mM, 4 eq) was added and continuously stirred at −5° C. for 20 minutes. Trifluoroacetic anhydride (9.80 mL, 4 eq) was slowly added dropwise within 0.5 hours. After the addition was completed, the reaction solution was dropped into 1 mol/L HCl and extracted with chloroform for 3-4 times. The organic phases were combined, washed 3 times with water, washed 2 times with 1 mol/L HCl, washed 3 times with saturated brine, dried with anhydrous magnesium sulfate, and the organic phase was concentrated to obtain the target product as a white solid, the white solid was dried, weighed as 5.11 g, and the yield was 89.74%. $^1$H-NMR (400M, DMSO-d6): δ 15.13 (1H), 9.11 (t, 1H), 6.40 (d, J=12.6 Hz, 1H), 6.25 (d, J=12.6 Hz, 1H), 3.17 (q, 2H), 2.81 (s, 4H), 2.76 (t, 2H), 1.639 (m, 2H), 1.50 (m, 2H), 1.38 (m, 2H). MS m/z 325.4 ([M−H]$^-$); 327.5 ([M+H]$^+$).

3) Preparation of Mm-$C_6$-OSu:

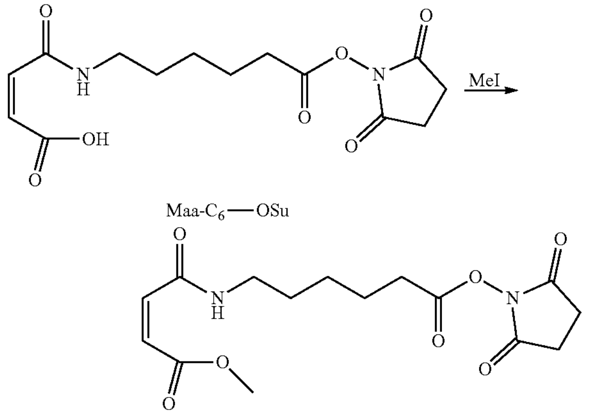

Maa-$C_6$—OSu

Mm-$C_6$—OSu

Maa-C6-OSu (1.50 g, 4.6 mM, 1 eq) was dissolved in DMF (25 mL), stirred to dissolve, anhydrous potassium carbonate (1.27 g, 9.2 mM, 2 eq) was added, then iodomethane (1.3 g, 9.2 mM, 2 eq) was added, and reacted at room temperature for 2 hours. After the reaction was completed, the insoluble substance was removed by filtration, the solvent was removed by concentration under reduced pressure, ethyl acetate was added to dissolve the residue, and then filtered, the filtrate was washed with saturated brine for 3 times, dried over anhydrous magnesium sulfate, concentrated under reduced pressure, re-dissolved in ethyl acetate and then mixed with silica gel, and purified by column chromatography to obtain the target product as a white solid, the white solid was dried, weighed as 1.1 g, and the yield was 66%. $^1$H-NMR (400M, $CDCl_3$): δ 8.21 (br, 1H), 6.35 (d, J=12.6 Hz, 1H), 6.13 (d, J=12.6 Hz, 1H), 3.80 (s, 3H), 3.35 (q, 2H), 2.84 (s, 4H), 2.63 (t, 2H), 1.80 (m, 2H), 1.63 (m, 2H), 1.49 (m, 2H). MS m/z 341.2 ([M+H]$^+$); 363.2 ([M+Na]$^+$).

Example 3: Synthesis of Linker Mm-$C_R$-OSu

1) Preparation of Maa-$C_R$—OH:

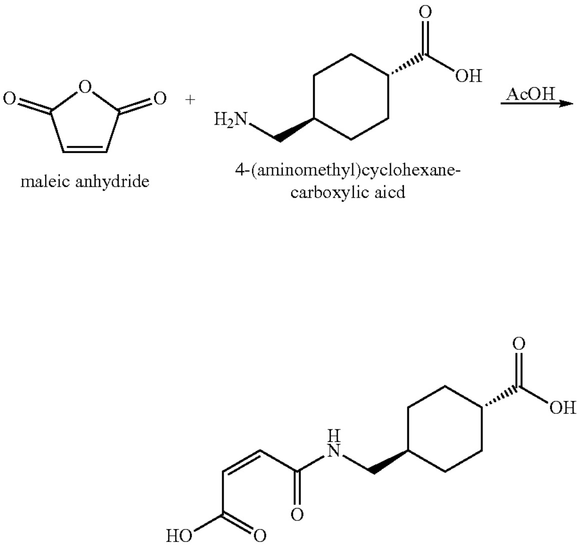

maleic anhydride 4-(aminomethyl)cyclohexane-carboxylic aicd

Maa-$C_R$—OH 4-(Aminomethyl)cyclohexane-1-carboxylic acid (2.0 g, 20.4 mM) was dissolved in acetic acid (100 mL), stirred to dissolve, maleic anhydride (3.2 g, 20.4 mM) was added, and stirred at room temperature, and the resulting reaction solution was clear and transparent, and stirred continuously to react for 1 hour at room temperature, white insoluble substance was precipitated out, and the reaction was continued for 10 hours. The reaction solution was filtered, the filter cake was washed with acetonitrile to obtain a white powdery solid, the white powdery solid was weighed as 2.91 g, and the yield was 56%. $^1$H-NMR (400M, DMSO-d6): δ 14.92 (br, 1H), 12.13 (br, 1H), 9.08 (t, 1H), 6.42 (d, J=12.6 Hz, 1H), 6.23 (d, J=12.6 Hz, 1H), 3.03 (t, 2H), 2.13 (tt, 1H), 1.90 (dd, 2H), 1.74 (dd, 2H), 1.43 (m, 1H), 1.26 (qd, 2H), 0.94 (qd, 2H). MS m/z 254.3 ([M−H]$^-$).

2) Preparation of Maa-$C_R$-OSu:

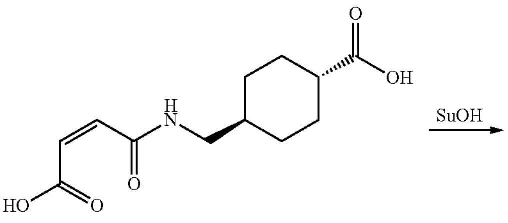

Maa-$C_R$—OH

-continued

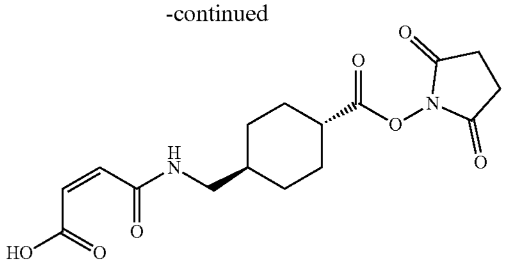

Maa-$C_R$—OSu

Maa-$C_R$—OH (0.64 g, 2.5 mM) was dissolved in DMF (15 mL), after the dissolution was completed, N-hydroxysuccinimide (0.58 g, 5.0 mM) was added, stirred to dissolve, placed in a −5° C. cold trap to cool down, 2,4,6-trimethylpyridine (1.3 mL, 10 mM) was added and continuously stirred for 10 minutes, and trifluoroacetic anhydride (1.40 mL, 10 mM) was slowly added dropwise. After the reaction was completed, the reaction solution was dropped into 1 mol/L HCl, 0.69 g of white fine powdery solid was precipitated out, and the yield was 78%. $^1$H-NMR (400M, DMSO-d6): δ 14.99 (br, 1H), 9.09 (t, 1H), 6.42 (d, J=12.6 Hz, 1H), 6.23 (d, J=12.6 Hz, 1H), 3.06 (t, 2H), 2.80 (s, 4H), 2.69 (tt, 1H), 2.02 (dd, 2H), 1.79 (dd, 2H), 1.43 (m, 1H), 1.50 (m, 1H), 1.42 (qd, 2H), 1.03 (qd, 2H).

3) Preparation of Mm-$C_R$-OSu:

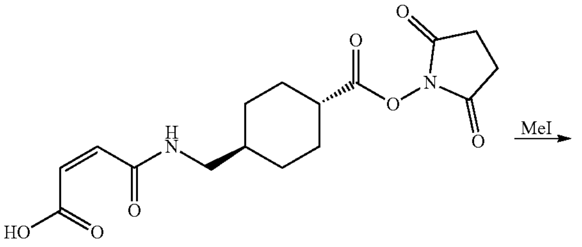

Maa-$C_R$—OSu

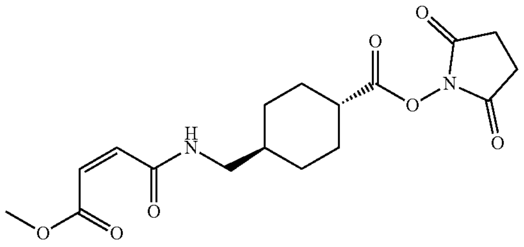

Maa-$C_R$—OSu

Maa-$C_R$-OSu (1.62 g, 4.6 mM) was dissolved in DMF (15 mL), stirred to dissolve, anhydrous potassium carbonate (1.27 g, 9.2 mM, 2 eq) was added, then iodomethane (1.3 g, 9.2 mM, 2 eq) was added dropwise, reacted at room temperature for 2 hours. After the reaction was completed, the insoluble substance was removed by filtration, the solvent was removed by concentration under reduced pressure, ethyl acetate was added to dissolve the residue, and then filtered, the filtrate was washed with saturated brine for 3 times, dried over anhydrous magnesium sulfate, concentrated under reduced pressure, re-dissolved in ethyl acetate and mixed with silica gel, and purified by column chromatography to obtain the target product as a white solid, the white solid was dried, weighed as 0.91 g, and the yield was 54%. $^1$H-NMR (400M, DMSO-d6): δ 9.09 (t, 1H), 6.40 (d, J=12.6 Hz, 1H), 6.18 (d, J=12.6 Hz, 1H), 3.81 (s, 3H), 3.06 (t, 2H), 2.80 (s, 4H), 2.69 (tt, 1H), 2.02 (dd, 2H), 1.79 (dd, 2H), 1.43 (m, 1H), 1.50 (m, 1H), 1.42 (qd, 2H), 1.03 (qd, 2H).

The structures of the linkers containing methyl maleate as prepared in Examples 1 to 3 are shown in the following table:

| Linker code | Linker structure |
|---|---|
| Mm-$C_3$-OSu | 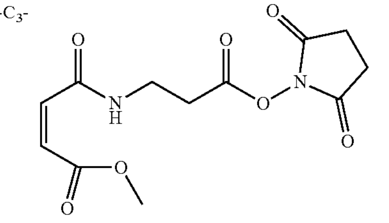 |
| Mm-$C_6$-OSu | 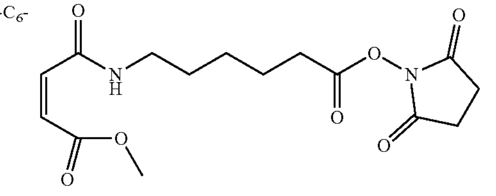 |
| Mm-$C_R$-OSu | 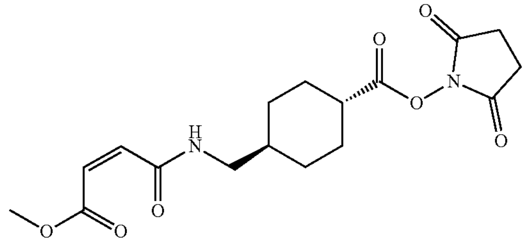 [SMILES: COC(=O)/C=C\C(=O)NC[C@H]1CC[C@H](C(=O)ON2C(=O)CCC2=O)CC1] |

Example 4: Synthesis of Linker Mm-$C_3$-Val-Ala-PAB-PNP

1) Preparation of Fmoc-Val-Ala:

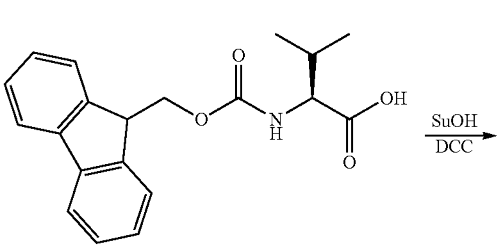

Fmoc-Val

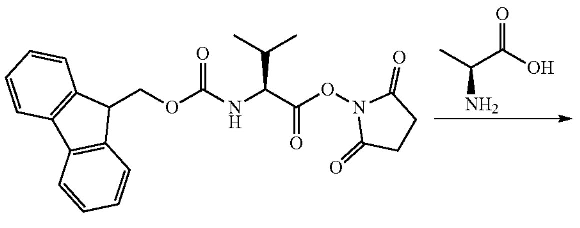

Fmoc-Val-OSu

-continued

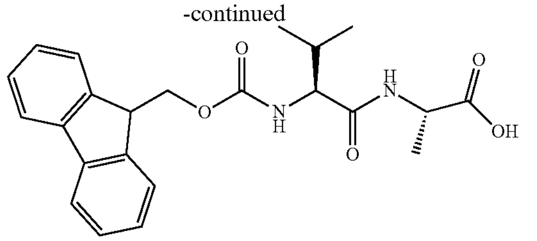

Fmoc-Val-Ala

Fmoc-Val (25.0 g, 74.0 mM), SuOH (NHS, 8.52 g, 74.0 mM) and dicyclohexyl-carbodiimide (DCC, 15.27 g, 74.0 mM) in THF solution (250 mL) were stirred at room temperature for 16 hours. The reaction mixture was cooled to 0° C. and stirred for 2 hours, and then filtered to remove insoluble solid by-product dicyclohexylurea (DCU), the filtrate was collected, the filter cake was further washed with THF, the washing liquid and the filtrate were combined, and concentrated under reduced pressure to obtain a crude product as a glassy solid, which was used directly in the next step without further purification.

The glassy solid was re-dissolved in a mixture of DME (200 mL) and THF (100 mL), and then L-alanine (6.95 g, 78 mM) in aqueous solution of sodium bicarbonate was added. The resulting reaction mixture was stirred at room temperature for 16 hours, poured into 15% citric acid in aqueous solution (400 mL), filtered, and the filter cake was dried under reduced pressure to obtain a crude product. The crude product was dispersed in diethyl ether, and purified 3 times by ultrasound and filtration to obtain a white solid (16.2 g, 53% yield). $^{1}$H-NMR (400 MHz, DMSO-d6): δ 12.48 (s, 1H), 8.25 (d, J=6.7 Hz, 1H), 7.89 (d, J=7.6 Hz, 2H), 7.74 (t, 2H), 7.43 (m, 3H), 7.33 (m, 2H), 4.22 (m, 4H), 3.89 (q, 1H), 1.96 (m, 1H), 1.27 (d, 3H), 0.88 (dd, 6H). MS(ESI) m/z: 411.3 $[M+H]^+$; 433.4 $[M+Na]^+$.

2) Preparation of Fmoc-Val-Ala-PAB:

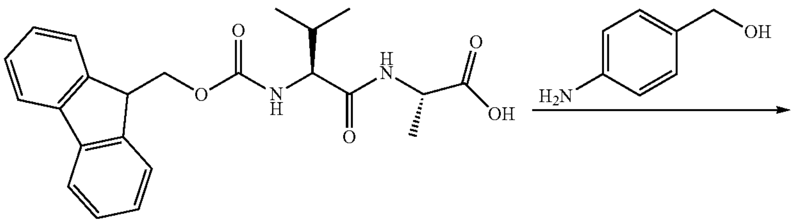

Fmoc-Val-Ala

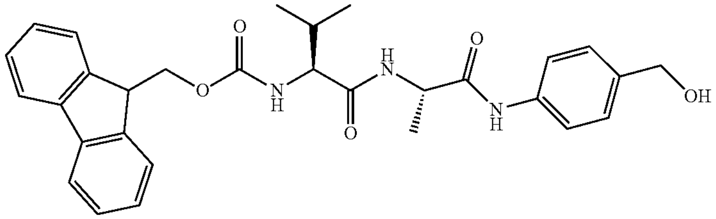

Fmoc-Val-Ala-PAB

Fmoc-Val-Ala (2 g, 4.87 mM) and 4-aminobenzyl alcohol (1.2 g, 9.75 mM) were dissolved in a dichloromethane/methanol mixed solvent (100 mL, the volume ratio of dichloromethane/methanol was 2:1), then 2-ethoxy-1-ethoxycarbonyl-1,2-dihydroquinoline (EEDQ, 2.41 g, 9.75 mM) was added, and the resulting mixed solution was placed in the dark at room temperature and stirred for 12 hours. The solvent was distilled off under reduced pressure to obtain a white solid residue, which was added to diethyl ether (300 mL), the resultant suspension was treated with ultrasonic for 5 minutes, then stood for 30 minutes, and then was filtered, the filter cake was washed with diethyl ether to obtain a white solid (1.92 g, 77% yield). $^{1}$H-NMR (400 MHz, DMSO-d6) δ 9.96 (s, 1H), 8.22 (d, J=6.7 Hz, 1H), 7.89 (d, J=7.6 Hz, 2H), 7.75 (t, 2H), 7.52 (q, 3H), 7.41 (t, 2H), 7.34 (t, 2H), 7.24 (t, 2H), 5.13 (t, J=5.6 Hz, 1H), 4.42 (d, J=5.6 Hz, 2H), 4.40 (br, 1H), 4.30 (t, 1H), 4.22 (q, 2H), 3.91 (t, J=8.4 Hz, 1H), 2.00 (m, 1H), 1.30 (d, J=7.0 Hz, 3H), 0.88 (dd, 6H). MS(ESI) m/z: 516.4 $[M+H]^+$; 538.3 $[M+Na]^+$.

3) Preparation of Val-Ala-PAB:

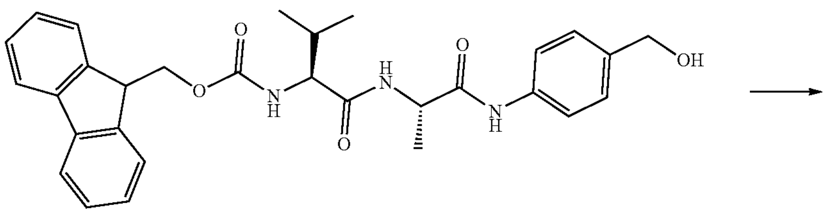

Fmoc-Val-Ala-PAB

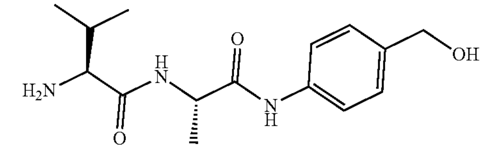

Val-Ala-PAB

Fmoc-Val-Ala-PAB (4.0 g, 7.76 mM) was dissolved in DMF (40 mL), and piperidine (2 mL) was added after the dissolution was completed. The resulting mixture was stirred at room temperature for 2 hours, the solvent was distilled off under reduced pressure to obtain a crude product, which was purified by silica gel column chromatography (DCM/MeOH (v/v)=20:1) to obtain a white solid (2.1 g, 90% yield). $^1$H-NMR (400 MHz, DMSO-d6): δ 10.0 (s, 1H), 8.18 (s, 1H), 7.53 (d, 2H), 7.24 (d, 2H), 5.13 (s, 1H), 4.48 (t, 1H), 4.43 (s, 1H), 3.00 (d, 1H), 2.80 (d, 1H), 1.92 (m, 1H), 1.29 (d, J=7.0 Hz, 3H), 0.85 (dd, 6H). MS(ESI) m/z: 294.2 $[M+H]^+$; 316.2 $[M+Na]^+$.

Preparation of Mm-$C_3$-Val-Ala-PAB:

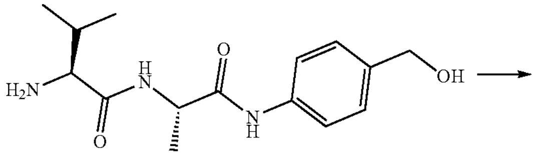

Val-Ala-PAB

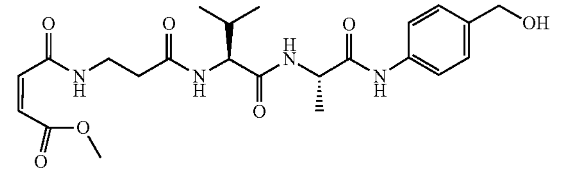

Mm-$C_3$-Val-Ala-PAB

The crude product of Mm-$C_3$-OSu (0.6 g, 2.0 mM) was dissolved in anhydrous DMF (20 mL), after the dissolution was completed, Val-Ala-PAB (0.59 g, 2.0 mM) was added, reacted under stirring overnight at room temperature. After the reaction was completed, DMF was removed by concentration under reduced pressure to obtain a crude product, which was further purified by column chromatography to obtain a white powdery solid (0.59 g, 62% yield). $^1$H-NMR (400 MHz, DMSO-d6)δ 9.85 (s, 1H), 8.24 (t, J=5.7 Hz, 1H), 8.19 (d, J=7.3 Hz, 2H), 7.96 (d, J=8.4 Hz, 2H), 7.54 (d, J=8.4 Hz, 2H), 7.23 (d, J=8.4 Hz, 2H), 6.27 (d, J=12.6 Hz, 1H), 6.23 (d, J=12.6 Hz, 1H), 5.11 (t, J=5.7 Hz, 1H), 4.42 (d, J=5.6 Hz, 2H), 4.39 (t, J=7.0 Hz, 1H), 4.19 (t, J=7.6 Hz, 1H), 3.64 (s, 3H), 3.27 (q, J=5.9 Hz, 2H), 2.38 (t, J=7.0 Hz, 2H), 1.97 (m, J=6.8 Hz, 1H), 1.30 (d, J=7.0 Hz, 3H), 0.85 (dd, $J_1$=15.7 Hz, $J_2$=6.8 Hz, 6H). MS(ESI) m/z: 477.24 $[M+H]^+$; 499.22 $[M+Na]^+$; 975.45 $[2M+Na]^+$.

Preparation of Mm-$C_3$-Val-Ala-PAB-PNP:

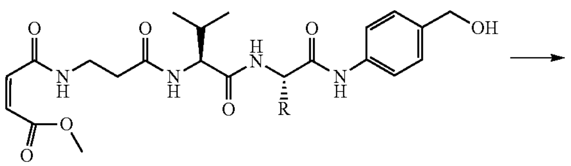

Mm-$C_3$-Val-Ala-PAB

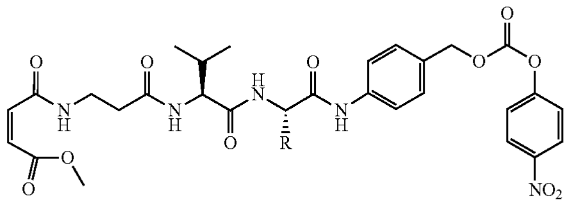

Mm-$C_3$-Val-Ala-PAB-PNP

Mm-$C_3$-Val-Ala-PAB was dissolved in anhydrous DMF (15 mL), after the dissolution was completed, bis(p-nitrophenyl) carbonate (360 mg, 1.2 mM) and DIPEA (104 mg, 0.9 mM) was added in sequence, and reacted under stirring at room temperature for 12 hours. After the reaction was completed, the solvent was removed by concentration under reduced pressure, and the residue was dispersed and slurried in diethyl ether and then filtrated to obtain a crude product, which was further purified by column chromatography to obtain the target product as a white solid powder (55% yield). $^1$H-NMR (400 MHz, DMSO-d6) δ 10.01 (s, 1H), 8.31 (d, J=9.2 Hz, 2H), 8.24 (m, 1H), 7.97 (d, J=8.4 Hz, 1H), 7.64 (d, J=8.7 Hz, 2H), 7.57 (d, J=9.3 Hz, 2H), 7.41 (d, J=8.7 Hz, 2H), 6.27 (d, J=12.6 Hz, 1H), 6.23 (d, J=12.6 Hz, 1H), 5.24 (s, 2H), 4.39 (m, 1H), 4.19 (t, J=15.1 Hz, 1H), 3.64 (s, 3H), 3.28 (q, J=7.0 Hz, 2H), 2.39 (t, J=7.2 Hz, 2H), 1.96 (m, 1H), 1.31 (d, J=7.0 Hz, 3H), 0.86 (dd, J=6.7 Hz, 6H). MS (ESI) m/z: 642.4 $[M+H]^+$; 664.5 $[M+Na]^+$; 680.4 $[M+K]^+$.

Example 5: Synthesis of Linker Mm-$C_6$-Val-Ala-PAB-PNP

1) Preparation of Mm-$C_6$-Val-Ala-PAB:

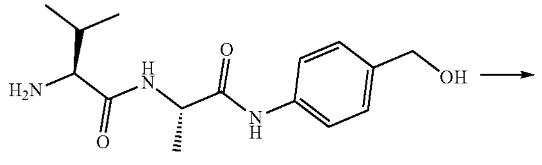

Val-Ala-PAB

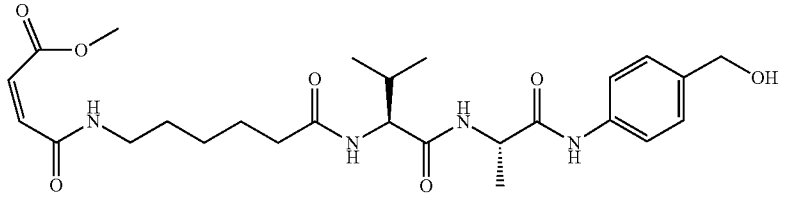

Mm-$C_6$-Val-Ala-PAB

Mm-$C_6$-OSu was used as raw material, and Mm-$C_6$-Val-Ala-PAB was synthesized by using a method similar to that of Mm-$C_3$-Val-Ala-PAB to obtain a pale yellow solid powder (60% yield). $^1$H-NMR (400 MHz, DMSO-d6)δ 9.99 (s, 1H), 8.12 (d, J=6.7 Hz, 1H), 7.89 (d, J=6.7 Hz, 2H), 7.74 (t, 2H), 7.54 (d, 2H), 7.46 (d, 1H), 7.41 (m, 2H), 7.32 (m, 2H), 7.23 (d, 2H), 5.98 (t, J=5.5 Hz, 1H), 5.42 (s, 2H), 5.12 (t, 1H), 4.41 (q, 3H), 4.30 (q, 1H), 4.23 (q, 2H), 3.92 (q, 1H), 3.00 (m, 2H), 1.98 (m, 1H), 1.69 (m, 1H), 1.57 (m, 1H), 1.41 (m, 2H), 0.86 (dd, 6H). MS(ESI) m/z: 602.7 $[M+H]^+$; 624.5 $[M+Na]^+$.

Preparation of Mm-$C_6$-Val-Ala-PAB-PNP:

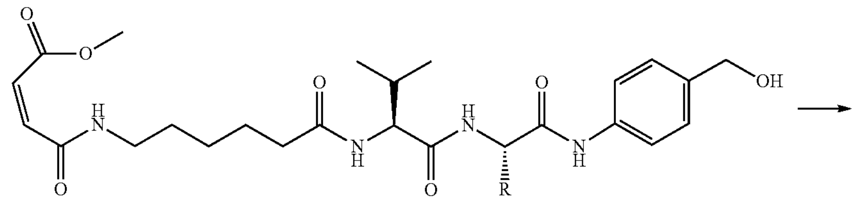

Mm-$C_6$-Val-Ala-PAB

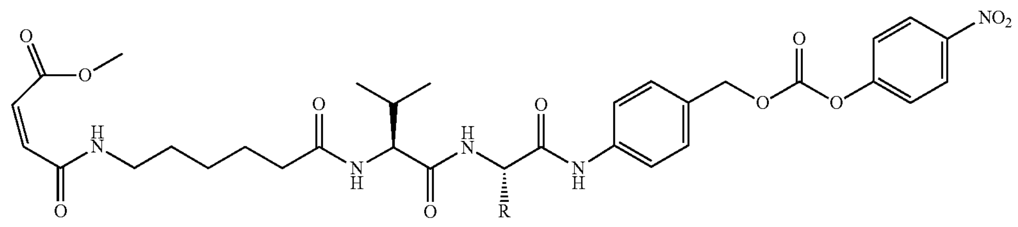

Mm-$C_6$-Val-Ala-PAB-PNP

Intermediate Mm-$C_6$-Val-Ala-PAB was used as raw material, Mm-$C_6$-Val-Ala-PAB-PNP was synthesized by using a preparation method similar to that of Mm-$C_3$-Val-Ala-PAB-PNP to obtain a pale yellow solid powder (86% yield). $^1$H-NMR (400 MHz, DMSO-d6)δ 10.03 (s, 1H), 8.31 (d, J=9.3 Hz, 2H), 8.20 (m, 1H), 7.84 (d, J=6.7 Hz, 1H), 7.64 (d, J=8.4 Hz, 2H), 7.57 (d, J=9.0 Hz, 2H), 7.41 (d, J=8.4 Hz, 2H), 6.28 (d, J=12.6 Hz, 1H), 6.23 (d, J=12.6 Hz, 1H), 5.24 (s, 2H), 4.38 (t, J=7.0 Hz, 1H), 4.18 (t, J=7.6 Hz, 1H), 3.62 (s, 3H), 3.05 (q, J=6.3 Hz, 2H), 2.15 (m, 2H), 1.96 (m, 1H), 1.49 (m, 2H), 1.40 (m, 2H), 1.31 (d, J=7.0 Hz, 3H), 1.25 (m, 2H), 0.86 (m, 6H). MS(ESI) m/z: 684.30 $[M+H]^+$; 706.28 $[M+Na]^+$.

Example 6: Synthesis of Linker Mm-$C_6$-Val-Cit-PAB-PNP

1) Preparation of Fmoc-Val-Cit:

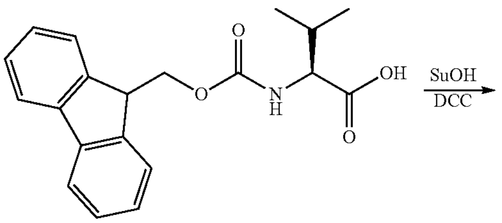

Fmoc-Val

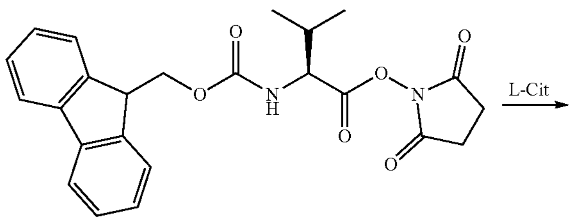

Fmoc-Val-OSu

-continued

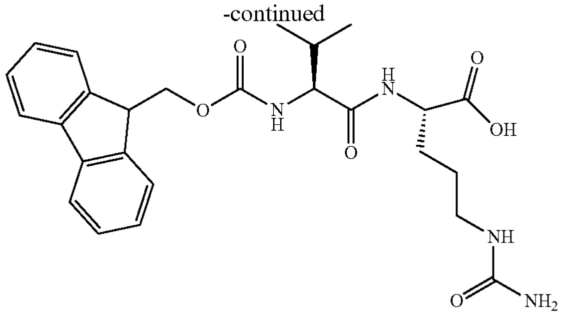

Fmoc-Val-Cit

Fmoc-Val-Cit was synthesized by using a preparation method similar to that of Fmoc-Val-Ala, and a pale yellow solid (70% yield) was obtained. $^1$H-NMR (400 MHz, DMSO-d6)δ 12.61 (s, 1H), 8.21 (d, J=6.7 Hz, 1H), 7.89 (d, J=6.7 Hz, 2H), 7.76 (t, 2H), 7.43 (q, 3H), 7.33 (t, 2H), 5.98 (t, J=5.2 Hz, 1H), 5.43 (s, 2H), 4.25 (m, 3H), 4.16 (q, 1H), 3.94 (t, 1H), 2.96 (q, 2H), 1.98 (m, 1H), 1.72 (m, 1H), 1.58 (m, 1H), 1.42 (m, 2H), 0.89 (dd, 6H). MS(ESI) m/z: 497.6 $[M+H]^+$; 519.6$[M+Na]^+$.

2) Preparation of Fmoc-Val-Cit-PAB:

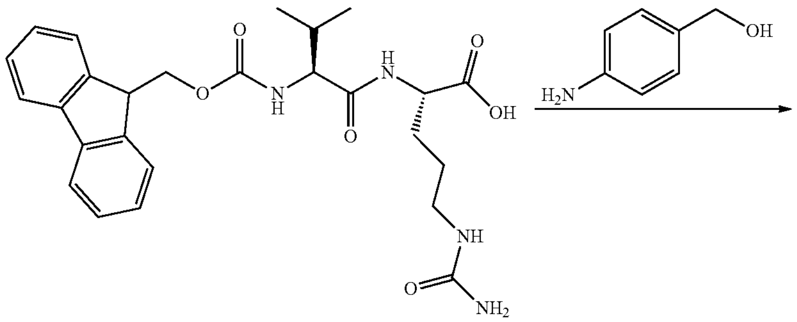

Fmoc-Val-Cit

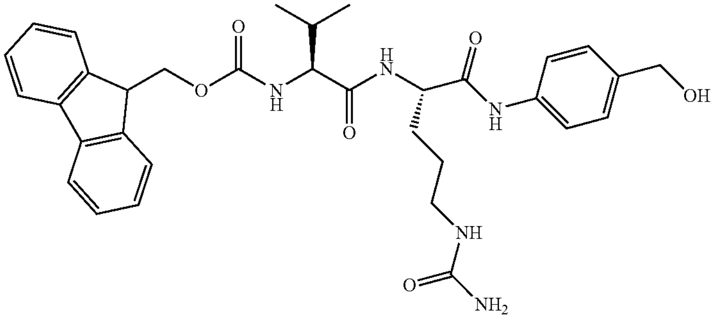

Fmoc-Val-Cit-PAB

Fmoc-Val-Cit was used as raw material, Fmoc-Val-Cit-PAB was synthesized by a preparation method similar to that of Fmoc-Val-Ala-PAB, and a pale yellow solid powder (60% yield) was obtained. $^1$H-NMR (400 MHz, DMSO-d6): δ 9.99 (s, 1H), 8.12 (d, J=6.7 Hz, 1H), 7.89 (d, J=6.7 Hz, 2H), 7.74 (t, 2H), 7.54 (d, 2H), 7.46 (d, 1H), 7.41 (m, 2H), 7.32 (m, 2H), 7.23 (d, 2H), 5.98 (t, J=5.5 Hz, 1H), 5.42 (s, 2H), 5.12 (t, 1H), 4.41 (q, 3H), 4.30 (q, 1H), 4.23 (q, 2H), 3.92 (q, 1H), 3.00 (m, 2H), 1.98 (m, 1H), 1.69 (m, 1H), 1.57 (m, 1H), 1.41 (m, 2H), 0.86 (dd, 6H). MS(ESI) m/z: 602.7 $[M+H]^+$; 624.5 $[M+Na]^+$.

3) Preparation of Val-Cit-PAB:
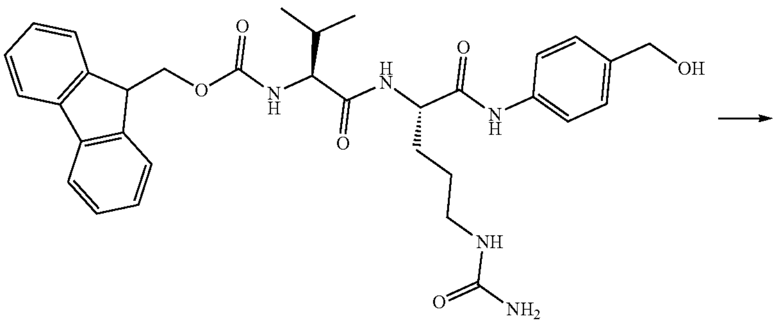
Fmoc-Val-Cit-PAB
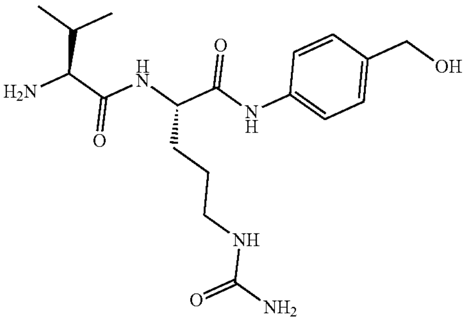
Val-Cit-PAB
Fmoc-Val-Cit-PAB was use as a raw material, Val-Cit-PAB was prepare using a preparation method similar to that of Val-Ala-PAB to obtain a pale yellow solid powder (84% yield). $^1$H-NMR (400 MHz, DMSO-d6)δ10.07 (s, 1H), 8.17 (br, 1H), 7.54 (d, 2H), 7.23 (d, 2H), 6.01 (br, 1H), 5.44 (d, 2H), 5.13 (br, 1H), 4.47 (s, 1H), 4.43 (s, 2H), 3.05 (d, 1H), 2.95 (m, 2H), 1.94 (m, 1H), 1.64 (m, 2H), 1.38 (m, 2H), 0.86 (dd, 6H). MS(ESI) m/z: 380.3 $[M+H]^+$; 402.3 $[M+Na]^+$.
4) Preparation of Mm-$C_6$-Val-Cit-PAB:
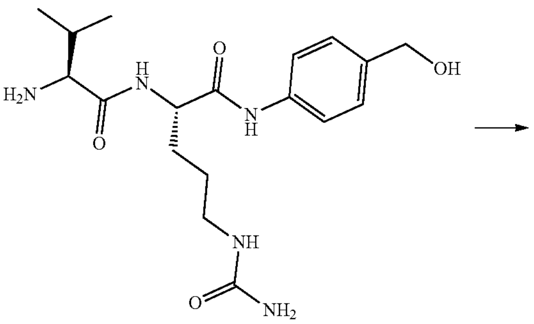
Val-Cit-PAB -continued

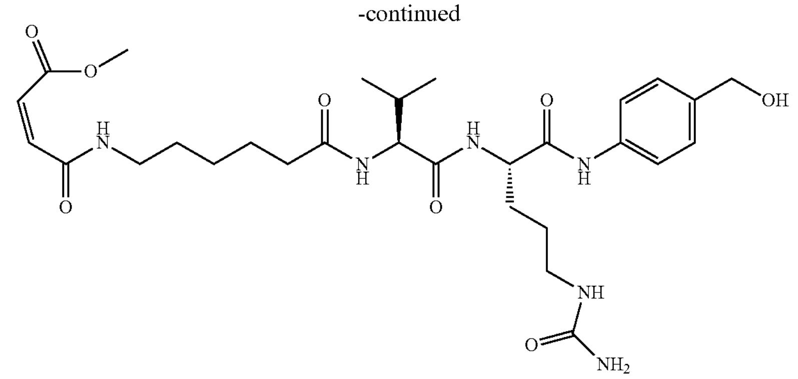

Mm-C6-Val-Cit-PAB

Mm-$C_6$-OSu (1.0 g, 2.94 mM) was dissolved in anhydrous DMF (30 mL), after the dissolution was completed, Val-Cit-PAB (1.11 g, 2.94 mM) was added, and reacted under stirring overnight at room temperature. After the reaction was completed, DMF was removed by concentration under reduced pressure to obtain a crude product as a yellow viscous substance, which was further purified by column chromatography to obtain a pale yellow powdery solid (1.19 g, 41% yield). $^1$H-NMR (400 MHz, DMSO-d6): δ 9.92 (s, 1H), 8.20 (t, 1H), 8.09 (d, 1H), 7.85 (d, 1H), 7.54 (d, 2H), 7.22 (d, 2H), 6.27 (d, J=12.6 Hz, 1H), 6.23 (d, J=12.6 Hz, 1H), 5.99 (br, 1H), 5.43 (s, 2H), 5.11 (t, 1H), 4.42 (d, 2H), 4.37 (m, 1H), 4.19 (t, 1H), 3.63 (s, 3H), 3.05 (q, 2H), 2.95 (m, 2H), 2.17 (m, 2H), 1.95 (m, 1H), 1.74-1.55 (m, 2H), 1.51-1.48 (m, 2H), 1.45-1.37 (m, 4H), 1.24 (m, 2H), 0.85 (dd, 6H). MS(ESI) m/z: 605.7 $[M+H]^+$; 627.7 $[M+Na]^+$.

5) Preparation of Mm-$C_6$-Val-Cit-PAB-PNP:

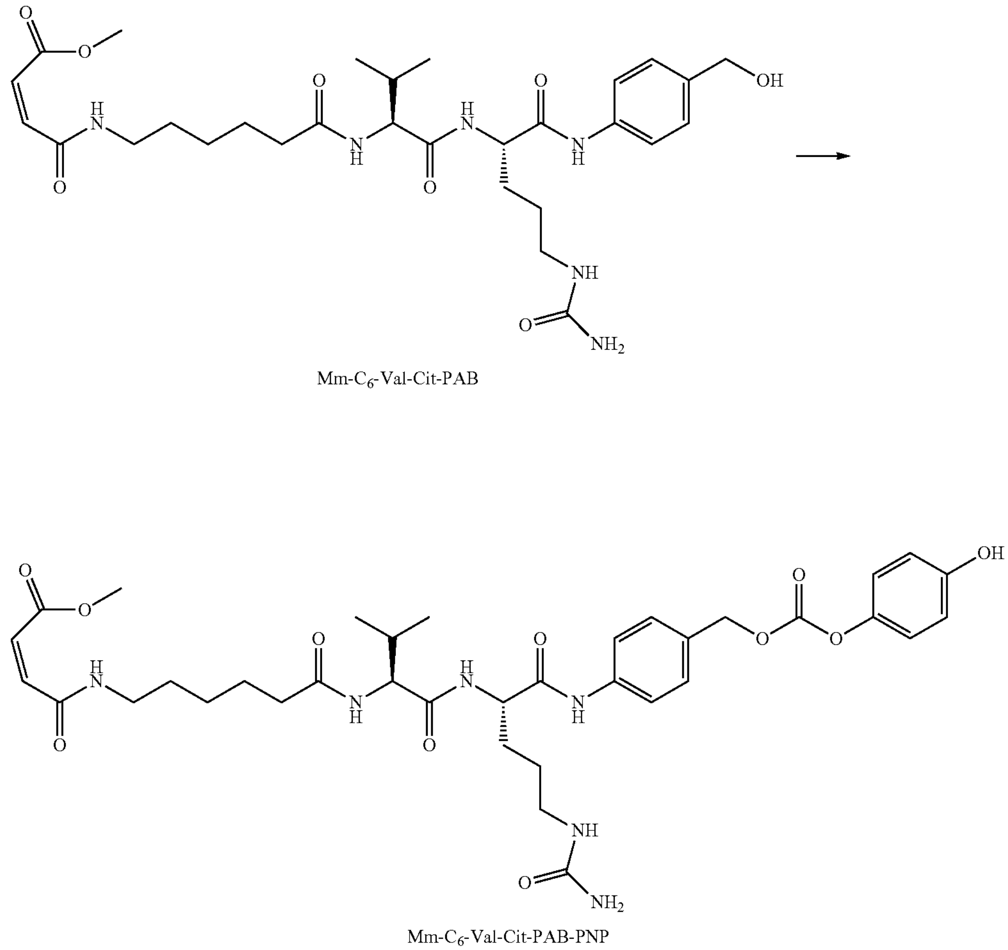

Mm-C6-Val-Cit-PAB

Mm-C6-Val-Cit-PAB-PNP

Intermediate Mm-$C_6$-Val-Cit-PAB was used as raw material, Mm-$C_6$-Val-Cit-PAB-PNP was synthesized using a preparation method similar to that of Mm-$C_6$-Val-Ala-PAB-PNP to obtain a pale yellow solid powder (85% yield). $^1$H-NMR (400 MHz, DMSO-d6): δ 10.08 (s, 1H), 8.31 (d, J=9.0 Hz, 2H), 8.20 (t, J=5.2 Hz, 1H), 8.13 (d, J=7.3 Hz, 2H), 7.83 (d, J=8.4 Hz, 1H), 7.65 (d, J=8.4 Hz, 2H), 7.57 (d, J=9.24 Hz, 2H), 7.41 (d, J=8.4 Hz, 2H), 6.28 (d, J=12.6 Hz, 1H), 6.23 (d, J=12.6 Hz, 1H), 5.99 (s, 1H), 5.43 (s, 2H), 5.24 (s, 2H), 4.38 (t, J=6.8 Hz, 1H), 4.19 (t, J=7.6 Hz, 1H), 3.63 (s, 3H), 3.08-2.92 (m, 4H), 2.17 (m, 2H), 1.71 (m, 1H), 1.60 (m, 2H), 1.52-1.37 (m, 6H), 1.25 (q, 2H), 0.85 (dd, 6H). MS(ESI) m/z: 770.7 [M+H]$^+$; 792.6 [M+Na]$^+$.

The structures of the linkers containing methyl maleate prepared in Examples 4 to 6 were shown in the following table:

| Linker code | Linker structure |
|---|---|
| Mm-$C_3$-Val-Ala-PAB-PNP | 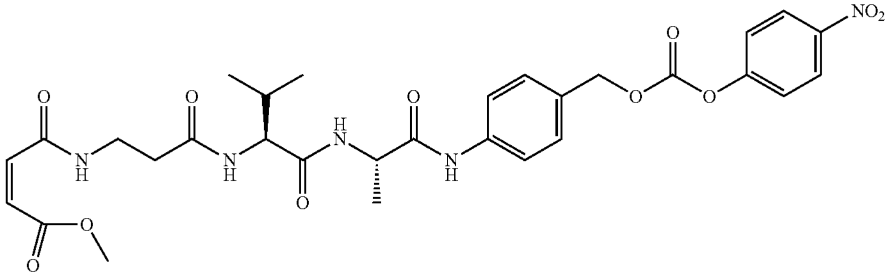 [SMILES: COC(=O)/C=C\C(=O)NCCC(=O)N[C@H](C(=O)N[C@@H](C)C(=O)Nc1ccc(COC(=O)Oc2ccc([N+](=O)[O-])cc2)cc1)C(C)C] |
| Mm-$C_6$-Val-Ala-PAB-PNP | 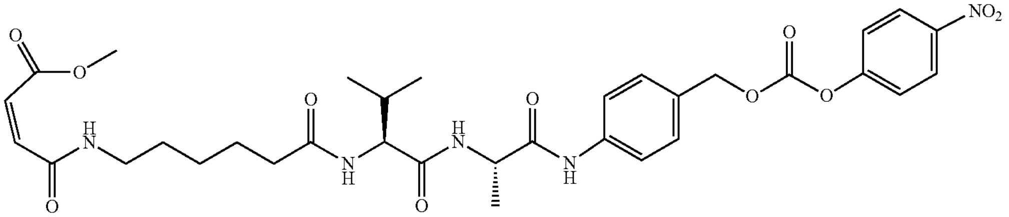 [SMILES: COC(=O)/C=C\C(=O)NCCCCCC(=O)N[C@H](C(=O)N[C@@H](C)C(=O)Nc1ccc(COC(=O)Oc2ccc([N+](=O)[O-])cc2)cc1)C(C)C] |
| Mm-$C_6$-Val-Cit-PAB-PNP | 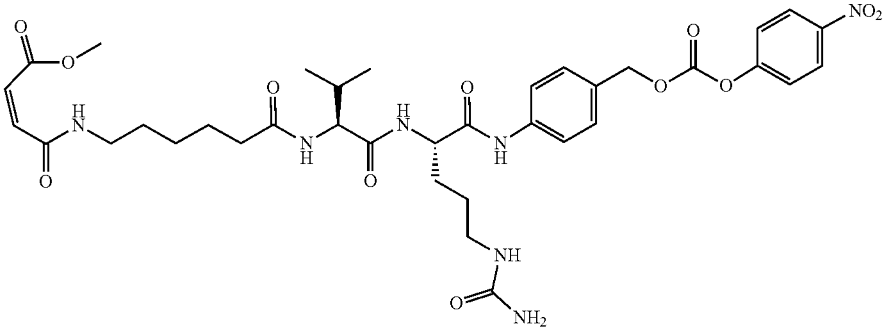 [SMILES: COC(=O)/C=C\C(=O)NCCCCCC(=O)N[C@H](C(=O)N[C@@H](CCCNC(N)=O)C(=O)Nc1ccc(COC(=O)Oc2ccc([N+](=O)[O-])cc2)cc1)C(C)C] |

Example 7-1: Synthesis of Linker-Cytotoxin Conjugate (1)

1) Preparation of Mm-$C_3$-Val-Ala-PAB-MMAE:

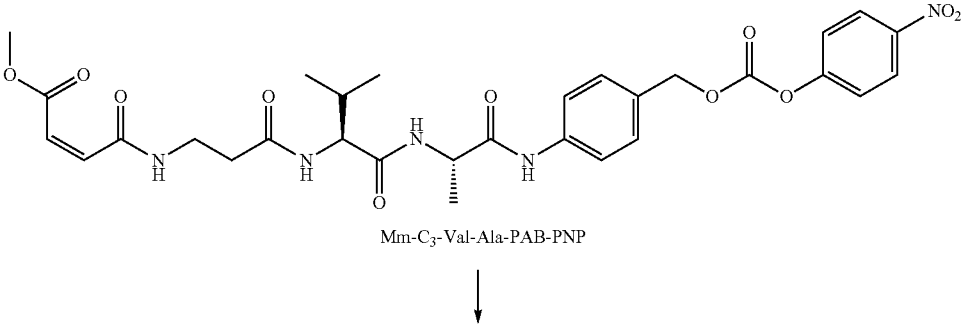

Mm-$C_3$-Val-Ala-PAB-PNP

-continued

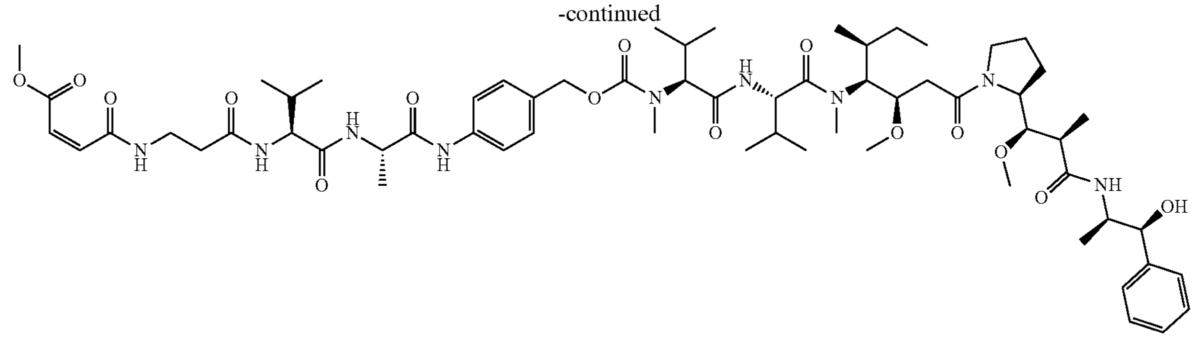

Mm-$C_3$-Val-Ala-PAB-MMAE

The linker Mm-$C_3$-Val-Ala-PAB-PNP was used as raw material, and dissolved in anhydrous DMF (3 mL), after the dissolution was completed, then HOBt (8.28 mg, 0.06 mM), MMAE (40 mg, 0.06 mM) and DIPEA (10.68 μL) were added, reacted under stirring at room temperature for 18 hours. After the reaction was completed, the solvent was removed by concentration under reduced pressure, and the residue was further purified by column chromatography to obtain the target product as a white solid powder (69% yield). MS(ESI) m/z: 1220.72 $[M+H]^+$; 610.87 $[M+2H]2^+$.

2) Preparation of Mm-$C_6$-Val-Ala-PAB-MMAE:

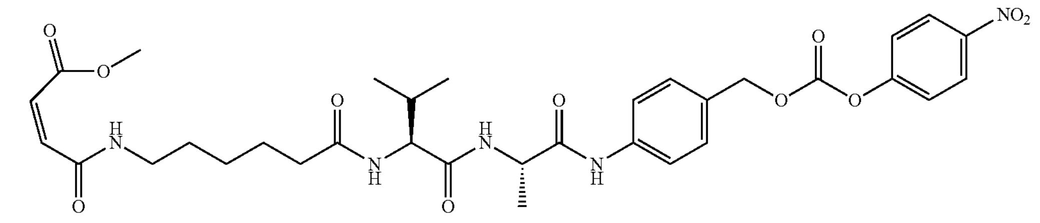

Mm-$C_6$-Val-Ala-PAB-PNP

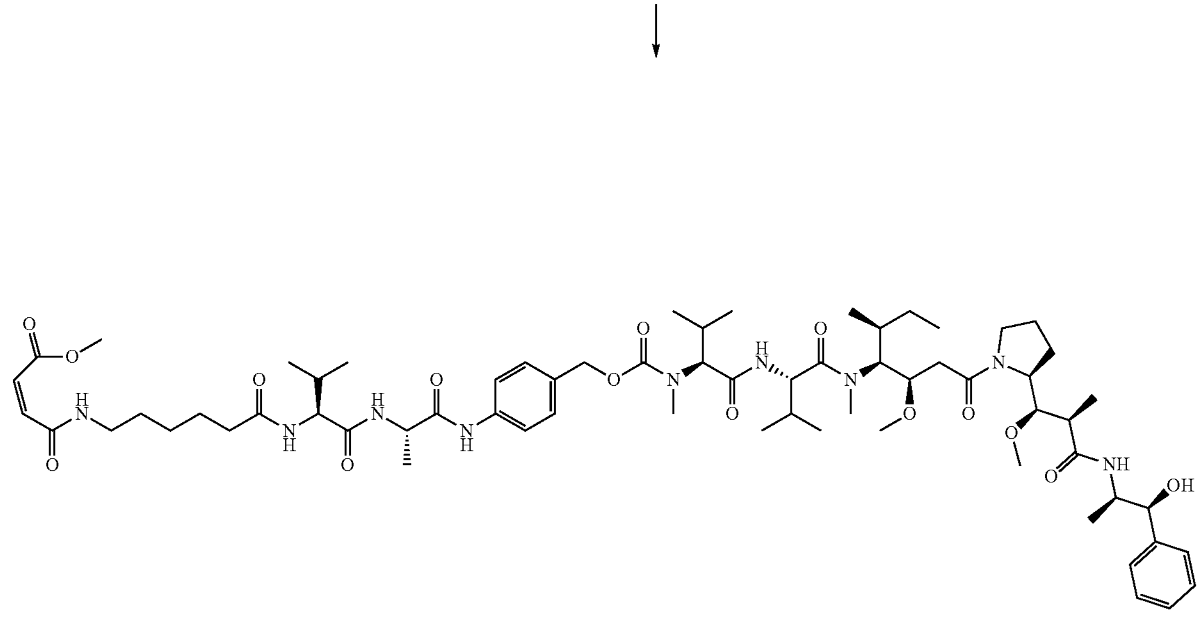

Mm-$C_6$-Val-Ala-PAB-MMAE

The linker Mm-$C_6$-Val-Ala-PAB-PNP was used as raw material, Mm-$C_6$-Val-Ala-PAB-MMAE was synthesized by using a preparation method similar to that of Mm-$C_3$-Val-Ala-PAB-MMAE to obtain a white solid Powder (75% yield). MS(ESI) m/z: 1284.75 $[M+H]^+$; 642.88 $[M+2H]^{2+}$.

3) Preparation of Mm-$C_6$-Val-Cit-PAB-MMAE:

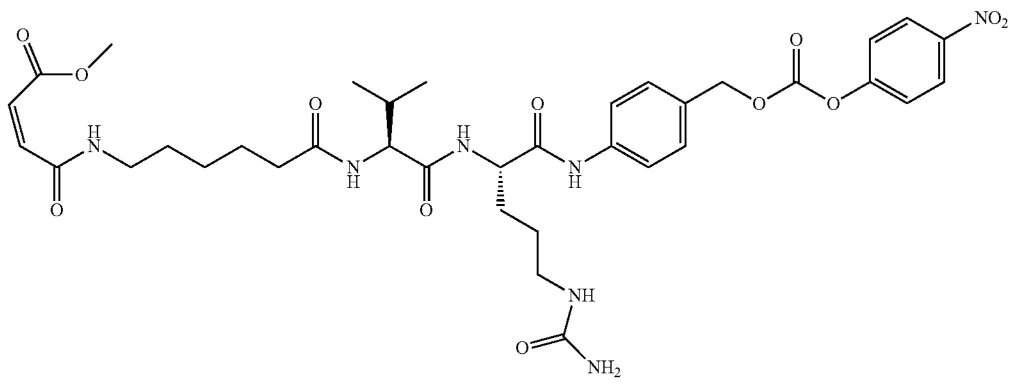

Mm-$C_6$-Val-Cit-PAB-PNP

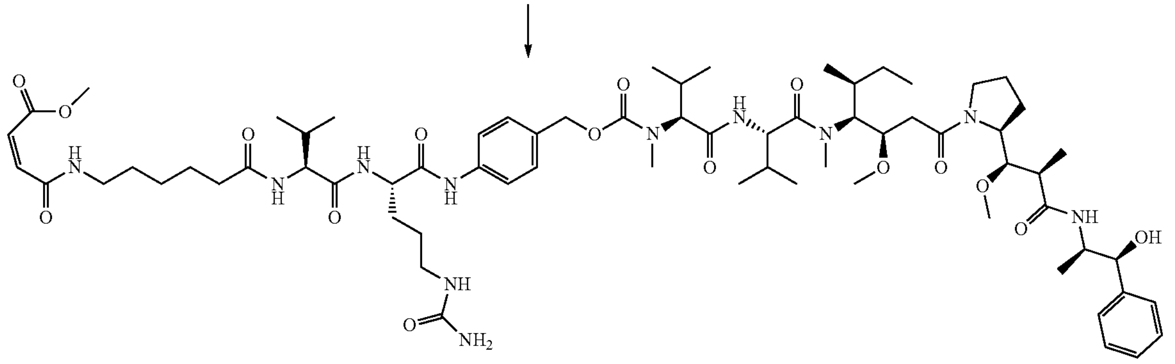

Mm-$C_6$-Val-Cit-PAB-MMAE

The linker Mm-$C_6$-Val-Cit-PAB-PNP was used as raw material, Mm-$C_6$-Val-Cit-PAB-MMAE was synthesized by using a preparation method similar to that of Mm-$C_3$-Val-Ala-PAB-MMAE to obtain a white solid Powder (68% yield). MS(ESI) m/z: 1349.6 $[M+H]^+$; 1371.3 $[M+Na]^+$; 675.6 $[M+2H]^{2+}$.

4) Preparation of Mm-$C_6$-PEG4-Val-Ala-PAB-MMAE 4.1) Preparation of Mm-$C_6$-PEG4-Val-Ala-PAB

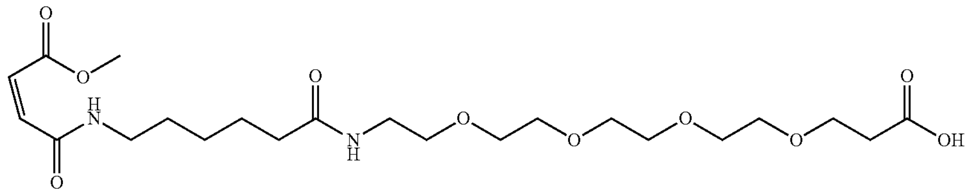

Mm-$C_6$-PEG4

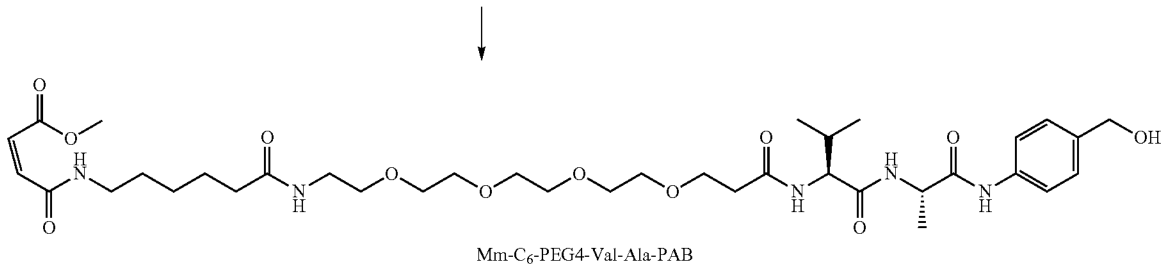

Mm-$C_6$-PEG4-Val-Ala-PAB

Mm-$C_6$-PEG4 (200 mg, 0.34 mM) was dissolved in anhydrous DMF (15 mL), after the dissolution was completed, Val-Ala-PAB (110 mg, 0.37 mM) was added, and then HoBt (69 mg, 0.51 mM) and DIPEA (65 mg, 0.51 mM) were added, reacted under stirring overnight at room temperature. After the reaction was completed, DMF was removed by concentration under reduced pressure to obtain a crude product as a pale yellow solid material, which was further purified by column chromatography to obtain a transparent colorless glassy solid (137 mg, 53% yield). MS(ESI) m/z: 766.4229$[M+H]^+$; 788.4050 $[M+Na]^+$. $^1$H-NMR (400 MHz, DMSO-d6): δ 9.86 (s, 1H), 8.19 (m, 2H), 7.92 (d, 1H), 7.85 (t, 1H), 7.55 (d, 2H), 7.24 (d, 2H), 6.26 (dd, 2H), 5.13 (t, 1H), 4.43 (d, 2H), 4.38 (m, 1H), 4.27 (m, 1H), 3.62 (s, 3H), 3.59 (m, 2H), 3.49 (m, 12H), 3.39 (m, 2H), 3.19 (m, 2H), 3.07 (m, 2H), 2.43 (m, 1H), 2.07 (m, 2H), 1.45 (m, 3H), 1.31 (d, 3H), 1.23 (m, 2H), 0.88 (d, 3H), 0.84 (d, 3H).

4.2) Preparation of Mm-$C_6$-PEG4-Val-Ala-PAB-MMAE

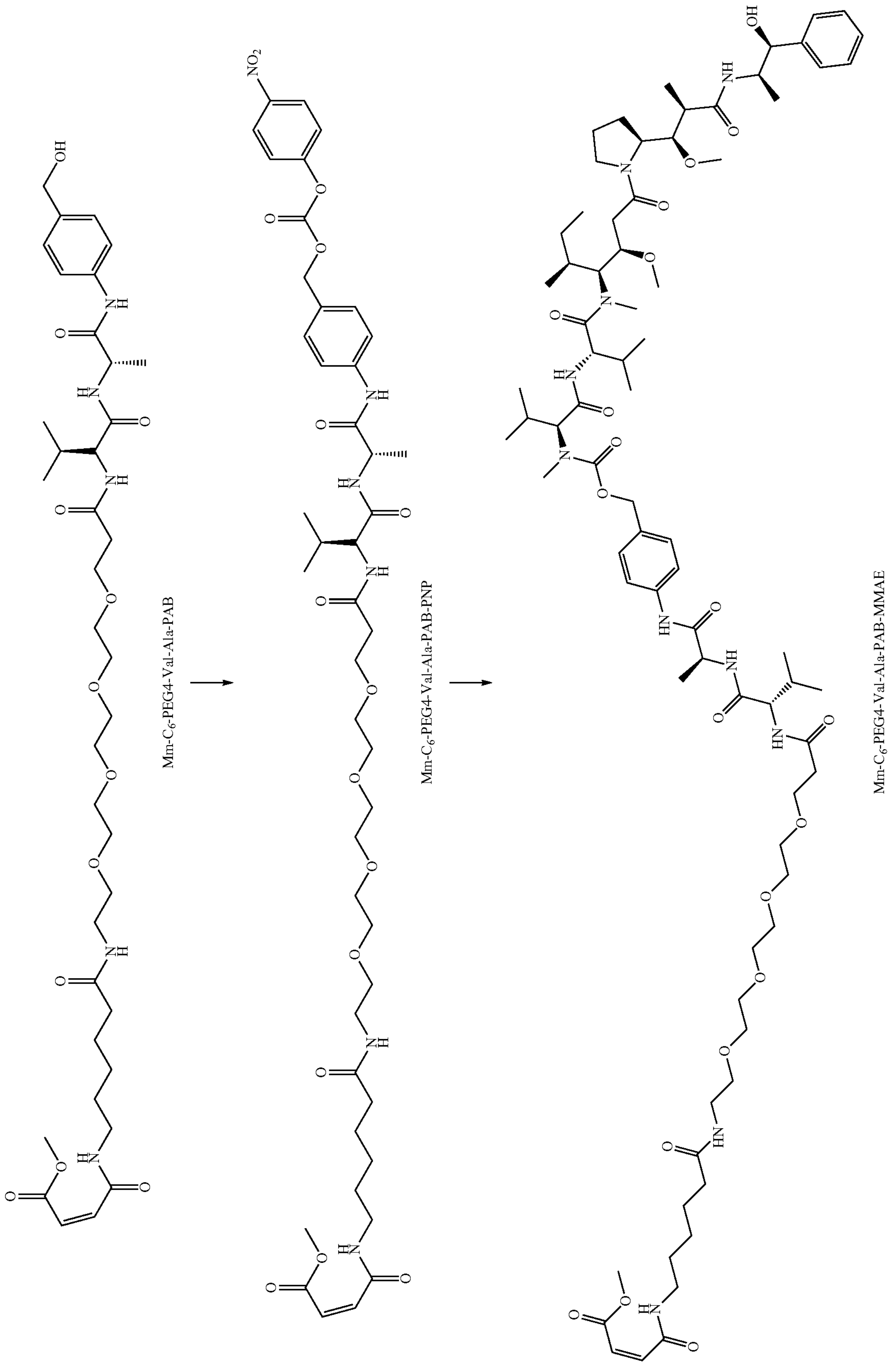
Mm-$C_6$-PEG4-Val-Ala-PAB
Mm-$C_6$-PEG4-Val-Ala-PAB-PNP
Mm-$C_6$-PEG4-Val-Ala-PAB-MMAE The intermediate Mm-$C_6$-PEG4-Val-Ala-PAB was used as raw material, Mm-$C_6$-PEG4-Val-Ala-PAB-PNP was synthesized by using a preparation method similar to that of Mm-$C_3$-Val-Ala-PAB-PNP to obtain a yellow viscous solid, which was purified by flash column chromatography with DCM to finally obtain a pale yellow viscous solid (70% yield). The Mm-$C_6$-PEG4-Val-Ala-PAB-PNP (128 mg, 0.14 mM) was immediately dissolved in anhydrous DMF (15 mL), after the dissolution was completed, MMAE (98 mg, 0.14 mM) was added, then HoBt (28 mg, 0.21 mM) and DIPEA (35 mg, 0.27 mM) were added, stirred at room temperature for 36 hours. After the reaction was completed, DMF was removed by concentration under reduced pressure to obtain a crude product as a pale yellow viscous substance, which was further purified by column chromatography to obtain a transparent colorless glassy solid (100 mg, 63% yield). MS(ESI) m/z: 755.4581[M+2H]$^{2+}$.

5) Preparation of Mm-$C_6$-PEG8-Val-Ala-PAB-MMAE 5.1) Preparation of Mm-$C_6$-PEG8-Val-Ala-PAB

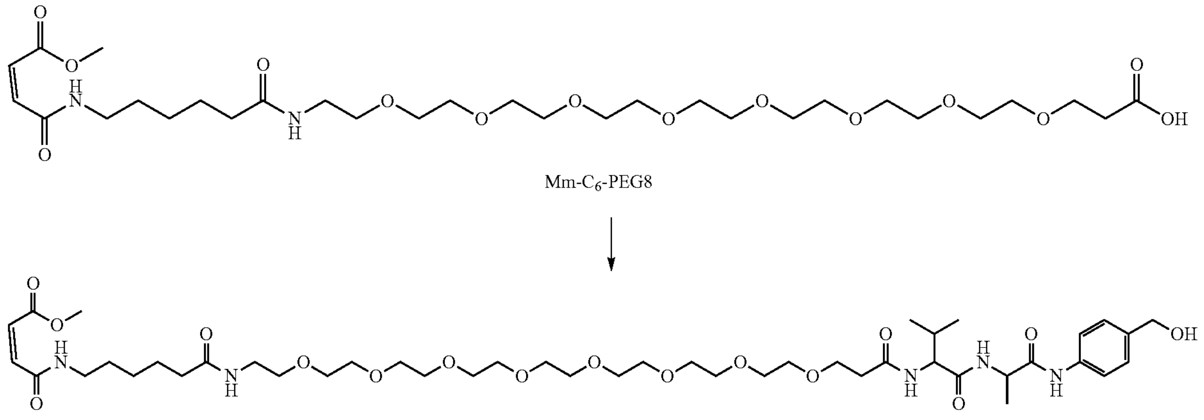

Mm-$C_6$-PEG8

Mm-$C_6$-PEG8-Val-Ala-PAB

Mm-$C_6$-PEG8 (220 mg, 0.33 mM) was dissolved in anhydrous DMF (15 mL), after the dissolution was completed, Val-Ala-PAB (96 mg, 0.33 mM) was added, and then HoBt (95 mg, 0.50 mM) and DIPEA (63 mg, 0.50 mM) were added, reacted under stirring for 24 hours at room temperature. After the reaction was completed, DMF was removed by concentration under reduced pressure to obtain a crude product as a pale yellow solid substance, which was further purified by column chromatography to obtain a transparent colorless glassy solid (260 mg, 78% yield). MS(ESI) m/z: 942.5281[M+H]$^+$; 964.5099 [M+Na]$^+$. $^1$H-NMR (400 MHz, DMSO-d6): δ 10.00 (s, 1H), 8.33 (m, 2H), 8.06 (d, 1H), 7.99 (t, 1H), 7.69 (d, 2H), 7.38 (d, 2H), 6.40 (dd, 2H), 4.56 (s, 2H), 4.36 (m, 1H), 3.76 (s, 3H), 3.73 (m, 2H), 3.62 (m, 30H), 3.53 (m, 2H), 3.19 (m, 2H), 2.61 (m, 2H), 1.57 (m, 2H), 1.44 (m, 3H), 1.23 (m, 4H), 1.02 (d, 3H), 0.97 (d, 3H).

5.2) Preparation of Mm-$C_6$-PEG8-Val-Ala-PAB-MM

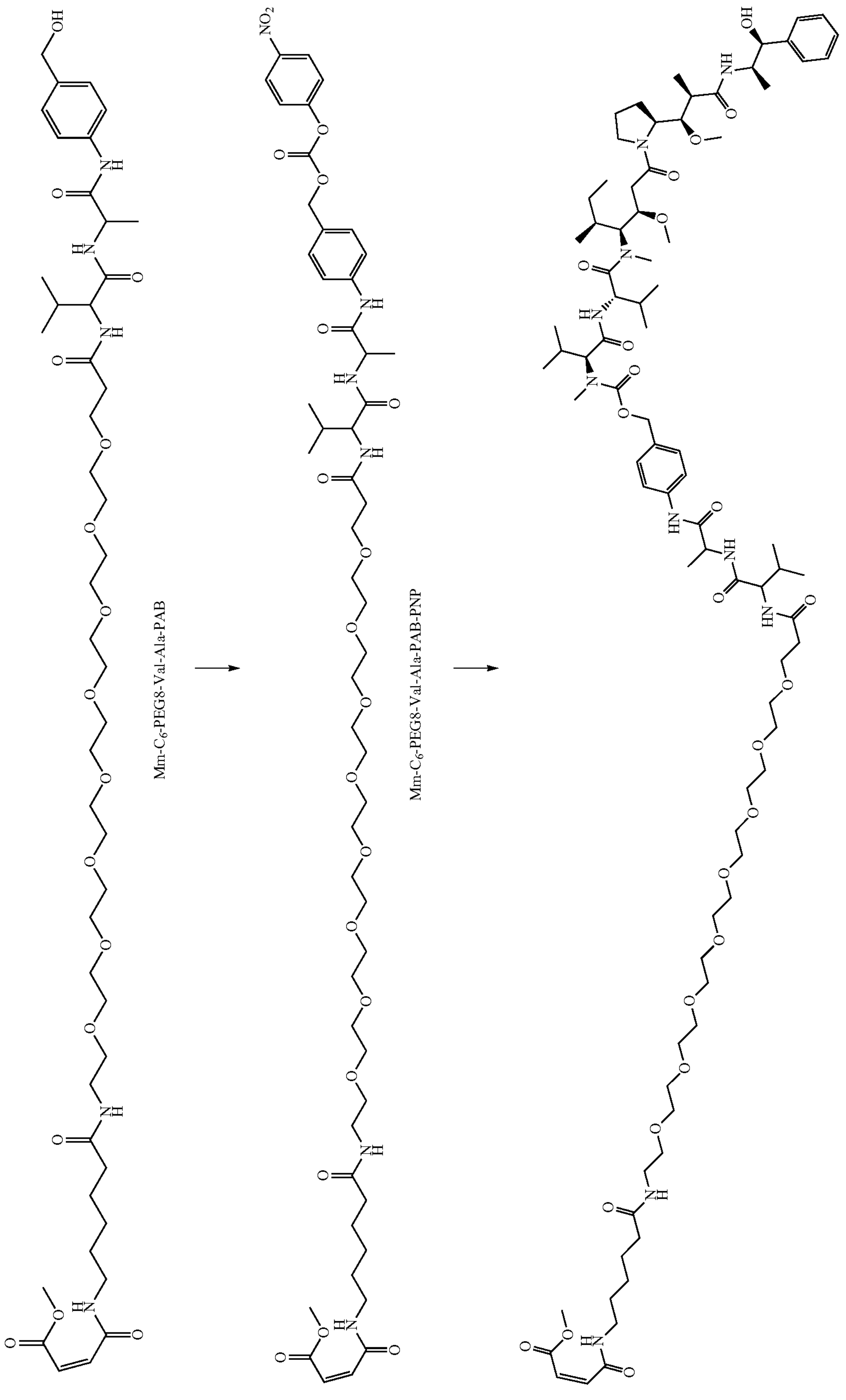
Mm-$C_6$-PEG8-Val-Ala-PAB
Mm-$C_6$-PEG8-Val-Ala-PAB-PNP
Mm-$C_6$-PEG8-Val-Ala-PAB-MMAE Mm-$C_6$-PEG8-Val-Ala-PAB-MMAE was synthesized by a preparation method similar to that of Mm-$C_6$-PEG4-Val-Ala-PAB-MMAE, and a colorless viscous solid (43% yield) was obtained. MS(ESI) m/z: 843.5101[M+2H]$^{2+}$.

6) Synthesis of Mm-$C_6$-PEG8'-Val-Ala-PAB-MMAE 6.1) Preparation of Mm-$C_6$-PEG8'-Val-Ala-PAB

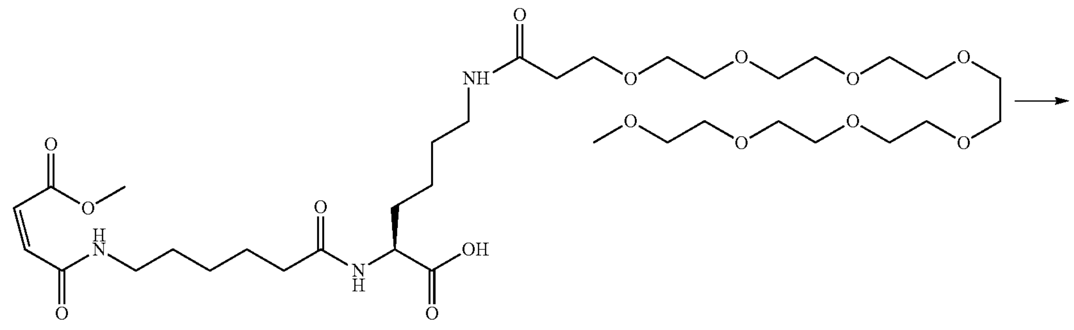

Mm-$C_6$-PEG8'-Val-Ala

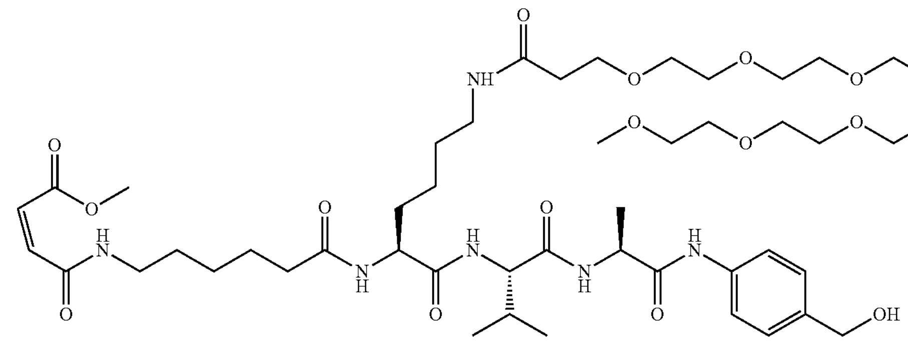

Mm-$C_6$-PEG8'-Val-Ala-PAB

Mm-$C_6$-PEG8' (252 mg, 0.33 mM) was dissolved in anhydrous DMF (15 mL), after the dissolution was completed, Val-Ala-PAB (96 mg, 0.33 mM) was added, and then HoBt (95 mg, 0.50 mM) and DIPEA (63 mg, 0.50 mM) were added, reacted under stirring for 24 h at room temperature. After the reaction was completed, DMF was concentrated under reduced pressure to obtain a crude product as a pale yellow solid substance, which was further purified by column chromatography to obtain a transparent colorless glassy solid (161 mg, 47% yield). MS(ESI) m/z: 1041.8958[M+H]$^+$; 1063.5775[M+Na]$^+$.

6.2) Preparation of Mm-$C_6$-PEG8'-Val-Ala-PAB-MMAE

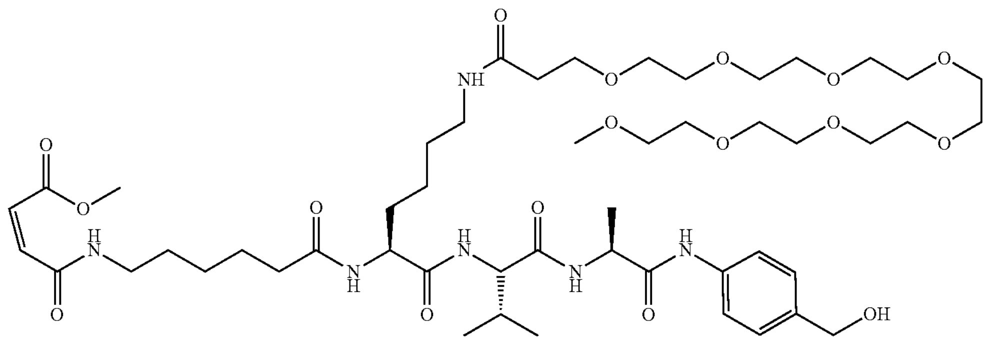

Mm-$C_6$-PEG8'-Val-Ala-PAB

-continued

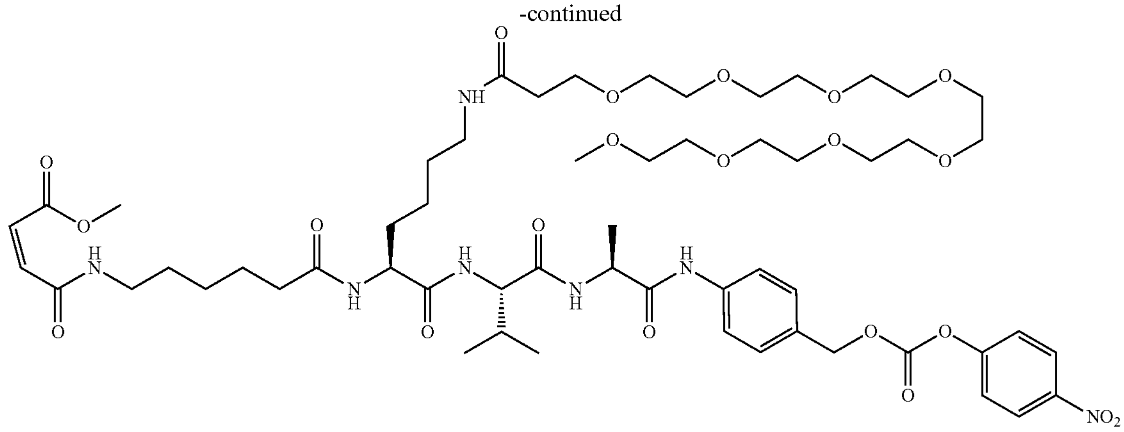

Mm-$C_6$-PEG8′-Val-Ala-PAB-PNP

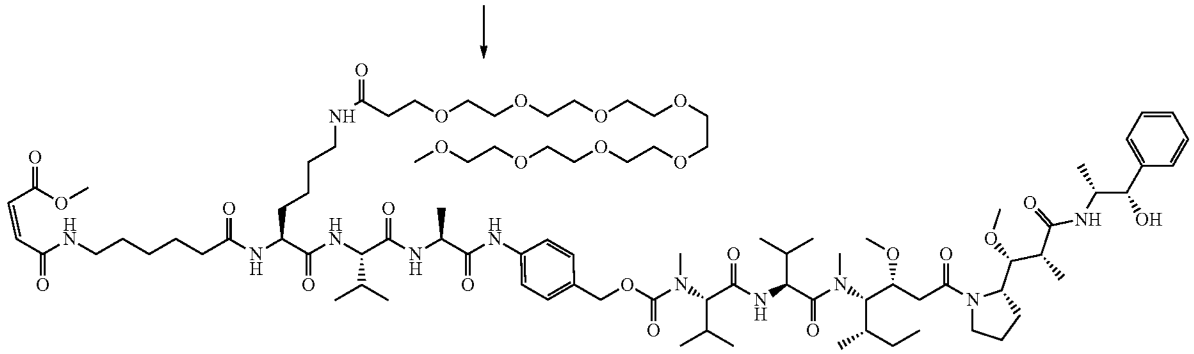

Mm-$C_6$-PEG8′-Val-Ala-PAB-MMAE

Mm-$C_6$-PEG8'-Val-Ala-PAB-MMAE was synthesized by using a preparation method similar to that of Mm-$C_6$-PEG4-Val-Ala-PAB-MMAE, and a pale yellow viscous solid (31% yield) was obtained. MS(ESI) m/z: 893.5463 $[M+2H]^{2+}$.

The structures of the conjugates of MMAE and the linkers containing methyl maleate prepared in Example 7 were shown in the following table:

| Linker-MMAE conjugate |
|---|
| Mm-$C_3$-Val-Ala-PAB-MMAE: 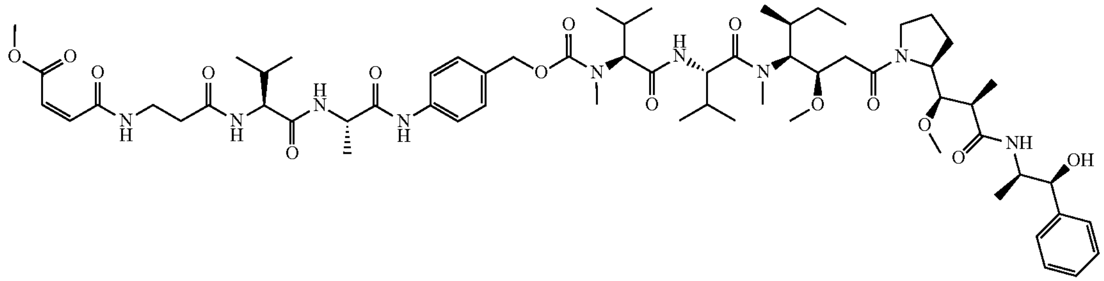 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](C)NC(=O)[C@@H](NC(=O)CCNC(=O)/C=C\C(=O)OC)C(C)C)cc1)C(C)C] |
| Mm-$C_6$-Val-Ala-PAB-MMAE: 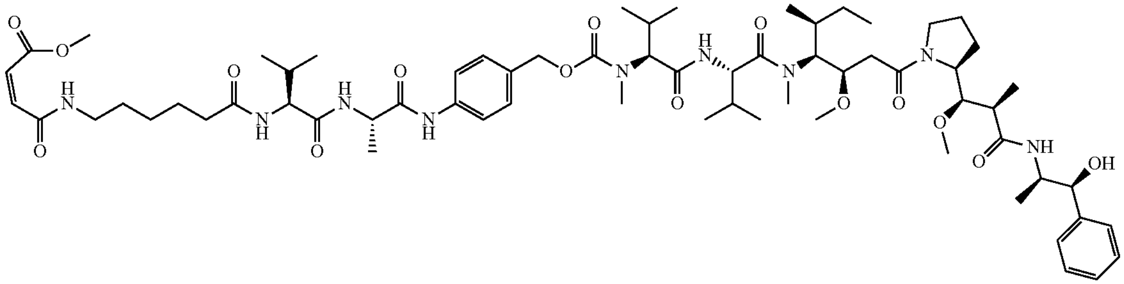 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](C)NC(=O)[C@@H](NC(=O)CCCCCNC(=O)/C=C\C(=O)OC)C(C)C)cc1)C(C)C] |
| Mm-$C_6$-Val-Cit-PAB-MMAE: 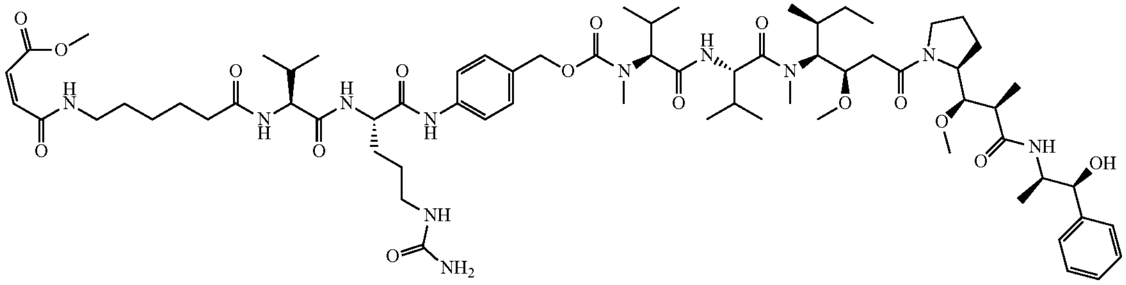 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)CCCCCNC(=O)/C=C\C(=O)OC)C(C)C)cc1)C(C)C] |
| Mm-$C_6$-PEG4-Val-Ala-PAB-MMAE: |

-continued
| Linker-MMAE conjugate |
| --- |
| 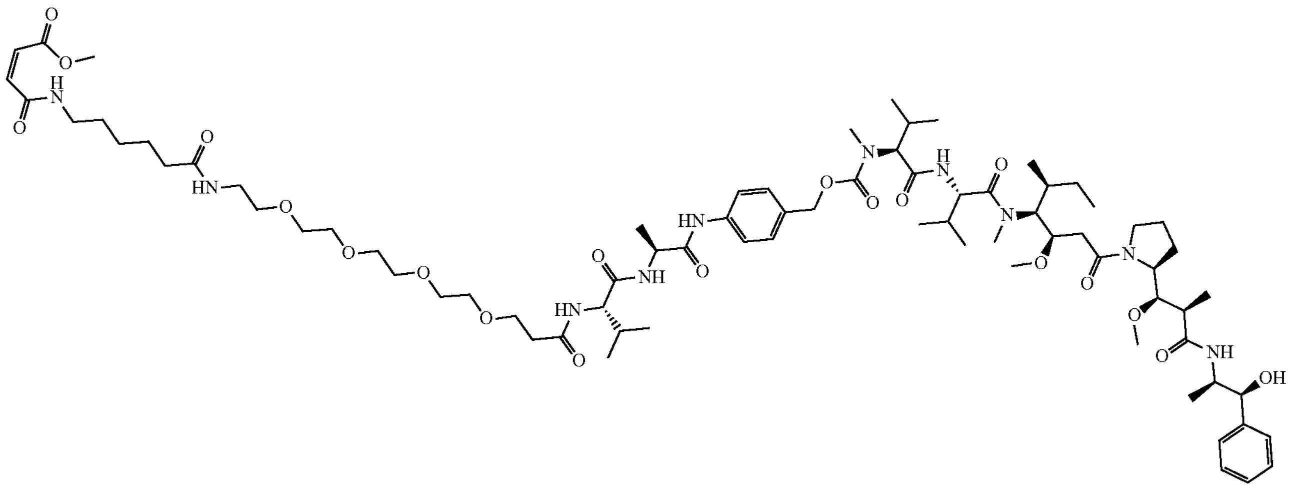 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](C)NC(=O)[C@@H](NC(=O)CCOCCOCCOCCOCCNC(=O)CCCCCNC(=O)/C=C\C(=O)OC)C(C)C)cc1)C(C)C] |
| Mm-$C_6$-PEG8-Val-Ala-PAB-MMAE: |

-continued
| Linker-MMAE conjugate |
|---|
| 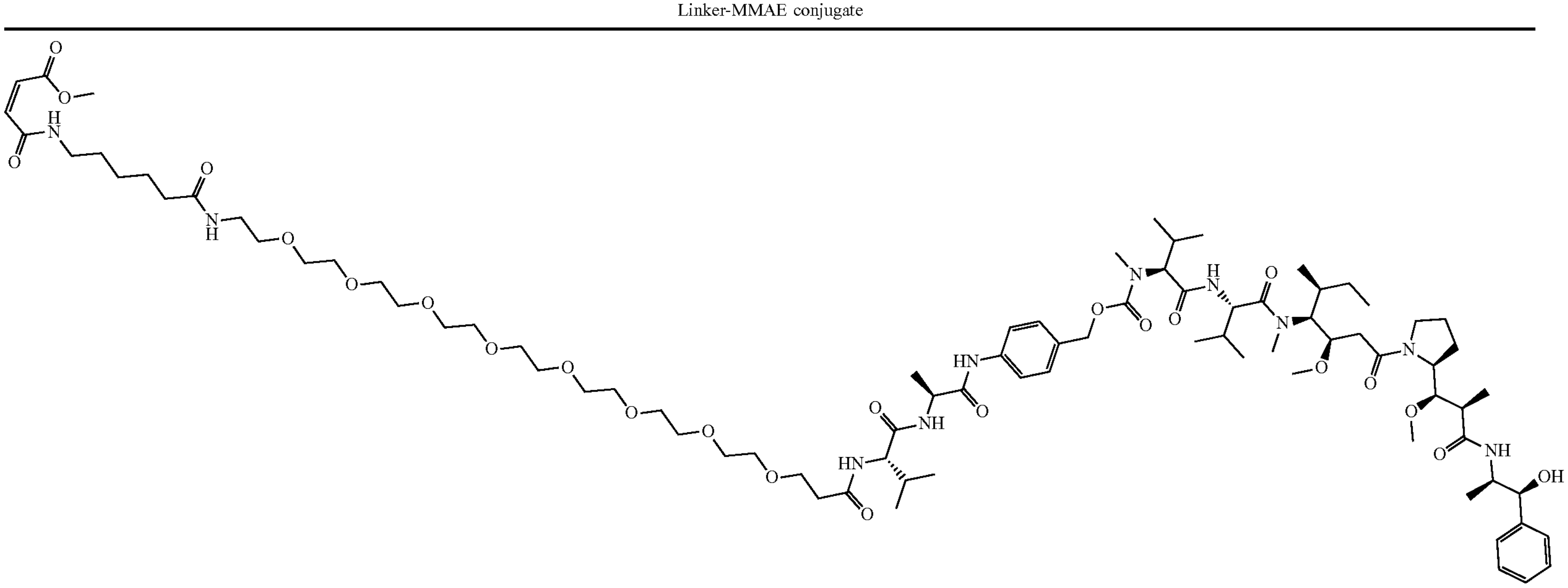 |
| Mm-$C_6$-PEG8'-Val-Ala-PAB-MMAE: |
| 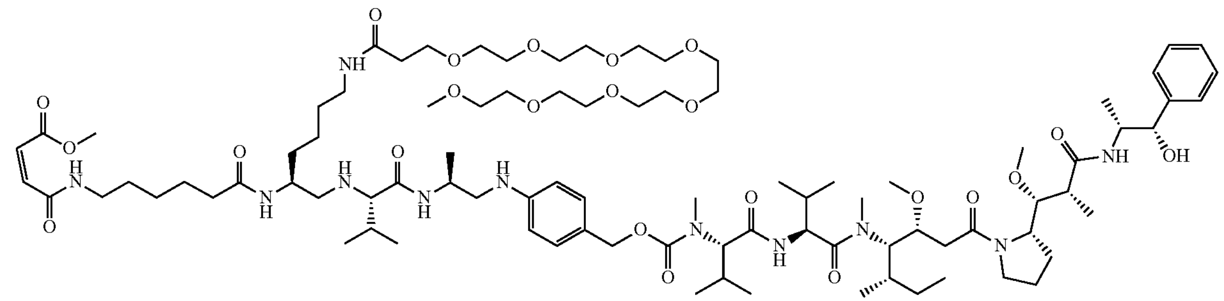 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC[C@H](C)NC(=O)[C@@H](NC[C@H](CCCCNC(=O)CCOCCOCCOCCOCCOCCOCCOCCOC)NC(=O)CCCCCNC(=O)/C=C\C(=O)OC)C(C)C)cc1)C(C)C] |

Example 8: Synthesis of Linker-(MMAE Substitute) Conjugate 8.1 Synthesis of MMAE substitute (Val'-Val-An)

The synthetic route was as follows:

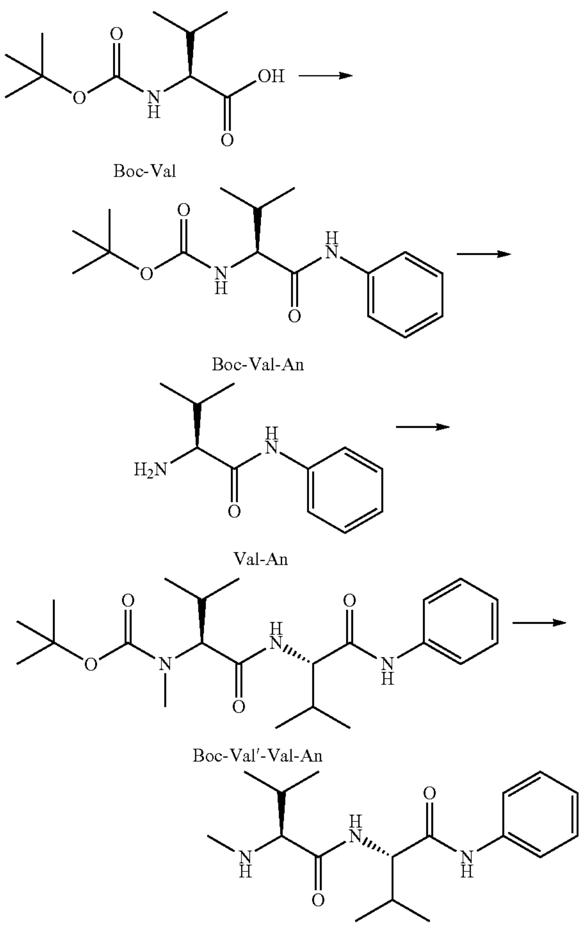

Boc-Val

Boc-Val-An

Val-An

Boc-Val'-Val-An

Val'-Val-An

1) Preparation of Boc-Val-An:

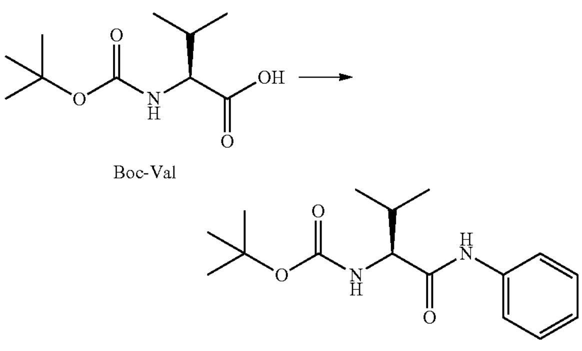

Boc-Val

Boc-Val-An

N-Boc-Valine (Boc-Val, 2.17 g, 10 mM) was dissolved in anhydrous THF (30 mL), then aniline (0.93 g, 10 mM) and DCC (2.39 g, 11 mM) were added, and reacted under stirring overnight at room temperature. After the reaction was completed, the insoluble substance (DCU) was removed by filtration, and the obtained filtrate was concentrated under reduced pressure and further purified by column chromatography to obtain the target product as a white solid powder (2.2 g, 75% yield). $^1$H-NMR (400 MHz, DMSO-d6): δ 9.98 (s, 1H), 7.60 (d, J=7.6 Hz, 2H), 7.30 (d, J=8.0 Hz, 2H), 7.04 (t, J=7.4 Hz, 1H), 6.90 (d, J=8.4 Hz, 1H), 3.91 (t, J=7.0 Hz, 1H), 1.96 (m, 1H), 1.39 (s, 9H), 0.88 (d, J=6.7 Hz, 6H). MS(ESI) m/z: 293.1 $[M+H]^+$; 315.2 $[M+Na]^+$.

2) Preparation of Val-An:

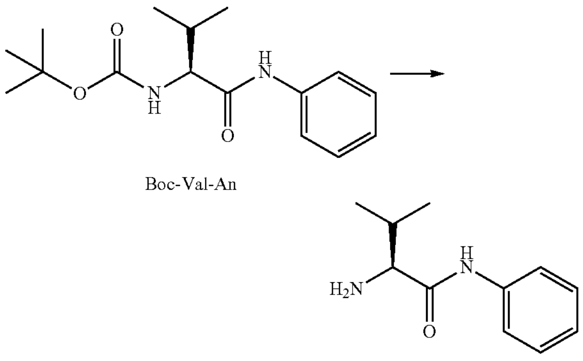

Boc-Val-An

Val-An

The product Boc-Val-An (5.85 g, 20 mM) obtained in step 1) was dissolved in DCM (50 mL), then TFA (12.5 mL) was added to the resulting reaction solution, and the reaction was carried out under stirring overnight at room temperature. After the reaction was completed, concentration under reduced pressure and further purification by column chromatography were carried out to obtain the target product as a pale yellow oily liquid (2.8 g, 88% yield). $^1$H-NMR (400 MHz, DMSO-d6): δ 9.84 (br, 1H), 7.63 (dd, J=8.7 Hz, 2H), 7.30 (d, J=8.0 Hz, 2H), 7.03 (td, J=7.4 Hz, 1H), 3.10 (d, J=5.6 Hz, 1H), 1.93 (m, 1H), 0.88 (d, J=6.7 Hz, 6H). MS(ESI) m/z: 193.1 $[M+H]^+$; 215.1 $[M+Na]^+$.

Preparation of Boc-Val'-Val-An:

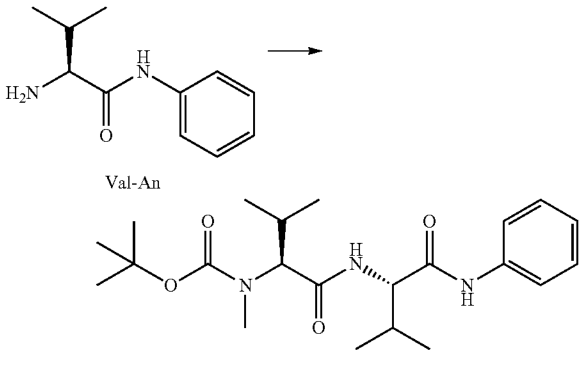

Val-An

Boc-Val'-Val-An

N-methyl-N-Boc-valine (Val', 0.58 g, 2.5 mM) was dissolved in DCM (10 mL), then EDCI (0.58 g, 3 mM), HOBt (0.41 g, 3 mM) and DIPEA (0.51 mL, 3.0 mM) were added in sequence, reacted under stirring at room temperature for 1 hour, then Val-An (0.48 g, 2.5 mM) was added, and the reaction was continued under stirring overnight at room temperature. After the reaction was completed, the solvent was removed by concentration to obtain a crude product, which was further dried to obtain a pale pink solid powder (0.43 g, 42% yield). $^1$H-NMR (400 MHz, DMSO-d6): δ

10.11 (d, 1H), 7.95 (d, J=8.3 Hz, 2H), 7.58 (d, J=7.6 Hz, 2H), 7.31 (t, J=8.0 Hz, 2H), 7.05 (t, J=7.4 Hz, 3H), 4.23 (t, J=9.4 Hz, 2H), 2.77 (s, 1H), 2.04 (m, 2H), 1.43 (s, 9H), 0.87-0.78 (m, 12H). MS(ESI) m/z: 406.2 $[M+H]^+$; 428.3 $[M+Na]^+$.

4) Preparation of Val'-Val-An:

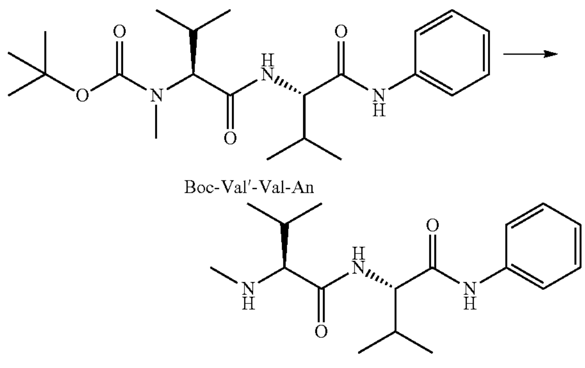

Boc-Val′-Val-An

Val′-Val-An

Boc-Val'-Val-An (0.42 g, 1.04 mM) obtained in step 3) was dissolved in DCM (5 mL), then TFA (1.25 mL) was added to the reaction solution, and the reaction was carried out under stirring for 3 hours at room temperature. After the reaction was completed, the concentration was carried out under reduced pressure, the residue was re-dissolved with ethyl acetate and washed twice with saturated sodium bicarbonate solution, then concentrated, the resulting product was recrystallized from ethyl acetate to obtain a product as a white powdery solid (0.31 g, 99% yield). $^1$H-NMR (400 MHz, DMSO-d6): δ 10.16 (s, 1H), 8.03 (d, J=9.0 Hz, 1H), 7.59 (d, J=8.7 Hz, 2H), 7.30 (t, J=7.1 Hz, 2H), 7.04 (t, J=7.4 Hz, 1H), 4.39 (t, J=8.0 Hz, 1H), 2.69 (d, J=6.2 Hz, 1H), 2.20 (s, 3H), 2.03 (m, 1H), 1.76 (m, 1H), 0.89 (m, 12H). MS(ESI) m/z: 306.22 $[M+H]^+$; 328.20 $[M+Na]^+$.

8.2 Synthesis of Linker-(MMAE Substitute) Conjugate

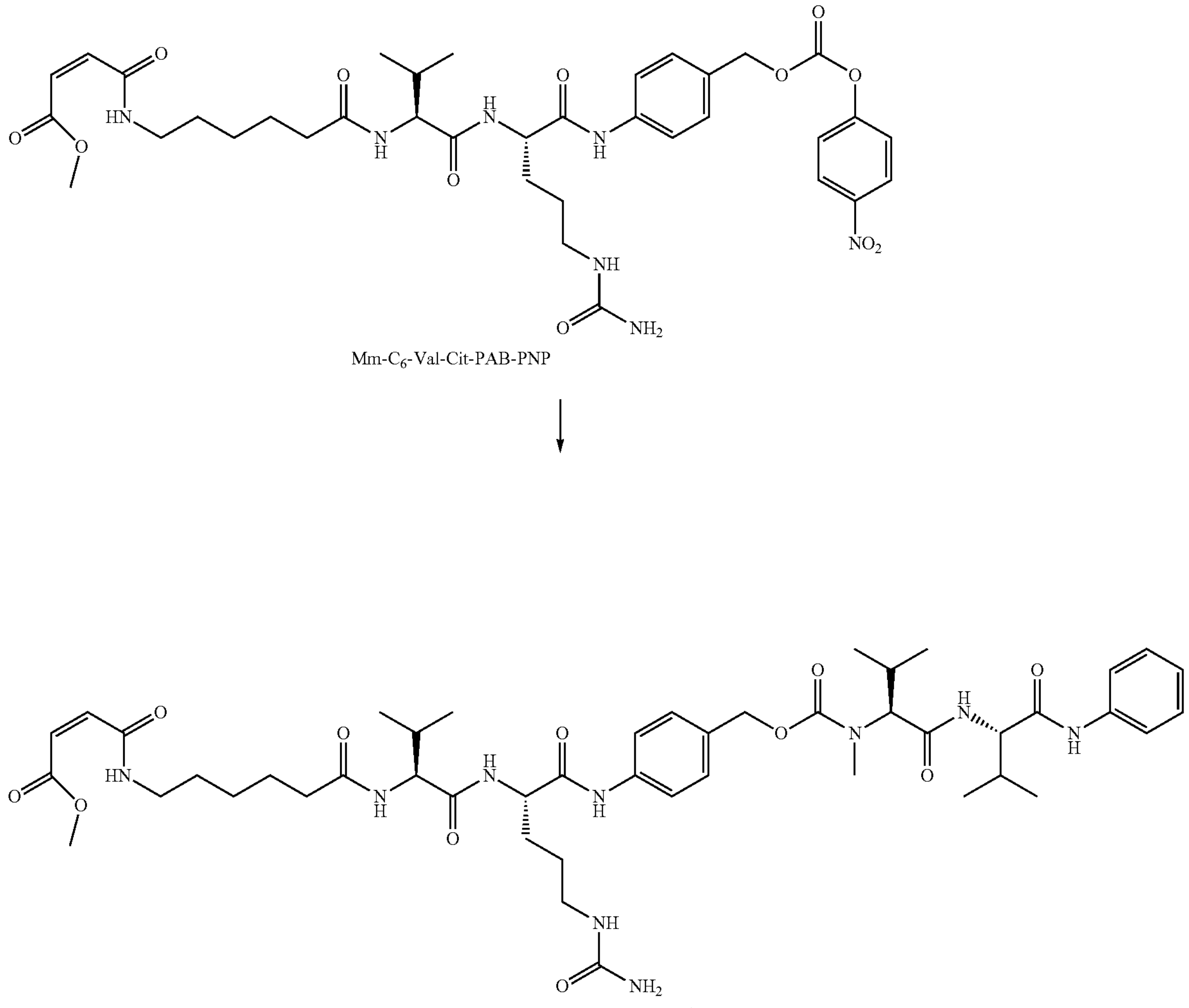

Mm-$C_6$-Val-Cit-PAB-PNP

Mm-$C_6$-Val-Cit-PAB-MMAE

The linker Mm-$C_6$-Val-Cit-PAB-PNP was used as raw material, dissolved in anhydrous DMF (10 mL), after the dissolution was completed, HOBt (44.6 mg, 0.33 mM), MMAE substitute (Val'-Val-An, 100 mg, 0.33 mM) and DIPEA (85.3 mg, 0.66 mM) were added in sequence, and reacted under stirring at room temperature for 18 hours. After the reaction was completed, the solvent was removed by concentration under reduced pressure, and the residue was further purified by column chromatography to obtain the target product as a white solid powder (86% yield). $^1$H-NMR (400 MHz, DMSO-d6): δ 10.07-9.97 (m, 2H), 8.19 (t, J=5.7 Hz, 1H), 8.12 (d, J=7.3 Hz, 1H), 7.94 (d, J=7.8 Hz, 1H), 7.83 (d, J=8.4 Hz, 2H), 7.60-7.57 (m, 4H), 7.34-7.28 (m, 4H), 7.05 (t, J=7.4 Hz, 1H), 6.27 (d, J=12.6 Hz, 2H), 6.23 (d, J=12.6 Hz, 2H), 5.98 (t, J=5.6 Hz, 1H), 5.43 (s, 1H), 5.11-5.01 (m, 2H), 4.39 (m, 2H), 4.18 (q, J=8.2 Hz, 2H), 3.63 (s, 3H), 3.08-2.95 (m, 4H), 2.85 (s, 3H), 2.17 (m, 2H), 2.09 (s, 1H), 1.97 (m, 1H), 1.69 (m, 1H), 1.61 (m, 1H), 1.53-1.31 (m, 6H), 1.23 (m, 2H), 0.87-0.77 (m, 18H). MS(ESI) m/z: 936.8 [M+H]$^+$; 959.1 [M+Na]$^+$.

The structure of the conjugate of the linker containing methyl maleate and the MMAE substitute prepared in Example 8 was shown in the following table:

-continued

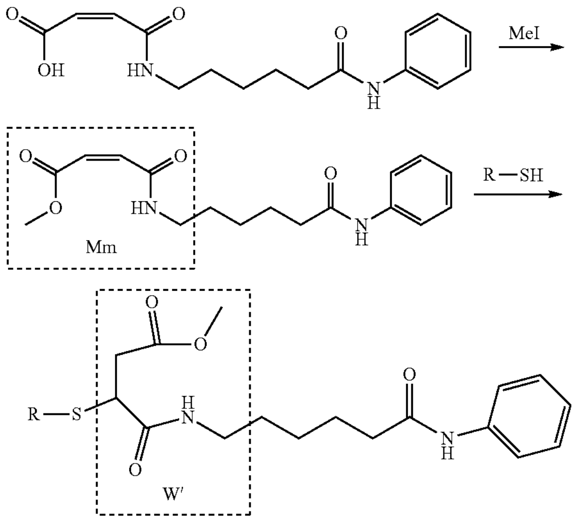

| Mm-$C_6$-Val-Cit-PAB-MMAE substitute: |
|---|
| 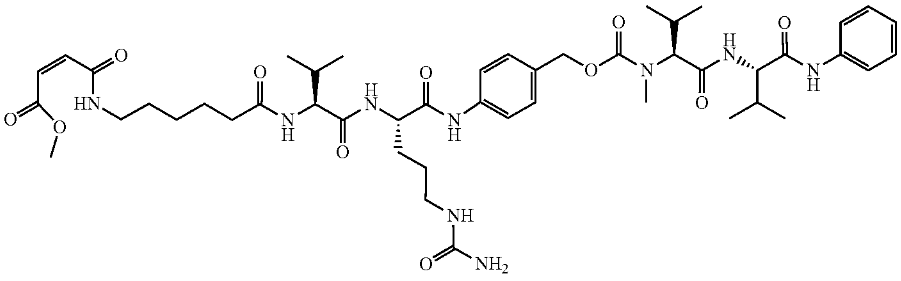 [SMILES: COC(=O)/C=C\C(=O)NCCCCCC(=O)N[C@H](C(=O)N[C@@H](CCCNC(N)=O)C(=O)Nc1ccc(COC(=O)N(C)[C@H](C(=O)N[C@H](C(=O)Nc2ccccc2)C(C)C)C(C)C)cc1)C(C)C] |

It was confirmed by Examples 7 and 8 that the linkers provided by the present application could be coupled with cytotoxin.

Example 9: Synthesis of Linker-(Sulfhydryl-Containing Small Molecule) Conjugate 9.1 Synthesis of W'-Containing Linker-(Sulfhydryl-Containing Small Molecule) Conjugate According to the Following Route:

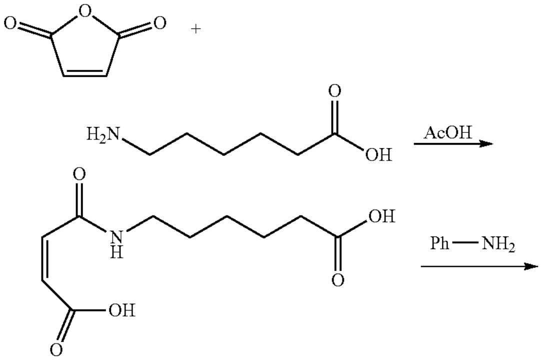

wherein, R was:

$R^1$

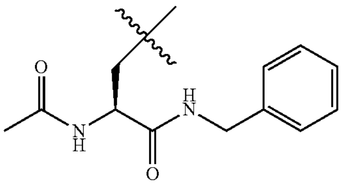

$R^2$

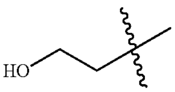

$R^3$

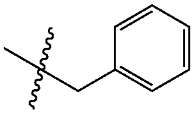

-continued

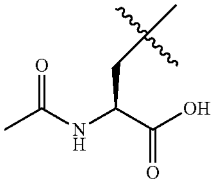

R4

R—SH was: SH SH

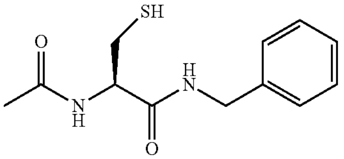

S1

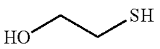

S2

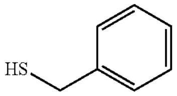

S3

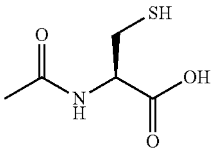

S4

1) Preparation of Maa-$C_6$-An:

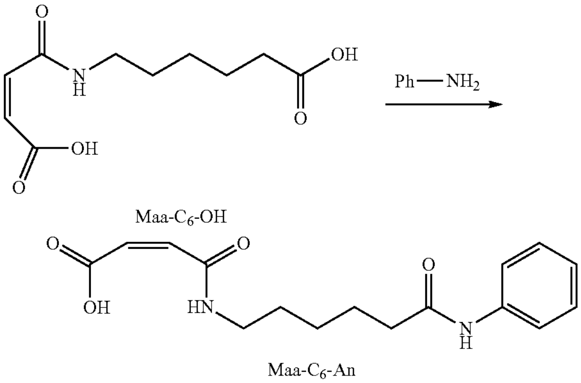

Maa-$C_6$-OH

Maa-$C_6$-An

Maa-$C_6$—OH (3.0 g, 13.1 mM) was dissolved in THF (50 mL), after the dissolution was completed, the resulting mixture was placed in a low-temperature reaction tank at −20° C. and stirred for 10 min for cooling down. NMM (1.59 g, 15.7 mM) and isobutyl chloroformate (2.14 g, 15.7 mM) were added dropwise, respectively, reacted for 20 min at a low temperature of −20° C., and then aniline (An, 1.83 g, 19.6 mM) was added dropwise, and stirred continuously to react for 2 hours. After the reaction was completed, 1 mol/L HCl was added to the reaction solution and extracted with ethyl acetate. The organic phases were combined, washed with saturated brine three times, dried over anhydrous sodium sulfate, concentrated and the residue was purified by silica gel column chromatography to obtain a pure product as a white solid (3.2 g, 81% yield). $^1$H-NMR (400 MHz, DMSO-d6): δ 11.98 (br, 1H), 11.35 (s, 1H), 8.68 (t, 1H), 7.61 (d, J=7.6 Hz, 2H), 7.32 (t, J=7.8 Hz, 2H), 7.07 (t, J=7.4 Hz, 2H), 6.26 (dd, 2H), 3.12 (q, 2H), 1.54-1.42 (m, 4H), 1.30 (m, 2H).

2) Preparation of Mm-$C_6$-An:

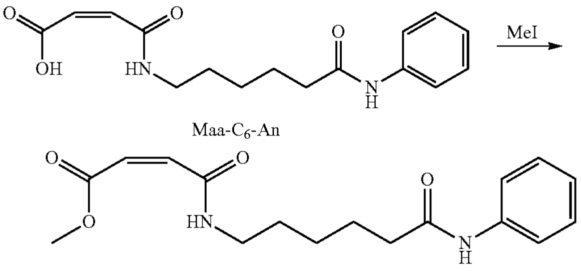

Maa-$C_6$-An

Mm-$C_6$-An

Maa-$C_6$-An (0.33 g, 1.1 mM) was dissolved in DMF, potassium carbonate (0.23 g, 1.63 mM) and methyl iodide (0.23 g, 1.63 mM) were added, and reacted under stirring at room temperature for 4 hours. After the reaction was completed, the insoluble salt was removed by filtration, and the resulting filtrate was dispersed in ethyl acetate, then mixed with silica gel and purified by column chromatography to obtain a white powdery solid (0.32 g, 93% yield). $^1$H-NMR (400 MHz, DMSO-d6): δ 11.33 (s, 1H), 8.67 (t, 1H), 7.61 (d, J=7.6 Hz, 2H), 7.32 (t, J=7.8 Hz, 2H), 7.07 (t, J=7.4 Hz, 2H), 6.26 (dd, 2H), 3.57 (s, 3H), 3.12 (q, 2H), 2.29 (t, 2H), 1.57-1.41 (m, 4H), 1.30 (m, 2H).

3) Preparation of S1-W'-$C_6$-An:

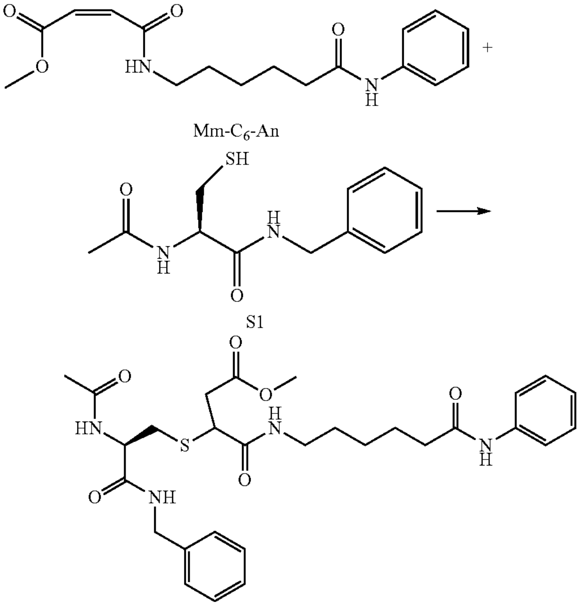

Mm-$C_6$-An

S1

S1-W'-$C_6$-An

Mm-$C_6$-An (0.11 g, 0.35 mM) was dissolved in methanol, then S1 (0.1 g, 0.38 mM) and a catalytic amount of triethylamine (TEA) were added to perform the reaction. After 30 minutes, the reaction was completed, the solvent was removed by concentration under reduced pressure, and the residue was purified by column chromatography to obtain a pair of enantiomers as white solid powder (0.2 g, about 100% yield), with contents of about 1:1. $^1$H-NMR (400 MHz, DMSO-d6): δ 10.00 (s, 1H), 8.53 (t, 1H), 8.23 (d, 2H), 7.97 (t, 1H), 7.55 (d, 2H), 7.32-7.21 (m, 7H), 7.02 (t, 1H), 4.49 (q, 1H), 4.27 (m, 2H), 3.75 (t, 2H), 3.57 (s, 3H), 3.03 (q, 2H), 2.98-2.88 (m, 2H), 2.80 (m, 1H), 2.66 (dd, 1H), 2.24 (t, 2H), 1.87 (s, 3H), 1.48 (m, 2H), 1.38 (m, 2H), 1.23 (m, 2H).

4) Preparation of S2-W'-$C_6$-An:

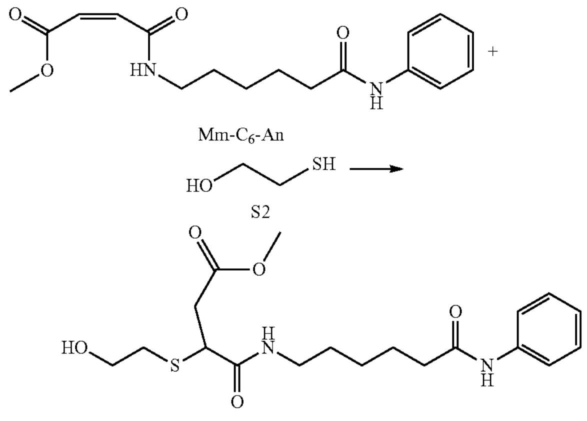

Mm-$C_6$-An

S2

S2-W'-$C_6$-An

Mm-$C_6$-An (0.15 g, 0.47 mM) was dissolved in methanol, then S2 (52 μL, 0.7 mM) was added to perform the reaction. After 30 minutes, the reaction was completed, the solvent was removed by concentration under reduced pressure, and the residue was purified by column chromatography to obtain a product as a white solid powder (0.2 g, 80% yield). $^1$H-NMR (400 MHz, DMSO-d6): δ 10.00 (s, 1H), 8.09 (d, 2H), 7.28 (t, 2H), 7.01 (t, 1H), 4.83 (br, 1H), 3.70 (t, 1H), 3.57 (s, 3H), 3.51 (t, 2H), 3.02 (m, 2H), 2.80 (m, 1H), 2.67 (m, 3H), 2.25 (t, 2H), 1.49 (m, 2H), 1.38 (m, 2H), 1.25 (m, 2H).

5) Preparation of S3-W'-$C_6$-An:

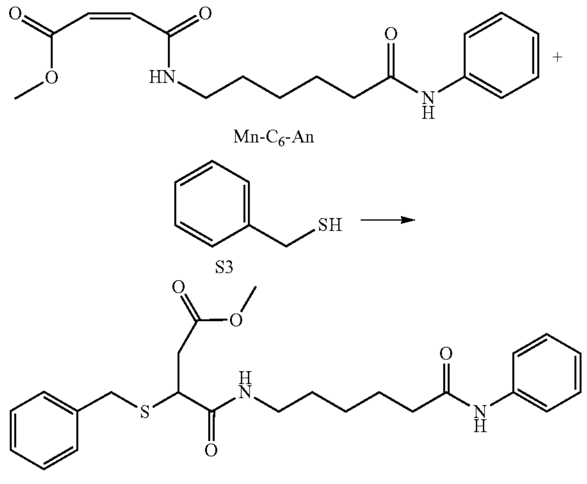

Mn-$C_6$-An

S3

S3-W'-$C_6$-An

Mm-$C_6$-An (0.15 g, 0.47 mM) was dissolved in methanol, then S3 (164 μL, 1.41 mM) was added to perform the reaction. After 30 minutes, the reaction was completed, the solvent was removed by concentration under reduced pressure, and the residue was purified by column chromatography to obtain a product as a white solid powder (0.17 g, 82% yield). $^1$H-NMR (400 MHz, CDCl3): δ 10.02 (s, 1H), 8.09 (t, 2H), 7.57 (d, 2H), 7.32-7.22 (m, 7H), 7.02 (t, 1H), 3.86 (m, 2H), 3.76 (t, 1H), 3.56 (s, 3H), 3.05 (m, 2H), 2.91 (m, 1H), 2.67 (m, 1H), 2.24 (m, 2H), 1.49 (m, 2H), 1.38 (m, 2H), 1.25 (m, 2H).

6) Preparation of S4-W'-$C_6$-An:

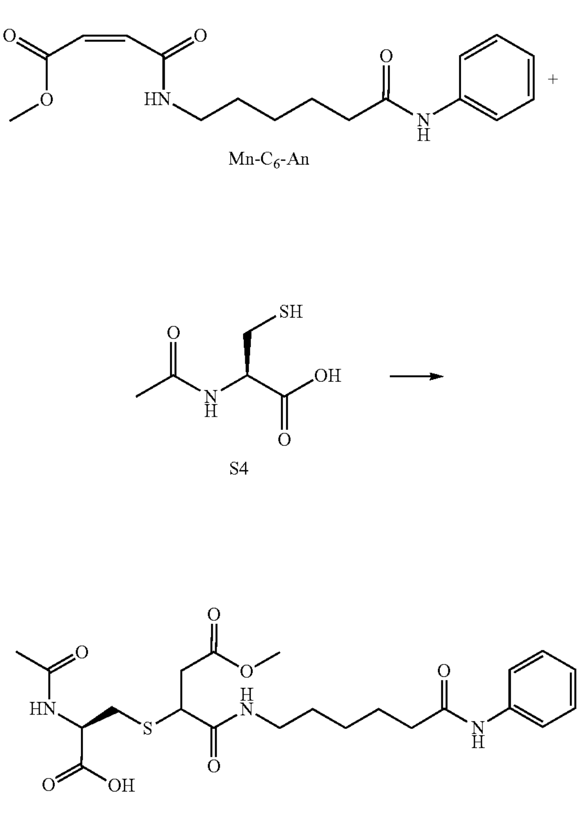

Mn-$C_6$-An

S4

S4-W'-$C_6$-An

Mm-$C_6$-An (0.15 g, 0.4/mM) was dissolved in a methanol/dichloromethane mixed so vent the volume ratio of the two was 1:2), and then S4 (0.23 g, 1.41 mM) and a catalytic amount of triethylamine were added to perform the reaction. After 4 hours, the reaction was completed, the solvent was removed by concentration under reduced pressure, and the residue was purified by column chromatography to obtain a product as a white solid powder (0.17 g, 75% yield). $^1$H-NMR (400 MHz, DMSO-d6): δ 12.77 (br, 1H), 10.00 (s, 1H), 8.23 (s, 1H), 7.55 (d, 2H), 7.22 (m, 2H), 7.02 (t, 1H), 4.49 (q, 1H), 4.27 (m, 2H), 3.75 (t, 2H), 3.57 (s, 3H), 3.03 (q, 2H), 2.98-2.88 (m, 2H), 2.80 (m, 1H), 2.66 (dd, 1H), 2.24 (t, 2H), 1.87 (s, 3H), 1.48 (m, 2H), 1.38 (m, 2H), 1.23 (m, 2H).

The structures of the conjugates of the linkers containing methyl maleate and the small molecule prepared in Example 9.1 were shown in the following table:

| Code | Linker-(small molecule) conjugate structure |
| --- | --- |
| S1-W'-$C_6$-An (Conjugate-1) | 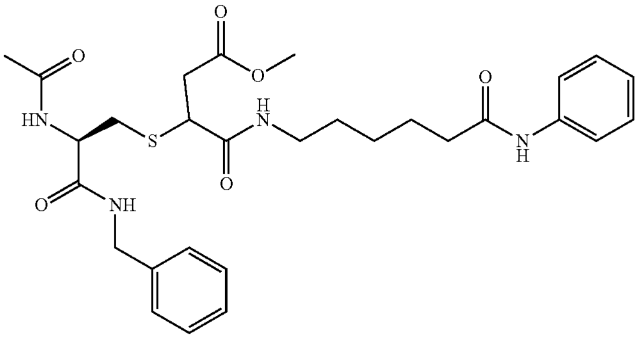 [SMILES: COC(=O)CC(SC[C@H](NC(C)=O)C(=O)NCc1ccccc1)C(=O)NCCCCCC(=O)Nc1ccccc1] |
| S2-W'-$C_6$-An (Conjugate-2) | 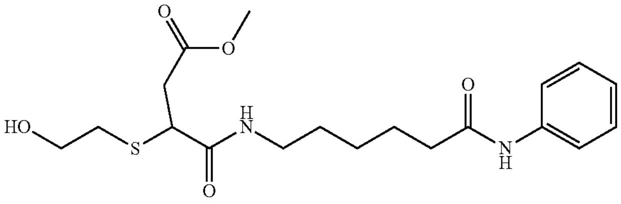 [SMILES: COC(=O)CC(SCCO)C(=O)NCCCCCC(=O)Nc1ccccc1] |
| S3-W'-$C_6$-An (Conjugate-3) | 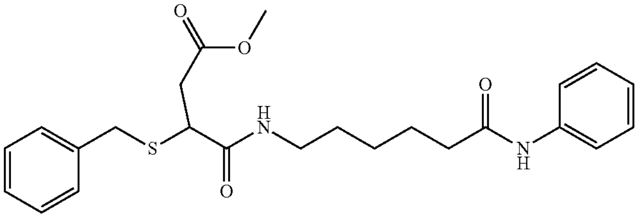 [SMILES: COC(=O)CC(SCc1ccccc1)C(=O)NCCCCCC(=O)Nc1ccccc1] |
| S4-W'-$C_6$-An (Conjugate-4) | 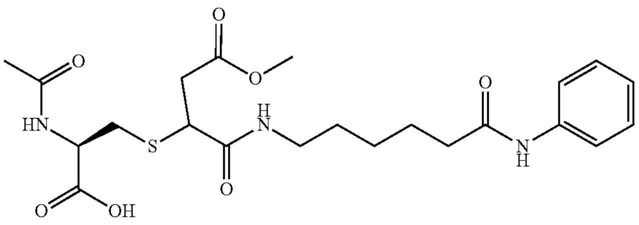 [SMILES: COC(=O)CC(SC[C@H](NC(C)=O)C(=O)O)C(=O)NCCCCCC(=O)Nc1ccccc1] |

It was confirmed by Example 9.1 that the methyl maleate group (Mm) in the linkers provided by the present application could be effectively coupled with various types of sulfhydryl group.

9.2 Synthesis of Succinimide (Su)-Containing Linker-(Sulfhydryl-Containing Small Molecule) Conjugate According to the Following Route:

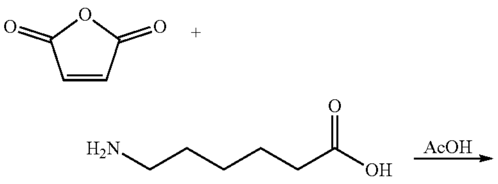

-continued

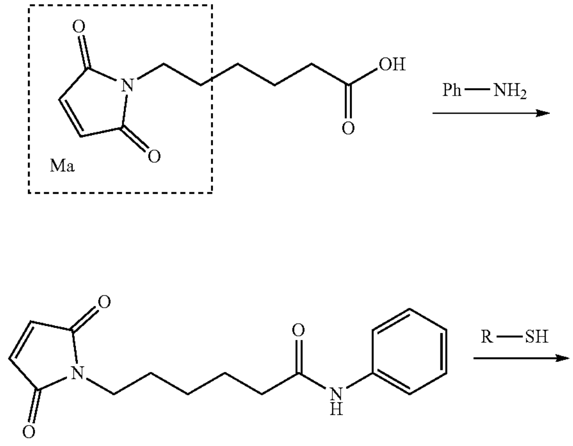

-continued

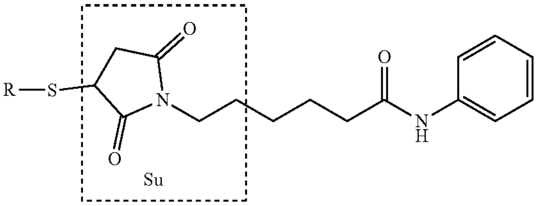

wherein, R was:

R[1]

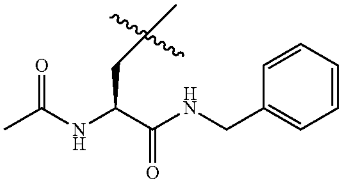

R[2]

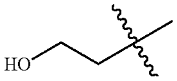

R[3]

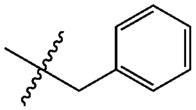

R[4]

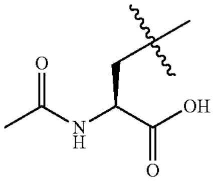

R—SH was:

S1

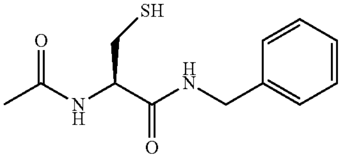

S2

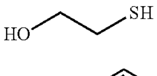

S3

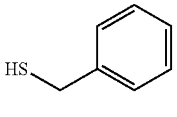

S4

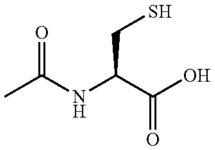

1) Preparation of Ma-$C_6$—OH:

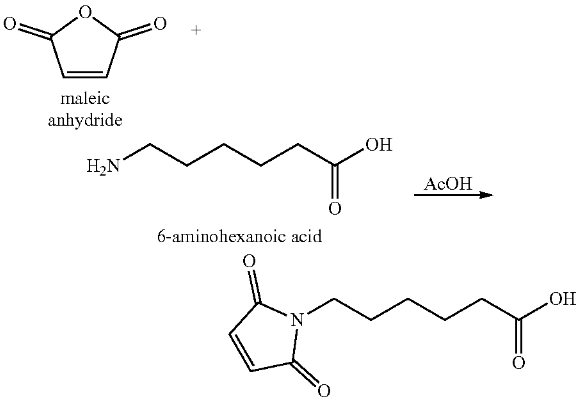

maleic anhydride 6-aminohexanoic acid

Ma-$C_6$-OH

Maleic anhydride (4.86 g, 49.55 mM) was dissolved in acetic acid (150 mL), after the dissolution was completed, 6-aminohexanoic acid (5.0 g, 38.11 mM) was added, and then the resulting reaction solution was heated to 120° C. and refluxed for 6 hours. After the reaction was completed, the reaction solution was cooled to room temperature and poured into distilled water, extracted multiple times with ethyl acetate, and the organic phases were combined. The ethyl acetate organic phase was washed with saturated NaCl solution and dried over anhydrous $Na_2SO_4$ overnight. The solvent was removed by concentration under reduced pressure, and the residue was purified by column chromatography to obtain a white powdery solid (5.92 g, 74% yield). $^1$H-NMR (400 MHz, DMSO-d6): δ 11.98 (br, 1H), 7.01 (s, 2H), 3.39 (t, J=7.3 Hz, 2H), 2.17 (t, J=7.3 Hz, 2H), 1.51-1.44 (m, 2H), 1.24-1.17 (m, 2H). MS(ESI) m/z: 210.0 $[M-H]^-$.

2) Preparation of Ma-$C_6$-An:

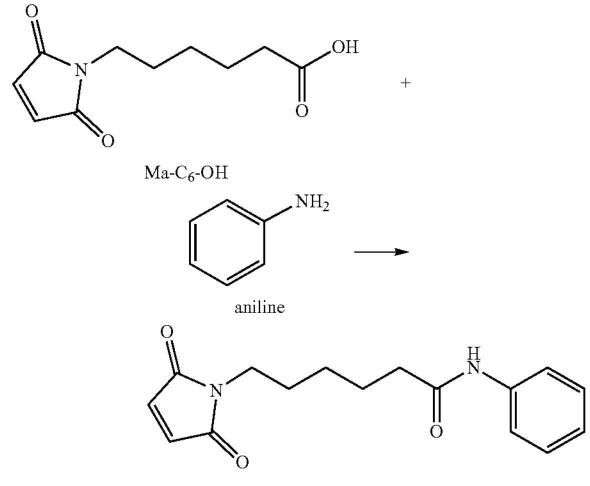

Ma-$C_6$-OH aniline

Ma-$C_6$An

Ma-$C_6$—OH (1.0 g, 4.73 mM) was dissolved in tetrahydrofuran (15 mL), after the dissolution was completed, the resulting mixture was placed in a low-temperature reaction tank at −20° C. to cool down, stirred for 10 minutes, and then NMM (0.63 mL, 5.68 mM) and isobutyl chloroformate (0.74 mL, 5.68 mM) were added dropwise in sequence, after the addition dropwise was completed, the resulting reaction solution was stirred continuously to react at −20° C. for 30 minutes. Then aniline (0.65 mL, 7.1 mM) was added dropwise, and the reaction was continued at −20° C. for 2 hours. After the reaction was completed, saturated aqueous sodium bicarbonate solution (30 mL) was added to the reaction solution, then the reaction solution was extracted with ethyl acetate, and the organic phases were combined. The resulting organic phase was washed with saturated NaCl solution and dried over anhydrous $Na_2SO_4$ overnight. The solvent was removed by concentration under reduced pressure, and the residue was purified by column chromatography to obtain a white powdery solid (0.8 g, 59% yield). $^1$H-NMR (400 MHz, DMSO-d6): δ 9.85 (s, 1H), 7.57 (d, 2H), 7.28 (t, 3H), 7.03-6.99 (m, 3H), 3.40 (t, 2H), 2.28 (t, 2H), 1.61-1.47 (m, 4H), 1.28-1.20 (m, 2H).

3) Preparation of S1-Su-$C_6$-An:

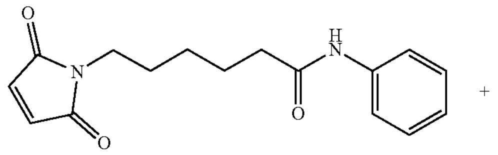

Ma-$C_6$-An

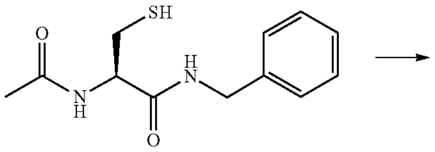

S1

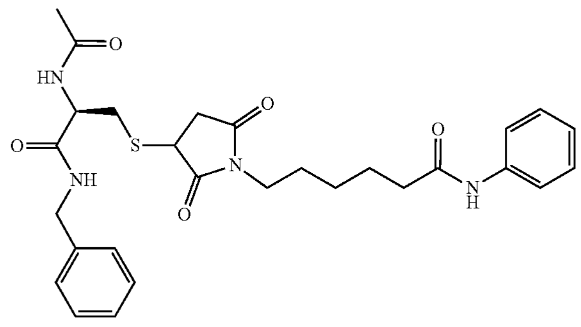

S1-Su-$C_6$-An

Ma-$C_6$-An (150 mg, 0.52 mM) was dissolved in a methanol/dichloromethane mixed solvent (15 mL, volume ratio 1:2), after the dissolution was completed, S1 (140 mg, 0.55 mM) was added, and reacted at room temperature for 10 minutes, the solvent was distilled off under reduced pressure to obtain a crude product. The crude product was dispersed and slurried in diethyl ether (10 mL) for purification to obtain a white solid powder (0.3 g, 82% yield). $^1$H-NMR (400 MHz, DMSO-d6): δ 9.87 (s, 1H), 8.63 (m, 1H), 8.28 (t, 1H), 7.58 (d, 2H), 7.33-7.21 (m, 7H), 7.01 (t, 1H), 4.52 (q, 1H), 4.29 (d, 2H), 4.00 (m, 1H), 3.37 (t, 2H), 3.19-3.11 (m, 2H), 3.00 (d, 1H), 2.82 (t, 1H), 2.28 (m, 2H), 1.87 (t, 3H), 1.61-1.46 (m, 4H), 1.26 (m, 2H).

4) Preparation of S2-Su-$C_6$-An:

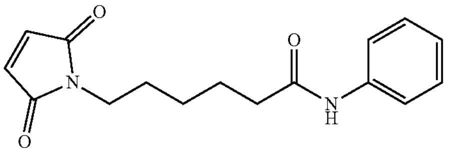

Ma-$C_6$-An

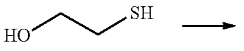

S2

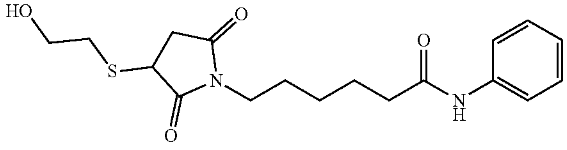

S2-Su-$C_6$-An

Ma-$C_6$-An (200 mg, 0.69 mM) was dissolved in a methanol/dichloromethane mixed solvent (15 mL, volume ratio 1:2), after the dissolution was completed, S2 (77 μL, 1.05 mM) was added, and reacted at room temperature for 10 minutes, the solvent was removed by distillation under reduced pressure to obtain a crude product, which was purified by column chromatography to obtain a white powdery solid (0.24 g, 99% yield). $^1$H-NMR (400 MHz, DMSO-d6): δ 9.86 (s, 1H), 7.57 (d, 2H), 7.28 (t, 2H), 7.01 (t, 1H), 4.90 (s, 1H), 3.58 (t, 2H), 3.37 (t, 2H), 3.16 (m, 1H), 2.87 (m, 1H), 2.71 (m, 1H), 2.52 (t, 1H), 2.48 (t, 1H), 2.28 (t, 2H), 1.58 (m, 2H), 1.49 (m, 2H), 1.26 (m, 2H).

5) Preparation of S3-Su-$C_6$-An:

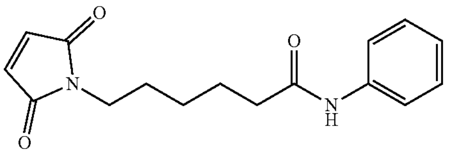

Ma-$C_6$-An

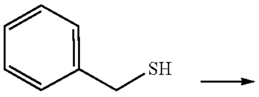

S3

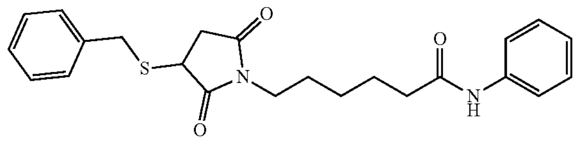

S3-Su-$C_6$-An

Ma-$C_6$-An (200 mg, 0.69 mM) was dissolved in a methanol/dichloromethane mixed solvent (15 mL, volume ratio 1:2), after the dissolution was completed, S3 (123 μL, 1.05 mM) was added, and reacted at room temperature for 10 minutes, the solvent was removed by distillation under reduced pressure to obtain a crude product, which was purified by column chromatography to obtain a white powdery solid (0.27 g, 95% yield). $^1$H-NMR (400 MHz, DMSO-d6): δ 9.86 (s, 1H), 7.58 (d, 2H), 7.37-7.24 (m, 7H), 7.01 (t, 1H), 4.05-4.00 (m, 2H), 3.91 (d, 1H), 3.75 (dd, 1H), 3.35 (t, 2H), 3.09 (m, 1H), 2.28 (t, 2H), 1.58 (m, 2H), 1.49 (m, 2H), 1.26 (m, 2H).

6) Preparation of S4-Su-$C_6$-An:

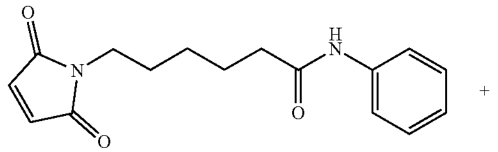

Ma-$C_6$-An

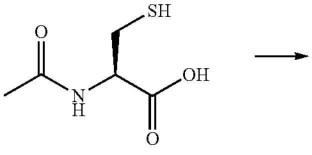

S4

-continued

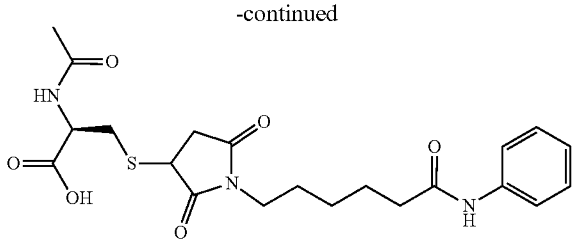

S4-Su-$C_6$-An

Ma-$C_6$-An (100 mg, 0.35 mM) was dissolved in a methanol/dichloromethane mixed solvent (15 mL, volume ratio 1:2), after the dissolution was completed, S4 (57 mg, 0.35 mM) was added, and reacted at room temperature for 10 minutes, the solvent was removed by distillation under reduced pressure to obtain a crude product, which was purified by column chromatography to obtain a white powdery solid (120 mg, 76% yield). $^1$H-NMR (400 MHz, DMSO-d6): δ 12.57 (br, 1H), 9.86 (s, 1H), 8.32 (t, 1H), 7.58 (d, 2H), 7.27 (d, 2H), 7.01 (t, 1H), 4.43 (m, 1H), 4.00 (m, 1H), 3.29 (t, 2H), 3.15 (m, 1H), 3.04 (m, 0.5H), 2.85 (m, 0.5H), 2.28 (d, 4H), 1.61-1.46 (m, 4H), 1.26 (m, 2H).

The structures of the conjugates of the succinimide-containing linkers and small molecule prepared in Example 9 were shown in the following table:

| Code | Linker-small molecule conjugate structure |
| --- | --- |
| S1-Su-$C_6$-An (Conjugate-1') | 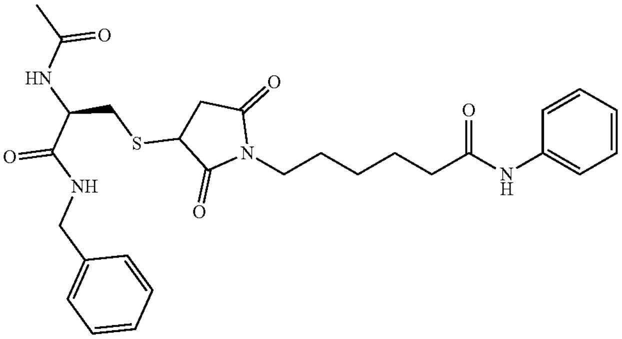 [SMILES: CC(=O)N[C@@H](CSC1CC(=O)N(CCCCCC(=O)Nc2ccccc2)C1=O)C(=O)NCc1ccccc1] |
| S2-Su-$C_6$-An (Conjugate-2') | 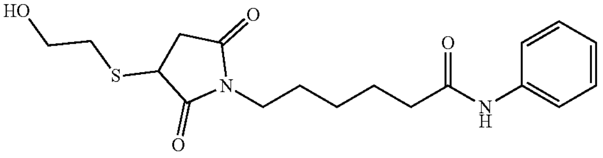 [SMILES: O=C(CCCCCN1C(=O)CC(SCCO)C1=O)Nc1ccccc1] |
| S3-Su-$C_6$-An (Conjugate-3') | 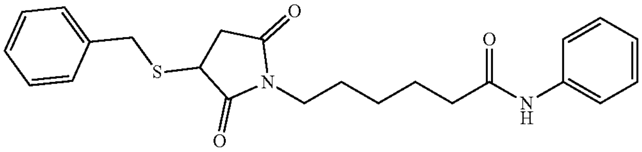 [SMILES: O=C(CCCCCN1C(=O)CC(SCc2ccccc2)C1=O)Nc1ccccc1] |
| S4-Su-$C_6$-An (Conjugate-4') | 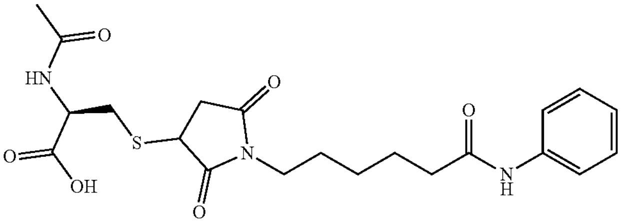 [SMILES: CC(=O)N[C@@H](CSC1CC(=O)N(CCCCCC(=O)Nc2ccccc2)C1=O)C(=O)O] |

Example 10: Preparation of Conjugate of Linker Containing Maleic Acid Amide Structure (Maa) and Cytotoxin MMAE 10.1 Preparation of Maa-$C_6$-Val-Ala-PAB-MMAE 1) Preparation of Maa-$C_6$-Val-Ala-PAB

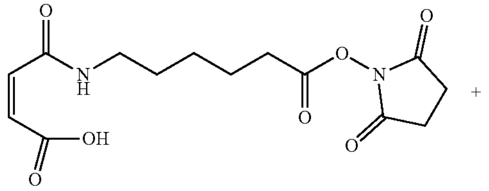

Maa-$C_6$-OSu

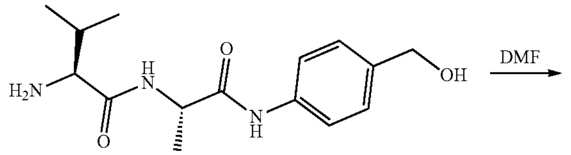

Val-Ala-PAB

-continued

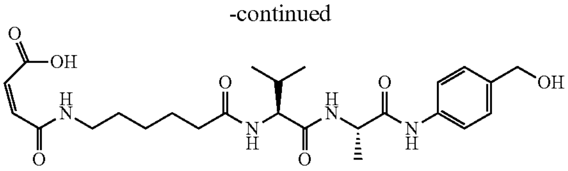

Maa-$C_6$-Val-Ala-PAB

Maa-$C_6$-OSu was used as raw material, Maa-$C_6$-Val-Ala-PAB was synthesized by a method similar to that of Mm-$C_6$-Val-Ala-PAB to obtain a pale yellow solid powder (78% yield). $^1$H-NMR (400 MHz, DMSO-d6)δ 15.09 (br, 1H), 12.03 (br, 1H), 9.86 (s, 1H), 9.43 (s, 1H), 8.12 (d, J=6.7 Hz, 1H), 7.84 (d, J=6.7 Hz, 2H), 7.53 (t, 2H), 7.23 (d, 2H), 6.31 (d, 1H), 6.21 (d, 1H), 5.12 (t, 1H), 4.42 (s, 2H), 4.37 (q, 1H), 4.17 (t, 1H), 3.14 (q, 2H), 2.24-2.10 (m, 2H), 1.97 (m, 1H), 1.48 (m, 4H), 1.31-1.24 (m, 5H), 0.85 (dd, 6H).

2) Preparation of Maa-$C_6$-Val-Ala-PAB-PNP:

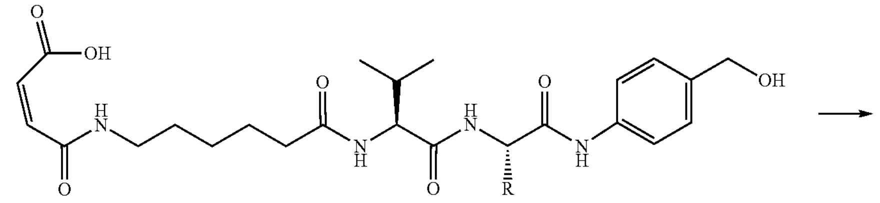

Maa-$C_6$-Val-Ala-PAB

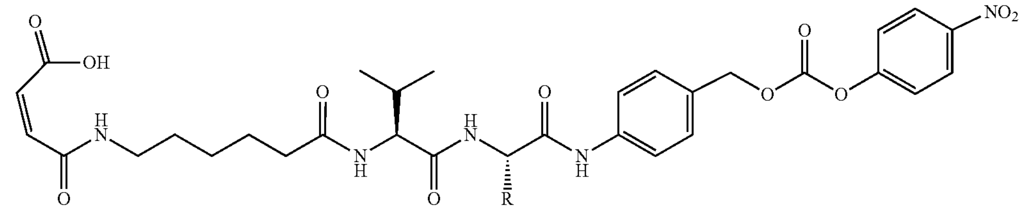

Maa-$C_6$-Val-Ala-PAB-PNP

The intermediate Maa-$C_6$-Val-Ala-PAB was used as raw material, Maa-$C_6$-Val-Ala-PAB-PNP was synthesized by using a preparation method similar to that of Mm-$C_3$-Val-Ala-PAB-PNP to obtain a pale yellow solid powder (20% yield). $^1$H-NMR (400 MHz, DMSO-d6)δ 15.22 (br, 1H), 10.03 (s, 1H), 9.18 (br, 1H), 8.32 (d, J=9.3 Hz, 2H), 8.22 (d, 1H), 7.84 (d, J=6.7 Hz, 1H), 7.64 (d, J=8.4 Hz, 2H), 7.57 (d, J=9.0 Hz, 2H), 7.41 (d, J=8.4 Hz, 2H), 6.37 (d, J=12.6 Hz, 1H), 6.24 (d, J=12.6 Hz, 1H), 5.24 (s, 2H), 4.40 (m, 1H), 4.18 (t, J=7.6 Hz, 1H), 3.16 (q, 2H), 2.22-2.18 (m, 2H), 1.96 (m, 1H), 1.47 (m, 4H), 1.28 (m, 5H), 0.86 (m, 6H).

3) Preparation of Maa-$C_6$-Val-Ala-PAB-MMAE

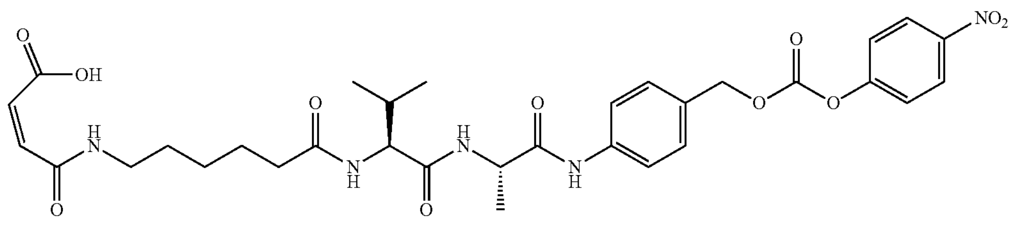

Maa-$C_6$-Val-Ala-PAB-PNP

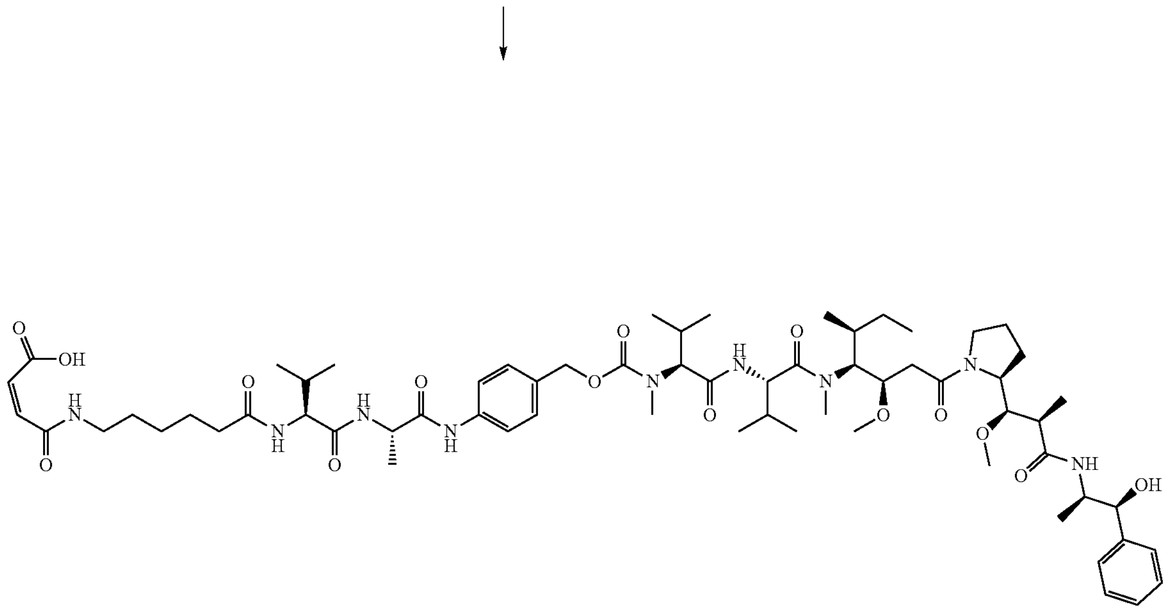

Maa-$C_6$-Val-Ala-PAB-MMAE

The linker Maa-$C_6$-Val-Ala-PAB-PNP was used as raw material, Maa-$C_6$-Val-Ala-PAB-MMAE was synthesized by using a preparation method similar to that of Mm-$C_6$-Val-Ala-PAB-MMAE to obtain a white solid Powder (57% yield). MS(ESI) m/z: 1249.2 $[M+H]^+$; 1266.2 $[M+NH_4]^+$; 625.3 $[M+2H]^{2+}$; 1247.1 $[M-H]^-$.

10.2 Preparation of Maa-$C_6$-Val-Cit-PAB-MMAE

1) Preparation of Maa-$C_6$-Val-Cit-PAB

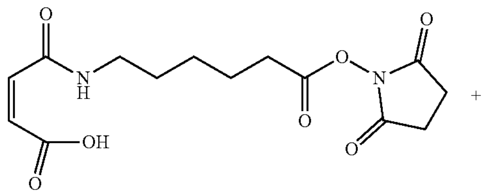

Maa-$C_6$-OSu

-continued

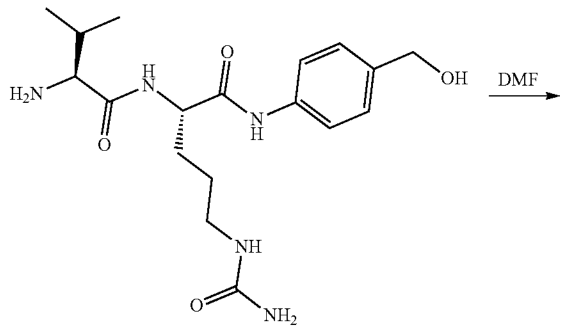

Val-Cit-PAB

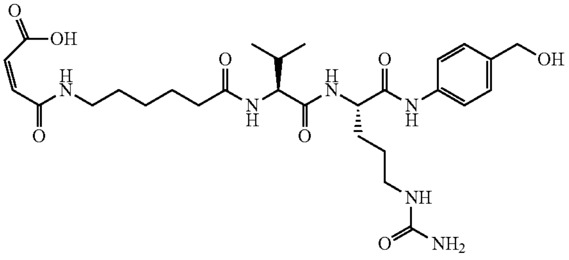

Maa-$C_6$-Val-Cit-PAB

Maa-$C_6$-OSu was used as raw material, and Maa-$C_6$-Val-Cit-PAB was synthesized by a method similar to that of Mm-$C_6$-Val-Cit-PAB to obtain a pale yellow solid powder (84% yield). $^1$H-NMR (400 MHz, DMSO-d6)δ 11.60 (br, 1H), 9.91 (s, 1H), 9.62 (br, 1H), 8.11 (d, J=6.7 Hz, 1H), 7.89 (d, J=6.7 Hz, 1H), 7.54 (d, 2H), 7.23 (d, 2H), 6.21 (m, 1H), 6.05 (m, 1H), 5.45 (d, 2H), 5.11 (br, 1H), 4.42 (s, 2H), 4.37 (t, 1H), 4.19 (t, 1H), 3.14 (m, 2H), 3.05-2.91 (m, 2H), 2.23-2.11 (m, 2H), 1.96 (m, 1H), 1.70 (m, 1H), 1.59 (m, 1H), 1.54-1.33 (m, 6H), 1.26 (m, 2H), 0.84 (dd, 6H).

2) Preparation of Maa-C-Val-Cit-PAB-PNP

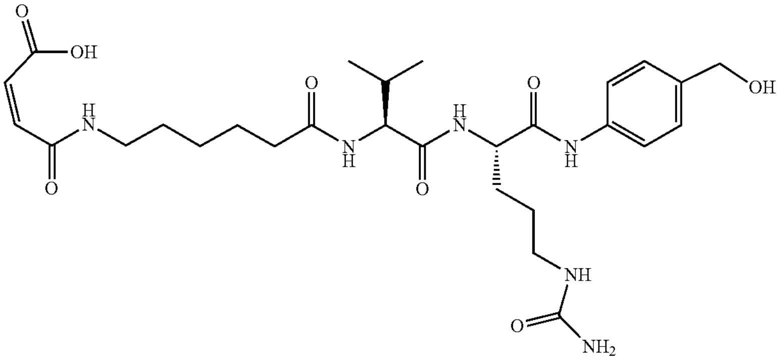

Maa-$C_6$-Val-Cit-PAB

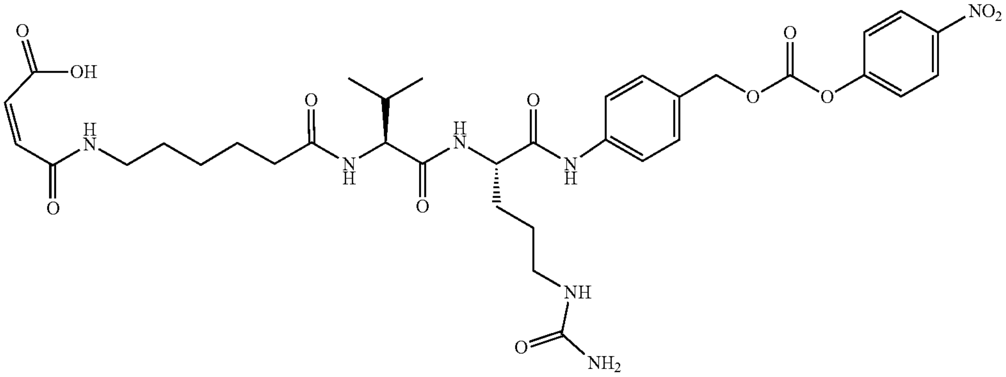

Maa-$C_6$-Val-Cit-PAB-PNP

The intermediate Maa-$C_6$-Val-Cit-PAB was used as raw material, and Maa-$C_6$-Val-Cit-PAB-PNP was synthesized by using a preparation method similar to that of Mm-$C_6$-Val-Ala-PAB-PNP to obtain a pale yellow solid powder (16% yield). $^1$H-NMR (400 MHz, DMSO-d6): δ 15.22 (br, 1H), 10.10 (s, 1H), 9.31 (br, 1H), 8.31 (d, J=9.0 Hz, 2H), 8.15 (t, J=5.2 Hz, 1H), 7.86 (d, J=8.4 Hz, 1H), 7.65 (d, J=8.4 Hz, 2H), 7.57 (d, J=9.24 Hz, 2H), 7.41 (d, J=8.4 Hz, 2H), 7.22 (d, 1H), 6.36 (d, J=12.6 Hz, 1H), 6.23 (d, J=12.6 Hz, 1H), 6.03 (s, 1H), 5.46 (s, 2H), 5.24 (s, 2H), 4.42 (m, 1H), 4.19 (m, 1H), 3.16 (q, 2H), 3.05-2.92 (m, 2H), 2.17 (m, 2H), 1.97 (m, 1H), 1.73-1.57 (m, 2H), 1.52-1.44 (m, 6H), 1.27 (m, 2H), 0.85 (dd, 6H). MS(ESI) m/z: 756.7 $[M+H]^+$; 778.4 $[M+Na]^+$; 754.6 $[M-H]^-$.

3) Preparation of Maa-$C_6$-Val-Cit-PAB-MMAE

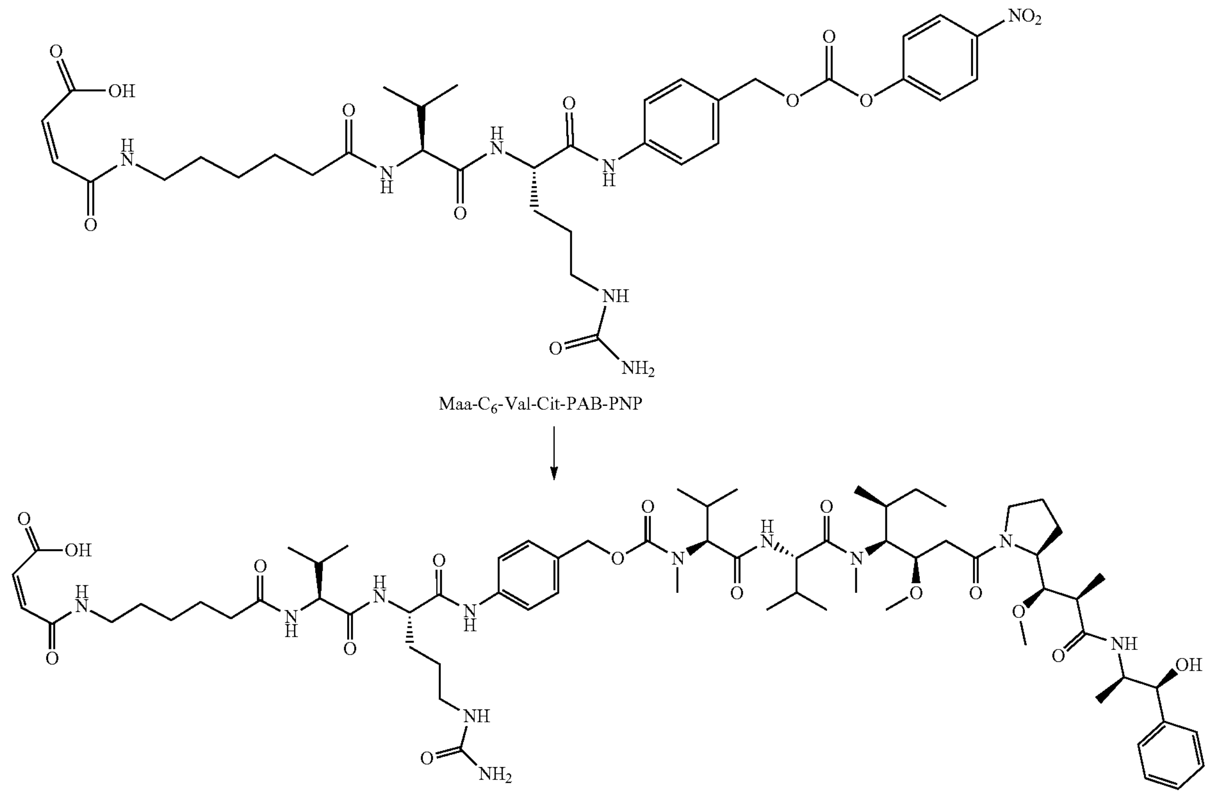

Maa-$C_6$-Val-Cit-PAB-PNP

Maa-$C_6$-Val-Cit-PAB-MMAE

The linker Maa-$C_6$-Val-Cit-PAB-PNP was used as raw material, and Maa-$C_6$-Val-Cit-PAB-MMAE was synthesized by using a preparation method similar to that of Mm-$C_6$-Val-Ala-PAB-MMAE to obtain a white solid powder (57% yield). MS(ESI) m/z: 1334.3 $[M+H]^+$; 689.5 $[M+2Na]^2$+.

The structures of the conjugates of the linkers containing maleic acid amide (Maa) and MMAE prepared in Example 10 were shown in the following table:

| Linker-MMAE conjugate |
| --- |
| Maa-$C_6$-Val-Ala-PAB-MMAE: 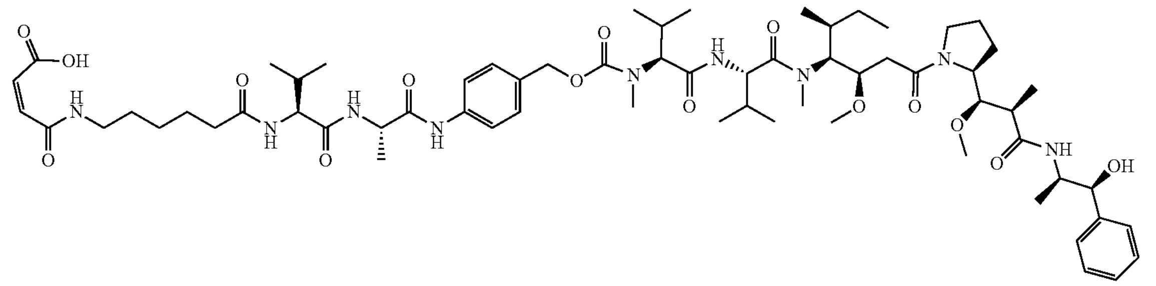 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](C)NC(=O)[C@@H](NC(=O)CCCCCNC(=O)/C=C\C(=O)O)C(C)C)cc1)C(C)C] |
| Maa-$C_6$-Val-Cit-PAB-MMAE: |

-continued

Linker-MMAE conjugate

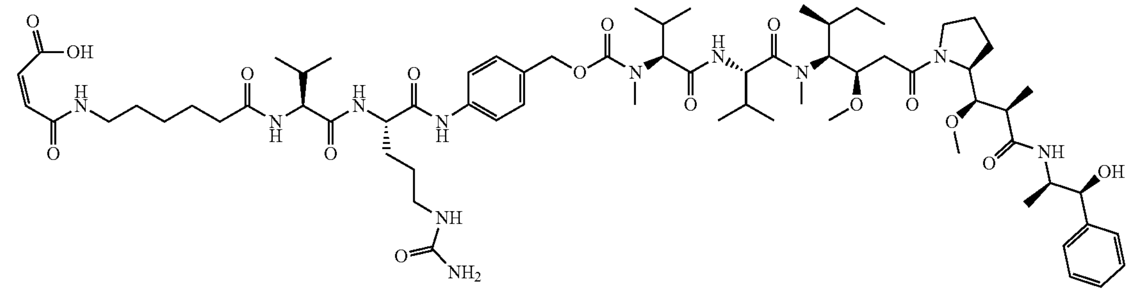 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)CCCCCNC(=O)/C=C\C(=O)O)C(C)C)cc1)C(C)C]

Example 11: Preparation of Conjugate of Linker Containing Methyl Fumarate Structure (Mf) and Cytotoxin MMAE

11.1 Preparation of Mf-$C_6$-Val-Ala-PAB-MMAE

1) Preparation of Mf-$C_6$—OH

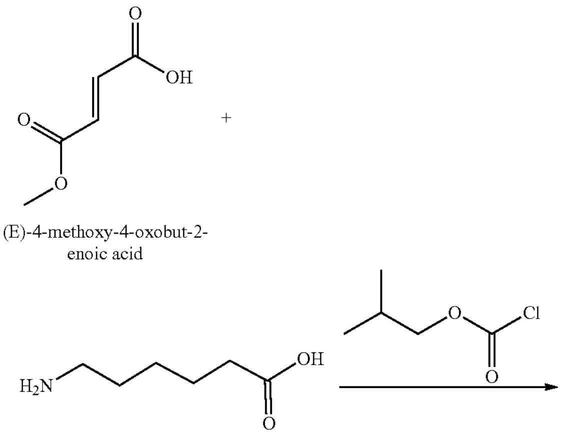

(E)-4-methoxy-4-oxobut-2-enoic acid 6-aminohexanoic acid

-continued

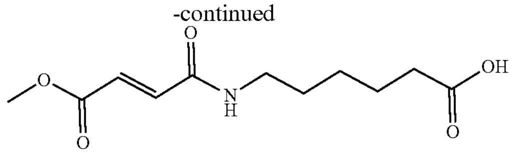

Mf-$C_6$-OH

Monomethyl fumarate (2.0 g, 15.37 mM) was dissolved in dichloromethane (50 mL), and 4-methylmorpholine (2.54 mL, 23.06 mM) was added, and the resulting mixed solution was cooled to −20° C. Isobutyl chloroformate (2 mL) was added dropwise, and stirred at −20° C. for 3 hours. A suspension of sonicated 6-aminohexanoic acid (2.02 g, 15.37 mM) in DMF (60 mL) was added, stirred for 1 hour at −20° C., and then warmed to room temperature and stirred for 2 hours, and then evaporated to remove the solvent. The resulting residue was an orange oil, water (150 mL) was added to the residue, and the resulting mixture was adjusted to have a pH of 1 with concentrated hydrochloric acid to precipitate out a solid, the solid was filtered by suction filtration, and dried to obtain a pale pink solid (3.33 g, 89% yield). $^1$H-NMR (400 MHz, DMSO-d6): δ 12.02 (s, 1H), 8.54 (t, 1H), 7.00 (d, 1H), 6.57 (d, 1H), 3.72 (s, 3H), 3.15 (m, 2H), 2.19 (t, 2H), 1.49 (m, 2H), 1.43 (m, 2H), 1.27 (m, 2H). MS(ESI) m/z: 242.10 $[M-H]^-$.

2) Preparation of Mf-$C_6$-VA-PAB

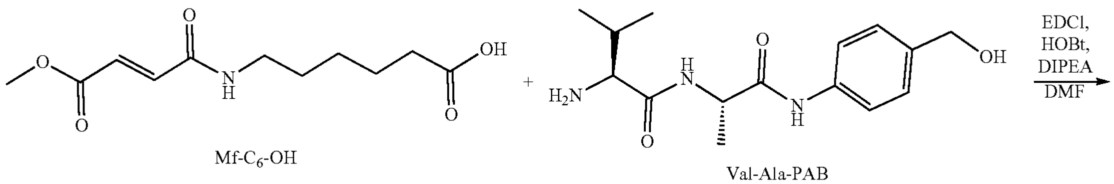

Mf-$C_6$-OH

Val-Ala-PAB

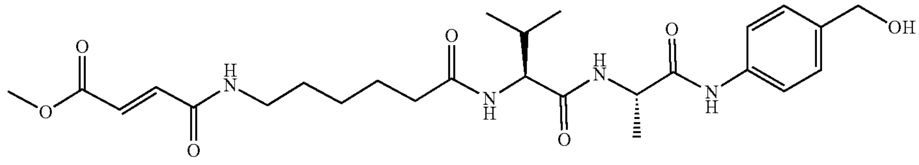

Mf-$C_6$-Val-Ala-PAB

Mf-$C_6$—OH (0.61 g, 2.5 mM) was dissolved in DMF (8 mL), and EDCI (0.71 g, 3.7 mM), HOBt (0.5 g, 3.7 mM) and DIPEA (0.61 mL, 3.7 mM) were added, stirred at room temperature for 1 hour, then Val-Cit-PABOH (0.87 g, 3.0 mM) in DMF (12 mL) solution was added, stirred at room temperature for 10 hours, evaporated to remove the solvent, and the resulting residue was mixed with crude silica gel, and separated on a silica gel column to obtain a white solid product (1.05 g, 81% yield). $^1$H-NMR (400 MHz, DMSO-d6): δ 9.91 (s, 1H), 8.56 (t, 1H), 8.19 (d, 1H), 7.86 (d, 1H), 7.54 (d, 2H), 7.23 (d, 2H), 7.01 (d, 1H), 6.56 (d, 1H), 5.13 (br, 1H), 4.42 (s, 2H), 4.38 (m, 1H), 4.17 (q, 1H), 3.72 (s, 3H), 3.12 (m, 2H), 2.16 (m, 2H), 1.96 (m, 1H), 1.43 (m, 4H), 1.31 (s, 2H), 1.30 (s, 3H), 0.85 (dd, 6H). MS(ESI) m/z: 541.26 $[M+H]^+$.

3) Preparation of Mf-$C_6$-VA-PAB-PNP

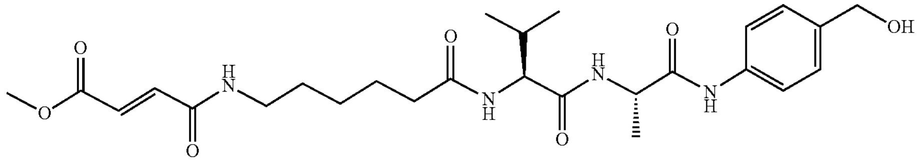

Mf-$C_6$-Val-Ala-PAB

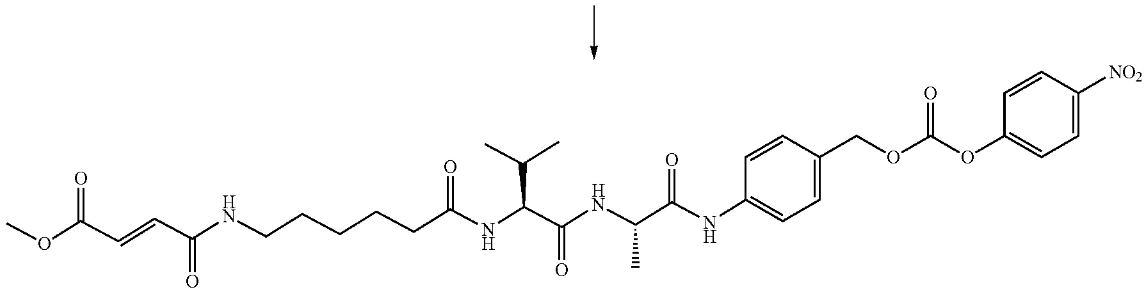

Mf-$C_6$-Val-Ala-PAB-PNP

Mf-$C_6$-VA-PAB (0.5 g, 0.96 mM) was dissolved in DMF (8 mL), bis(4-nitrophenyl) carbonate (0.88 g, 2.89 mM) and DIPEA (0.34 mL, 1.92 mM) were added, stirred at room temperature for 10 hours, then evaporated to remove the solvent, sonicated with anhydrous diethyl ether, filtered by suction filtration, dried and then pulverized, ethyl acetate was added at a ratio of 20 mL/g, stirred at room temperature for 3 hours, and filtered by suction filtration to obtain a solid (0.49 g, 75% yield). $^1$H-NMR (400 MHz, DMSO-d6): δ 10.04 (s, 1H), 8.53 (br, 1H), 8.31 (d, 2H), 8.22 (d, 1H), 7.85 (d, 1H), 7.64 (d, 2H), 7.57 (d, 2H), 7.41 (d, 2H), 7.01 (d, 1H), 6.56 (d, 1H), 5.24 (s, 2H), 4.39 (t, 1H), 4.18 (t, 1H), 3.71 (s, 3H), 3.13 (q, 2H), 2.16 (m, 2H), 1.95 (m, 1H), 1.49 (br, 2H), 1.43 (t, 2H), 1.31 (d, 3H), 1.24 (m, 2H), 0.85 (dd, 6H). MS(ESI) m/z: 684.29 $[M+H]^+$; 706.27 $[M+Na]^+$; 722.24 $[M+K]^+$.

4) Preparation of Mf-$C_6$-VA-PAB-MMAE

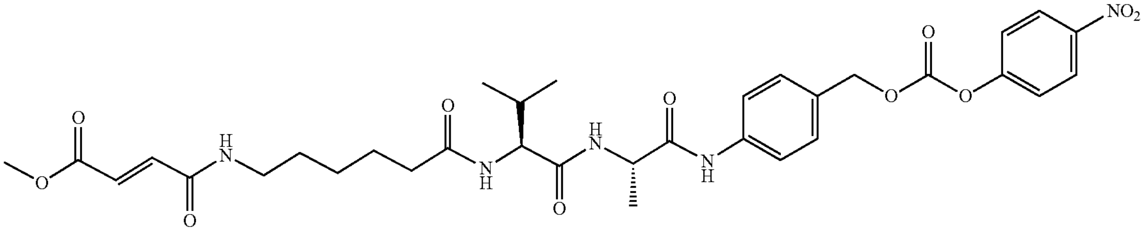

Mf-$C_6$-Val-Ala-PAB-PNP

-continued

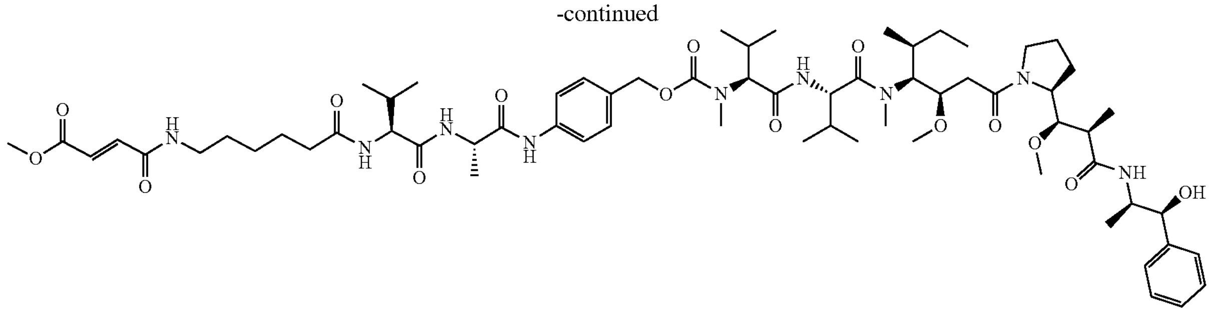

Mf-$C_6$-Val-Ala-PAB-MMAE

Mf-$C_6$-Val-Ala-PAB-PNP (29.99 mg, 0.04387 mM) was dissolved in DMF (2 mL), and HOBt (5.93 mg, 0.04387 mM), MMAE (30 mg, 0.04178 mM) and DIPEA (0.0056 g, 0.04387 mM) were added in sequence, and stirred at room temperature for 8 hours. The resulting reaction solution was transferred to a separatory funnel, 15 mL of water was added, the resulting mixture was extracted 4 times with 20 mL of ethyl acetate. The organic phases were combined, washed twice with saturated sodium chloride solution, then stood for 1 hour, and then evaporated to remove the solvent, the resulting residue was mixed with 100 mg of crude silica gel, separated by silica gel column with gradient elution to obtain a product as a white solid (37 mg, 71% yield). $^1$H-NMR (400 MHz, $CDCl_3$): δ 9.21 (br, 1H), 7.52 (t, 4H), 7.31 (m, 5H), 7.21 (m, 3H), 6.84 (dd, 1H), 6.74 (m, 1H), 6.56 (m, 0.5H), 5.06 (m, 2H), 4.91 (s, 1H), 4.73 (m, 3H), 4.46 (t, 1H), 4.23 (m, 1H), 4.12 (m, 1H), 4.02 (m, 1H), 3.79 (s, 4H), 3.46 (m, 1H), 3.36 (s, 5H), 3.25 (d, 4H), 3.12 (d, 1H), 2.99 (s, 2H), 2.88 (d, 3H), 2.73 (d, 0.5H), 2.43 (m, 2H), 2.28 (s, 2H), 2.17 (m, 1H), 2.02 (m, 3H), 1.81 (s, 2H), 1.63 (m, 3H), 1.51 (m, 2H), 1.38 (d, 2H), 1.30 (t, 3H), 1.21 (d, 4H), 1.01 (m, 8H), 0.79 (m, 24H). MS(ESI) m/z: 1280.3 $[M+NH_4]^+$; 1285.0 $[M+Na]^+$.

11.2 Preparation of Mf-$C_3$-Val-Ala-PAB-MMAE

1) Preparation of Mf-$C_3$—OH

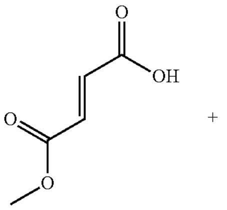

(E)-4-methoxy-4-oxobut-2-enoic acid

-continued

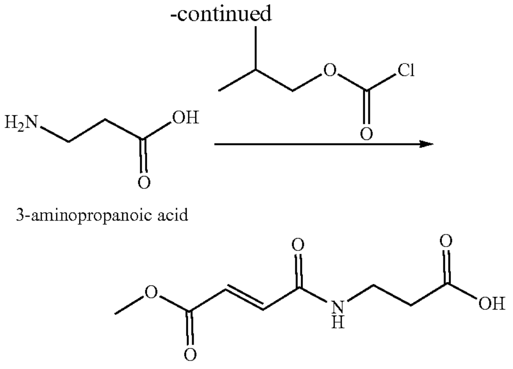

3-aminopropanoic acid

Mf-$C_3$-OH

Monomethyl fumarate (2.0 g, 15.37 mM) was dissolved in dichloromethane (50 mL), and 4-methylmorpholine (2.54 mL, 23.06 mM) was added, and the resulting solution was cooled to −20° C. Isobutyl chloroformate (2 mL) was added dropwise, and stirred at −20° C. for 3 hours. A suspension of sonicated $-alanine (1.37 g, 15.37 mM) in DMF (60 mL) was added, stirred for 1 hour at −20° C., then warmed to room temperature and stirred for 2 hours, and then evaporated to remove the solvent, sonicated with anhydrous diethyl ether, filtered by suction filtration to obtain a brown solid, the brown solid was mixed with crude silica gel and subjected to silica gel column chromatography to obtain a white powdery solid (0.72 g, 23% yield). $^1$H-NMR (400 MHz, DMSO-d6): δ 12.32 (s, 1H), 8.68 (t, 1H), 7.01 (d, 1H), 6.60 (d, 1H), 3.72 (s, 3H), 3.36 (t, 2H), 2.44 (t, 2H). MS(ESI) m/z: 200.06 $[M-H]^-$ 2) Preparation of Mf-$C_3$-Val-Ala-PAB

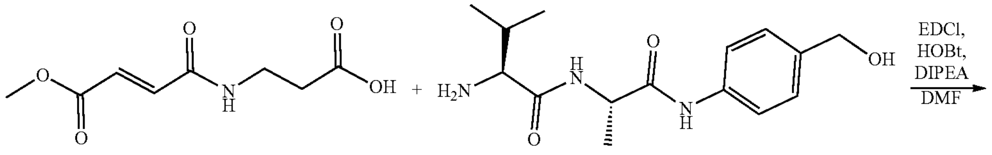

Mf-$C_3$-OH Val-Ala-PAB

-continued

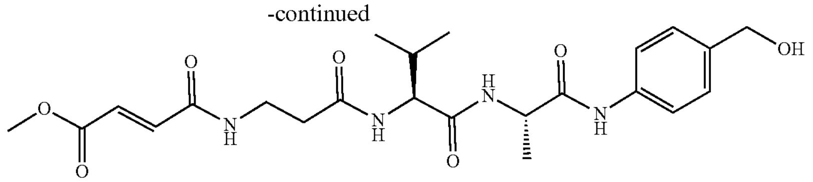

Mf-$C_3$-Val-Ala-PAB

Mf-$C_3$—OH (0.51 g, 2.53 mM) was dissolved in DMF (10 mL), EDCI (0.73 g, 3.79 mM), HOBt (0.51 g, 3.75 mM) and DIPEA (0.66 mL, 3.79 mM) were added in sequence, stirred at room temperature for 1 hour, then Val-Ala-PABOH (0.89 g, 3.03 mM) in DMF solution (20 mL) was added, stirred for 12 h at room temperature, then evaporated to remove the solvent. The resulting residue was mixed with crude silica gel and separated by a silica gel column to obtain a pale yellow solid (0.7 g, 58% yield). $^1$H-NMR (400 MHz, DMSO-d6): δ 9.86 (s, 1H), 8.63 (t, 1H), 8.21 (d, 1H), 7.98 (d, 1H), 7.54 (d, 2H), 7.23 (d, 2H), 7.01 (d, 1H), 6.56 (d, 1H), 5.12 (t, 1H), 4.42 (d, 2H), 4.39 (m, 1H), 4.19 (t, 1H), 3.71 (s, 3H), 2.41 (m, 2H), 1.96 (m, 1H), 1.30 (d, 3H), 0.85 (q, 6H). MS(ESI) m/z: 477.3 $[M+H]^+$; 494.4 $[M+NH_4]^+$; 499.4 $[M+Na]^+$.

3) Preparation of Mf-$C_3$-Val-Ala-PAB-PNP

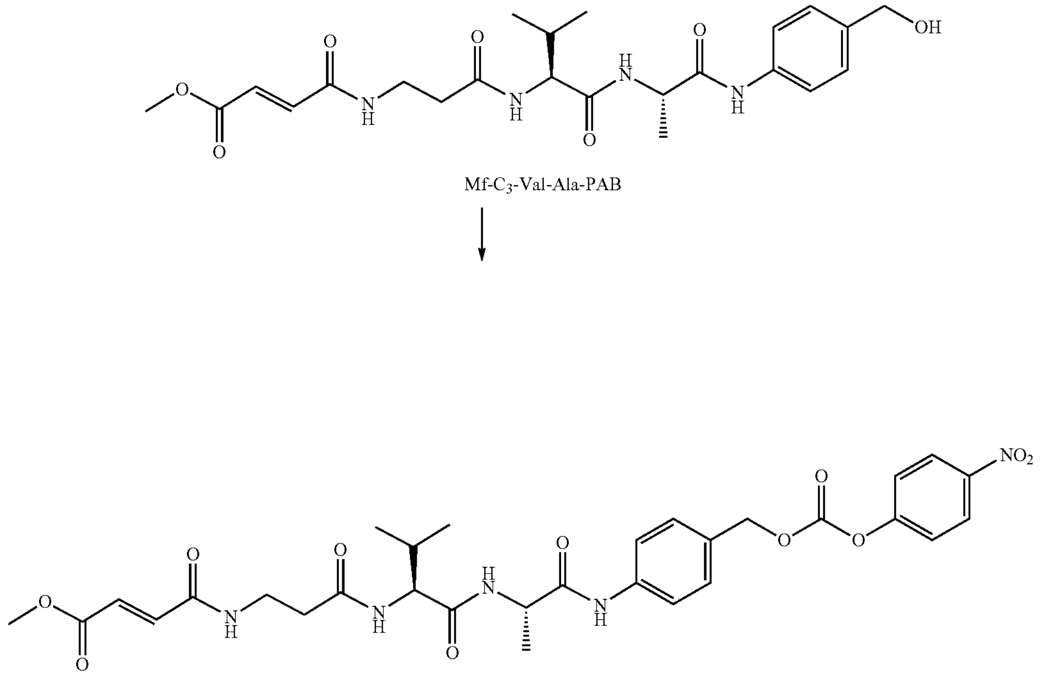

Mf-$C_3$-Val-Ala-PAB

Mf-$C_3$-Val-Ala-PAB-PNP

Mf-$C_3$-VA-PAB (0.3 g, 0.63 mM) was dissolved in DMF (6 mL), bis(4-nitrophenyl) carbonate (0.57 g, 1.89 mM) and DIPEA (0.22 mL, 1.26 mM) were added, stirred at room temperature for 10 hours. The resulting reaction solution was added dropwise into distilled water (60 mL) and filtered by suction filtration to obtain a gray solid. The gray solid was dried, and sonicated with anhydrous diethyl ether (15 mL), filtered by suction filtration, the resulting residue was mixed with ethyl acetate (15 mL) and stirred at room temperature for 3 hours to obtain a dark red solid (0.3 g, 74% yield). $^1$H-NMR (400 MHz, DMSO-d6): δ 10.02 (s, 1H), 8.62 (br, 1H), 8.32 (d, 2H), 8.26 (d, 1H), 8.00 (d, 1H), 7.64 (d, 2H), 7.57 (d, 2H), 7.41 (d, 2H), 7.01 (d, 1H), 6.56 (d, 1H), 5.24 (s, 2H), 4.38 (m, 1H), 4.20 (t, 1H), 3.71 (s, 3H), 2.41 (br, 2H), 1.96 (m, 1H), 1.31 (d, 3H), 0.86 (dd, 6H). MS(ESI) m/z: 642.3 $[M+H]^+$; 659.6 $[M+NH_4]^+$; 664.4 $[M+Na]^+$.

4) Preparation of Mf-$C_3$-Val-Ala-PAB-MMAE

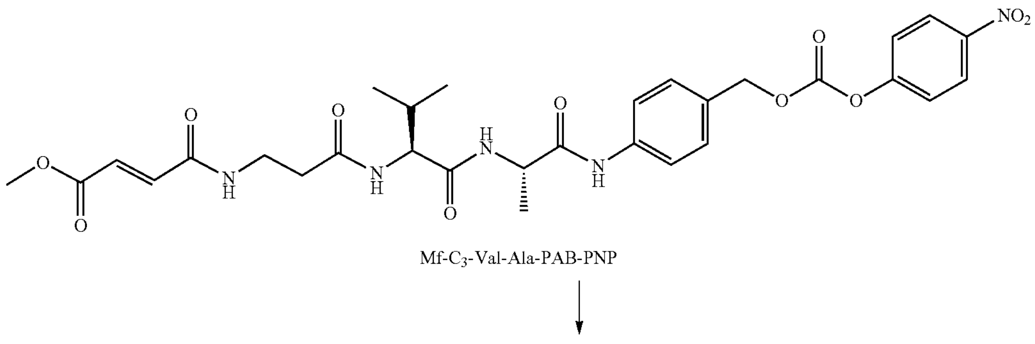

Mf-$C_3$-Val-Ala-PAB-PNP

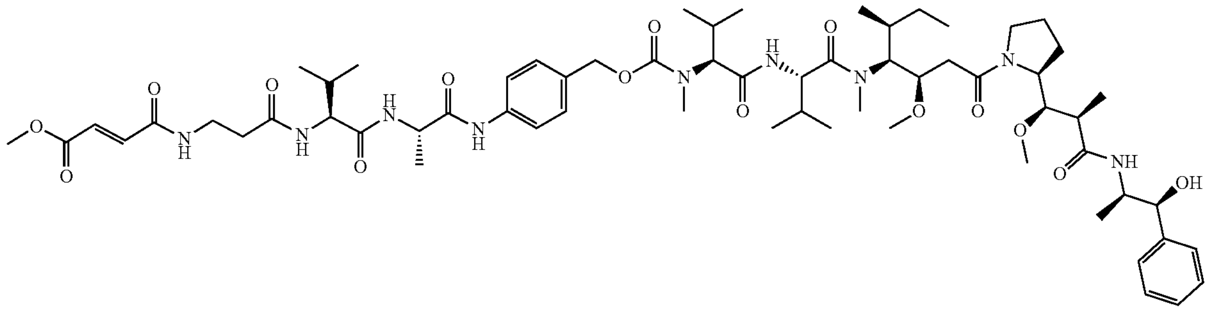

Mf-$C_3$-Val-Ala-PAB-MMAE

Mf-$C_3$-VA-PAB-PNP (46.89 mg, 0.07312 mM) was dissolved in DMF (4 mL), HOBt (9.88 mg, 0.07312 mM), MMAE (50 mg, 0.07312 mM) and DIPEA (13 μL, 0.07312 mM) were added in sequence, stirred at room temperature for 8 hours. The resulting reaction solution was poured into a separatory funnel, 40 mL of water was added, and the resulting mixture was extracted with 20 mL of ethyl acetate for three times. The organic phases were combined, washed twice with saturated sodium chloride solution, and the resulting saturated sodium chloride solution was extracted once with ethyl acetate. The organic phases were combined, stood for 1 hour, and evaporated to remove the solvent, the resulting residue was mixed with 180 mg of crude silica gel, and separated by a silica gel column to obtain a product as a white solid (61 mg, 68% yield). $^1$H-NMR (400 MHz, $CDCl_3$): δ 7.63 (m, 1H), 7.34 (m, 6H), 7.16 (d, 1H), 6.78 (d, 1H), 5.30 (s, 2H), 5.01 (m, 0.5H), 4.92 (m, 1H), 4.73 (m, 1H), 4.64 (m, 1H), 4.42 (m, 0.5H), 4.21 (m, 3H), 4.03 (m, 0.5H), 3.88 (m, 0.5H), 3.76 (s, 4H), 3.54 (m, 3H), 3.40 (s, 5H), 3.36 (m, 1H), 3.29 (s, 3H), 3.01 (s, 2H), 2.89 (t, 4H), 2.64 (m, 2H), 2.42 (m, 2H), 2.19 (m, 1H), 2.03 (m, 5H), 1.84 (br, 6H), 1.45 (m, 4H), 0.98 (m, 8H), 0.84 (m, 24H). MS(ESI) m/z: 1221.0 $[M+H]^+$; 1238.0 $[M+NH_4]^+$; 1243.1 $[M+Na]^+$.

11.3 Preparation of Mf-$C_6$-Val-Cit-PAB-MMAE

1) Preparation of Mf-$C_6$—VC-PAB

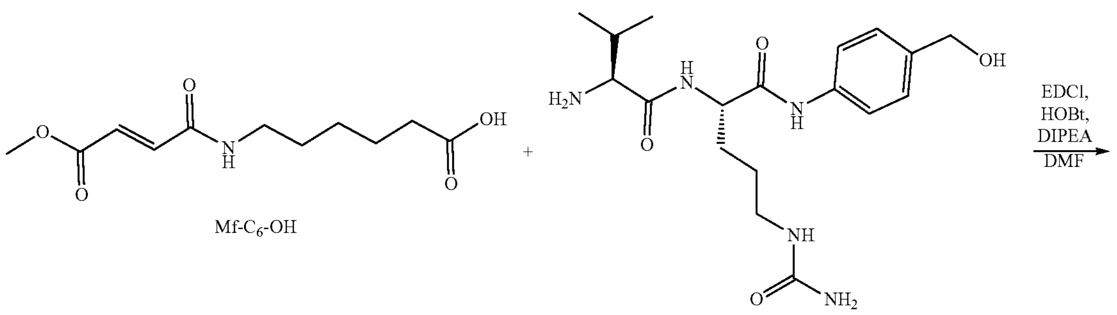

Mf-$C_6$-OH

Val-Cit-PAB

-continued

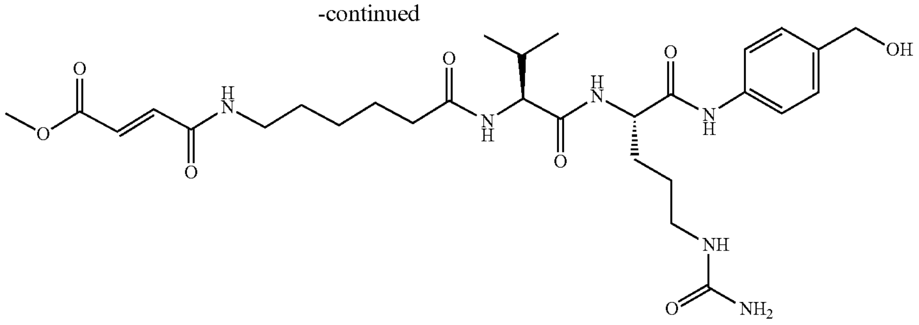

Mf-C6-Val-Cit-PAB

Mf-$C_6$—OH (0.53 g, 2.20 mM) was dissolved in DMF (10 mL), and EDCI (0.63 g, 3.29 mM), HOBt (0.44 g, 3.29 mM) and DIPEA (0.57 mL, 3.29 mM) were added, stirred at room temperature for 1 hour; Val-Cit-PABOH (1 g, 2.64 mM) in DMF solution (20 mL) was added, stirred at room temperature for 10 hours, evaporated to remove the solvent, the resulting residue was mixed with crude silica gel, and separated by silica gel column to obtain a white solid product (0.52 g, 39% yield). $^1$H-NMR (400 MHz, DMSO-d6): δ 9.93 (s, 1H), 8.54 (t, 1H), 8.07 (d, 1H), 7.83 (d, 1H), 7.55 (d, 2H), 7.22 (d, 2H), 7.01 (d, 1H), 6.56 (d, 1H), 6.03 (t, 1H), 5.42 (s, 2H), 5.10 (t, 1H), 4.42 (d, 2H), 4.37 (m, 1H), 4.19 (m, 1H), 3.72 (s, 3H), 3.15 (m, 2H), 2.99 (m, 2H), 2.16 (m, 2H), 1.98 (m, 1H), 1.66 (m, 2H), 1.44 (m, 6H), 1.25 (m, 2H), 0.84 (dd, 6H). MS(ESI) m/z: 605.5 $[M+H]^+$; 627.5 $[M+Na]^+$.

2) Preparation of Mf-$C_6$—VC-PAB-PNP

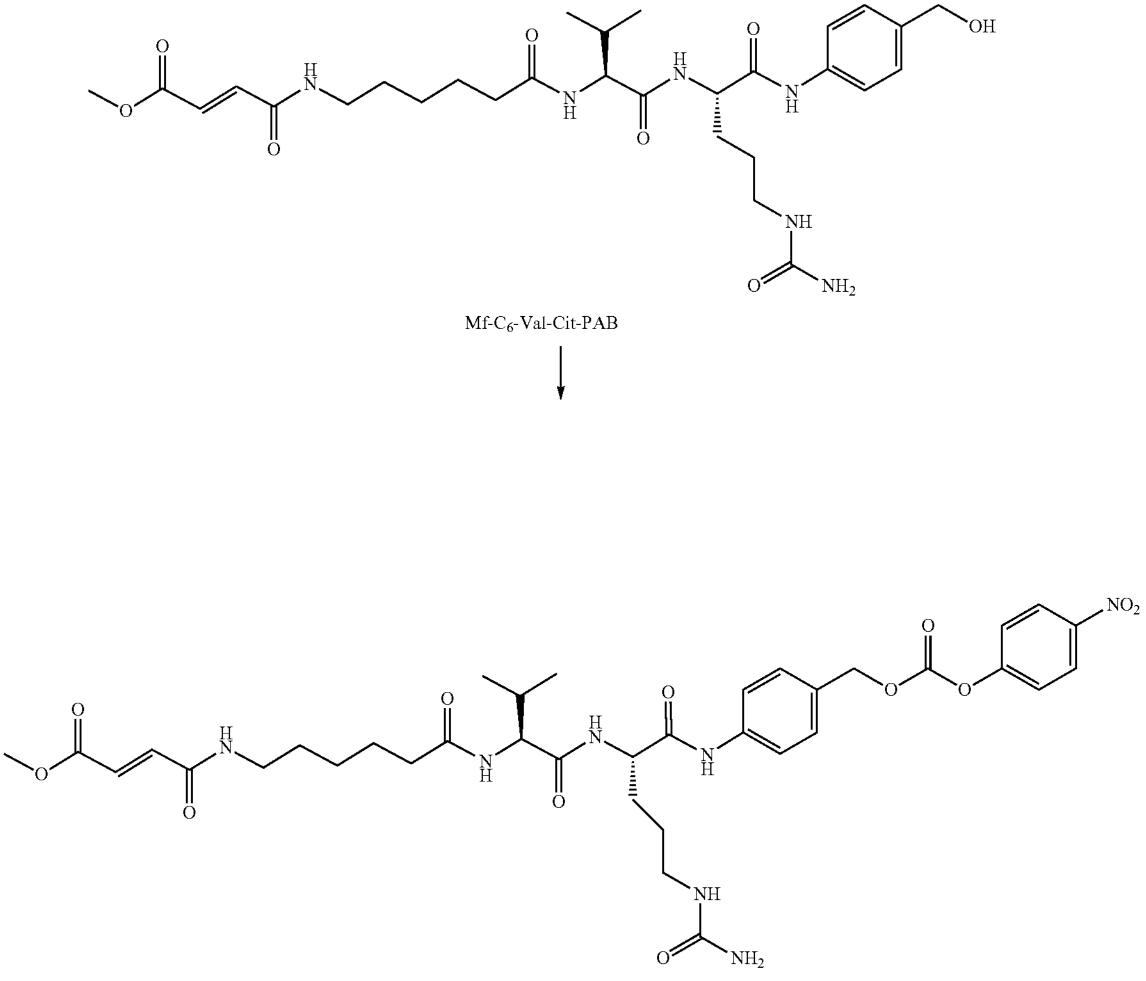

Mf-C6-Val-Cit-PAB

Mf-C6-Val-Cit-PAB-PNP

Mt—$C_6$-Vit-Cit-PAB (0.3 g, 0.496 mM) was dissolved in DMF (8 mL), bis(4-nitrophenyl) carbonate (0.45 g, 1.49 mM) and DIPEA (0.17 mL, 0.99 mM) were added, stirred at room temperature for 12 hours. The resulting reaction solution was added dropwise into 70 mL of distilled water, filtered by suction filtration, and the obtained solid was dried, treated with anhydrous diethyl ether, mixed with ethyl acetate at a ratio of 20 mL/g and stirred at room temperature for 3 hours, and filtered by suction filtration to obtain a pale yellow solid (0.27 g, 71% yield). $^1$H-NMR (400 MHz, DMSO-d6): δ 10.09 (s, 1H), 8.53 (br, 1H), 8.32 (d, 2H), 8.15 (d, 1H), 7.84 (d, 1H), 7.65 (d, 2H), 7.57 (d, 2H), 7.41 (d, 2H), 6.98 (d, 1H), 6.56 (d, 1H), 5.99 (br, 1H), 5.45 (s, 2H), 5.24 (s, 2H), 4.38 (br, 1H), 4.19 (t, 1H), 3.71 (s, 3H), 3.13 (d, 2H), 3.03 (m, 1H), 2.93 (m, 1H), 2.16 (m, 2H), 1.99 (s, 1H), 1.93 (m, 1H), 1.69 (m, 1H), 1.60 (m, 1H), 1.49 (m, 1H), 1.43 (t, 2H), 1.25 (m, 4H), 0.84 (dd, 6H). MS(ESI) m/z: 770.6 $[M+H]^+$; 792.4 $[M+Na]^+$.

3) Preparation of Mf-$C_6$-Vit-Cit-PAB-MMAE

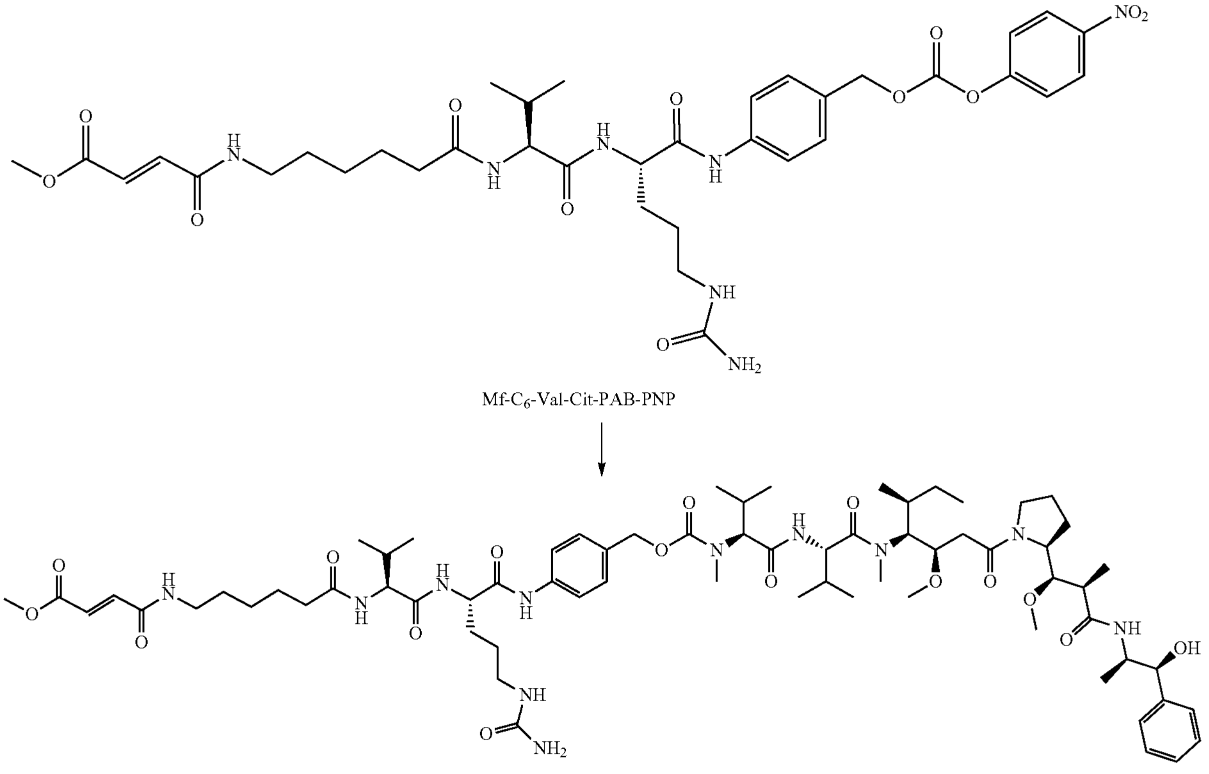

Mf-$C_6$-Val-Cit-PAB-PNP

Mf-$C_6$-Val-Cit-PAB-MMAE

Mf-$C_6$-Val-Cit-PAB-PNP (68 mg, 0.0877 ml) was dissolved in DMF (6 m), HOBt (11.86 mg, 0.0877 mM), MMAE (60 mg, 0.0836 mM) and DIPEA (15 μL, 0.0877 mM) were added in sequence, stirred at room temperature for 8 hours. The resulting reaction solution was poured into a separatory funnel, 40 mL of water was added, and the resulting mixture was extracted 6 times with 20 mL of ethyl acetate. The organic phases were combined, washed twice with saturated sodium chloride solution, and the resulting saturated sodium chloride solution was extracted twice with ethyl acetate. The organic phases were combined, stood for 1 hour, and evaporated to remove the solvent, and the resulting residue was mixed with 200 mg of crude silica gel, and separated by silica gel column to obtain a product as a white solid. (63 mg, 56% yield). $^1$H-NMR (400 MHz, DMSO-d6): δ 10.01 (br, 1H), 8.54 (t, 1H), 8.13 (d, 1H), 7.92 (d, 0.5H), 7.84 (d, 1H), 7.67 (d, 0.5H), 7.58 (d, 2H), 7.30 (m, 6H), 7.16 (m, 1H), 7.01 (d, 1H), 6.57 (d, 1H), 6.00 (br, 1H), 5.45 (br, 2H), 5.37 (d, 0.5H), 5.01 (m, 2H), 4.74 (m, 0.5H), 4.64 (m, 0.5H), 4.42 (m, 3H), 4.23 (m, 2H), 3.98 (m, 2H), 3.71 (s, 3H), 2.91 (m, 8H), 2.41 (d, 1H), 2.21 (m, 6H), 1.98 (m, 4H), 1.74 (m, 4H), 1.49 (m, 8H), 1.26 (m, 6H), 1.02 (m, 9H), 0.91 (m, 4H), 0.82 (m, 24H). MS(ESI) m/z: 1349.3 [M+H]; 1371.0 [M+Na].

The structures of the conjugates of the linkers containing methyl fumarate and MMAE as prepared in Example 11 were shown in the following table:

Linker-MMAE conjugate

Mf-$C_6$-Val-Ala-PAB-MMAE:

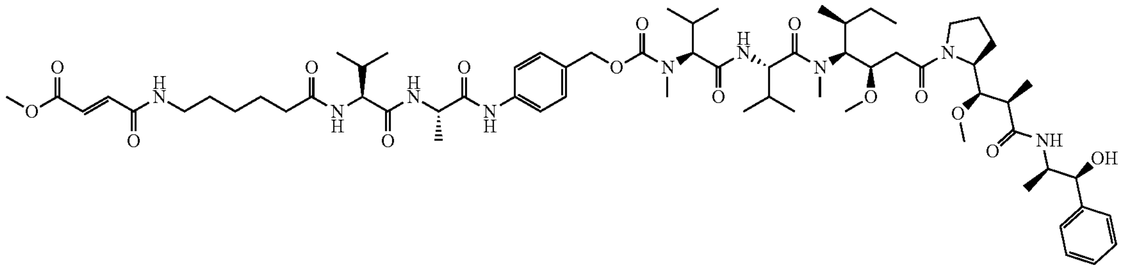 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](C)NC(=O)[C@@H](NC(=O)CCCCCNC(=O)/C=C/C(=O)OC)C(C)C)cc1)C(C)C]

Mf-$C_3$-Val-Ala-PAB-MMAE:

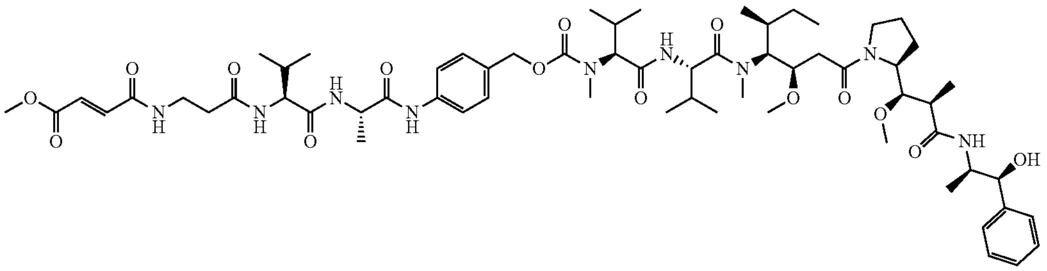 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](C)NC(=O)[C@@H](NC(=O)CCNC(=O)/C=C/C(=O)OC)C(C)C)cc1)C(C)C]

Mf-$C_6$-Val-Cit-PAB-MMAE:

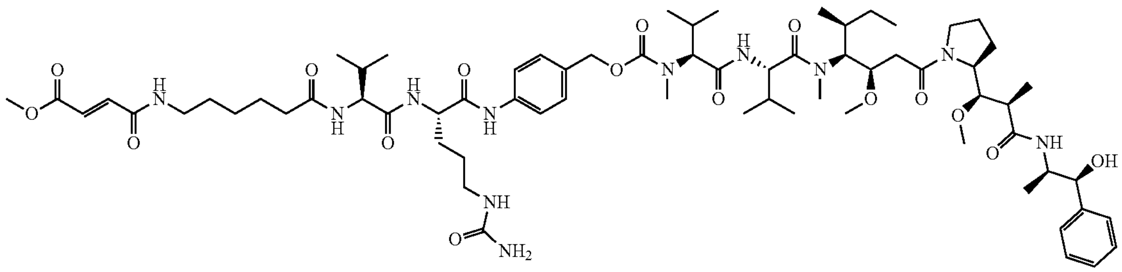 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)CCCCCNC(=O)/C=C/C(=O)OC)C(C)C)cc1)C(C)C]

Example 12: Preparation of ADC

The linker-MMAE conjugate prepared in Example 7 was coupled to anti-HER2 humanized monoclonal antibody.

1) Preparation of Commonly Used Buffer Salt Solutions:

Buffer salt solution-1 (buffer-1): 3.11 g of L-histidine was taken and dissolved in 1 L of double-distilled water, after the dissolution was completed, the resulting mixture was adjusted by using medical glacial acetic acid to have pH of about 5.50 (+0.05), then sterilized by filtration with a 0.22 μm filter membrane, bottled and stored at 4° C. for short-term storage until use.

Buffer salt solution-2 (buffer-2): 6.06 g of TRIS·base and 0.93 g of EDTA·2Na were weighed, dissolved and diluted to 100 mL; 7.88 g of TRIS·HCl and 0.93 g of EDTA·2Na were weighed, dissolved and diluted to 100 mL as well; the resulting TRIS·HCl solution was added to the resulting TRIS·base solution, mutually adjusted to have pH=8.50 (+0.05); the resulting mixture was sterilized by filtration with a 0.22 μm filter membrane, bottled and stored at 4° C. for short-term storage until use.

Buffer salt solution-3 (buffer-3): 1.715 mL of medical glacial acetic acid was taken by using a pipette, dissolved in 200 mL of double-distilled water, mixed well, sterilized by filtration with a 0.22 μm filter membrane, and then bottled and stored at 4° C. for short-term storage until use.

2) Antibody coupling reaction:

① Replacement of medicinal antibody: The anti-HER2 humanized monoclonal antibody mil40 (purchased from Zhejiang Hisun Pharmaceutical Co., Ltd.) used for coupling was a biosimilar of Herceptin, and its initial preparation solution contained histidine hydrochloride (monohydrate) 0.616 mg/ml, L-histidine 0.364 mg/ml, trehalose 22.727 mg/mL, Tween-20 100 mg/mL and other pharmaceutical excipients. In order to remove the interference of excipients, the stock solution of frozen and thawed antibody was slowly thawed at room temperature, and transferred into buffer-1 via replacement by passing through a G25 dextran gel column. After the replacement was completed, the resulting antibody in buffer-1 solution was concentrated by ultrafiltration and centrifugation (final concentration >5 mg/mL), and the concentration of which was measured by an ultraviolet spectrophotometer.

② Preparation of coupling reaction solution: According to the required amount of coupling antibody (1 eq), the antibody in buffer-1 solution was accurately pipetted using a pipette, to which a certain amount of buffer-1 was added to make the antibody concentration approximately 10 mg/mL. The resulting antibody in buffer-1 solution was adjusted with buffer-2 to having a pH of about 6 to 8, and transferred to a clean reaction vial with a pipette.

③ Reduction of antibody: The reaction solution in the vial was slowly stirred (100 rpm), and 2 to 5 eq of 2.87 mg/mL TCEP·HCl solution was added. After the addition was completed, it was stirred slowly at room temperature for 60 to 180 minutes.

④ Antibody coupling: The volume of organic solvent (DMAC or DMSO) to be added was calculated to account for 5% to 15% of the total volume; at the same time, the mass of the small molecule load (linker-MMAE conjugate) to be added was calculated, in which the small molecule load usually was slightly excessive (usually was 8 eq), and then the concentration of the load in the organic solvent to be added was calculated. The loaded solution was accurately prepared, and then slowly dropped into the reduced antibody reaction solution, stirred slowly at room temperature, and the reaction was carried out for 0.5 to 5 hours according to the specific coupling situation.

⑤ Termination of reaction: After reaching the predetermined coupling time, an excessive amount of water-soluble reductive sulfhydryl-containing small molecule N-acetylcysteine solution (1.63 mg/mL) was added to the reaction solution, and stirred slowly to continue the reaction for 30 minutes.

⑥ Preliminary purification of product: After the termination reaction of coupling was completed, buffer-3 was added to adjust the reaction solution to have a pH of about 5.50; the resulting reaction solution was filtered, and then purified using a G25 dextran gel column for preliminary purification. The forepart (approximately 80%) of the component eluate was collected, concentrated by ultrafiltration, then aseptically filtered and subjected to subpackage; except for some samples that were reserved for product analysis was placed at 4° C. for short-term storage, other products were stored at −80° C. for later use.

By using the above method, Mm-$C_3$-Val-Ala-PAB-MMAE, Mm-$C_6$-Val-Ala-PAB-MMAE, Mm-$C_6$-Val-Cit-PAB-MMAE and Mm-$C_6$-Val-Cit-PAB-MMAE substitutes were coupled to antibodies, respectively, and the following ADCs were prepared:

ADC-I: MAB-W'-$C_3$-Val-Ala-PAB-MMAE:

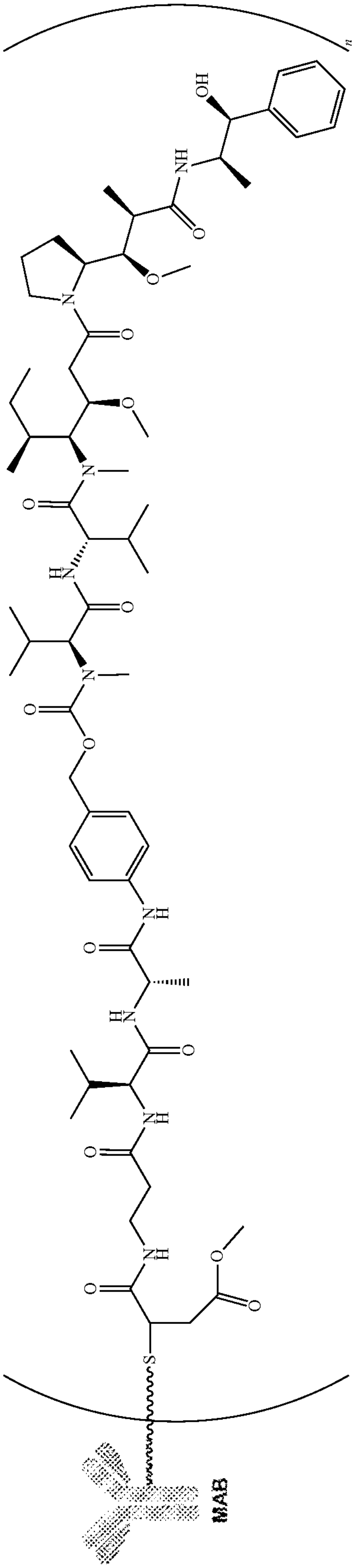

wherein: MAB was an antibody, and n was about 4 or 8.

ADC-II: MAB-W'-$C_6$-Val-Ala-PAB-MMAE:

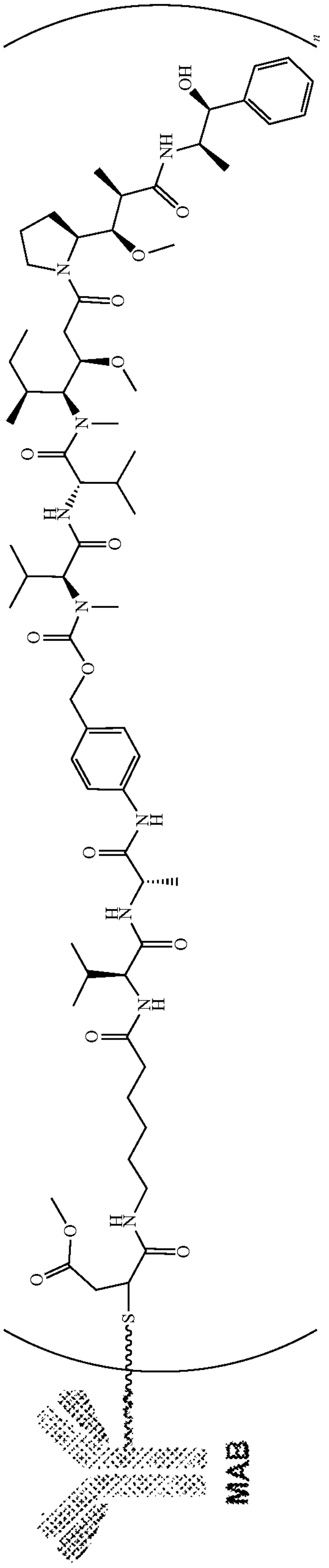

wherein: MAB was an antibody, and n was about 4 or 8.
ADC-III: MAB-W'-$C_6$-Val-Cit-PAB-MMAE:
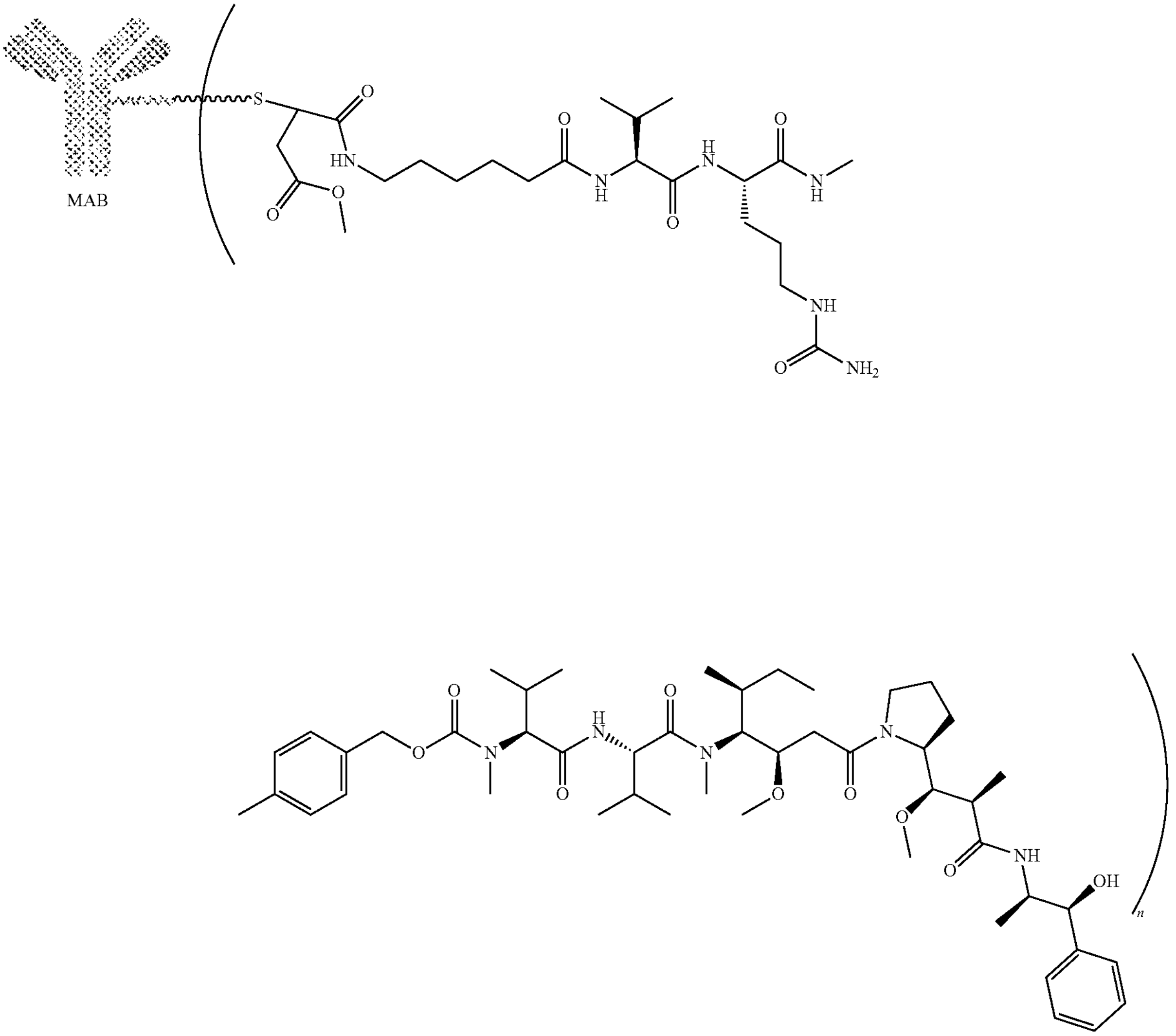
wherein: MAB was an antibody, and n was about 4 or 8.
ADC-IV: MAB-W'-$C_6$-Val-Cit-PAB-MMAE substitute:
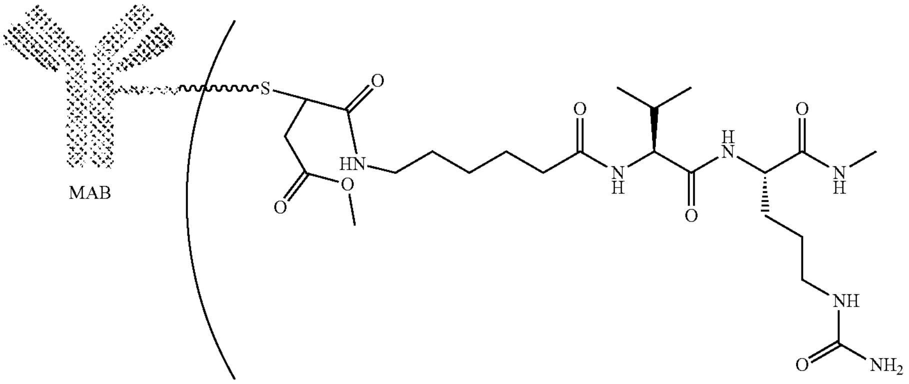

-continued
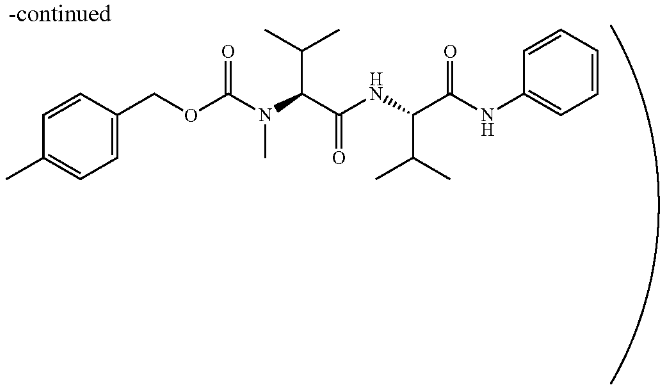
wherein: MAB was an antibody, and n was about 4 or 8.
ADC-A: MAB-W'-$C_6$-PEG4-Val-Ala-PAB-MMAE:
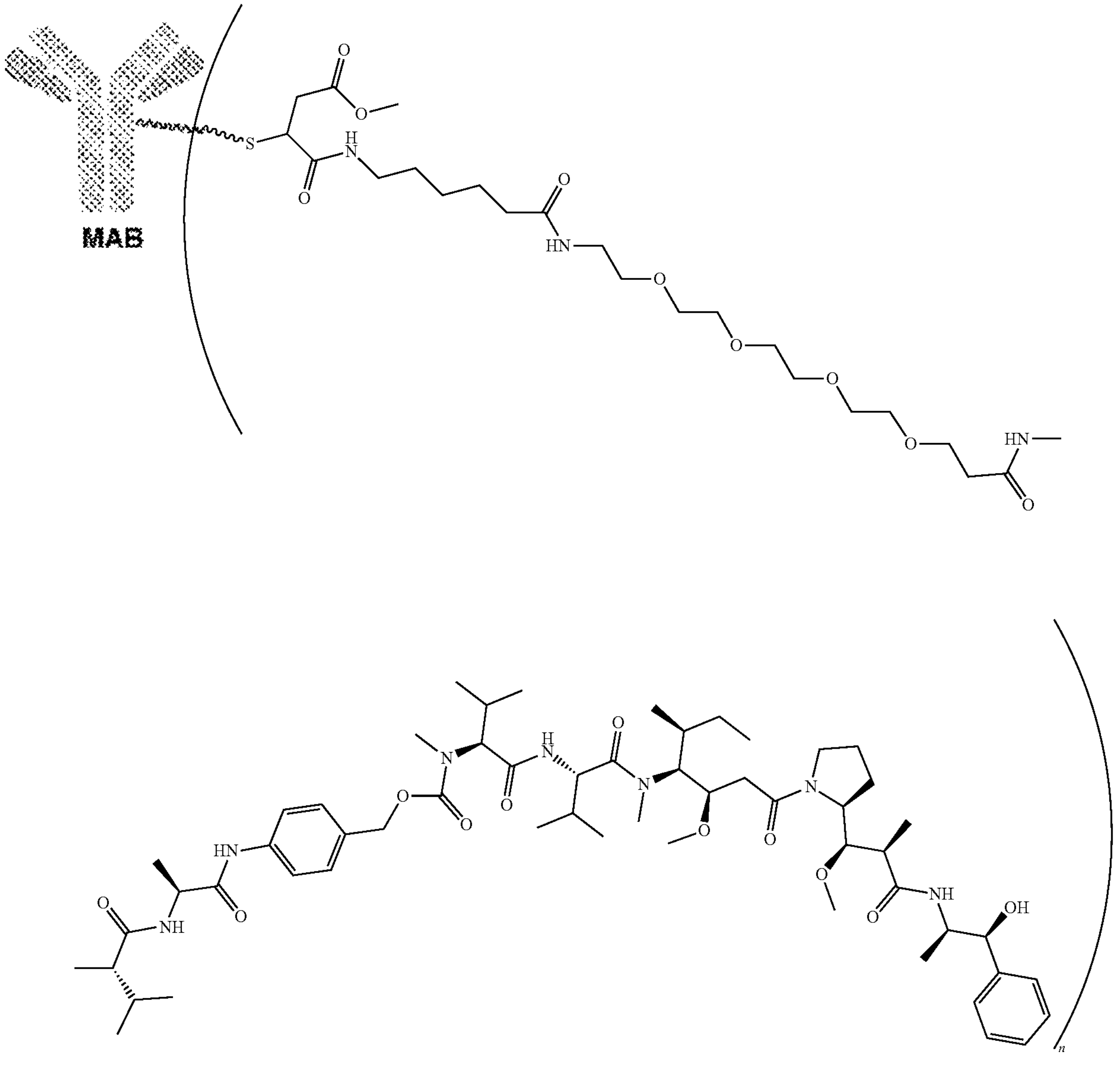
wherein: MAB was an antibody, and n was about 4 or 8.

ADC-B: MAB-W'-$C_6$-PEG8-Val-Ala-PAB-MMAE:
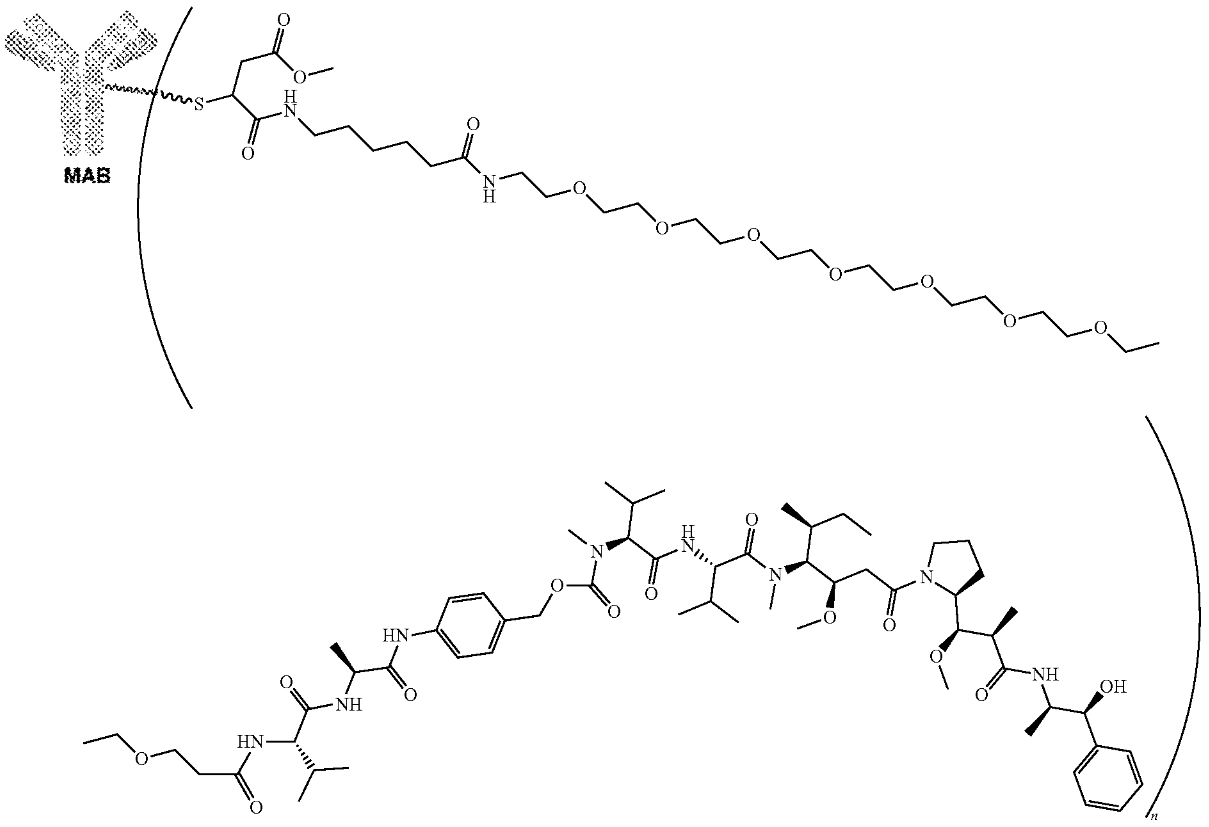
wherein: MAB was an antibody, and n was about 4 or 8.
ADC-C: MAB-W'-$C_6$-PEG8'-Val-Ala-PAB-MMAE:
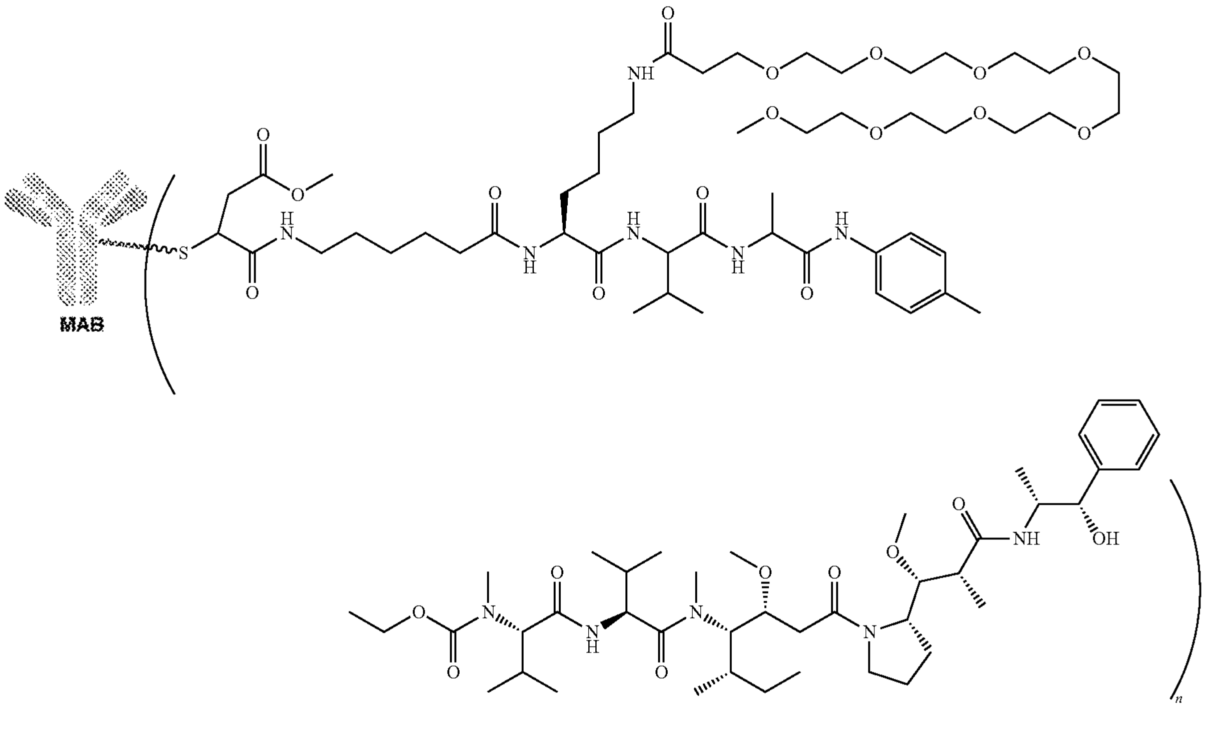
wherein: MAB was an antibody, and n was about 4 or 8.

Example 13: Stability Experiment of ADCs (DAR: About 8) Containing Linkers with Different Structures In this example, the ADC containing succinimide linker (MAB-Su-$C_6$-Val-Cit-PAB-MMAE, Su-E8; the preparation method of which was referred to Int *J Mol Sci.,* 2017, 18(9): 1860.) and the ADC containing methyl maleate linker (MAB-W'-$C_6$-Val-Cit-PAB-MMAE, W'-E8, prepared in Example 12) were evaluated to determine their toxin off-targeting situations in the presence of excess free sulfhydryl substance N-acetylcysteine (NAC), in which the monitoring indicators were changes of DAR over time for the two ADCs. The ADCs to be tested were transferred by replacement in PBS buffer (which contained NAC, 0.41 mg/mL, pH=7.4) and incubated in a 37° C. incubator, and 200 μL of sample was separately collected at each of the predetermined time points (0, 1, 2, 4, 8, 12, 24, 48, 72 h, and 7 days), which was frozen at −20° C. after sampling. After the end of sampling, HPLC-HIC was used to detect the changes of DAR over time for the ADCs (FIG. 6), where the initial value of DAR was about 8.

Figure 6:
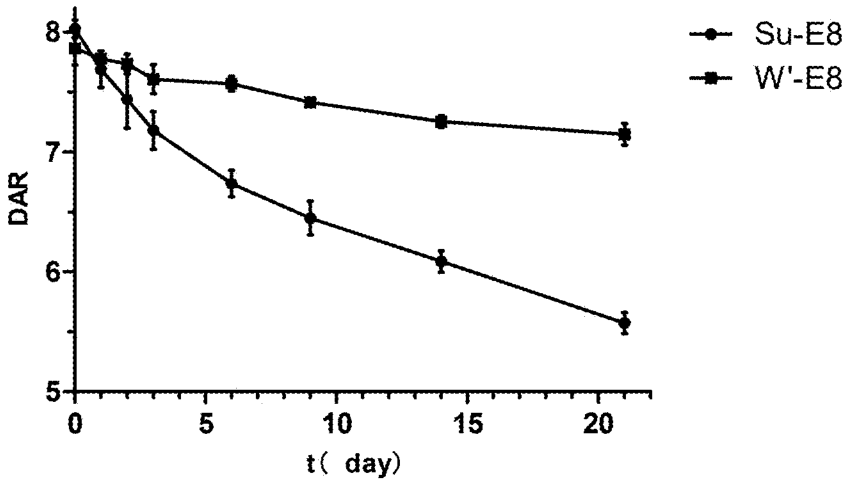
FIG. 6 shows the curves of DAR of ADCs containing linkers of different structures over time, wherein the initial value of DAR was about 8. The results showed that the ADCs containing methyl maleate linker (W') had significantly better in vitro stability than the ADCs with succinimide linker (Su), and showed no significant toxin off-targeting within 21 days in the presence of capture agent NAC; by contrast, the ADCs containing succinimide linker (Su) showed about 35% of toxin off-targeting under the same conditions.

The experimental data shown in FIG. 6 indicated that the ADC containing methyl maleate linker (W') had significantly better in vitro stability than the ADC containing succinimide linker (Su), and showed no significant toxin off-targeting in the presence of trapping agent NAC within 21 days; by contrast, the ADC containing succinimide linker (Su) showed a toxin off-targeting rate of about 35% under the same condition.

The structural formulas of the compounds MAB-W'-$C_6$-Val-Cit-PAB-MMAE and MAB-Su-$C_6$-Val-Cit-PAB-MMAE (DAR: about 8) used in this example were as follows:

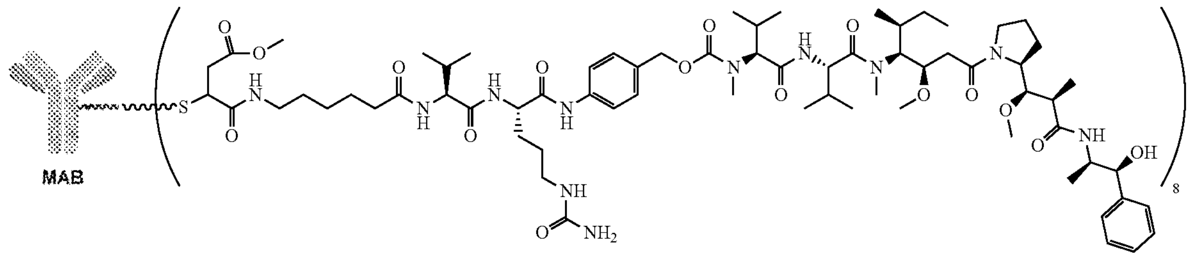

MAB-W'-$C_6$-Val-Cit-PAB-MMAE

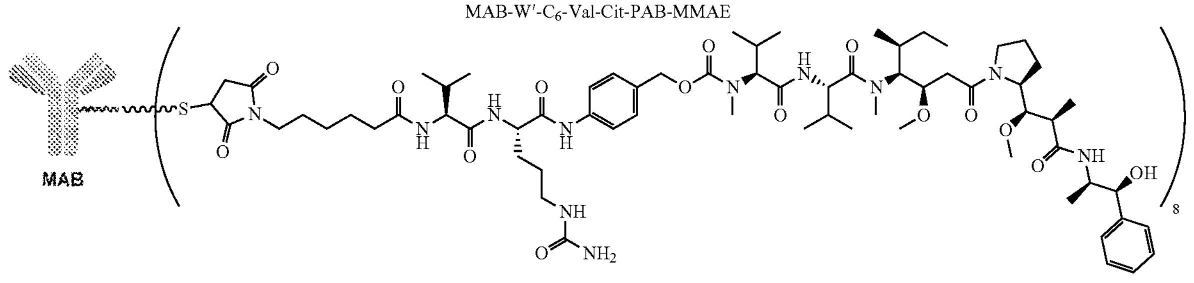

MAB-Su-$C_6$-Val-Cit-PAB-MMAE

Example 14: Stability Experiment of Conjugates of Small Molecules and Linkers with Different Structures In this example, the small molecule conjugates containing methyl maleate linker (Conjugate-1, Conjugate-2 and Conjugate-3, prepared in Example 9) and small molecule conjugates containing succinimide linker (Conjugate-1', Conjugate-2' and Conjugate-3', prepared in Example 9) were evaluated to determine their stability situations in the presence of excess free sulfhydryl (Cys), in which the monitoring indicators were the changes of the remaining amounts of the small molecule conjugates containing two different linkers in the solution over time. The substances to be tested were each dissolved in DMSO, diluted with 10 times volume of PBS buffer containing cysteine (in which the concentration of Cys was 0.41 mg/mL, pH=7.4) and incubated in a 37° C. incubator; at t=0, another 200 μL of each sample was taken and stored at −80° C. as control. After each solution was incubated for 7 days, samples were taken separately, and RP-HPLC was used to detect the changes of their remaining amounts of substrate over time, in which the peak area of substrate at t=0 was defined as 100%. The experimental results were shown in the table below.

| Code | Conjugate structure | Remaining amount |
|---|---|---|
| Conjugate-1 | 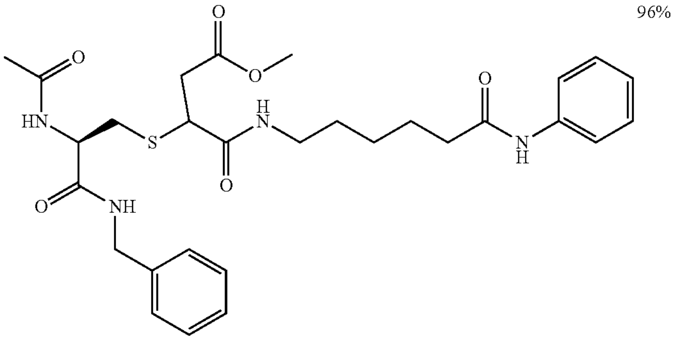 | 96% |
| Conjugate-1' | 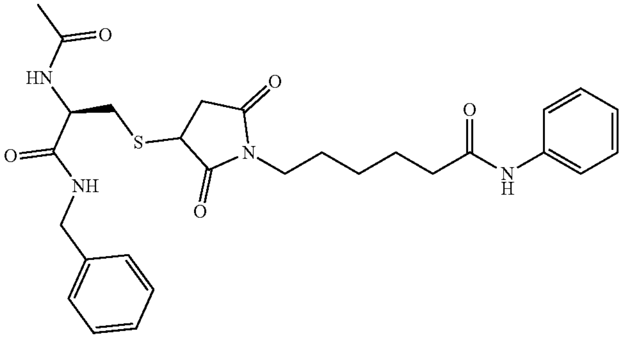 [SMILES: CC(=O)N[C@@H](CSC1CC(=O)N(CCCCCC(=O)Nc2ccccc2)C1=O)C(=O)NCc1ccccc1] | 53% |
| Conjugate-2 | 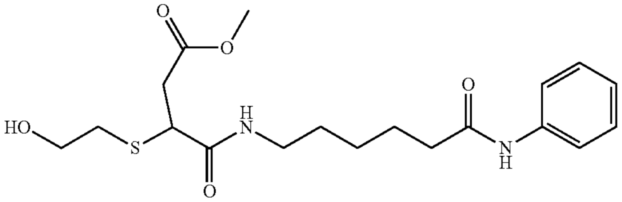 [SMILES: COC(=O)CC(SCCO)C(=O)NCCCCCC(=O)Nc1ccccc1] | 98% |
| Conjugate-2' | 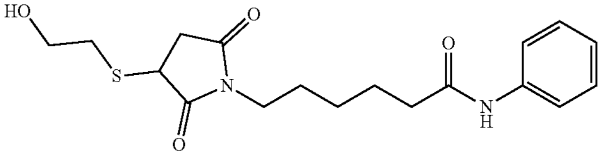 [SMILES: O=C(CCCCCN1C(=O)CC(SCCO)C1=O)Nc1ccccc1] | 61% |
| Conjugate-3 | 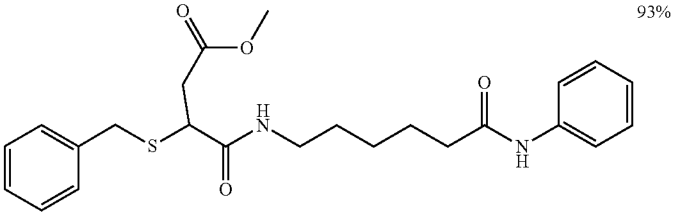 | 93% |
| Conjugate-3' | 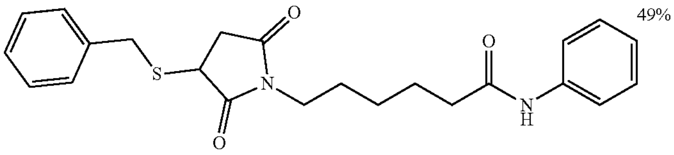 | 49% |

The above experimental data of stability showed that in the presence of the trapping agent Cys, the small molecule conjugates (Conjugate-1, Conjugate-2 and Conjugate-3) containing the linker of ring-opening maleyl monomethyl ester (W') had significantly better in vitro stability in comparison with the small molecule conjugates (Conjugate-1', Conjugate-2' and Conjugate-3') containing succinimide linker (Su). Under mild conditions of 37° C. and pH=7.4, after 7 days of incubation, the small molecule conjugates containing maleimide linker showed no significant off-targeting (<10%); by contrast, the small molecule conjugates containing succinimide linker showed an off-targeting rate of about 50% under the same conditions.

Example 15: Coupling Experiment of Antibody and Linkers with Different Structures

15.1 Coupling of Antibody with Linker Containing the Maleic Acid Amide Structure (Maa)

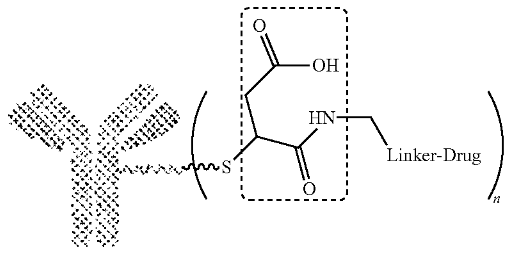

Maa

ADC with Maa Linker

In the present application, it was attempted to perform antibody coupling by using a linker of maleic acid amide structure (Maa) obtained by ring-opening of maleimide, so as to realize the preparation of a stable ADC with Maa linker through a one-step method. First, linkers with maleic acid amide structure (Maa) were synthesized and coupled with toxin MMAE to obtain two corresponding loads: Maa-$C_6$-Val-Ala-PAB-MMAE and Maa-$C_6$-Val-Cit-PAB-MMAE (prepared according to the method described in Example 10). The aforementioned two conjugate loads with maleic acid amide structure (Maa) were coupled with antibody, respectively, and it was expected to obtain target ADCs with stable carboxylic acid-type linker through process optimization. However, in phosphate buffer (PBS), histidine buffer (L-His), tris(hydroxymethyl)aminomethane buffer (TRIS) and other systems, after optimization of conditions in terms of pH, temperature, reaction time, material ratio, etc., it was only realized that a very small amount of Maa-$C_6$-Val-Ala-PAB-MMAE or Maa-$C_6$-Val-Cit-PAB-MMAE was coupled to the antibody, and the coupling results were shown in Table 1. In the obtained ADCs, the amount of carried toxin MMAE was too low, and thus the product did not meet the requirements. The ideal DAR (Drug-Antibody ratio, DAR) was about 4.

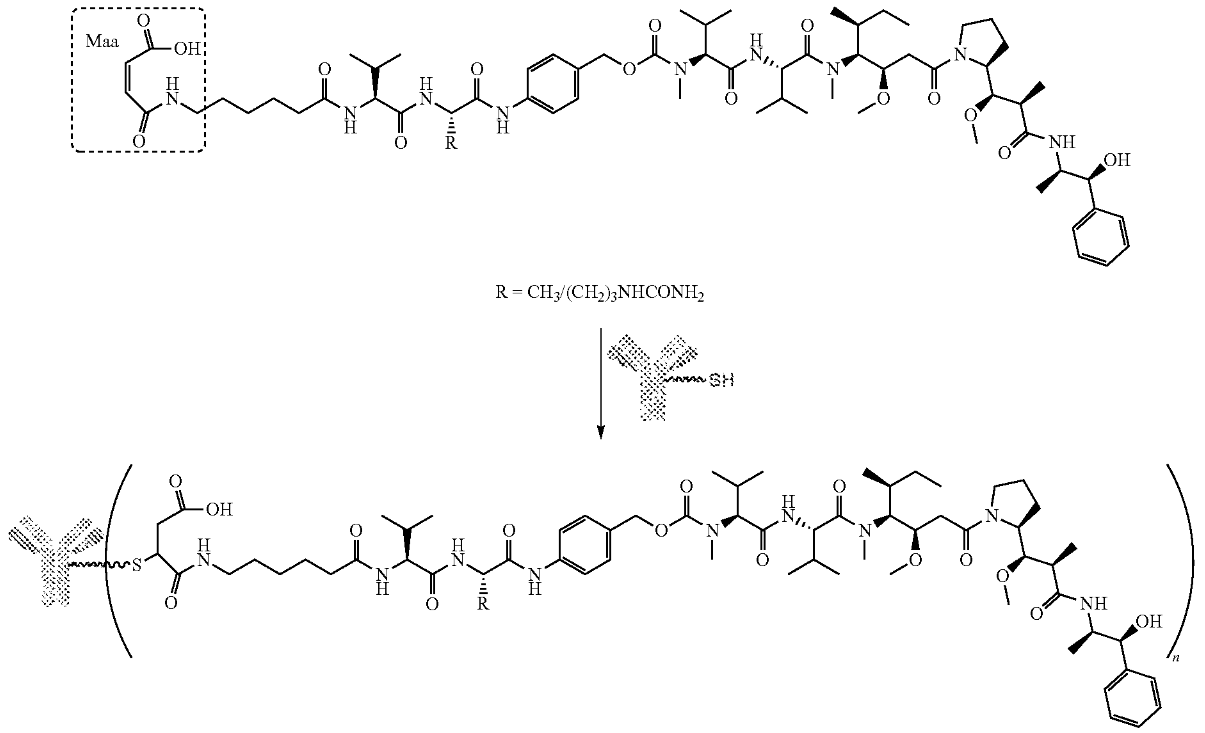

R = $CH_3/(CH_2)_3NHCONH_2$

R = $CH_3/(CH_2)_3NHCONH_2$

TABLE 1
| Results of coupling linkers containing maleic acid amide (Maa) structure with antibody | |
|---|---|
| ADC structure | n(DAR) |
| 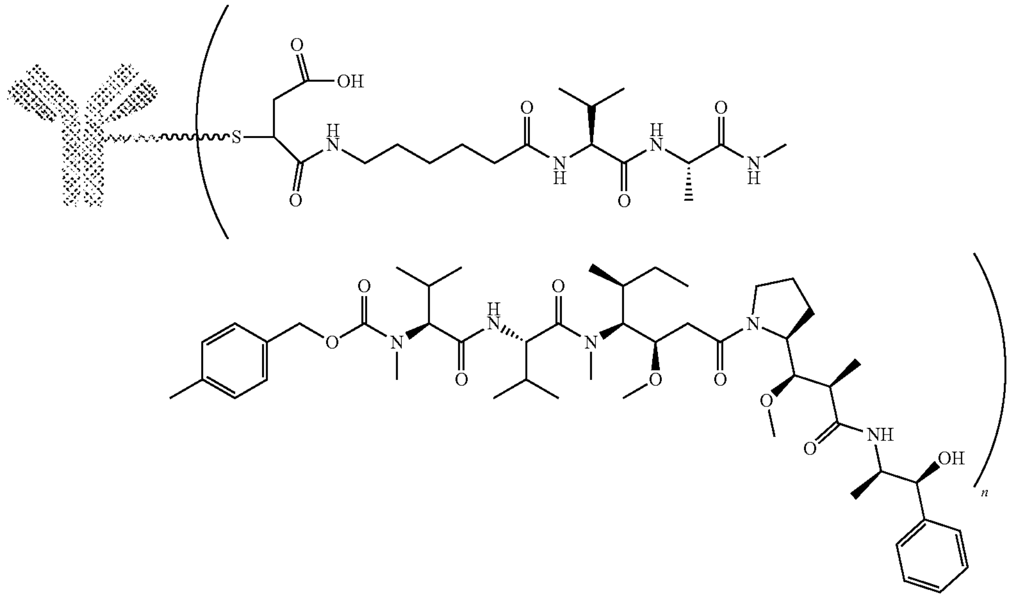 | 0.27 |
| 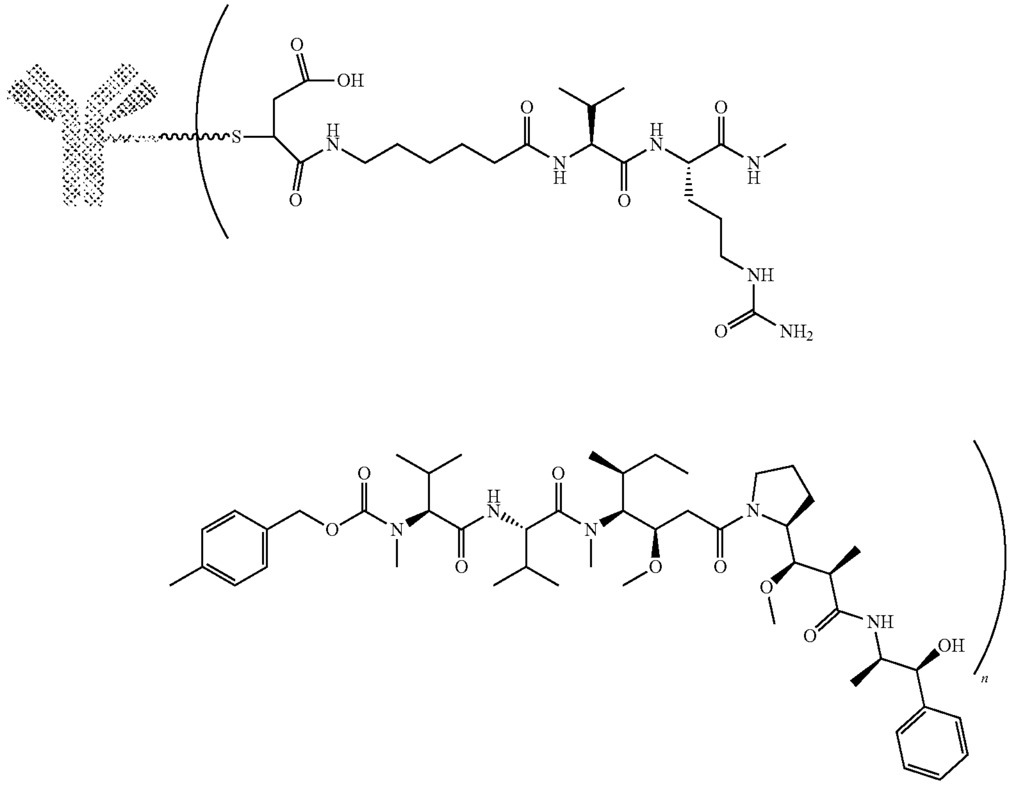 | 0.22 |

The above experiment showed that the ADCs containing linker with maleic acid amide structure (Maa), i.e., the ADCs containing linker with succinimide ring-opening structure, cannot be directly obtained by preparation.

15.2 Coupling Antibody with Linker Containing Methyl Fumarate (Mf) Structure

Through reverse synthesis analysis, we further designed conjugates with methyl fumarate linker (Mf) and methyl maleate linker (Mm), in order to obtain synthetically easy-to-obtain and structurally stable ADCs that contained new stable linker structure. Theoretically, both methyl fumarate linker (Mf) and methyl maleate linker (Mm) could undergo Michael addition reaction with sulfhydryl to obtain methyl ester-type products with a ring-opening linker structure.

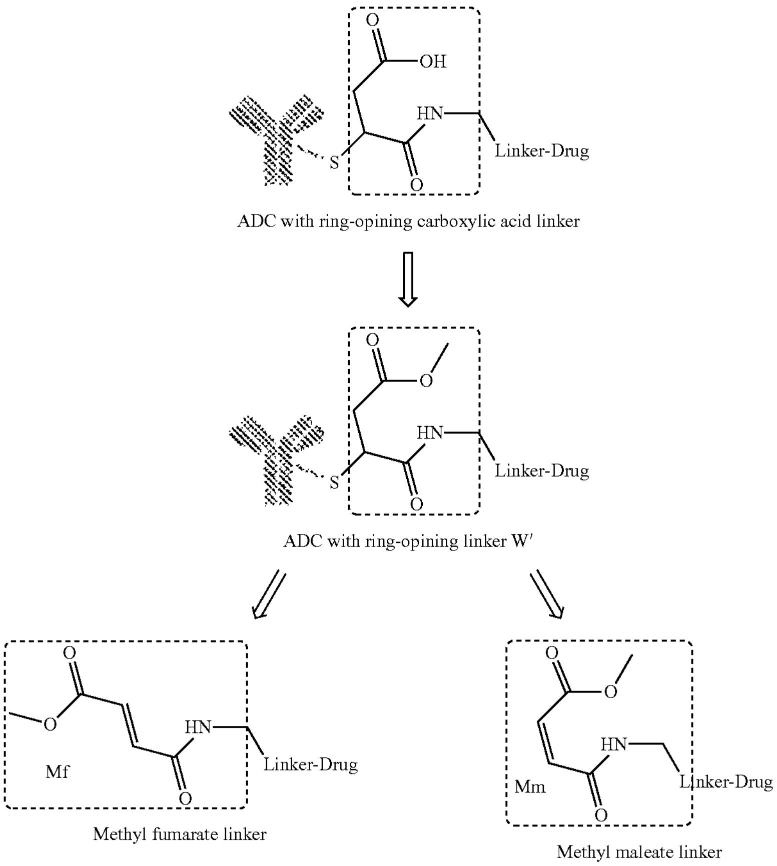

In this example, three linker-cytotoxin conjugates containing methyl fumarate structure (Mf), Mf-$C_6$-Val-Ala-PAB-MMAE, Mf-$C_3$-Val-Ala-PAB-MMAE and Mf-$C_6$-Val-Cit-PAB-MMAE were first prepared (prepared according to the method described in Example 11), and were coupled to antibody, respectively, and the coupling results were shown in Table 2. Similar to 14.1, after optimization of a variety of coupling conditions, only a small amount of linker-cytotoxin conjugates could be modified on the antibody, which confirmed that the methyl fumarate linker could not achieve the coupling of ring-opening ADC. The coupling mode was as follows:

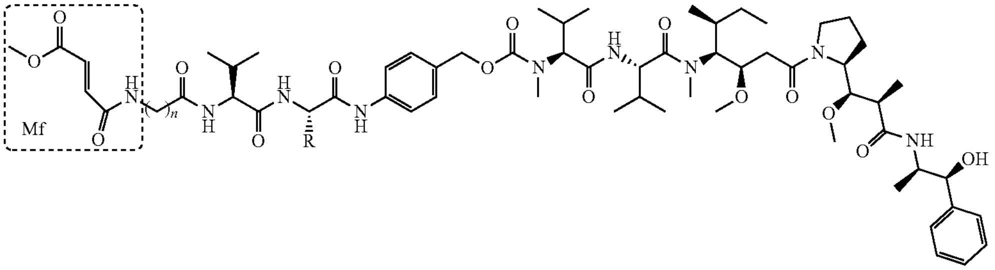
n = 2/5
R = $CH_3/(CH_2)_3NHCONH_2$
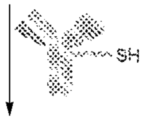
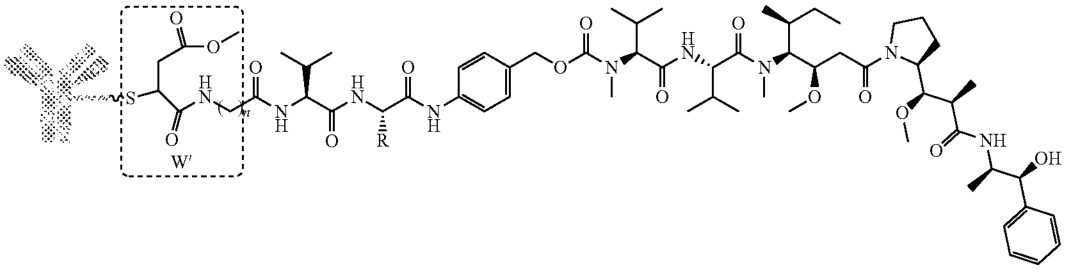
n = 2/5
R = $CH_3/(CH_2)_3NHCONH_2$
TABLE 2
| []Coupling results of antibody and linkers containing methyl fumarate (Mf) structure | |
|---|---|
| ADC structure | n(DAR) |
| 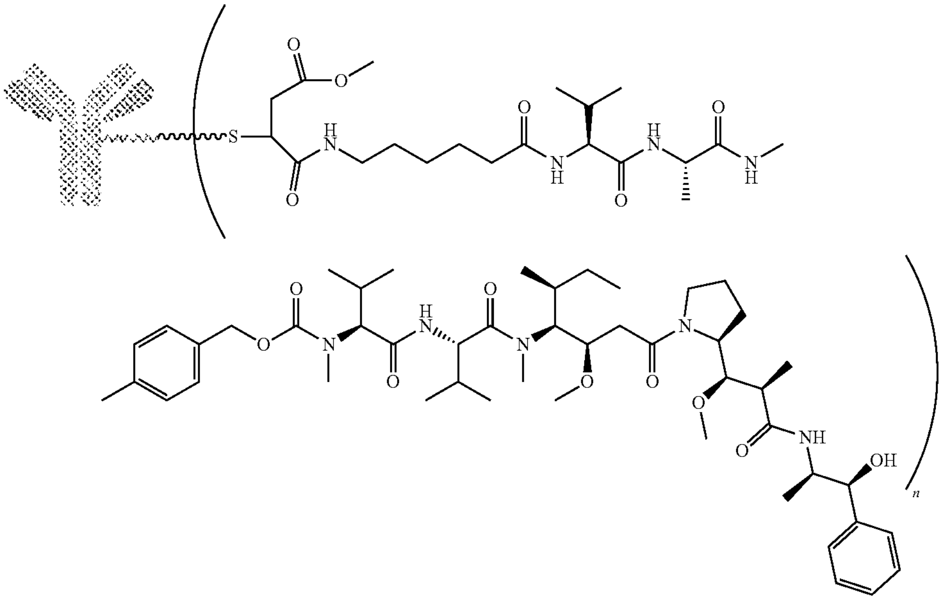 | 0.31 |

TABLE 2-continued

| []Coupling results of antibody and linkers containing methyl fumarate (Mf) structure | |
|---|---|
| ADC structure | n(DAR) |
| 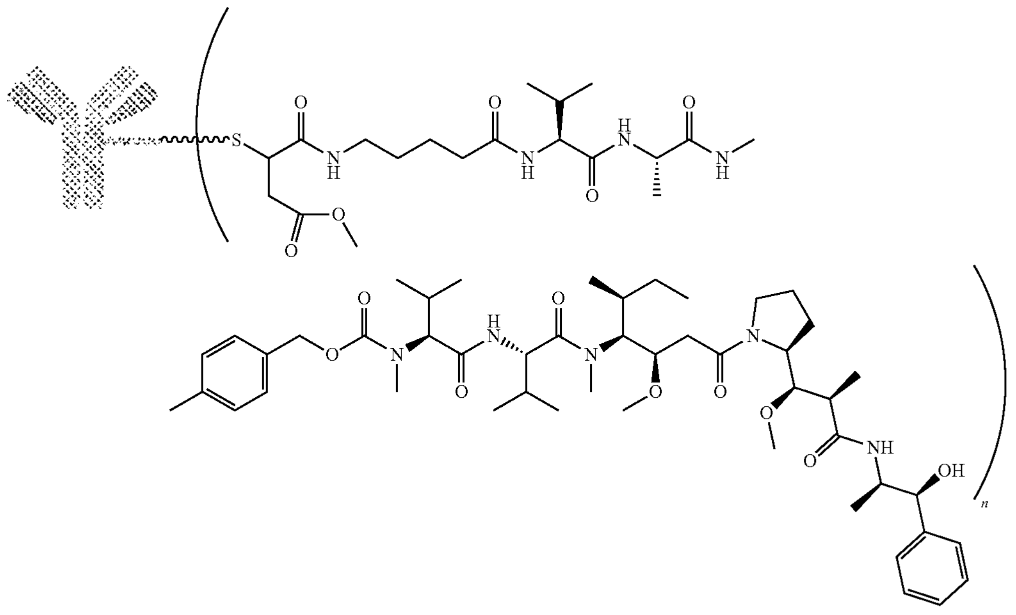 | 0.58 |
| 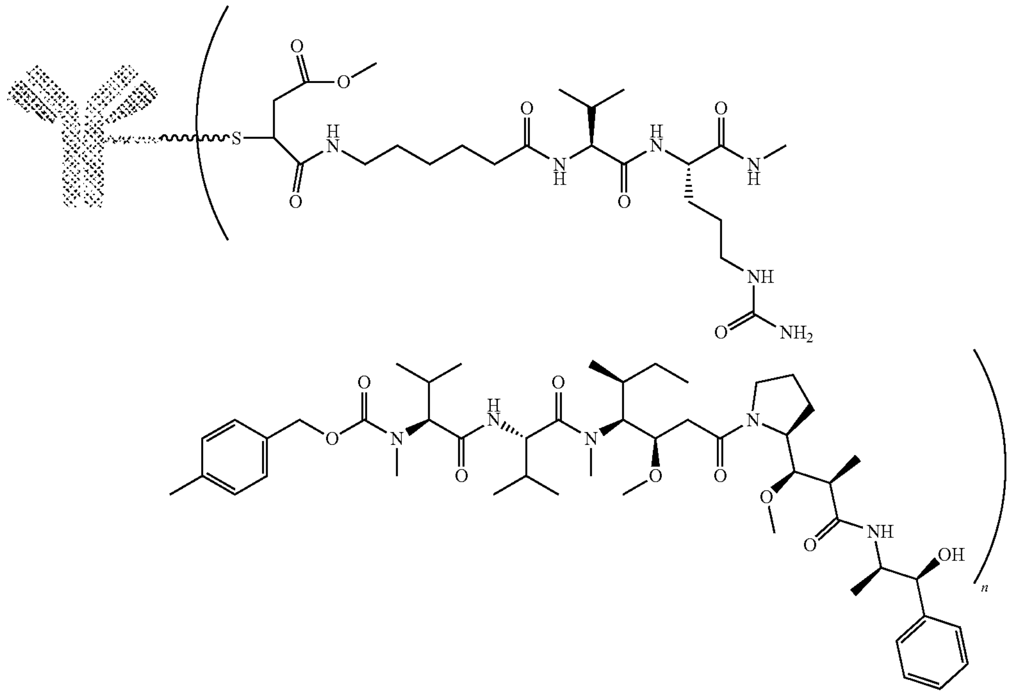 | 0.79 |

15.3 Coupling of Antibody and Linkers Containing Methyl Maleate (Mm) Structure

The linker-cytotoxin conjugates containing methyl maleate structure (Mm) prepared in Example 7 of the present application: Mm-$C_6$-Val-Ala-PAB-MMAE, Mm-$C_3$-Val-Ala-PAB-MMAE, Mm-$C_6$-Val-Cit-PAB-MMAE, Mm-$C_6$-PEG4-Val-Ala-PAB-MMAE, Mm-$C_6$-PEG8-Val-Ala-PAB-MMAE, Mm-$C_6$-PEG8'-Val-Ala-PAB-MMAE, were conjugated with antibody, respectively. The coupling results were completely different from the coupling results of 15.1 and 15.2. The linkers containing methyl maleate structure (Mm) had ideal antibody coupling performance, and could achieve quick and effective coupling in a variety of buffer systems (PBS, L-His, TRIS) under mild conditions (pH=5 to 10, 0° C. to 40° C.). The coupling results were shown in Table 3, and the coupling modes were as follows:

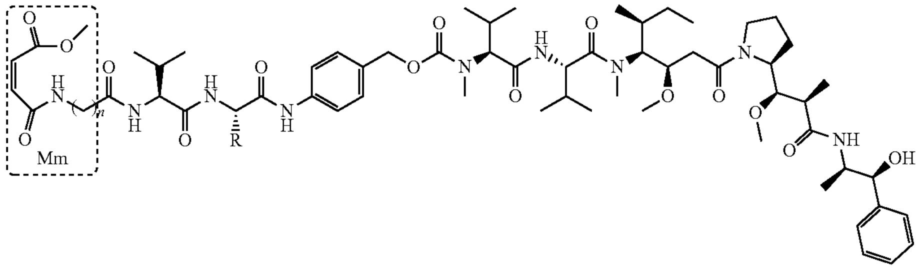
n = 2/5
R = $CH_3/(CH_2)_3NHCONH_2$
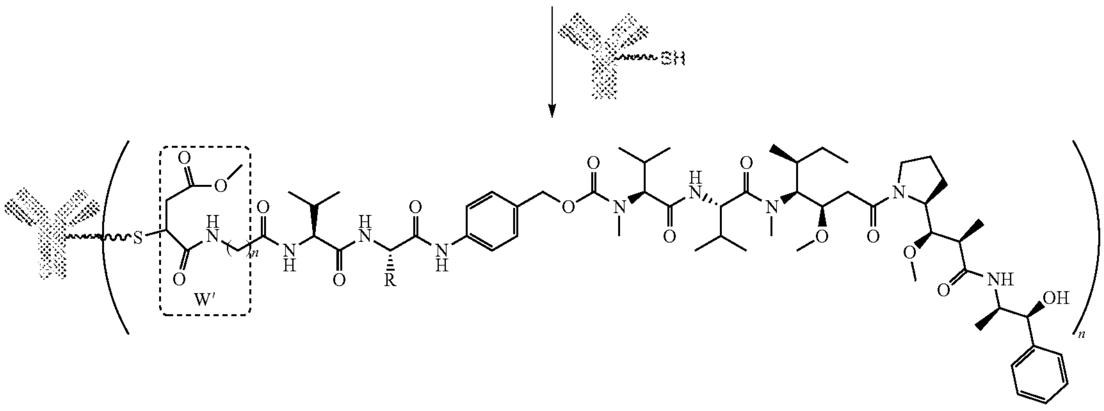
n = 2/5
R = $CH_3/(CH_2)_3NHCONH_2$
TABLE 3
| Coupling results of antibody and linkers containing methyl maleate (Mm) structure | |
|---|---|
| ADC structure | n(DAR) |
| 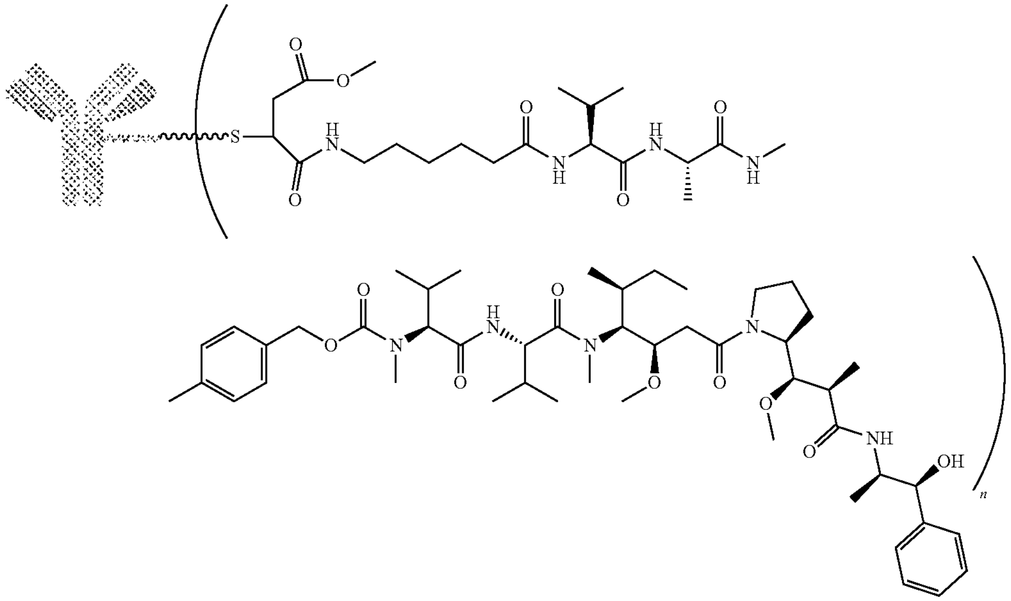 | 3.91 |

TABLE 3-continued
Coupling results of antibody and linkers containing methyl maleate (Mm) structure
| ADC structure | n(DAR) |
| --- | --- |
| 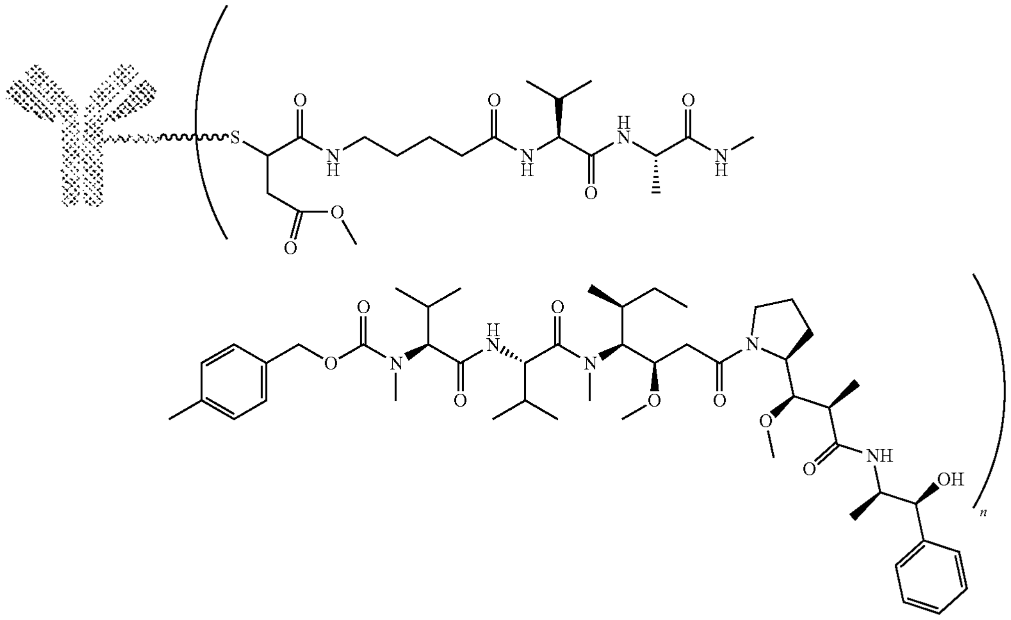 | 3.99 |
| 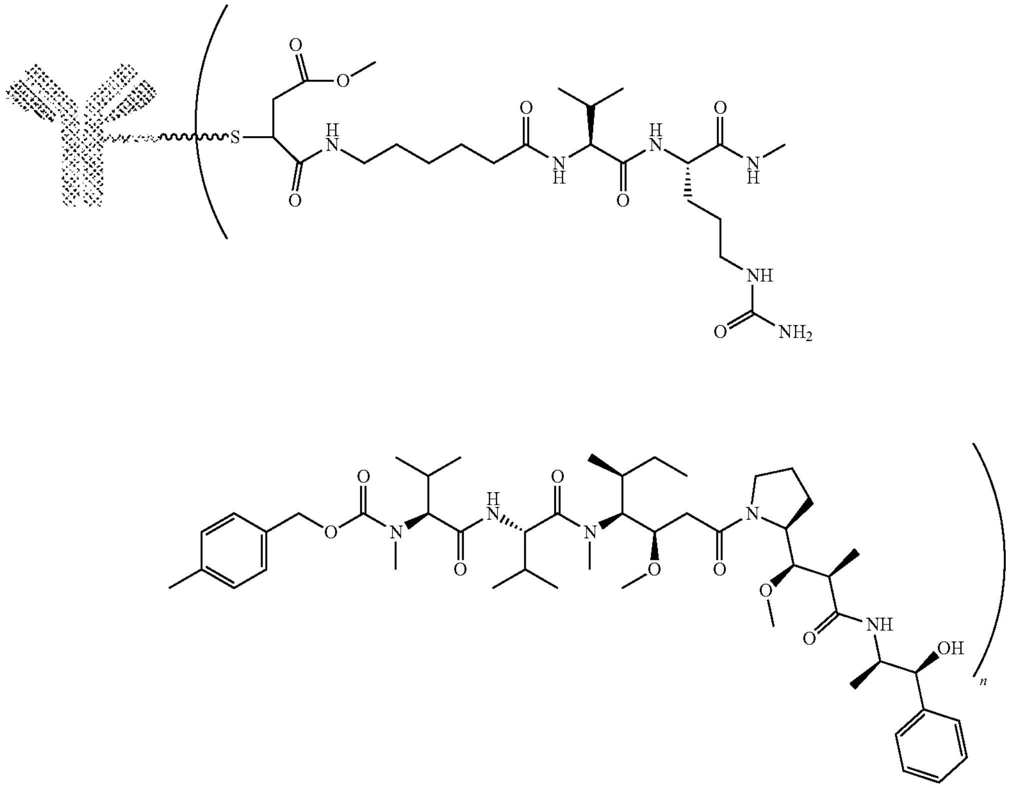 | 3.96 |

TABLE 3-continued
| Coupling results of antibody and linkers containing methyl maleate (Mm) structure | |
|---|---|
| ADC structure | n(DAR) |
| 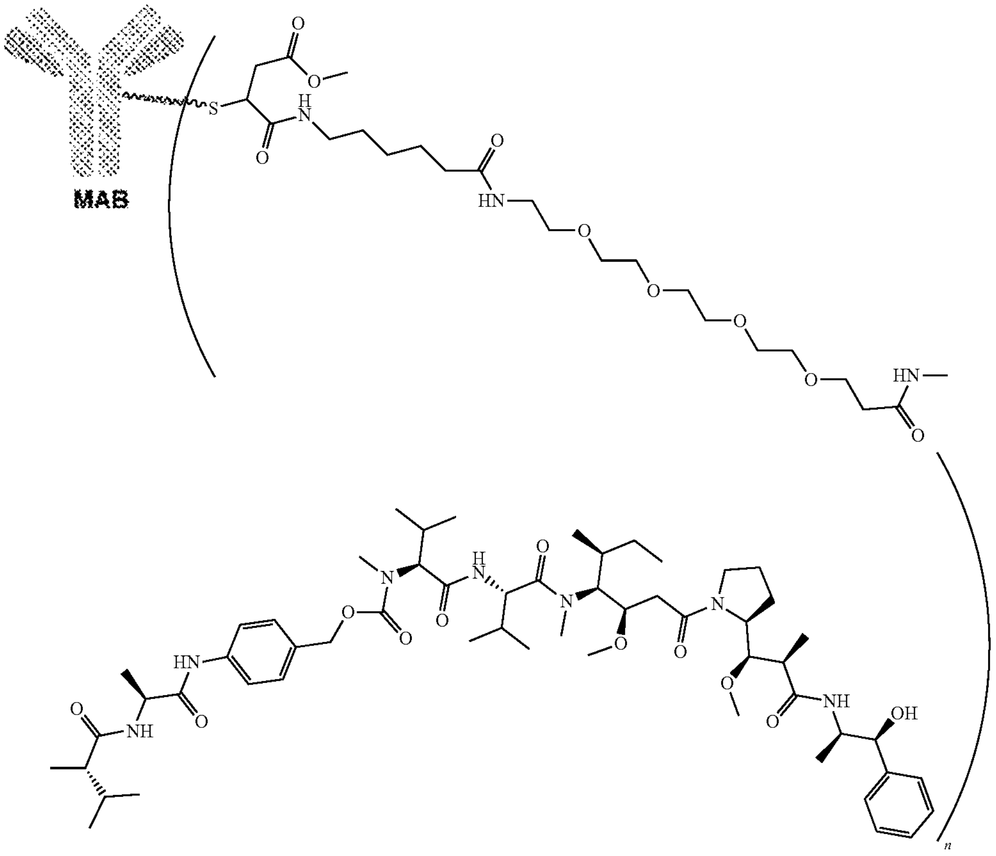 | 3.55 |
| 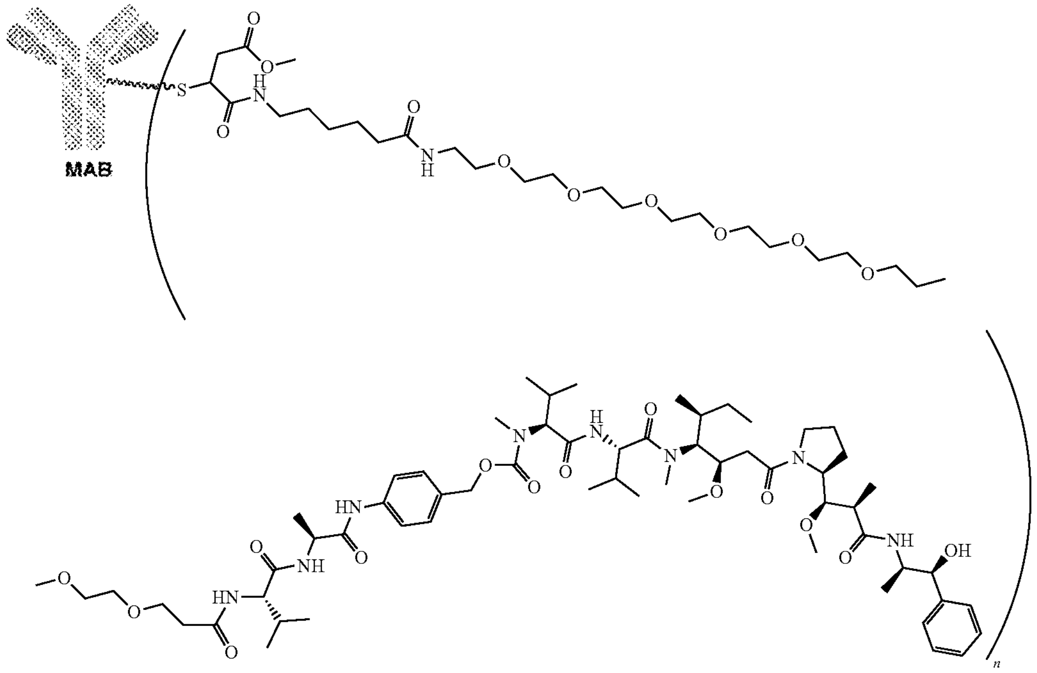 | 4.11 |

TABLE 3-continued

Coupling results of antibody and linkers containing methyl maleate (Mm) structure

| ADC structure | n(DAR) |
| --- | --- |
| 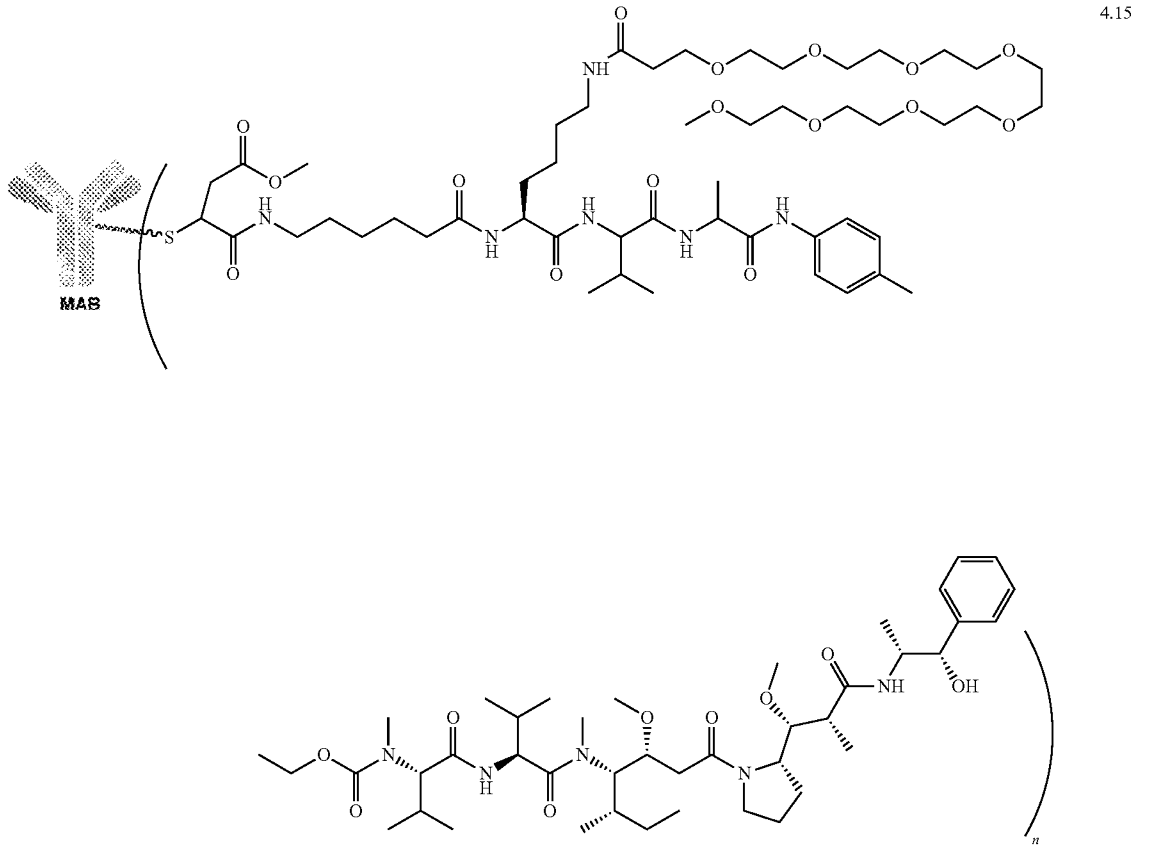 | 4.15 |

The above experimental results showed that the linkers with methyl maleate linker structure (Mm) provided in the present application had achieved unexpected effects. The methyl maleate linker structure (Mm) could be quickly coupled to sulfhydryl in antibody under mild biological conditions, and active agent conjugates with ring-opening methyl ester linker structure (W') could be prepared by a one-step method, in which the coupling process was fast and effective, and the preparation processes of linkers with methyl maleate linker structure (Mm) and the related linker-cytotoxin conjugates were simple and could be easily performed in large-scale.

Example 16: In Vitro Cytotoxicity Test of ADCs with Ring-Opening and Ring-Closing Linkers (DAR; About 4)

The test compounds included 3 pairs: MAB-W'-$C_6$-Val-Cit-PAB-MMAE (W'-$C_6$—VC) and MAB-Su-$C_6$-Val-Cit-PAB-MMAE (Su-$C_6$—VC), MAB-W'-$C_6$-Val-Ala-PAB-MMAE (W'-$C_6$-VA) and MAB-Su-$C_6$-Val-Ala-PAB-MMAE (Su-$C_6$-VA), MAB-W'-$C_3$-Val-Ala-PAB-MMAE (W'-$C_3$-VA) and MAB-Su-$C_3$-Val-Ala-PAB-MMAE (Su-$C_3$-VA), and 3 ADCs (ADC-A, ADC-B, ADC-C) containing PEG structure linker. The structures thereof were as follows:

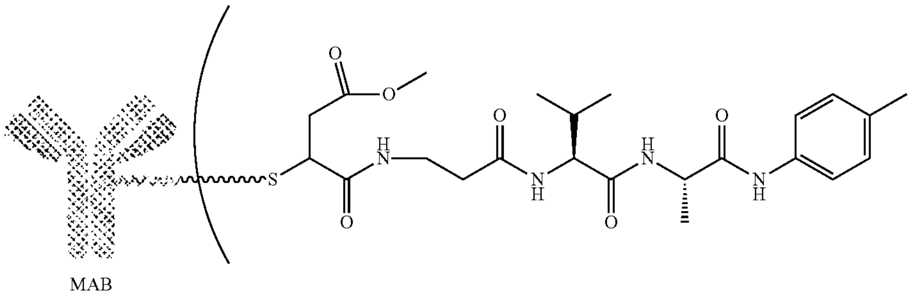

-continued
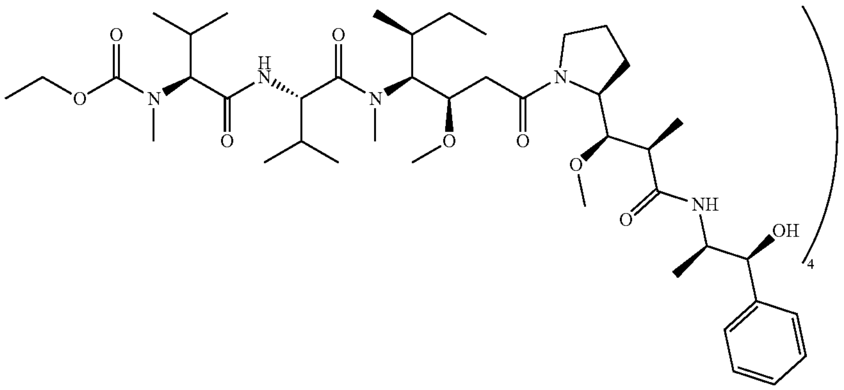
MAB-W′-C$_3$-Val-Ala-PAB-MMAE
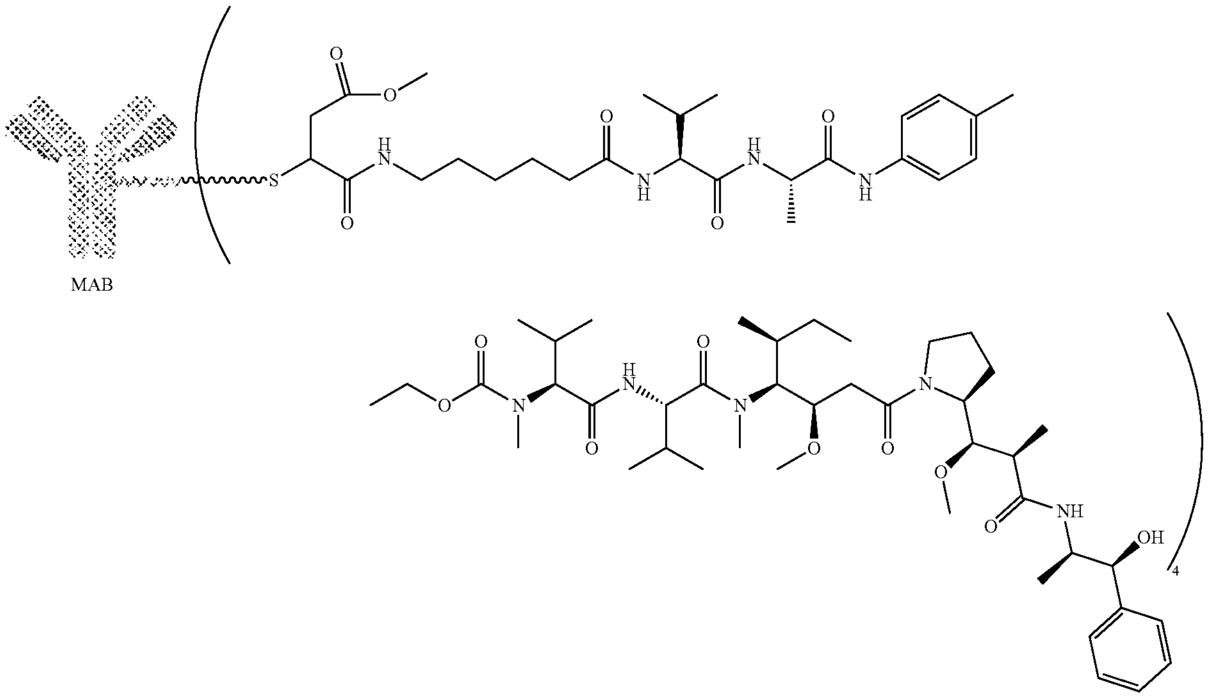
MAB-W′-C$_6$-Val-Ala-PAB-MMAE
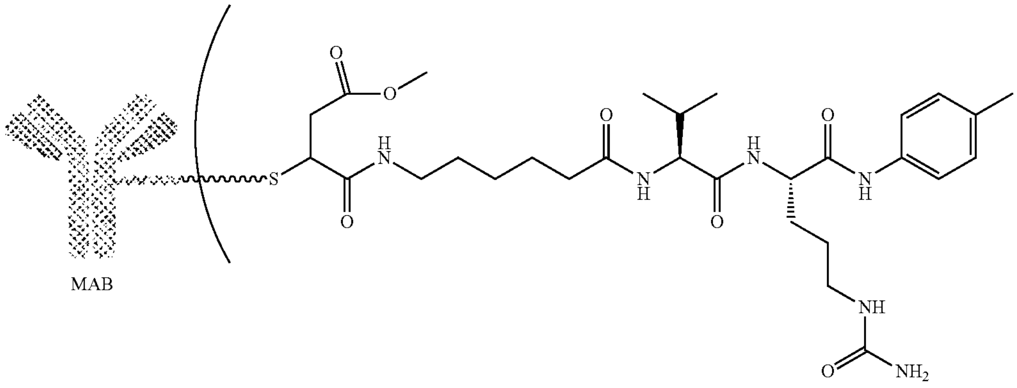

-continued
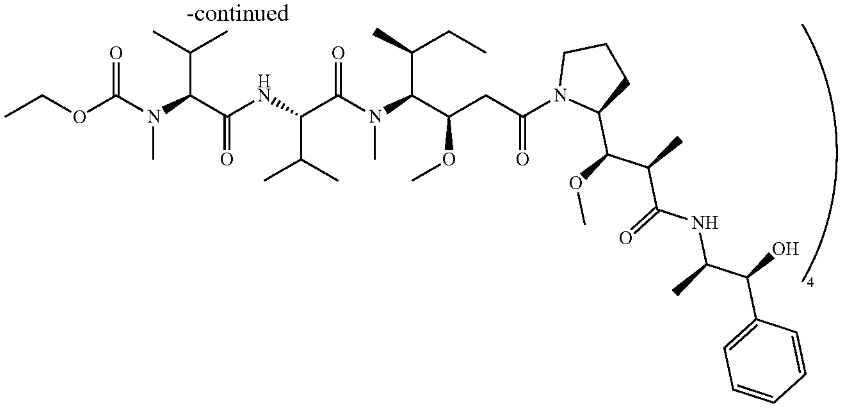
MAB-W'-$C_6$-Val-Cit-PAB-MMAE
Controls: ADCs with ring-closing structure (their preparation method were referred to: *Int J Mol Sci.,* 2017, 18(9): 1860.):
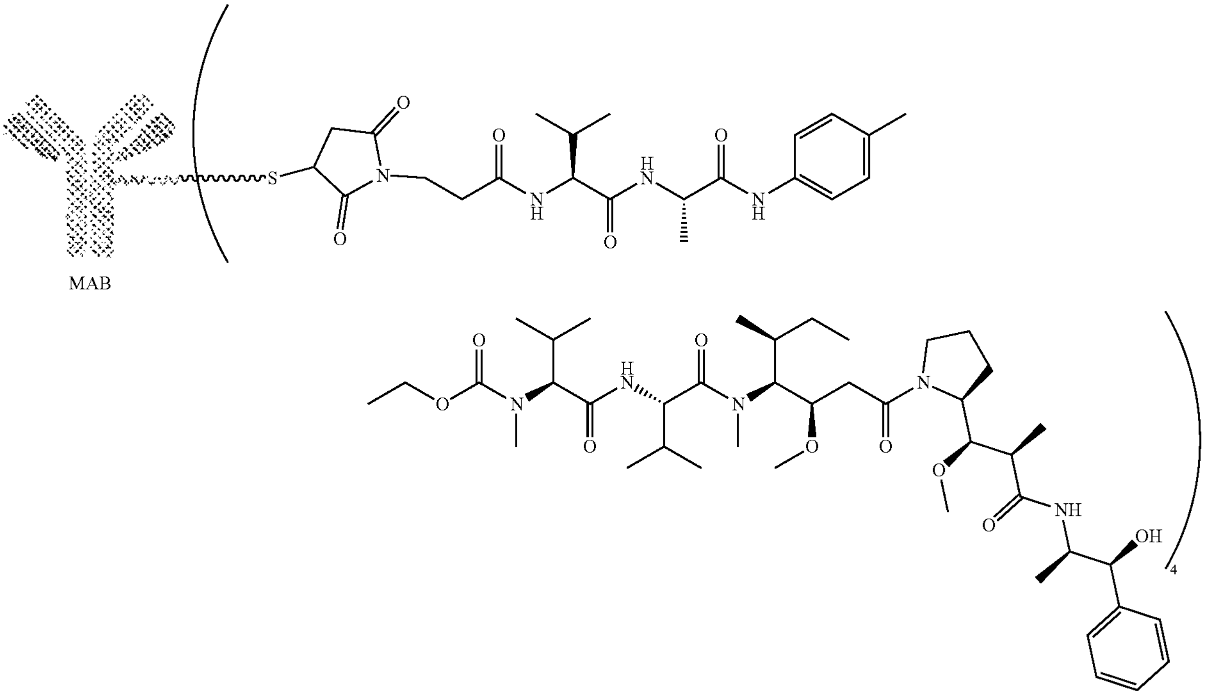
MAB-Su-$C_3$-Val-Ala-PAB-MMAE
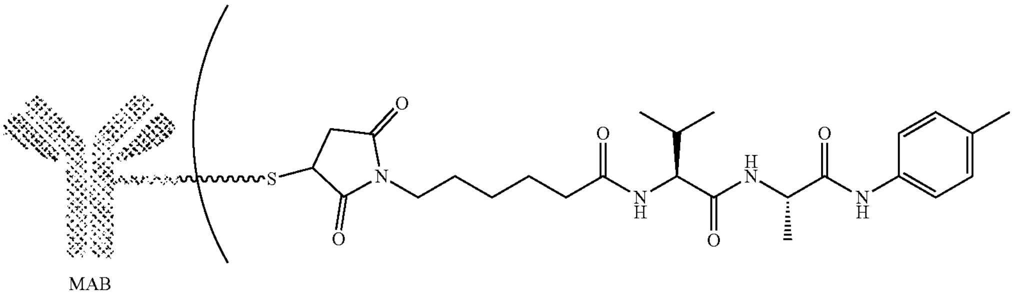

-continued

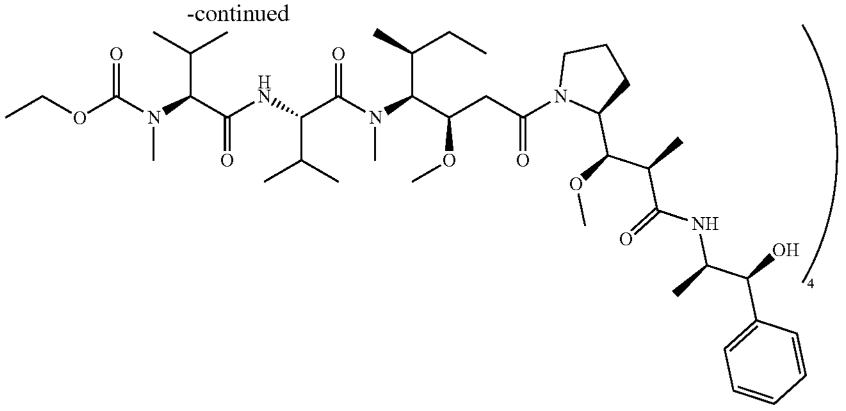

MAB-Su-$C_6$-Val-Ala-PAB-MMAE

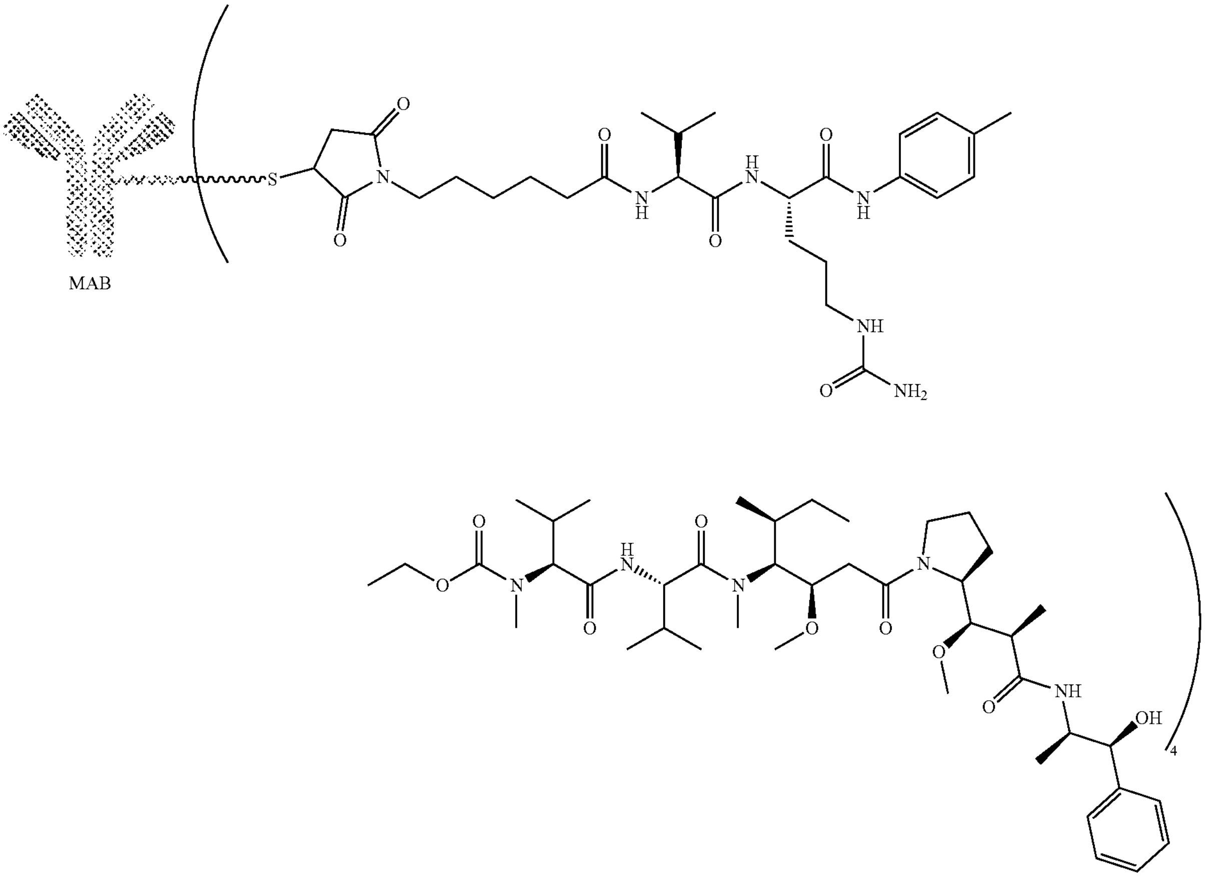

MAB-Su-$C_6$-Val-Cit-PAB-MMAE

The positive control drugs were anti-HER2 humanized monoclonal antibody mil40 (MAB) (purchased from Zhejiang Hisun Pharmaceutical Co., Ltd.), and cytotoxin MMAE (purchased from Concortis Biosystems). The selected cell lines included antigen HER2-positive breast cancer cell lines BT-474 and HCC1954, antigen HER2-positive ovarian cancer cell line SK-OV-3, antigen HER2-positive gastric cancer cell line NCI-N87, and antigen HER2-weakly positive breast cancer cell line MCF-7, and antigen HER2-negative breast cancer cell line MDA-MB-468 (purchased from ATCC).

The reagents, instruments and consumables used during the test were described in the following table:

| Reagents and consumables | Vendor | Cat# |
|---|---|---|
| RPMI 1640 | Invitrogen | A10491-01 |
| FBS | Invitrogen | 10099 |
| Penicillin-Streptomycin | Invitrogen | 15140 |
| Mccoy's 5A | Invitrogen | 16600-082 |
| DMEM | Invitrogen | 10569010 |
| CellTiter Glo kit | Promega | G9243 |
| **Instruments** | **Vendor** | **Cat#** |
| Enspire | PE | 2300 |

The test process was as follows:

1) Cell Thawing a) Vial was gently shaken in a 37° C. water bath to be thawed; b) after all the contents had been thawed, the vial was taken out from the water bath, and disinfected by immersion in or spraying with 70% ethanol; c) the contents of the vial was transferred into a centrifuge tube containing 9 mL of complete medium (DMEM medium was used for cell lines BT-474 and MCF-7; RPMI1640 medium was used for cell lines NCI-N87, HCC1954 and MDA-MB-468; and Mccoy's 5A medium was used for cell line SK-OV-3; the media described below were the same as here), and centrifuged at about 200 xg for 5 minutes; d) the cell pellet was re-suspended in a medium and distributed into a 75 $cm^2$ culture flask; e) the resulting culture was incubated in a 37° C., 5% $CO_2$ incubator.

2) Expansion of Cells a) The cells were passaged three times a week at a ratio of 1:4 in a medium containing 10% FBS (heat inactivated) and 1% penicillin/streptomycin solution; b) for the passaged cells, the adherent cells were firstly washed with 0.05% trypsin/EDTA solution (3 mL), then trypsin/EDTA (3 mL) was added and vortexed to coat the cells evenly. The resulting culture was incubated at 37° C. until the cells were detached (observed with microscope to verify that the cells were detached). An equal volume of cell culture medium was added to inactivate trypsin, the detached cells were collected, and centrifuged at 200×g for 5 minutes and then re-suspended in fresh culture medium.

3) Preparation of Compound a) the compound stock solution was diluted in series in a ratio of 1:3 to produce 10 diluted solutions with different concentrations (the compound stock solution was an L-His buffer salt solution with a concentration of about 2 mg/mL, which was diluted with PBS, and the initial maximum concentration at test point was about 500 μg/mL); b) 4 μL of the compound diluted solutions with different concentrations was distributed into a 384-well plate.

4) Cell Seeding a) The cells were collected and counted to determine the number of cells; b) 36 μL of the cell suspension with an adjusted density was added to the designated 384-well cell culture plate; and the final cell density was about 1,000 cells/well; c) the plate was covered with a lid, and placed in an incubator to perform incubation at 37° C., 5% $CO_2$ and 0.1% $O_2$ for 96 hours.

5) Reading Plate a) After 96 hours, the plate was taken from the incubator and equilibrated at room temperature for 10 minutes; b) CellTiter Glo reagent was incubated at 37° C. before the experiment; c) 40 μL of CellTiter-Glo reagent was added to each well to be tested (the ratio of CellTiter-Glo reagent to medium was 1:1); d) the plate was then placed at room temperature for 30 minutes, and then reading was carried out on an EnSpire reader for cell counting.

6) Data Analysis

Remaining activity was calculated using the following formula:

$$\text{Remaining activity (\%)}=100\%\times(S-M)/(V-M)$$

S: Readout of test sample

V: Readout of vehicle sample

M: Readout of well with compounds treatment

Xlfit (v5.3.1.3), equation 201 was used to fit curve, and calculate $IC_{50}$ value.

7) Experimental Results

The experimental results were shown in Table 4. The results indicated that the ADCs containing ring-opening methyl maleate linker and the ADCs containing ring-closing succinimide linker had substantially comparable in vitro cytotoxicity.

TABLE 4

Results of in vitro cytotoxicity test

| | Test cmpds ($IC_{50}$ nM) | | | | | | | |
|---|---|---|---|---|---|---|---|---|
| Cell lines | MAB | MMAE | W'-$C_3$-VA | W'-$C_6$-VC | Su-$C_3$-VA | W'-$C_3$-VA | Su-$C_6$-VC | Su-$C_6$-VA |
| BT-474 | 1.5406 | 0.2986 | 0.0937 | 0.1026 | 0.0900 | 0.1038 | 0.0777 | 0.0783 |
| NCI-N87 | 0.3599 | 0.1611 | 0.0513 | 0.0536 | 0.0498 | 0.0587 | 0.0523 | 0.0563 |
| HCC1954 | 0.2739 | 0.1164 | 0.0201 | 0.0258 | 0.0229 | 0.0232 | 0.0242 | 0.0231 |
| Sk-OV-3 | 2762.6134 | 0.6444 | 0.2151 | 0.2074 | 0.2181 | 0.2372 | 0.1627 | 0.1518 |
| MCF-7 | >3438 | 0.2227 | >1.4570 | >1.5316 | >1.6314 | >1.6814 | >1.6590 | >1.6495 |
| MDA-MB-468 | 552.5534 | 0.0669 | >1.4570 | >1.5316 | >1.6314 | >1.6814 | >1.6590 | >1.6495 |

The results of the in vitro cytotoxicity test of the ADCs containing PEG structure linkers were shown in Table 5. The results showed that the three tested ADCs (ADC-A, ADC-B, ADC-C) containing PEG structure linkers had very significant in vitro cytotoxicity (0.064 to 0.075 nmol/L) to HER2-positive BT-474; in comparison with antigen HER2-negative MCF-7, the in vitro cytotoxicity of the ADCs containing PEG structure linkers to HER2-positive BT-474 could be significantly increased by 472 to 1865 times, indicating that the type of ADCs had a higher antigen selectivity.

TABLE 5

Results of in vitro cytotoxicity test of ADCs containing PEG structure linkes

| | Test $IC_{50}$ (nM) | |
|---|---|---|
| ADCs | BT-474($HER2^+$) | MCF-7($HER2^-$) |
| ADC-A | 0.069 | 98.357 |
| ADC-B | 0.075 | 139.901 |
| ADC-C | 0.064 | 30.219 |

Example 17: In Vivo Pharmacodynamics of ADCs Containing Ring-Opening and Ring-Closing Linkers (DAR: About 4)

In this experiment, a xenograft model of human breast cancer cell line BT-474 expressed by HER2 (purchased from ATCC) was used to evaluate the pharmacodynamics of the test compound, in which the test compound was MAB-W'-$C_6$-Val-Ala-PAB-MMAE (W'-$C_6$-VA, ADC-II), three dose groups were set, and the doses were 1 mg/kg, 2.5 mg/kg, 5 mg/kg, respectively. At the same time, positive control groups and solvent control group were set. The positive control group 1 was given an equal dose of a mixture of anti-HER2 humanized monoclonal antibody mil40 (MAB) and MMAE, and the positive control group 2 was given an equal dose of ADC (MAB-Su-$C_6$-Val-Ala-PAB-MMAE (Su-$C_6$-VA)) that contained a ring-closing succinimide linker (Su). The solvent control group was given an equal dose of physiological saline. The test drug was dissolved in physiological saline and administered by tail vein injection. Since MMAE was insoluble in water, when a mixture solution of anti-HER2 humanized monoclonal antibody mil40 (MAB) and MMAE was prepared, MMAE was first dissolved in DMSO to prepare a 1 mg/mL solution, and then the solution was dissolved in physiological saline containing mil40 antibody, and mixed well.

BT-474 human breast cancer cells (purchased from ATCC) in a DMEM medium containing 10% inactivated fetal bovine serum, 100 U/mL penicillin, 100 μg/mL streptomycin and 2 mM glutamine were cultured in a 37° C., 5% $CO_2$ incubator. The initial concentration of cell was $1\times10^6$ cells/ml during cultivation, and the cells were divided into bottles for passage every 3 to 4 days. The cancer cells in the logarithmic growth phase were inoculated under skin of right lateral thorax of SCID mice (female, 6-8 weeks old, 18-22 g, purchased from Beijing Ankai Yibo Biotechnology Co., Ltd.), and when the tumor grew to a volume of 150 $mm^3$, the modeling was successful. Then the administration was started, 6 mice in each dose group were administered at a set dose once a week, the administration volume was 5 mL/kg, and the administration was 4 times in total. All mice were injected subcutaneously with estrogen (veterinary estradiol benzoate injection, 4 mg/2 mL, purchased from Sichuan Lansheng Pharmaceutical Co., Ltd.) from the day before the cancer cell inoculation until the end of the experiment, 2 times per week, 40 μg/20 μL each time. The tumor volume was measured twice a week by measurement of the long and short diameters of tumor with a vernier caliper. The volume calculation formula was: volume=0.5×long diameter×short diameter$^2$. While measuring the tumor volume, the mice were weighed. The relationship between the change of mouse body weight and the time of administration was recorded. At the same time, the survival and health status of mice, such as animal activity and eating during the administration period were observed.

Figure 7:
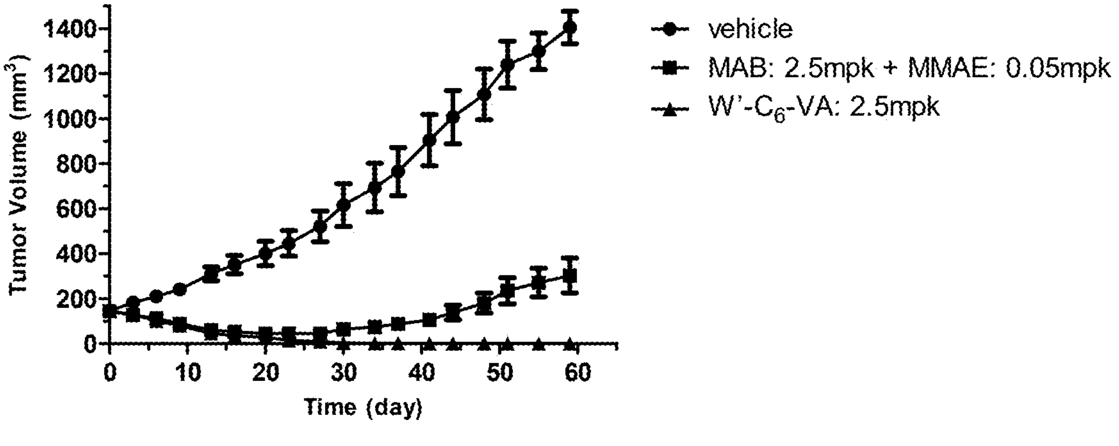
FIG. 7 shows the curves of tumor volume over time after administration. The results showed that compared with the solvent control group, the tumors of all animals in the positive control group 1 shrank, but were only partially inhibited, and the tumors of all animals still existed; while in the test compound treatment group (2.5 mg/kg), the tumors of all tested animals disappeared and did not appear for a long time, and no animal had tumor recurrence one month after drug withdrawal.

The curve of tumor volume over time after administration was shown in FIG. 7. The results showed that compared with the solvent control group, the tumors of all animals in the positive control group 1 shrank but were only partially inhibited, and the tumors of all animals still existed; while in the test compound treatment group (2.5 mg/kg), the tumors of all test animals disappeared and did not appear for a long time, and no animal had tumor recurrence one month after drug withdraw.

Figure 8:
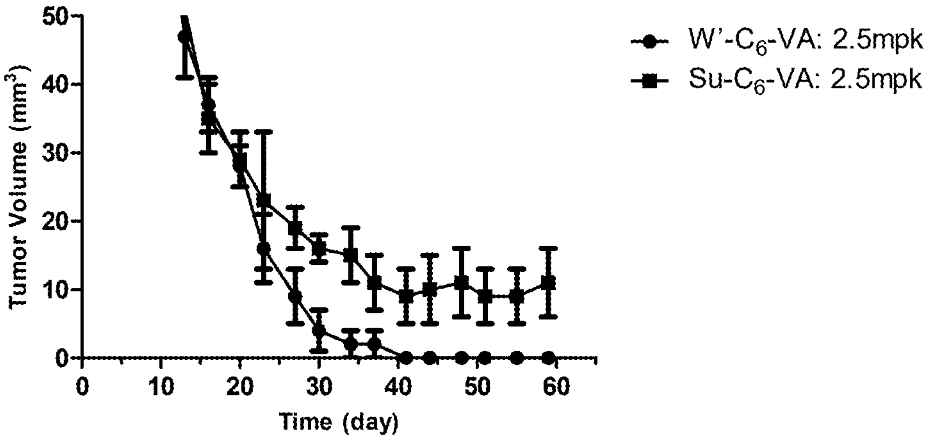
FIG. 8 shows the anti-tumor effects of ADCs containing different structural linkers at the same dosage. The results showed that at a dose of 2.5 mg/kg, tumors of mouse in the positive control group 2 did not completely disappear, while tumors of mouse in the test compound treatment group completely disappeared (at the end of treatment, p=0.0061), which indicated that compared with the ADC containing ring-closing succinimide linker, the ADCs containing ring-opening methyl maleate linker provided in the present application had better efficacy.

At the same dosage, the anti-tumor effects of ADCs containing linkers with different structures were shown in FIG. 8. The results showed that at a dose of 2.5 mg/kg, the tumors of mice in the positive control group 2 did not completely disappear, while the tumors of mice in the test compound treatment group disappeared completely, which indicated that, as compared with the ADC containing ring-closing succinimide linker, the ADC containing ring-opening methyl maleate linker provided in the present application had better efficacy (p=0.0061).

Figure 9:
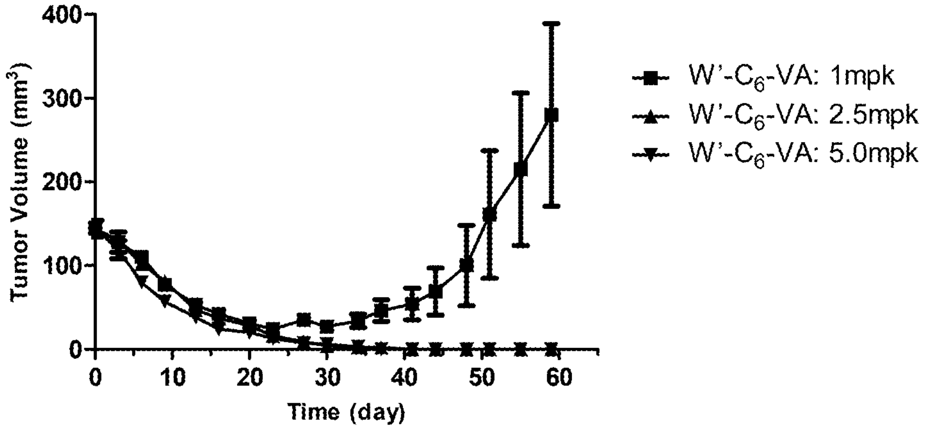
FIG. 9 shows the anti-tumor effects of ADCs under different dosages. The results showed that the ADCs containing open-ring methyl maleate linker (W') of the present application exhibited a significant dose-dependent anti-tumor activity, and tumors in both the medium and high dose groups disappeared.

In the study of dose dependence, three dose groups of 1.0 mg/kg, 2.5 mg/kg and 5.0 mg/kg were set for the test compound. At different dosages, the anti-tumor effects of the ADC was shown in FIG. 9. The results showed that the anti-tumor activity of the ADC containing ring-opening methyl maleate linker (W') of the present application showed a significant dose-dependence, in which the tumors disappeared in the middle and high dose groups.

Figure 10:
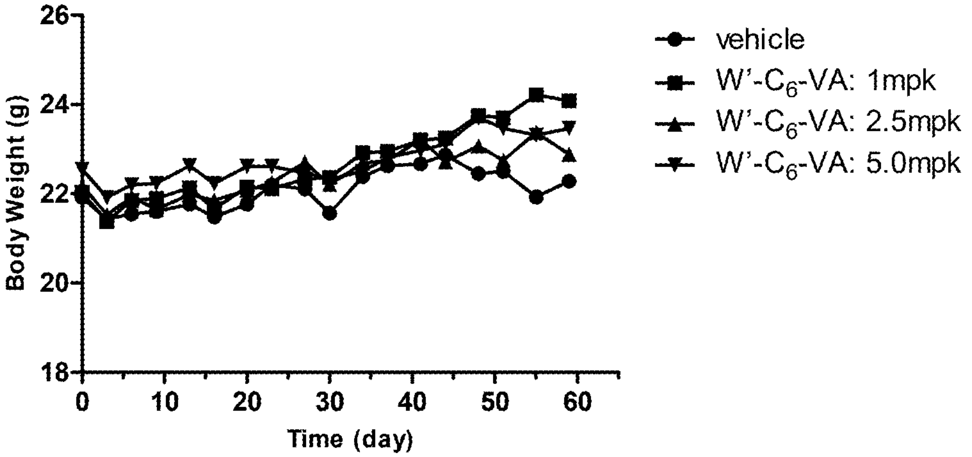
FIG. 10 shows a curve of animal body weight change after receiving the treatment of ADC containing the ring-opening methyl maleate linker (W') of the present application. The results showed that there was basically no significant difference between the test compound treatment group and the solvent control group, and all the test animals showed a steady increase in body weight, indicating that the ADC containing the ring-opening methyl maleate linker provided in the present application had little side effects.

After receiving the treatment of the ADC containing ring-opening methyl maleate linker (W') of the present application, the curve of animal body weight change was shown in FIG. 10. The results showed that there was basically no significant difference between the test compound treatment group and the solvent control group, and all the test animals showed a steady increase in body weight, indicating that the ADC provided in the present application had little side effects.

Example 18: Hematological Analysis of MAB-W'-$C_6$-Val-Ala-PAB-MMAE at Therapeutic Dose in Xenograft Model In order to further verify the safety of using the ADC (MAB-W'-$C_6$-Val-Ala-PAB-MMAE) containing methyl maleate linker (W'), the test animals were subjected to blood sampling and whole blood analysis when the administration in BT-474 xenograft model was completed (i.e., the 28$^{th}$ day after the first administration) and when the observation period was completed (i.e., that is, the 58$^{th}$ day after the first administration). The main hematological test indicators included white blood cells (WBC), red blood cells (RBC), platelets (PLT), neutrophils (Neuts) and lymphocytes (Lymph), etc. 100 μL of whole blood was collected from each test animal. Due to the limitation of volume, these samples were diluted 3 times to achieve the final blood cell counts. On basis of the quantitative analysis of the modified dilution factor, the results were expressed as mean±SD.

Figure 11:
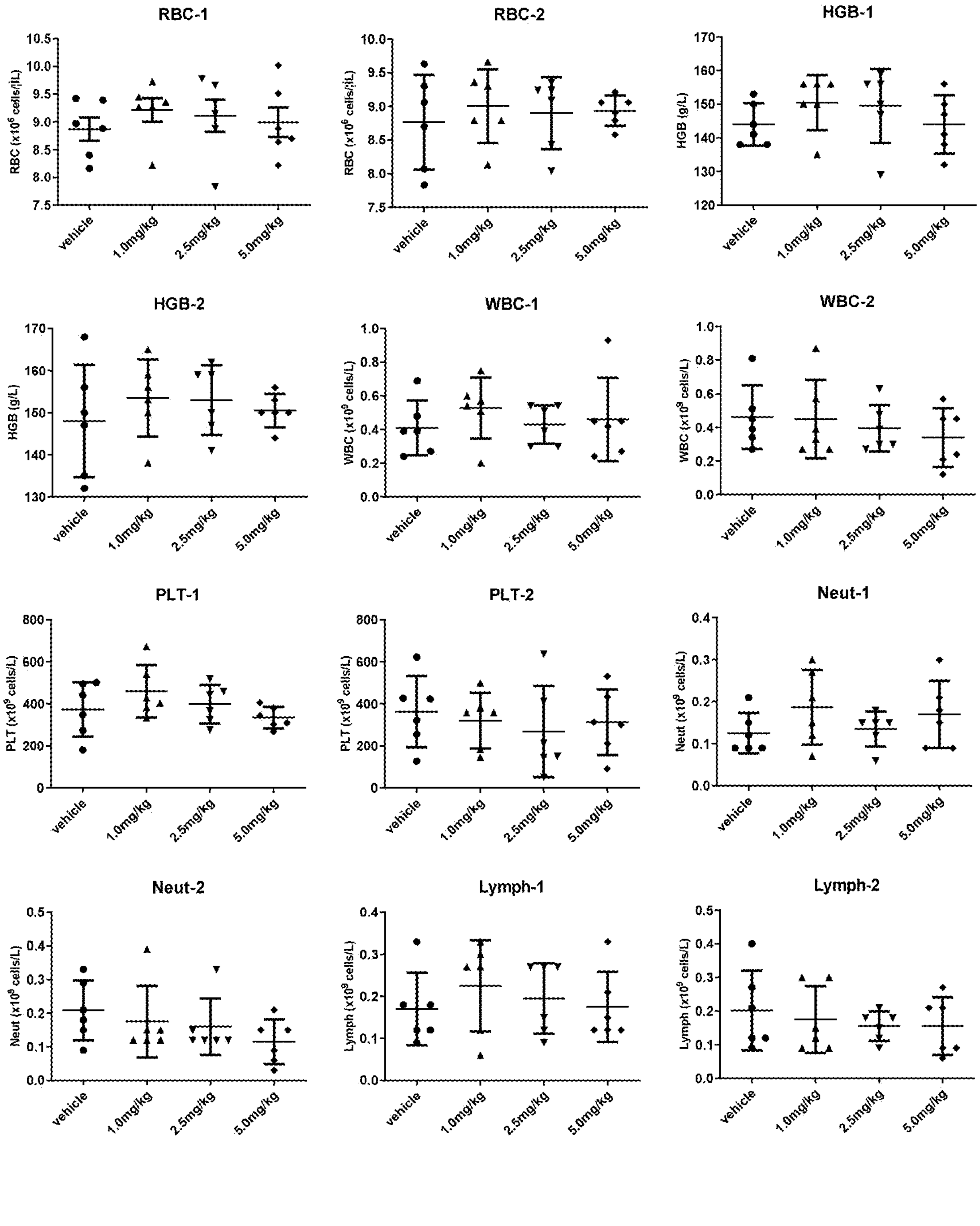
FIG. 11 shows the results of blood analysis for the animals in three dose groups (1 mg/kg, 2.5 mg/kg, 5 mg/kg) after receiving the treatment of ADC containing the ring-opening methyl maleate linker (W') of the present application, wherein the numbers "1" and "2" represented the results of the whole blood analysis of the test animals on the $28^{th}$ and $58^{th}$ day after administration, respectively. The results showed that there was no significant difference between the solvent control group and the test compound treatment groups (1 mg/kg, 2.5 mg/kg, and 5 mg/kg). The above conclusions indicated that the ADC containing the ring-opening methyl maleate linker provided in the present application had low blood toxicity and off-target bone marrow toxicity, which was also likely to be the main reason why it was well tolerated.

After receiving the treatment of the ADC containing ring-opening methyl maleate linker (W') of the present application, the animals of three dose groups (1 mg/kg, 2.5 mg/kg, 5 mg/kg) were subjected to hematological analysis and the results were shown in FIG. 11, in which the numbers "1" and "2" represented the results of whole blood analysis of test animal on the 28$^{th}$ and 58$^{th}$ days after administration, respectively. The ANOVA analysis results of the hematological parameters of the two batches of blood samples showed that there was no significant difference between the solvent control group and the test compound treatment groups (1 mg/kg, 2.5 mg/kg, and 5 mg/kg). The above conclusions indicated that the ADC containing ring-opening methyl maleate linker provided in the present application had low blood toxicity and off-target bone marrow toxicity, which could also be the main reason why it was well tolerated.

Figure 12:
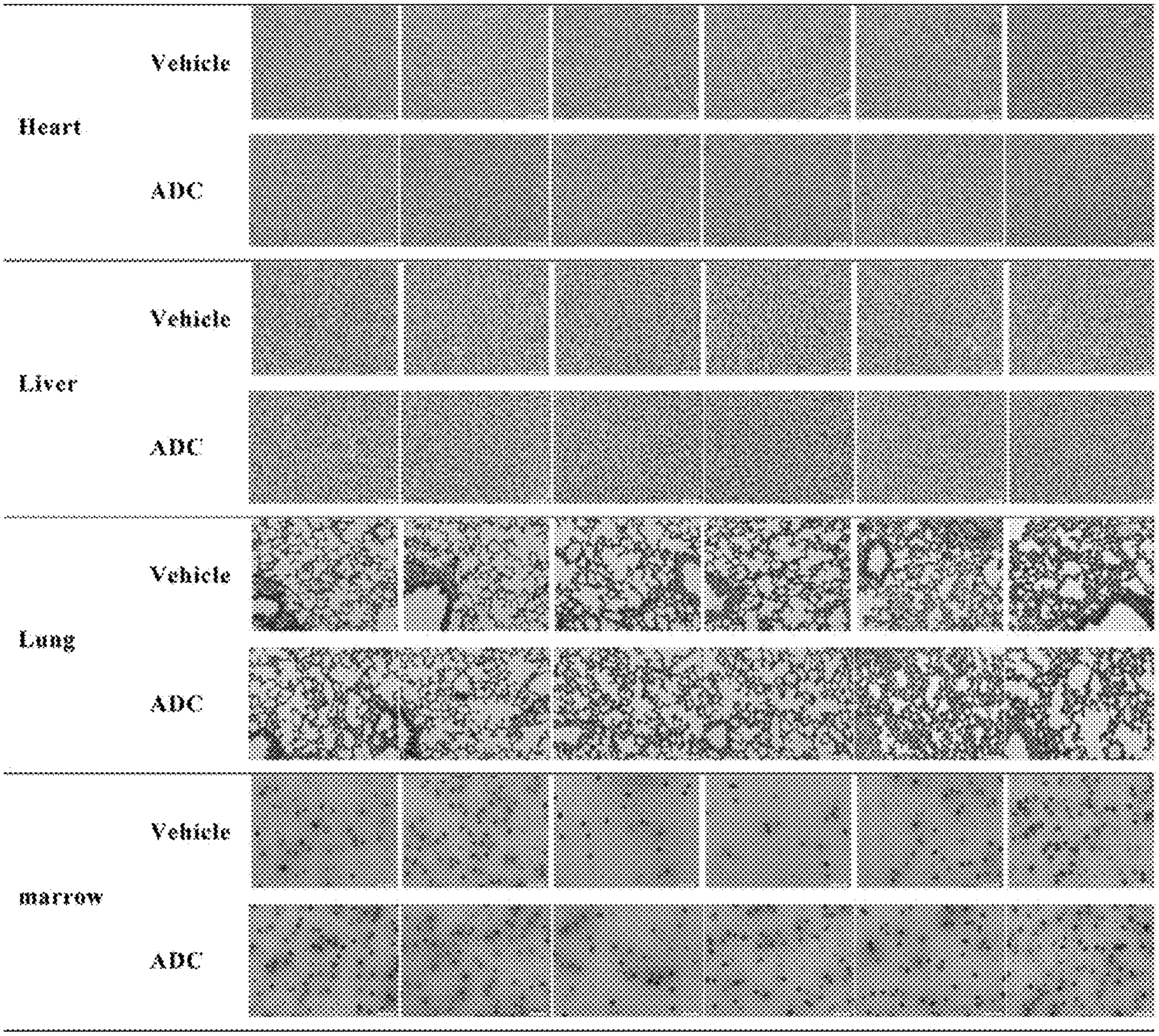
FIG. 12 shows the results of tissue sections and bone marrow smears taken under a microscope, wherein each administration group contained 6 animals, and the original size of picture was 425×320 μm. The results showed that compared with the solvent control group, the test compound treatment group did not show a significant difference. This experiment further confirmed the drug safety of the ADC provided in the present application.

Example 19: Histopathological Analysis of MAB-W'-$C_6$-Val-Ala-PAB-MMAE at Therapeutic Dose in Xenograft Model When the test in BT-474 xenograft model was completed, the inventors performed histopathological study on the animals treated with the ADC (MAB-W'-$C_6$-Val-Ala-PAB-MMAE) containing ring-opening methyl ester linker (W'). The test organs mainly included bone marrow, heart, liver and lung. Tissue samples of heart, liver, and lung were fixed in 10% formalin for 24 hours and transferred to 70% ethanol, dehydrated with 70% ethanol, 85% ethanol, 90% ethanol, 95% ethanol, 100% ethanol, and treated with xylene for 3 times, then embedded with paraffin, sectioned and subjected to H&E staining. The bone marrow was made into a smear. The tissue sections and bone marrow smear were observed with magnifying glass, and pictures were taken under microscope. The results were shown in FIG. 12. Each administration group contained 6 animals, and the original size of picture was 425×320 μm.

The results showed that compared with the solvent control group, the test compound treatment groups also showed no significant difference. This experiment further confirmed the safety of using the ADC provided in the present application.

Example 20: Large-Dose Tolerance Test of MAB-W'-$C_6$-Val-Ala-PAB-MMAE (DAR: About 4)

In this example, on a normal CD-1 mouse model, the maximal tolerance dose of the ADC (MAB-W'—$C_6$-Val-Ala-PAB-MMAE, DAR was about 4) containing ring-opening methyl ester linker (W') was evaluated.

The CD-1 mice [Crl: CD-1 (ICR)] used in the experiment were purchased from Beijing Vital River Laboratory Animal Technology Co., Ltd., about 7 to 9 weeks old, about 22 to 40 g for males, and 20 to 35 g for females. Each test drug dose group had 6 animals (half male and half female); the animals were separately fed in mouse boxes with polycarbonate solid bottom and with corn cobs as bedding. The animals freely ate rodent feed and freely drank water in bottle. The environment was controlled to maintain temperature at 20° C. to 26° C. and relative humidity at 40% to 70%, and the lighting of animal room was maintained at light/dark alternation per 12 hours.

The test drug was dissolved in physiological saline and then injected through tail vein. Five dose groups were set for administration: 10 mg/kg, 20 mg/kg, 40 mg/kg, 80 mg/kg and 120 mg/kg. The volume for administration was 5 mL/kg. The observation period of animals after administration was 15 days, the animals at termination of experiment or the dying animals during experiment were euthanized by inhalation of 70% $CO_2$/30% $O_2$. During the observation period after administration, cage-side observation (including the death or dying of animals, the general health condition and symptoms of drug toxicity of animals) was performed twice a day; one day before the administration and 14 consecutive days thereafter, the test animals were subjected to body weight test and detailed clinical observation once per day (including changes in skin, coat, eyes and mucous membranes of animals, as well as changes in respiratory system, circulatory system, autonomic and central nervous systems, physical movement and behavior patterns, etc.).

In the aforementioned tolerance study of the test drug, after the animals of the dose groups of 10 mg/kg, 20 mg/kg, 40 mg/kg and 80 mg/kg were administrated with the test drug ADC-II (MAB-W'-$C_6$-Val-Ala-PAB-MMAE), no significant tolerable toxicity and animal death occurred. In the maximum dose group of 120 mg/kg, the body weight of the mice continuously decreased on the $1^{st}$ to $5^{th}$ day after the administration, and death occurred in test animals (in 6 test animals 2 died); in addition, all the surviving animals in the test group of 120 mg/kg showed varying degrees of hair loss on the neck, abdomen and limbs from the $9^{th}$ day after the administration, some test animals had scabs on the hair-loss sites and granular protrusions under skin, and these symptoms were not improved significantly until the termination of the test period (the $15^{th}$ day after administration). It showed that the dose of 120 mg/kg had reached the maximal tolerance dose (MTD) of ADC-II (MAB-W'-$C_6$-Val-Ala-PAB-MMAE).

Taking ADC-II as an example, in the mouse xenograft model test of the HER2-expressing human breast cancer cell line BT-474, when the dose was 2.5 mg/kg, all tumors in the test animals disappeared and did not reoccur within 1 month after the withdraw of drug (Example 16). In the tolerability and safety evaluation study, the dose of 80 mg/kg did not show dose-related toxicity of the test substance, and some animals died when the dose was 120 mg/kg, which indicated that the ADC test compound MAB-W'-$C_6$-Val-Ala-PAB-MMAE had relatively better tolerability and higher therapeutic index.

Finally, it should be noted that the above examples are only used to illustrate the technical solutions of the present application and not to limit it; although the present application has been described in detail with reference to the preferred examples, those of ordinary skill in the art should understand that: the specific implementation of the present application can be modified or some technical features can be equivalently replaced without departing from the spirit of the technical solution of the present application, and all of them shall be covered by the scope of the technical solutions that are sought to be protected by the present application.

What is claimed is:

1. A compound represented by Formula III, a salt or a solvate thereof,

III

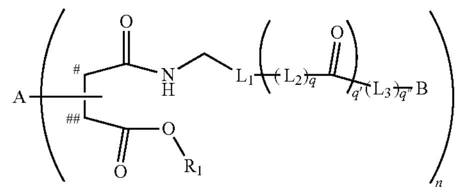

wherein:

A is a targeting compound selected from antibody; A is coupled to the site # or ## through a S atom in the B targeting compound;

B is an active compound selected from the group consisting of auristatin, methyl-auristatin E (MMAE), maytansine, maytansinoid, DM1, DM3, DM4, paclitaxel, calicheamicin, duocarmycin, doxorubicin, camptothecin, and pyrrolobenzodiazepine, wherein DM1, DM3 and DM4 are defined as:

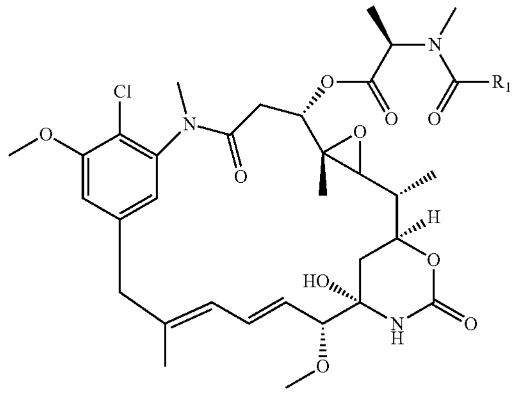

$R_1 = CH_2CH_2SH$ DM1
$R_1 = CH_2CH_2CH(CH_3)SH$ DM3
$R_1 = CH_2CH_2C(CH_3)_2SH$ DM4,

B is coupled to the site * through a N atom or O atom in the active compound; or B is coupled to $L^3$ through a N atom or O atom in the active compound;

n is a number between 0.5 and 8.5;

$R_1$ is a $C_{1-6}$ linear or branched alkyl, and $R_1$ is optionally mono- or multi-substituted by one or more substituents selected from the group consisting of: halogen and $C_{1-4}$ alkoxy;

$L^1$ is selected from the group consisting of: $-(CH_2)_m-$, $-(CH_2)_tO-$, $-(CH_2CH_2O)_r-$, $-O-$, $-NH-$, $-S-$, $-S(O)-$, $-S(O)_2-$, $-NCH_3-$, $-NH(CH_2)_2NH-$, $-C(O)-$, $-(CH_2)_e-C(O)NH-(CH_2CH_2O)_f-(CH_2)_g-$, $-(CH_2)_h-C(O)NH-CH[(CH_2)_i-NHC(O)-(CH_2CH_2O)-(CH_2)_k-CH_3]-$,

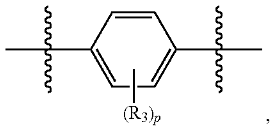
,
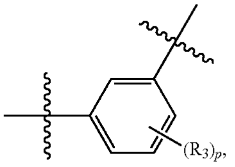

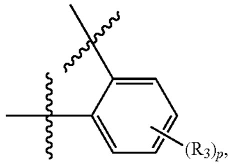
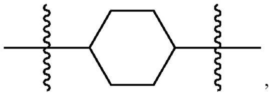
,

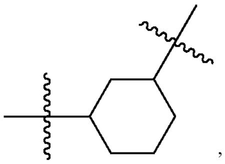
,
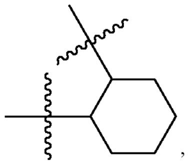
, and
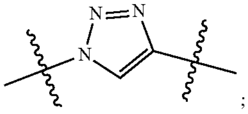
;

$L^2$ is
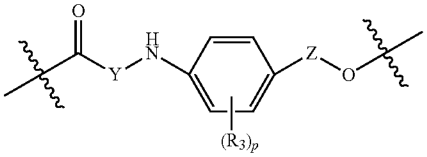
or
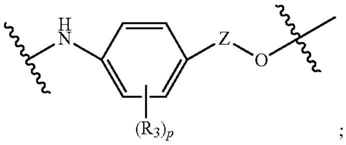
;

$L^3$ is
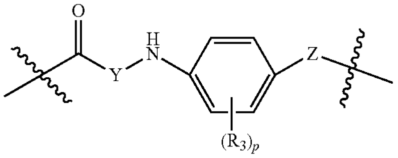
;

q' is 1 and q" is 0, or q' is 0 and q" is 1;

$R_3$ is selected from the group consisting of: hydrogen, halogen, methyl, ethyl, nitro, methoxy, and ethoxy;

q is 0 or 1;

m, r, t, e, f, g, h, i, j and k are each independently selected from the group consisting of 0, 1, 2, 3, 4, 5, 6, 7, 8, 9, 10 and 11;

each p is independently 0, 1, 2, 3 or 4;

Y is an amino acid residue formed by a dipeptide selected from the group consisting of: Val-Cit, Val-Ala, Val-Lys, Val-Gly, Val-Thr, Val-Val, Val-Leu, Val-Ile, Val-Asn and Phe-Lys, wherein the N-terminus is connected to the carbonyl and the C-terminus is connected to the N atom;

Z is $-CH_2-$, $-CH(CH_3)-$ or $-C(CH_3)_2-$.

2. The compound represented by Formula III according to claim 1, a salt or a solvate thereof, wherein $L^1$ is selected from the group consisting of: $-(CH_2)_m-$, $-(CH_2)_tO-$, $-(CH_2CH_2O)_r-$, $-O-$, $-NH-$, $-S-$, $-S(O)-$, $-S(O)_2-$, $-NCH_3-$, $-NH(CH_2)_2NH-$, $-C(O)-$,

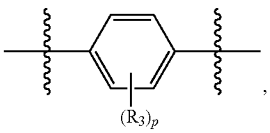
,
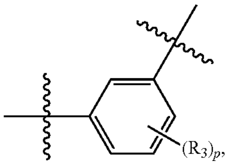

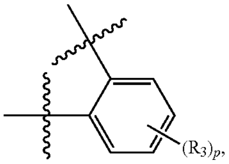
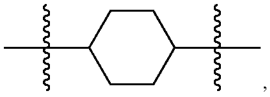
,

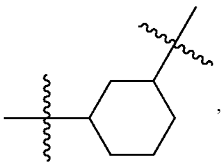
,
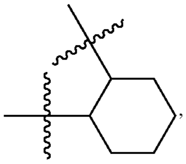
, and
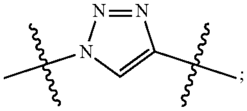
;

wherein m, t and r are each independently selected from the group consisting of 0, 1, 2, 3, 4, 5, 6, 7, 8, 9, 10 and 11, or $L^1$ is $-(CH_2)_e-C(O)NH-(CH_2CH_2O)_f-(CH_2)_g-$, or $-(CH_2)_h-C(O)NH-CH[(CH_2)_i-NHC(O)-(CH_2CH_2O)_j-(CH_2)_k-CH_3]-$, wherein e, f, g, h, i, j and k are each independently selected from the group consisting of 0, 1, 2, 3, 4, 5, 6, 7, 8, 9, 10 and 11.

3. The compound according to claim 1, a salt or a solvate thereof, wherein the compound is a compound represented by Formula VI,

VI

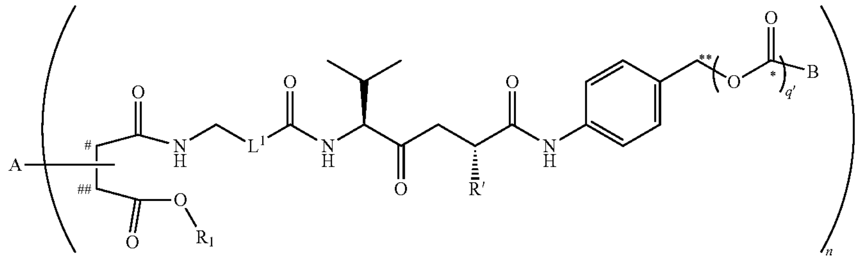

wherein,

A is a targeting compound selected from antibody; A is coupled to the site # or ## through a S atom in the targeting compound;

q' is 0 or 1;

B is an active compound selected from the group consisting of auristatin, methyl-auristatin E (MMAE), maytansine, maytansinoid, DM1, DM3, DM4, paclitaxel, calicheamicin, duocarmycin, doxorubicin, camptothecin, and pyrrolobenzodiazepine, wherein DM1, DM3 and DM4 are defined as:

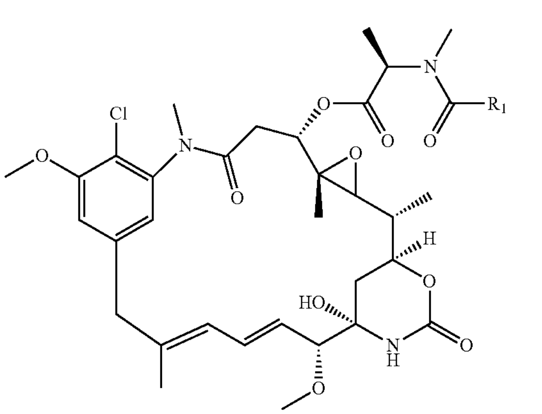

$R_1 = CH_2CH_2SH$ DM1
$R_1 = CH_2CH_2CH(CH_3)SH$ DM3
$R_1 = CH_2CH_2C(CH_3)_2SH$ DM4,

B is coupled to the site * through a N atom or O atom in the active compound when q' is 1; or B is coupled to the site ** through a N atom or O atom in the active compound when q' is 0;

n is a number between 0.5 and 8.5;

$R_1$ is a $C_{1-6}$ linear or branched alkyl group, and $R_1$ is optionally mono- or multi-substituted by one or more substituents selected from the group consisting of: halogen and $C_{1-4}$ alkoxy;

$L^1$ is selected from the group consisting of: $—(CH_2)_m—$, $—(CH_2)_tO—$, $—(CH_2CH_2O)_r—$, —O—, —NH—, —S—, —S(O)—, $—S(O)_2—$, $—NCH_3—$, $—NH(CH_2)_2NH—$, —C(O)—, $—(CH_2)_e—C(O)NH—(CH_2CH_2O)_f—(CH_2)_g—$, $—(CH_2)_h—C(O)NH—CH[(CH_2)_i—NHC(O)—(CH_2CH_2O)_j—(CH_2)—CH_3]—$,

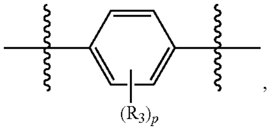
,
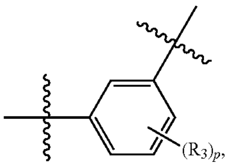
,
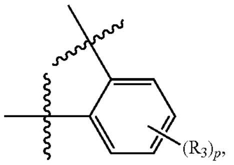
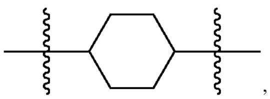
,
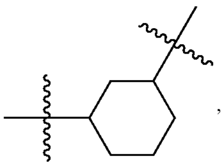
,
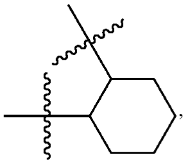
, and
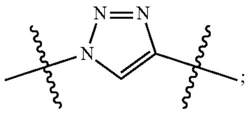
;

R' is a substituent side chain in the variable group (R) of the amino acid residue; R' is $—CH_3$, $—(CH_2)_3NHCONH_2$, $—(CH_2)_4—NH_2$, —H, $—CH(CH_3)—OH$, $—CH—(CH_3)_2$, $—CH_2—CH(CH_3)_2$, $—CH(CH_3)—CH_2—CH_3$ or $—CH_2—CONH_2$;

$R_3$ is independently selected from the group consisting of: hydrogen, halogen, methyl, ethyl, nitro, methoxy and ethoxy;

m, r and t are each independently selected from the group consisting of 0, 1, 2, 3 and 4;

e, f, g, h, i, j and k are each independently selected from the group consisting of 0, 1, 2, 3, 4, 5, 6, 7, 8, 9 and 10;

each p is independently 0, 1, 2, 3 or 4.

4. The compound according to claim 1, a salt or a solvate thereof, wherein the compound is selected from the group consisting of:

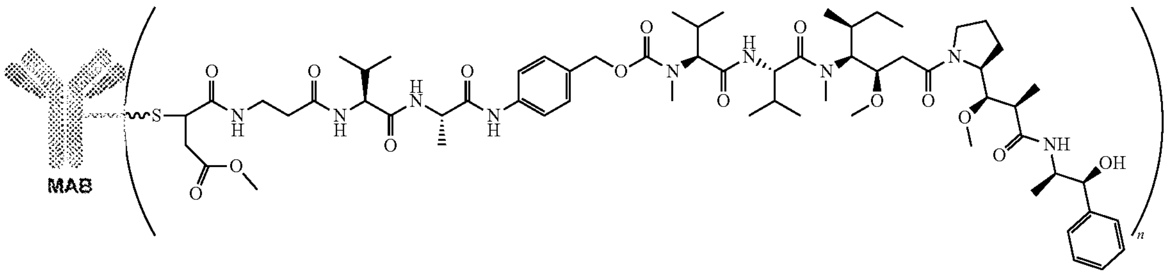
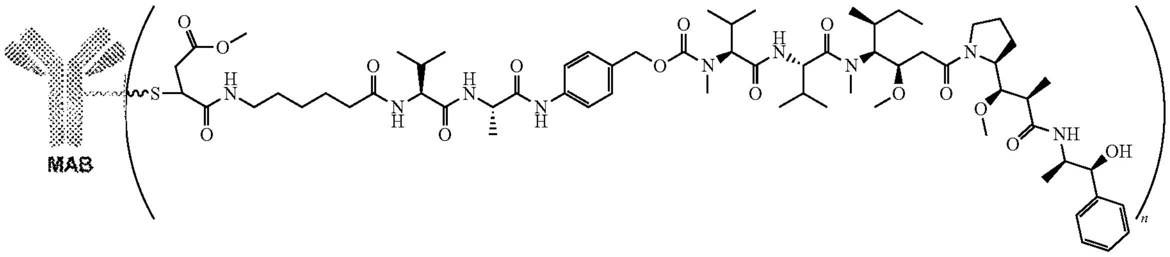
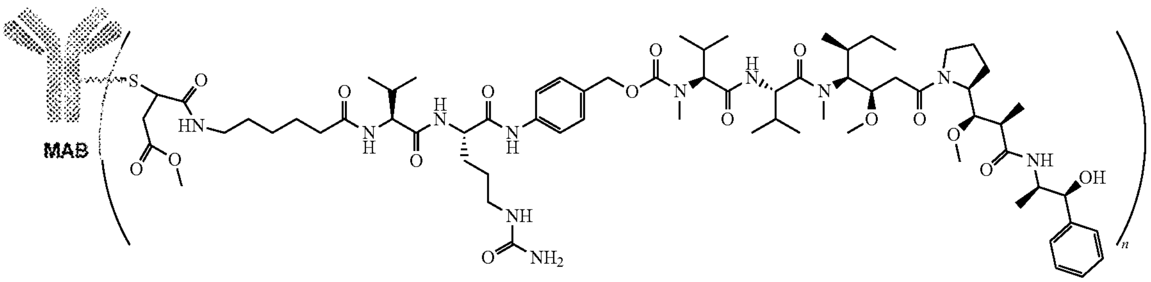
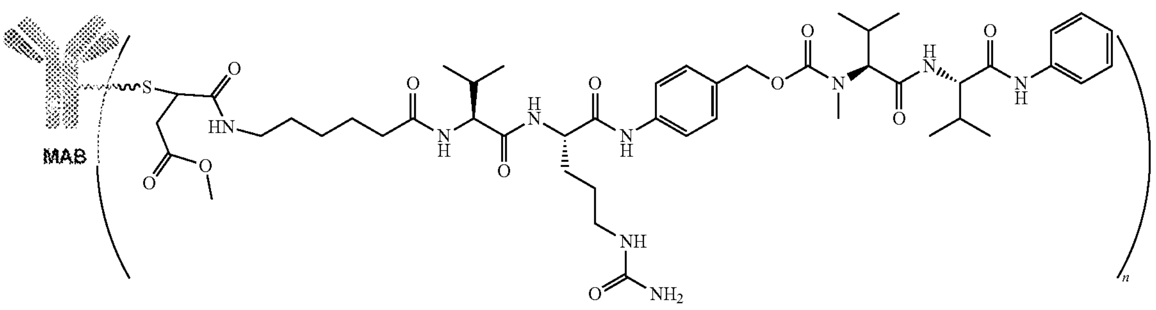
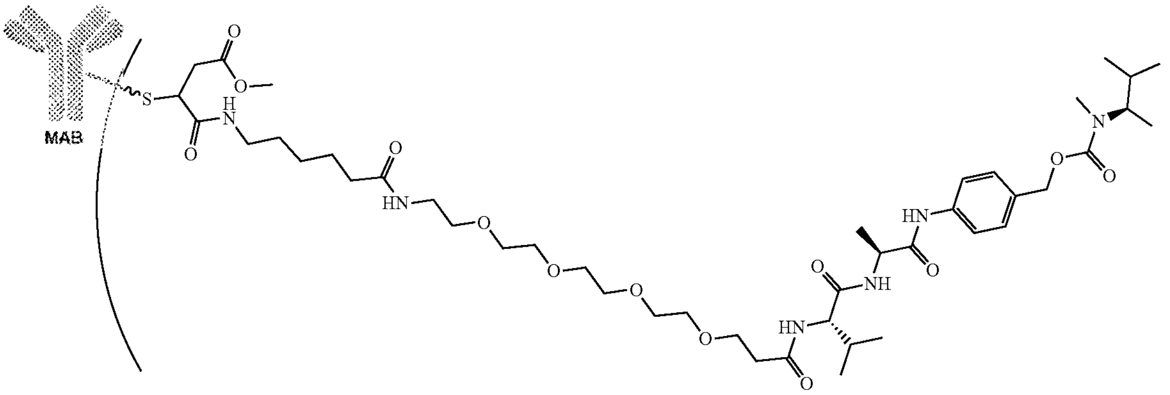

-continued
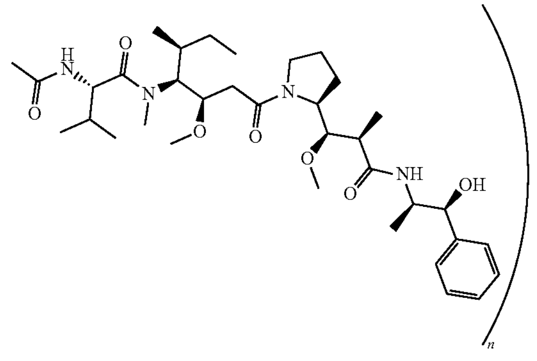
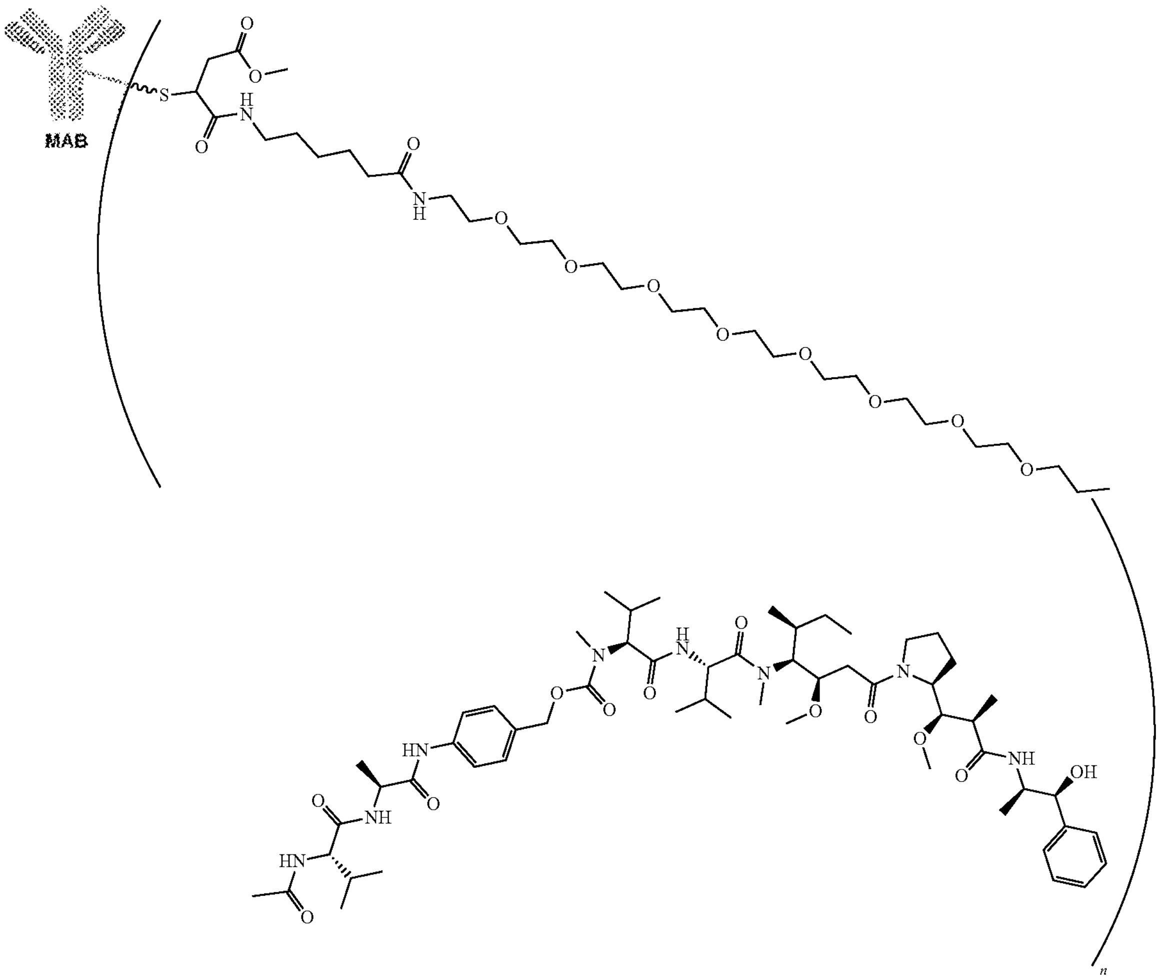
and
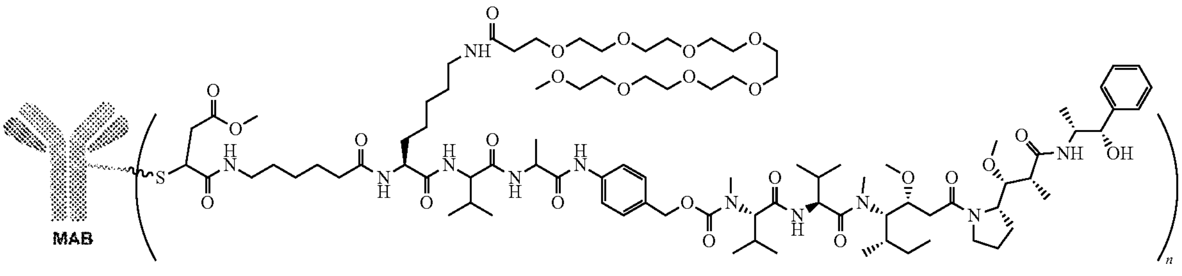
wherein MAB is an antibody, and n is defined as described in claim 1.

5. A pharmaceutical composition, which comprises at least one compound according to claim 1, a salt or a solvate thereof, and one or more pharmaceutically acceptable carriers or excipients.

6. A method for preparing the compound represented by Formula III according to claim 1, a salt or a solvate thereof, comprising the following steps:

reacting a compound represented by Formula II or a salt or a solvate thereof with A, wherein A is coupled to the site # through a S atom in the targeting compound to obtain the compound represented by Formula III,

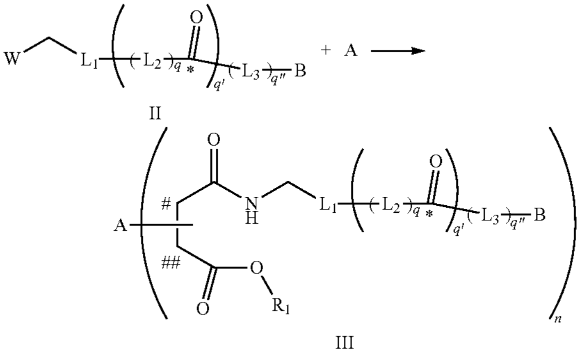

wherein:

W is

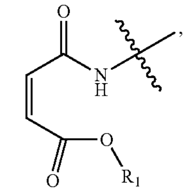

wherein the two carbonyl groups are located on the same side of the C═C double bond, which is a cis structure, $R_1$ is a $C_{1-6}$ linear or branched alkyl, and $R_1$ is optionally mono- or multi-substituted by one or more substituents selected from the group consisting of: halogen and $C_{1-4}$ alkoxy;

the definitions of $L^1$, $L^2$, $L^3$, q, q', q'', and B are same as described in claim 1.

7. A method for diagnosis or treatment of a disease or condition or reducing a severity of the disease or condition, the method comprising administering to a patient in need of such treatment an effective amount of the compound according to claim 1, salt or a solvate thereof, wherein the disease or condition is selected from the group consisting of tumor, infectious disease, hematological disease, metabolic disease and inflammation.

8. The compound according to claim 4, a salt or a solvate thereof, wherein MAB is selected from the group consisting of: anti-HER2 humanized monoclonal antibody mil40, trastuzumab, pertuzumab, cetuximab, panitumumab, rituximab, alemtuzumab, ibritumomab, tositumomab, ofatumumab, bevacizumab, ipilimumab, denosumab, pembrolizumab, nivolumab, Avelumab, Atezolizumab, durvalumab, sacituzumab, and rovalpituzumab.

9. The method according to claim 7, wherein the tumor is selected from the group consisting of cancer, lymphoma, lymphoid tumor, blastoma, sarcoma and leukemia.

10. The method according to claim 9, wherein the cancer is selected from the group consisting of: breast cancer; squamous cell carcinoma; lung cancer; peritoneal cancer; liver cancer; gastric cancer; gastrointestinal cancer; pancreatic cancer; glioblastoma; cervical cancer; ovarian cancer; liver cancer; bladder cancer; urethral cancer; hepatocellular tumor; breast cancer; intestinal cancer; colon cancer; rectal cancer; colorectal cancer; endometrial cancer; uterine cancer; salivary gland cancer; renal or kidney cancer; prostate cancer; vulvar cancer; thyroid cancer; liver cancer; anal cancer; penile cancer; melanoma; multiple myeloma and B-cell lymphoma; brain cancer; gallbladder cancer; esophageal cancer; cholangiocarcinoma; head and neck cancer and related metastatic tumor.

11. The method according to claim 10, wherein the breast cancer is HER2-positive breast cancer, the squamous cell carcinoma is epithelial squamous cell carcinoma, the lung cancer is small cell lung cancer, non-small cell lung cancer, adenocarcinoma of lung or squamous cell carcinoma of lung.

* * * * *